United States Patent
Kim et al.

(10) Patent No.: US 11,737,356 B2
(45) Date of Patent: Aug. 22, 2023

(54) ORGANIC ELECTROLUMINESCENCE DEVICE AND AMINE COMPOUND FOR ORGANIC ELECTROLUMINESCENCE DEVICE

(71) Applicant: Samsung Display Co., Ltd., Yongin-si (KR)

(72) Inventors: Dongjun Kim, Suwon-si (KR); Minji Kim, Hwaseong-si (KR); Eunjae Jeong, Hwaseong-si (KR); Sohee Jo, Seoul (KR); Sanghyun Han, Hwaseong-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 288 days.

(21) Appl. No.: 16/997,595

(22) Filed: Aug. 19, 2020

(65) Prior Publication Data

US 2021/0175430 A1 Jun. 10, 2021

(30) Foreign Application Priority Data

Nov. 29, 2019 (KR) .................. 10-2019-0157409

(51) Int. Cl.
*H10K 50/15* (2023.01)
*H10K 50/17* (2023.01)
(Continued)

(52) U.S. Cl.
CPC ......... *H10K 85/636* (2023.02); *C07D 421/12* (2013.01); *H10K 50/15* (2023.02);
(Continued)

(58) Field of Classification Search
CPC ...... H10K 85/636; H10K 50/15; H10K 50/17; H10K 85/6572; H10K 85/6574;
(Continued)

(56) References Cited

U.S. PATENT DOCUMENTS 8,580,399 B2   11/2013   Dyatkin et al.
10,340,464 B2 *  7/2019   Ma .................. H10K 85/615
(Continued)

FOREIGN PATENT DOCUMENTS

CN   101238122 A  *  8/2008  ........... C07D 471/04
CN   102668160 B  *  6/2016  ............. C09K 11/06
(Continued)

*Primary Examiner* — Mohammed Shamsuzzaman
(74) *Attorney, Agent, or Firm* — Lewis Roca Rothgerber Christie LLP

(57) ABSTRACT

An organic electroluminescence device includes a first electrode, a second electrode facing the first electrode, and a plurality of organic layers between the first electrode and the second electrode, wherein at least one of the plurality of organic layers includes an amine compound, the amine compound includes a central nitrogen atom, a carbazole group substituted to the central nitrogen atom, and a dibenzoselenophene group substituted to the central nitrogen atom, and a nitrogen atom of the carbazole group is substituted with a substituted or unsubstituted aryl group or a substituted or unsubstituted heteroaryl group. The organic electroluminescence device thereby has high efficiency and long-life.

9 Claims, 2 Drawing Sheets

(51) Int. Cl.
*H10K 85/60* (2023.01)
*C07D 421/12* (2006.01)

(52) U.S. Cl.
CPC ......... *H10K 50/17* (2023.02); *H10K 85/6572* (2023.02); *H10K 85/6574* (2023.02); *H10K 85/6576* (2023.02)

(58) Field of Classification Search
CPC ............. H10K 85/6576; H10K 50/156; H10K 85/615; H10K 85/633; H10K 85/657; C07D 421/12
See application file for complete search history.

(56) References Cited

U.S. PATENT DOCUMENTS

| | | | | |
|---|---|---|---|---|
| 10,673,000 | B2* | 6/2020 | Fuchiwaki | H10K 85/6574 |
| 11,165,029 | B2* | 11/2021 | Ueno | H10K 85/615 |
| 2005/0129982 | A1* | 6/2005 | Fukuoka | H10K 85/615 |
| | | | | 313/506 |
| 2007/0278938 | A1* | 12/2007 | Yabunouchi | H10K 85/633 |
| | | | | 313/504 |
| 2008/0106190 | A1* | 5/2008 | Yabunouchi | H10K 50/00 |
| | | | | 313/504 |
| 2009/0009065 | A1* | 1/2009 | Nishimura | H05B 33/14 |
| | | | | 313/504 |
| 2009/0309491 | A1* | 12/2009 | Kwon | C09K 11/06 |
| | | | | 313/504 |
| 2013/0032788 | A1* | 2/2013 | Lee | C07D 403/12 |
| | | | | 257/E51.026 |
| 2013/0112951 | A1* | 5/2013 | Xia | H10K 71/00 |
| | | | | 438/46 |
| 2014/0209880 | A1* | 7/2014 | Choi | H10K 85/6572 |
| | | | | 257/40 |
| 2014/0361259 | A1* | 12/2014 | Hwang | C07D 401/10 |
| | | | | 546/64 |
| 2015/0207084 | A1* | 7/2015 | Hwang | H10K 85/342 |
| | | | | 257/40 |
| 2017/0179416 | A1 | 6/2017 | Lim et al. | |
| 2019/0067599 | A1* | 2/2019 | Kravchuk | C07F 15/0033 |
| 2019/0123284 | A1 | 4/2019 | Yen et al. | |
| 2020/0020859 | A1* | 1/2020 | Hatakeyama | H10K 85/322 |
| 2023/0013038 | A1* | 1/2023 | Sakamoto | H10K 85/631 |

FOREIGN PATENT DOCUMENTS

| | | | | |
|---|---|---|---|---|
| CN | 110226241 B | * | 8/2022 | ............. C09K 11/06 |
| EP | 2617712 A1 | * | 7/2013 | ........... C07D 209/86 |
| JP | 2000169448 A | * | 6/2000 | ........... C07C 211/54 |
| JP | 2000186066 A | * | 7/2000 | ........... C07C 211/54 |
| JP | 2000247932 A | * | 9/2000 | ........... C07C 211/54 |
| JP | 2007112729 A | * | 5/2007 | ........... C07C 211/54 |
| KR | 10-2017-0075116 A | | 7/2017 | |
| KR | 10-2018-0052543 A | | 5/2018 | |
| KR | 10-1950045 B1 | | 2/2019 | |
| WO | WO-2013118507 A1 | * | 8/2013 | .......... C07F 9/65517 |
| WO | WO-2018139662 A1 | * | 8/2018 | ............. C09K 11/06 |

* cited by examiner

ORGANIC ELECTROLUMINESCENCE DEVICE AND AMINE COMPOUND FOR ORGANIC ELECTROLUMINESCENCE DEVICE

CROSS-REFERENCE TO RELATED APPLICATION

This application claims priority to and the benefit of Korean Patent Application No. 10-2019-0157409, filed on Nov. 29, 2019, the entire content of which is hereby incorporated by reference.

BACKGROUND

1. Field

One or more aspects of embodiments of the present disclosure herein relate to an organic electroluminescence device and an amine compound used therein.

2. Description of the Related Art

The development of an organic electroluminescence device (e.g., organic electroluminescence display) as an image display apparatus is being actively conducted. The organic electroluminescence device is a self-luminescent display apparatus, in which holes and electrons injected from a first electrode and a second electrode, respectively, recombine in an emission layer to generate excitons, and these excitons fall to the ground state to emit light, thereby implementing display of images.

Meanwhile, in the development of materials for a hole transport region, although the development of an amine compound continues, there is a demand (or desire) for the development of a highly efficient and long-life amine compound and an organic electroluminescence device including the same.

SUMMARY

One or more aspects of embodiments of the present disclosure are directed toward an organic electroluminescence device having an increased lifetime (lifespan).

One or more aspects of embodiments of the present disclosure are directed toward an amine compound having an improved lifetime.

An embodiment of the present disclosure provides an organic electroluminescence device including a first electrode, a second electrode facing the first electrode, and a plurality of organic layers between the first electrode and the second electrode, wherein at least one of the plurality of organic layers includes an amine compound, the amine compound includes a central nitrogen atom, a carbazole group substituted to the central nitrogen atom, and a dibenzoselenophene group substituted to the central nitrogen atom, and a nitrogen atom of the carbazole group is substituted with a substituted or unsubstituted aryl group or a substituted or unsubstituted heteroaryl group.

In an embodiment of the present disclosure, the amine compound may further include a substituted or unsubstituted aryl group and a substituted or unsubstituted heteroaryl group substituted to the central nitrogen atom.

In an embodiment of the present disclosure, the amine compound may further include a substituted or unsubstituted arylene group or a substituted or unsubstituted heteroarylene group connecting the central nitrogen atom and the carbazole group, and the central nitrogen atom and the dibenzoselenophene group, respectively.

In an embodiment of the present disclosure, the plurality of organic layers may include a hole transport region, an emission layer, and an electron transport region, and the amine compound may be included in the hole transport region.

In an embodiment of the present disclosure, the hole transport region may include a hole transport layer and a hole injection layer, and the amine compound may be included in the hole transport layer.

In an embodiment of the present disclosure, the amine compound may be represented by Formula 1 below.

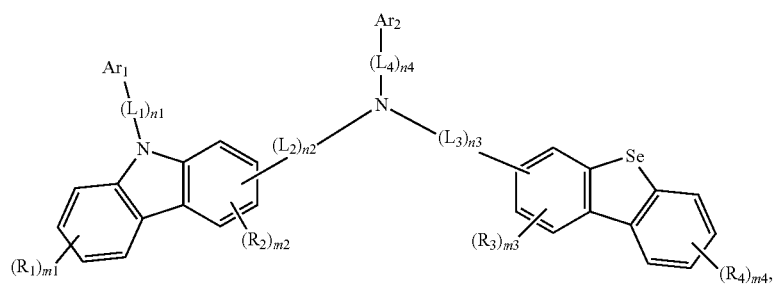

Formula 1

In Formula 1 above, $Ar_1$ and $Ar_2$ may be each independently a substituted or unsubstituted aryl group having 6 to 60 ring-forming carbon atoms, or a substituted or unsubstituted heteroaryl group having 3 to 60 ring-forming carbon atoms.

$L_1$ to $L_4$ may be each independently a direct linkage, a substituted or unsubstituted arylene group having 6 to 60 ring-forming carbon atoms, or a substituted or unsubstituted heteroarylene group having 3 to 60 ring-forming carbon atoms.

$R_1$ to $R_4$ may be each independently a hydrogen atom, a deuterium atom, a halogen atom, a substituted or unsubstituted alkyl group having 1 to 20 carbon atoms, a substituted or unsubstituted aryl group having 6 to 60 ring-forming carbon atoms, or a substituted or unsubstituted heteroaryl group having 3 to 60 ring-forming carbon atoms.

$m_1$ to $m_4$ may be each independently an integer of 0 to 4.

$n_1$ to $n_4$ may be each independently an integer of 0 to 1.

In an embodiment of the present disclosure, the amine compound represented by Formula 1 above may be represented by Formula 1-1 below.

Formula 1-1

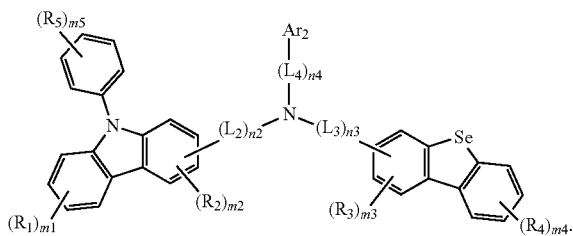

In Formula 1-1 above,

Ar$_2$, L$_2$ to L$_4$, R$_1$ to R$_4$, m$_1$ to m$_4$, and n$_2$ to n$_4$ are the same as defined in Formula 1.

R$_5$ may be a hydrogen atom, a deuterium atom, a halogen atom, a substituted or unsubstituted alkyl group having 1 to 20 carbon atoms, a substituted or unsubstituted aryl group having 6 to 60 ring-forming carbon atoms, or a substituted or unsubstituted heteroaryl group having 3 to 60 ring-forming carbon atoms.

m$_5$ may be an integer of 0 to 5.

In an embodiment of the present disclosure, the amine compound represented by Formula 1 above may be represented by any one of Formulae 2-1 to 2-4 below.

Formula 2-1

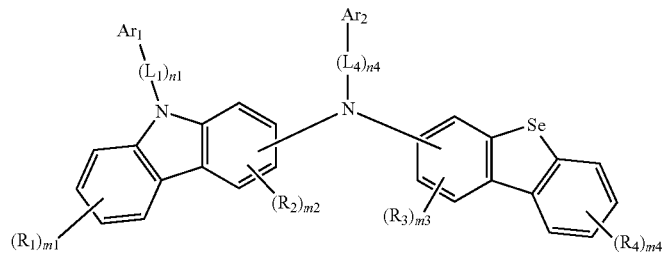

Formula 2-2

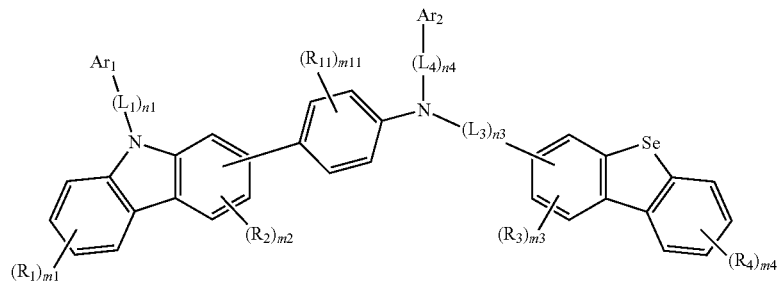

Formula 2-3

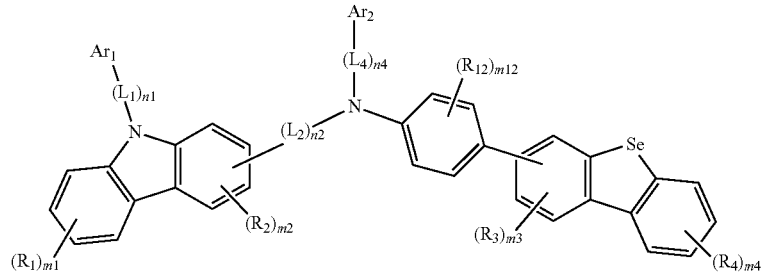

Formula 2-4

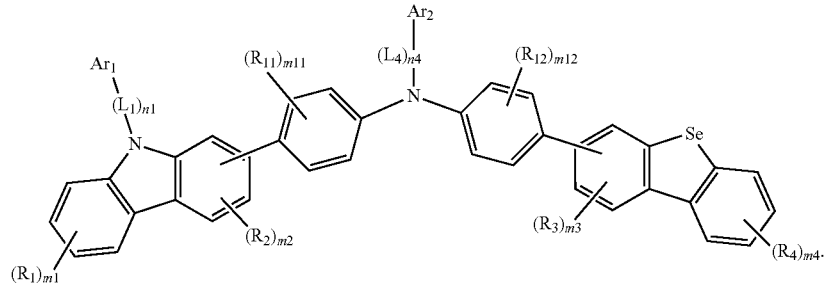

In Formulae 2-1 to 2-4 above, $Ar_1$, $Ar_2$, $L_1$ to $L_4$, $R_1$ to $R_4$, $m_1$ to $m_4$, and $n_1$ to $n_4$ are the same as defined in Formula 1.

$R_{11}$ and $R_{12}$ may be each independently a hydrogen atom, a deuterium atom, a halogen atom, a substituted or unsubstituted alkyl group having 1 to 20 carbon atoms, a substituted or unsubstituted aryl group having 6 to 60 ring-forming carbon atoms, or a substituted or unsubstituted heteroaryl group having 3 to 60 ring-forming carbon atoms.

$m_{11}$ and $m_{12}$ may be each independently an integer of 0 to 4.

In an embodiment of the present disclosure, the amine compound represented by Formula 1 above may be represented by any one of Formulae 3-1 to 3-4 below.

In an embodiment of the present disclosure, $Ar_2$ above may be a substituted or unsubstituted phenyl group, a substituted or unsubstituted naphthyl group, a substituted or unsubstituted phenanthrenyl group, a substituted or unsubstituted dibenzofuranyl group, or a substituted or unsubstituted dibenzothiophenyl group.

In an embodiment of the present disclosure, the amine compound represented by Formula 1 above may be any one of compounds represented by Compound Group 1 below.

Compound Group 1

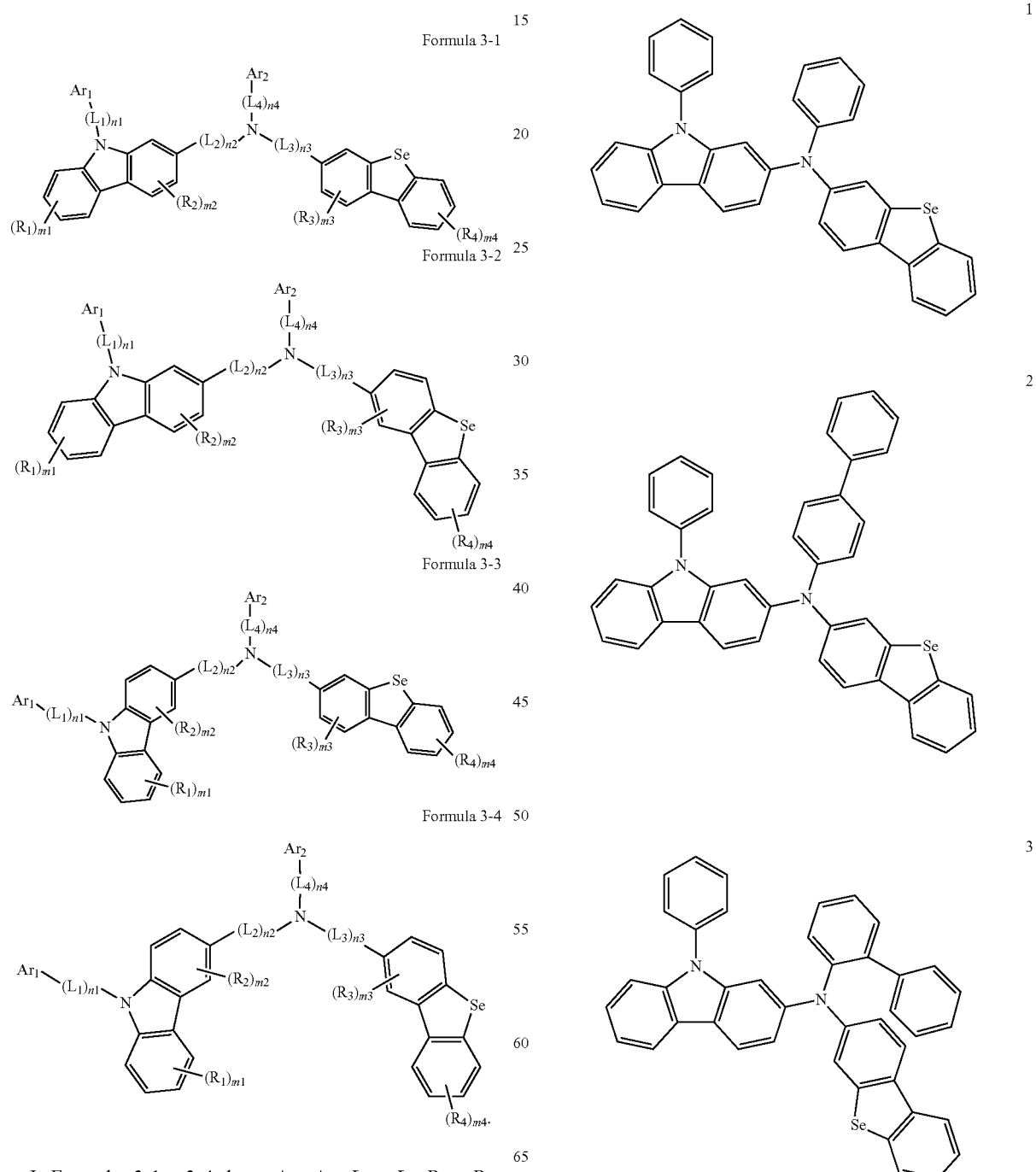

Formula 3-1

Formula 3-2

Formula 3-3

Formula 3-4

In Formulae 3-1 to 3-4 above, $Ar_1$, $Ar_2$, $L_1$ to $L_4$, $R_1$ to $R_4$, $m_1$ to $m_4$, and $n_1$ to $n_4$ are the same as defined in Formula 1.

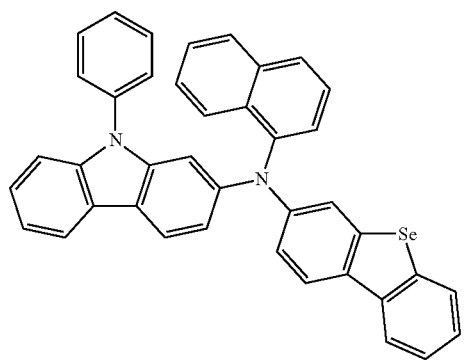
4
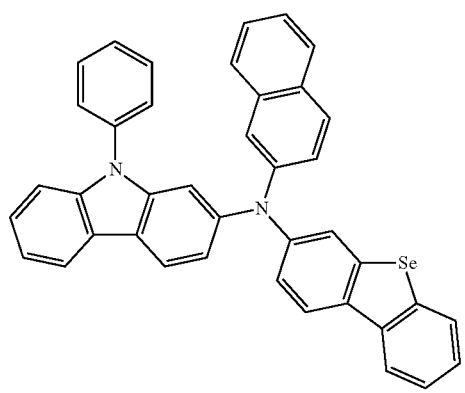
5
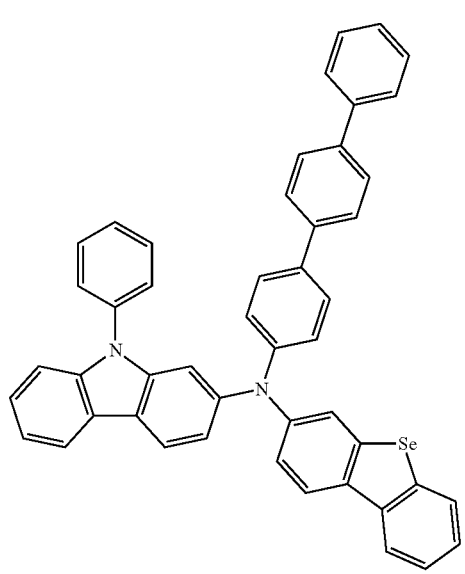
6
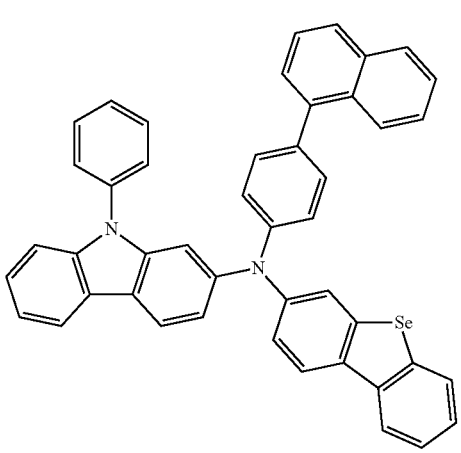
7
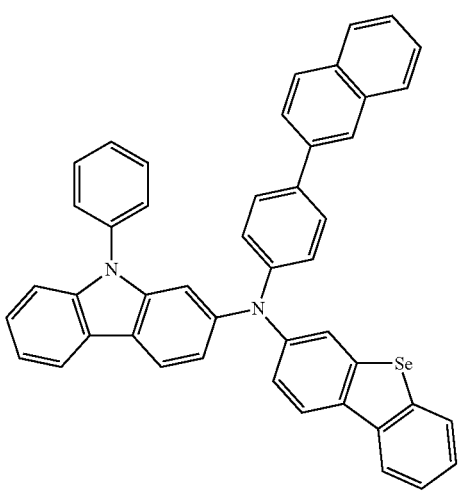
8
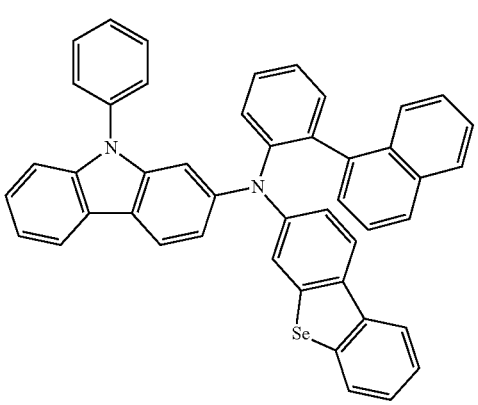
9

10
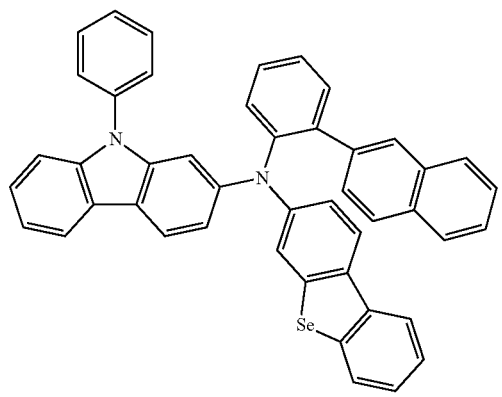
11
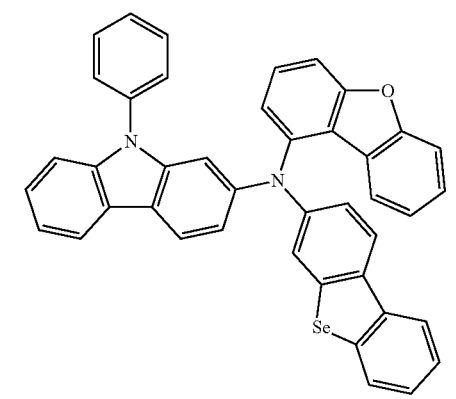
12
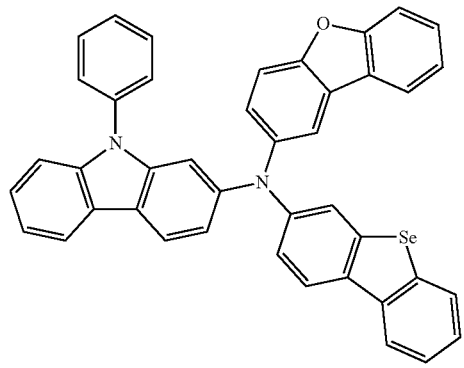
13
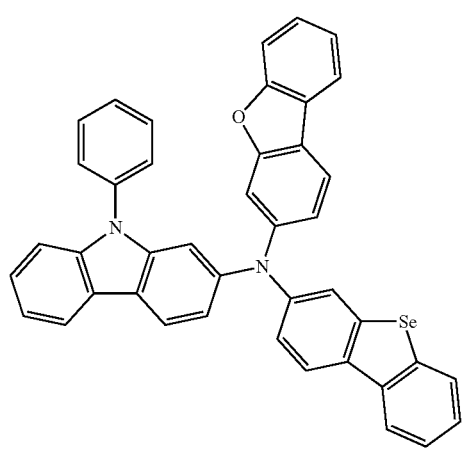
14
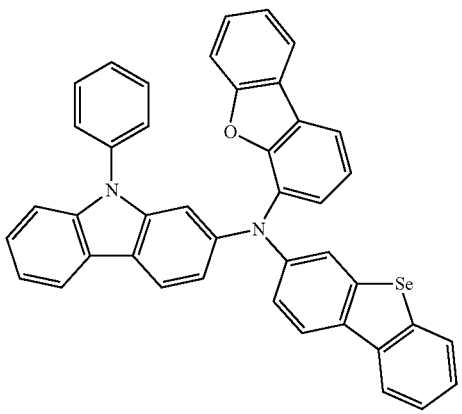
15
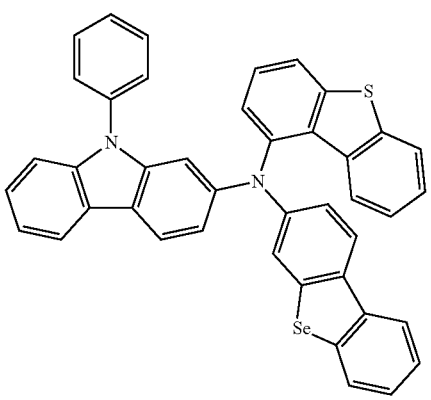
16
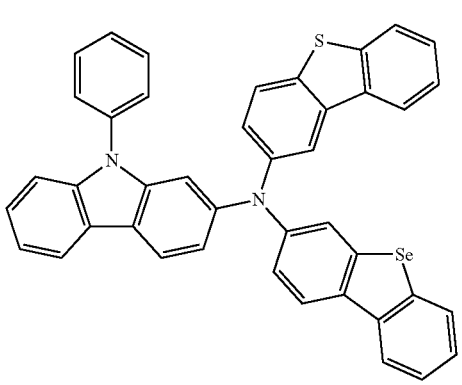
17
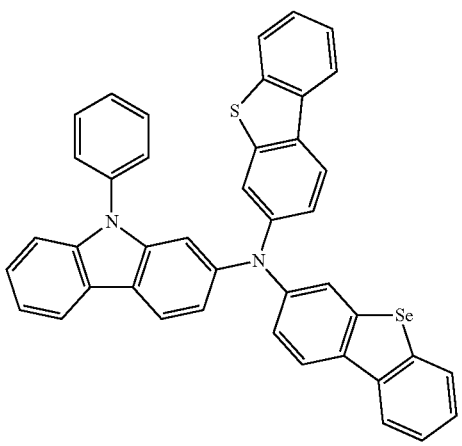

18
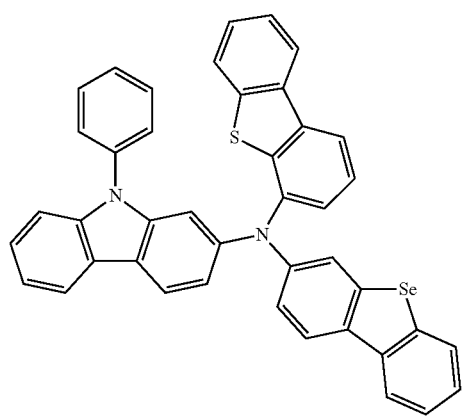
19
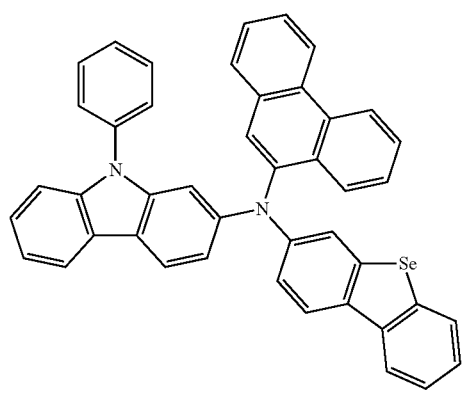
20
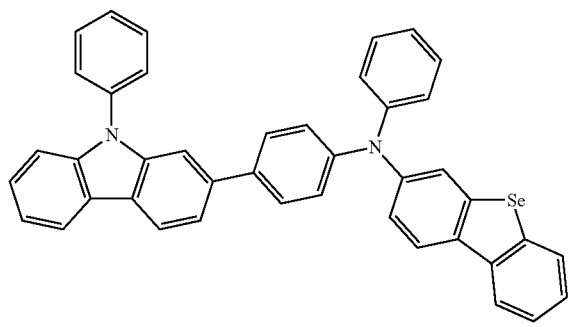
21
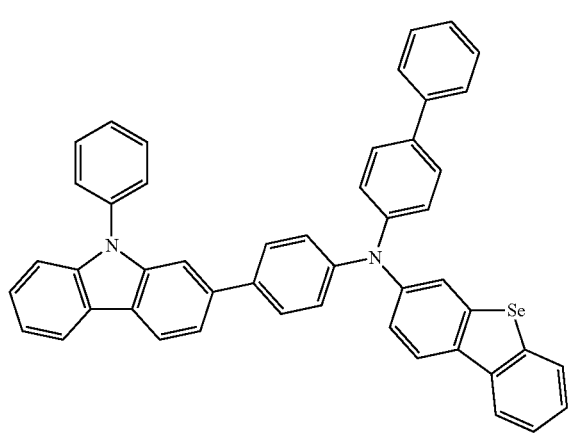
22
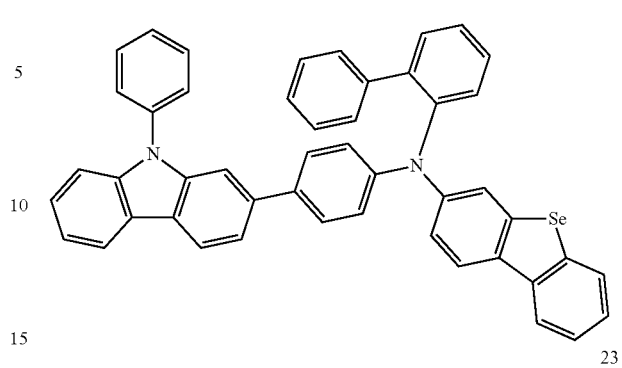
23
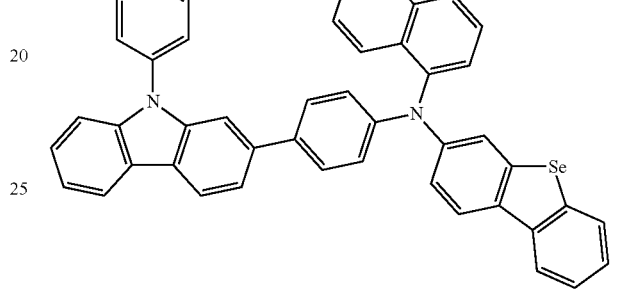
24
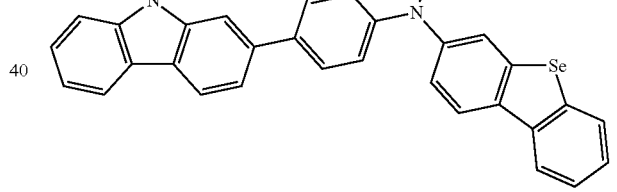
25

-continued
26
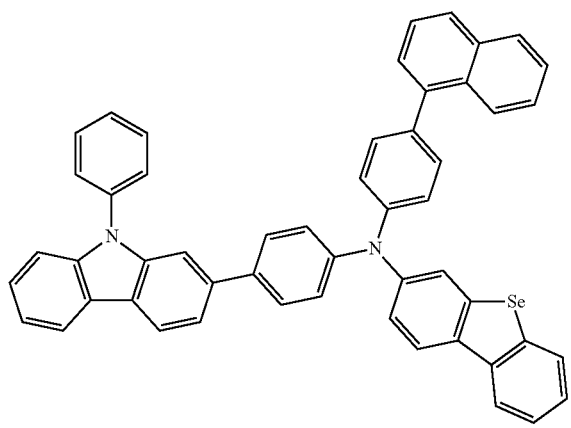
27
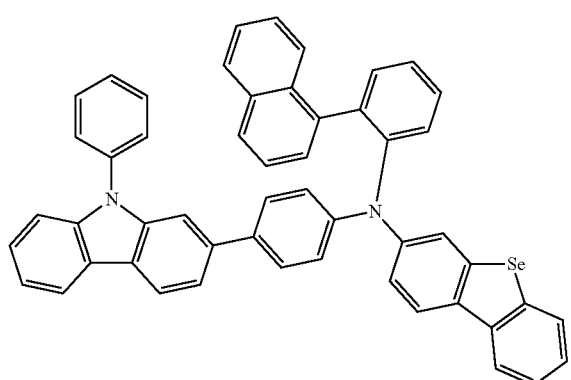
28
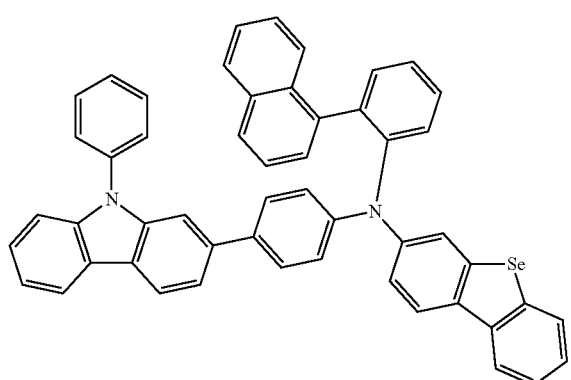
-continued
29
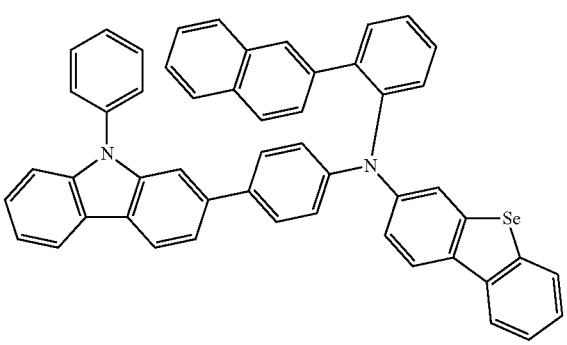
30
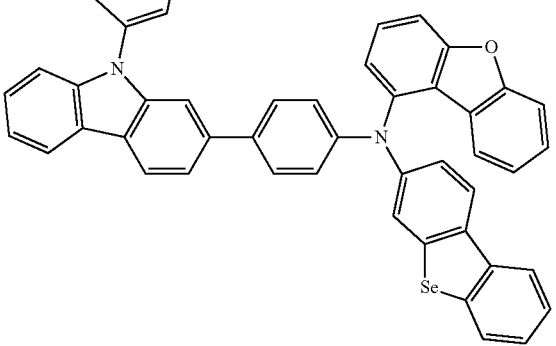
31
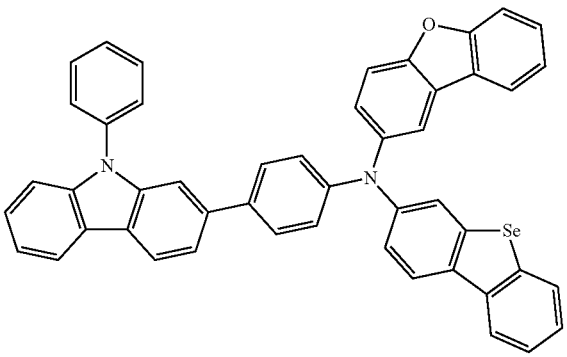
32
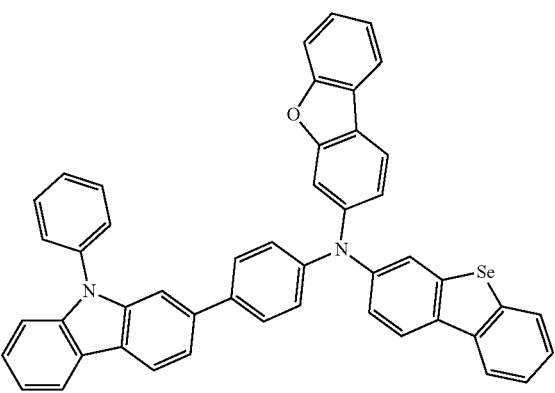

33
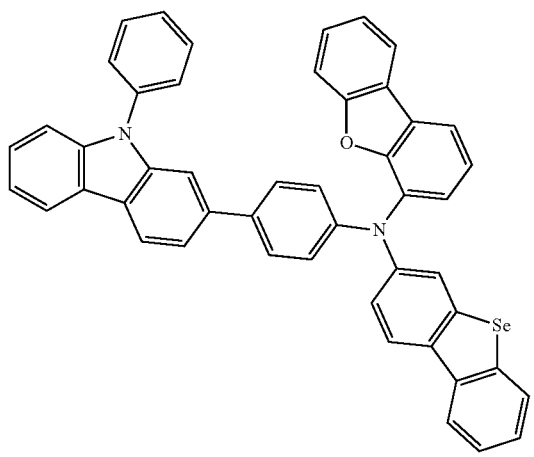
34
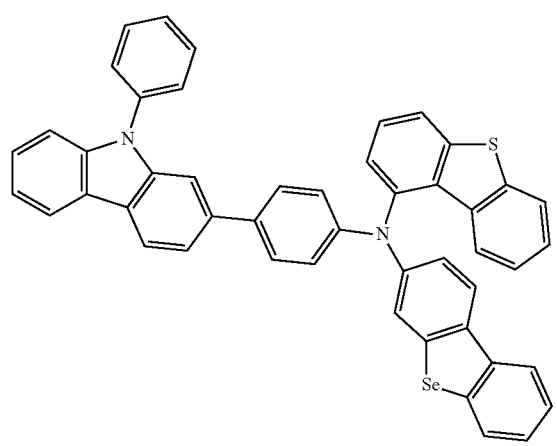
35
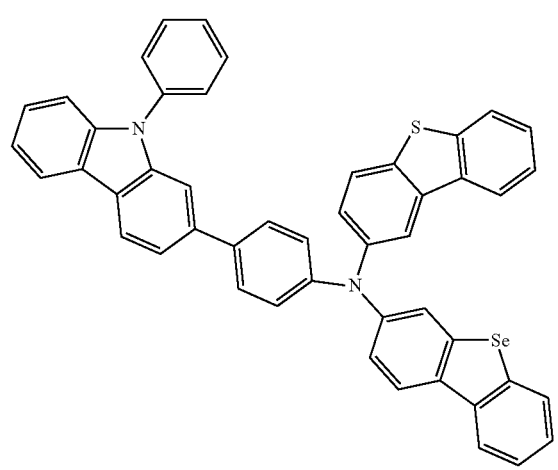
36
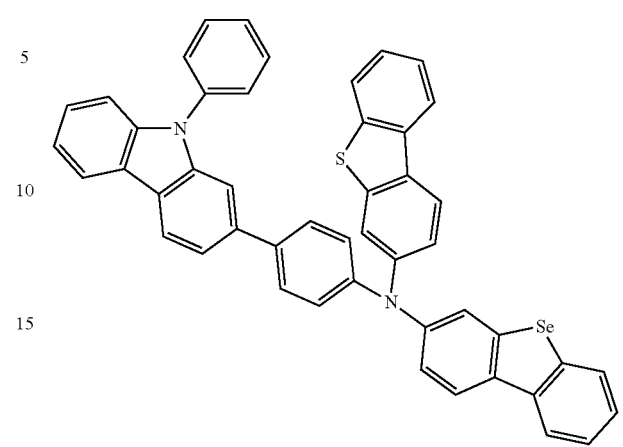
37
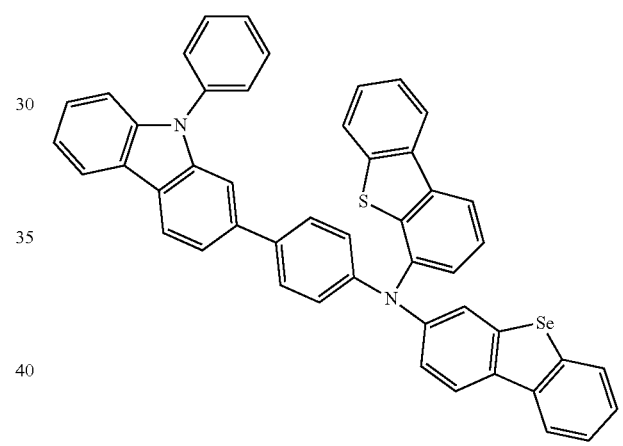
38
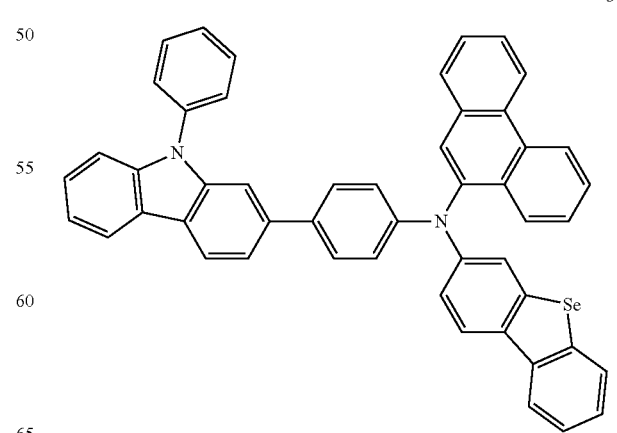

39
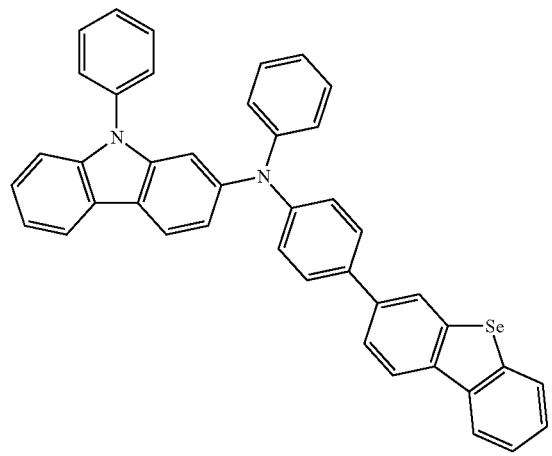
40
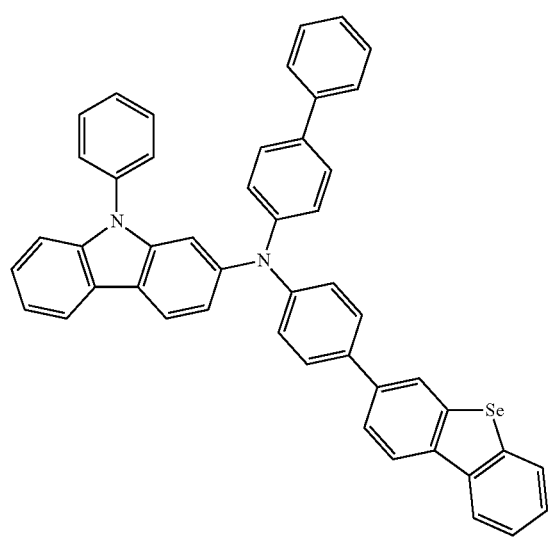
41
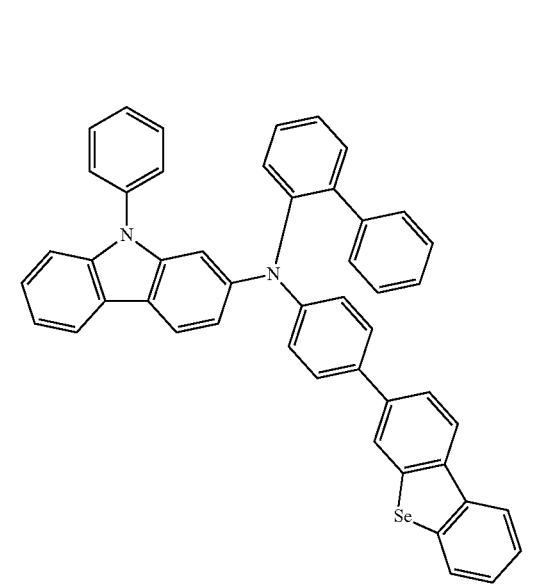
42
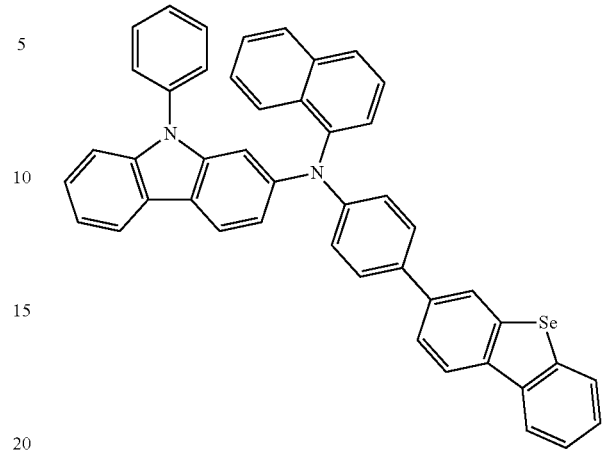
43
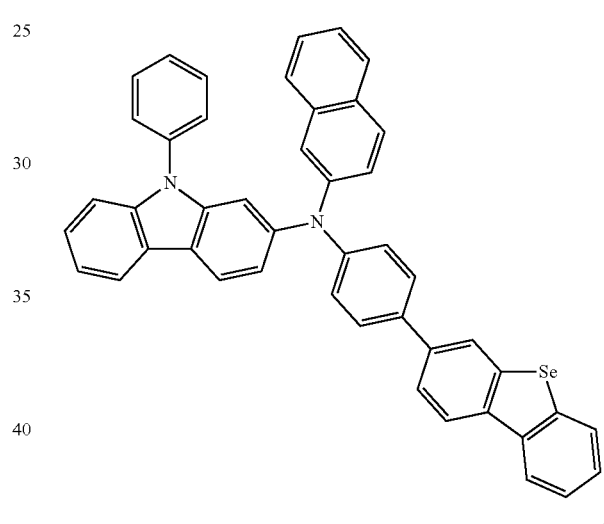
44
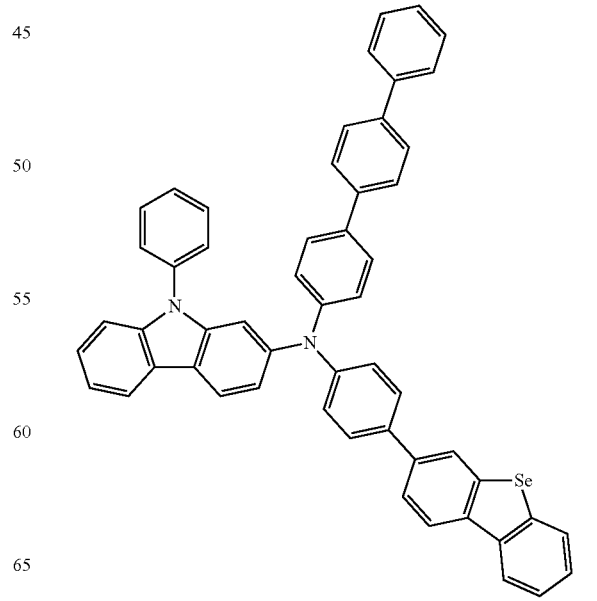

45
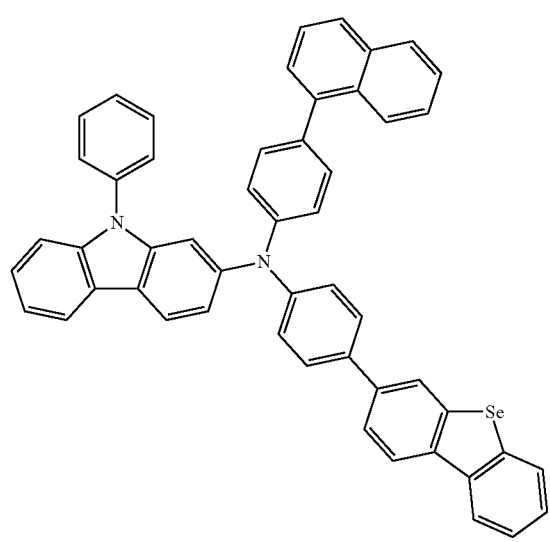
46
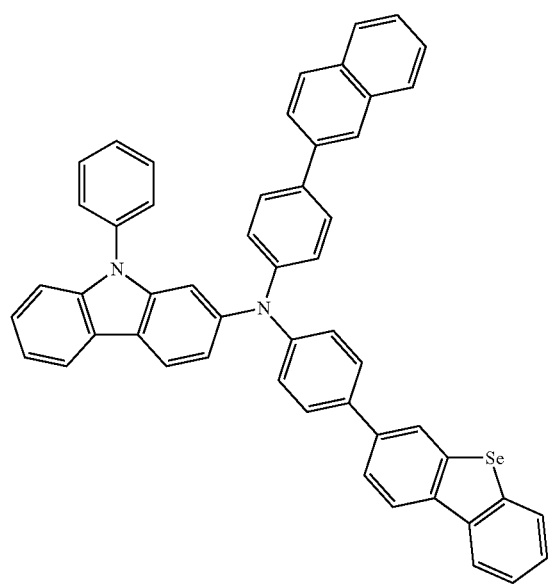
47
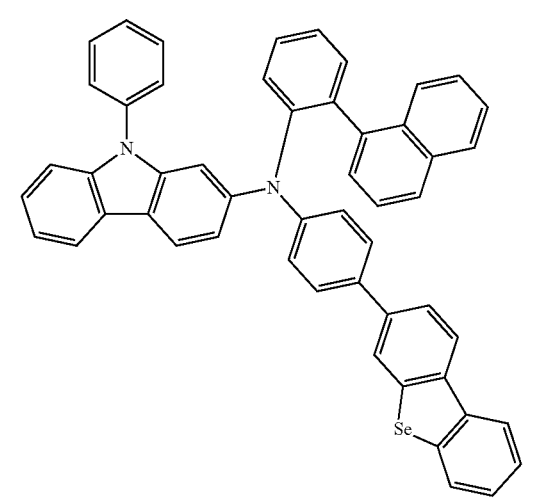
48
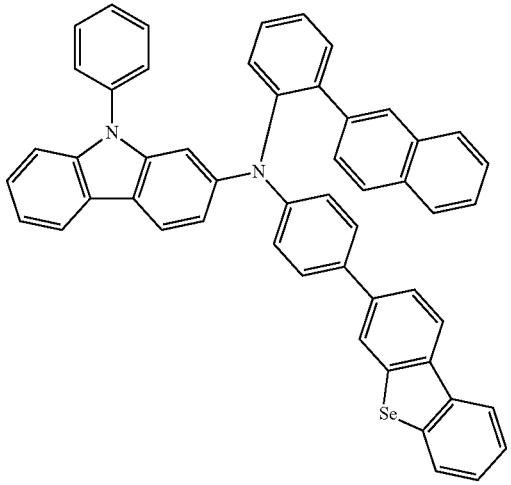
49
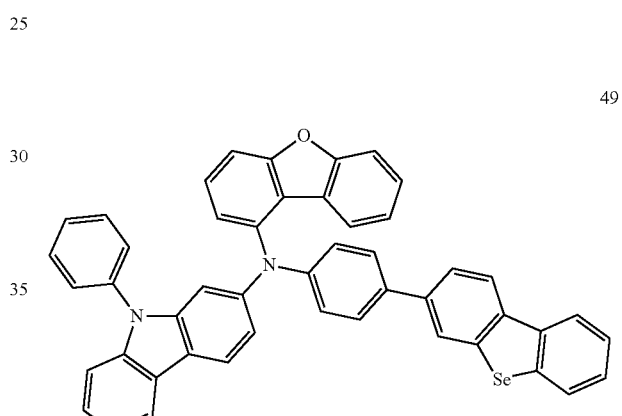
50
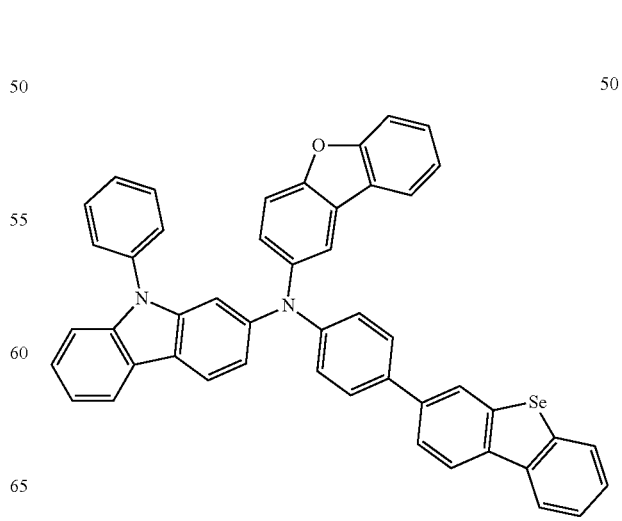

51
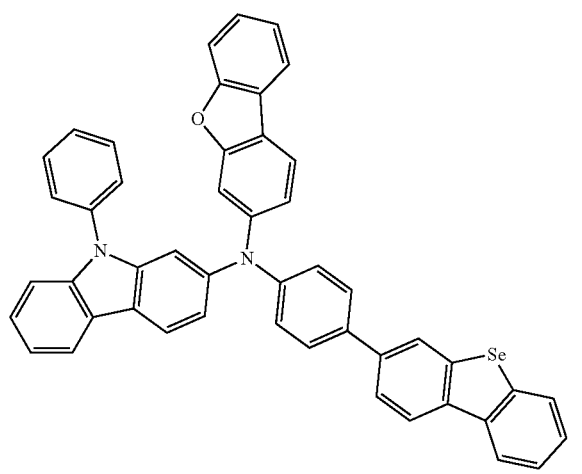
52
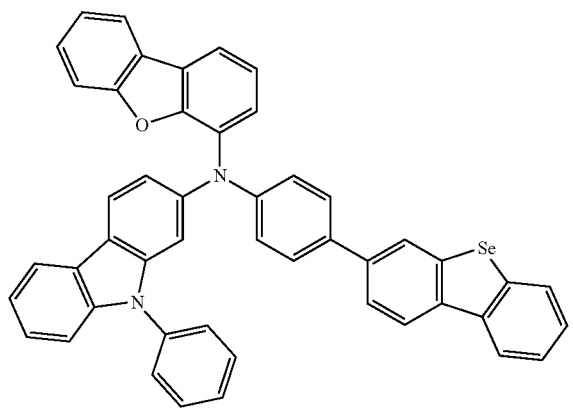
53
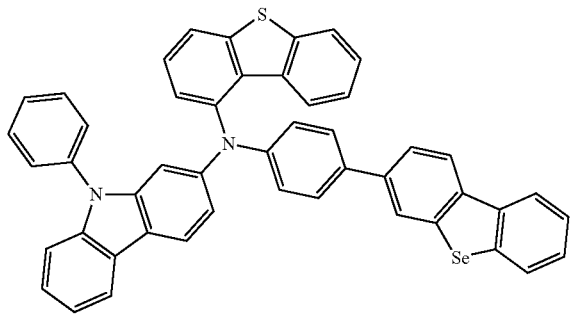
54
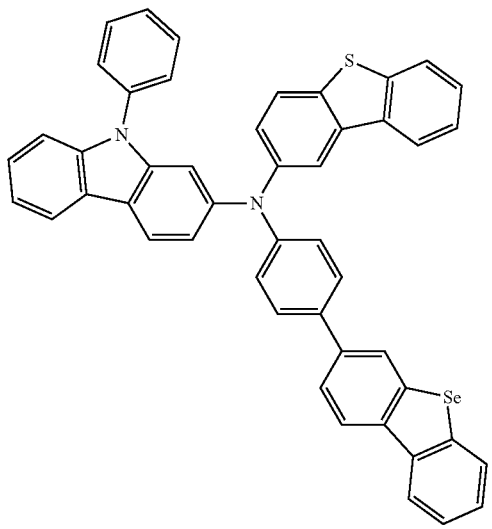
55
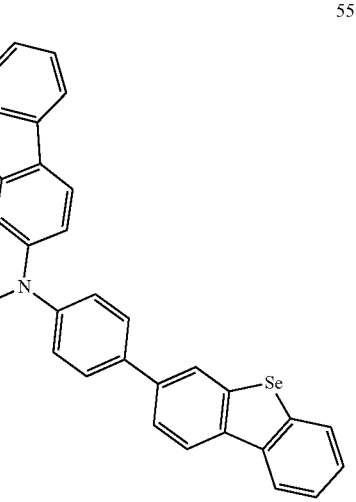
56
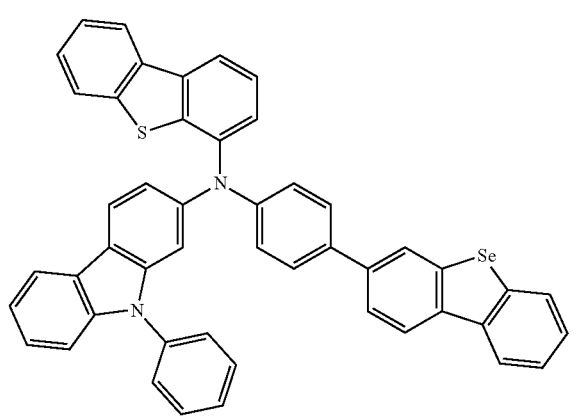

57
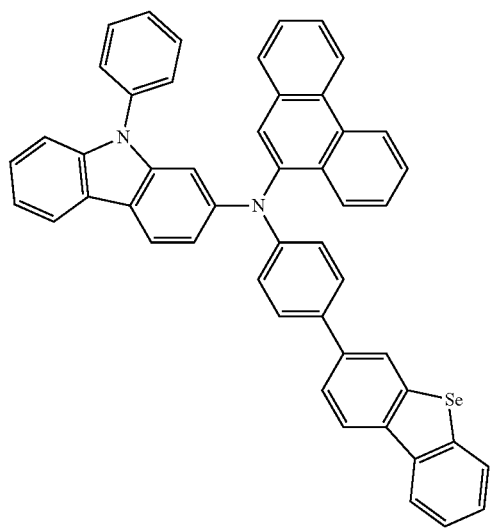
58
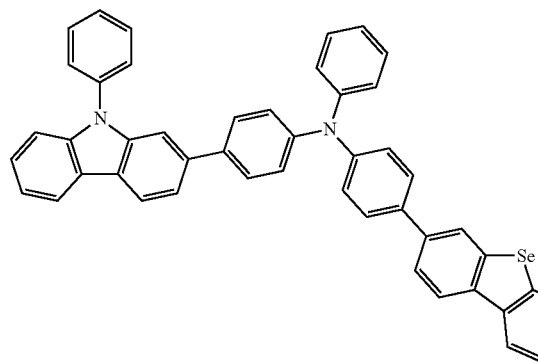
59
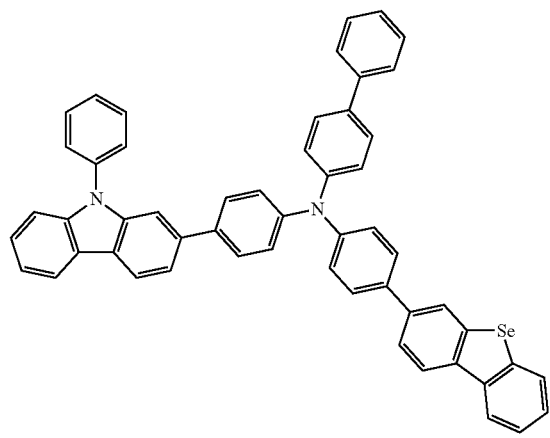
60
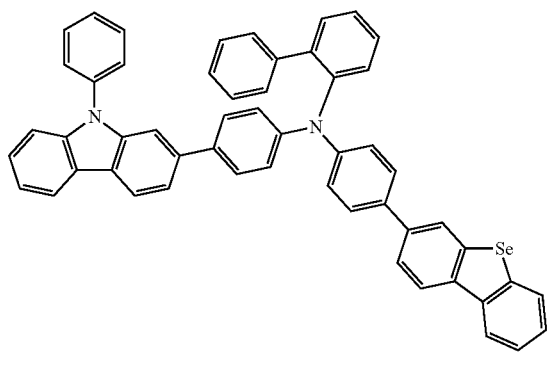
61
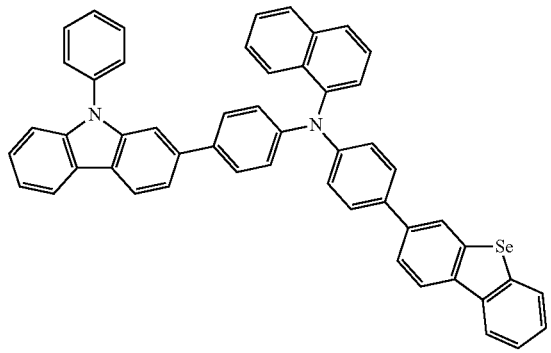
62
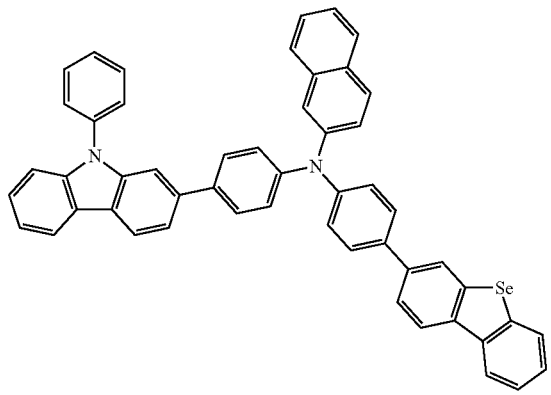

63
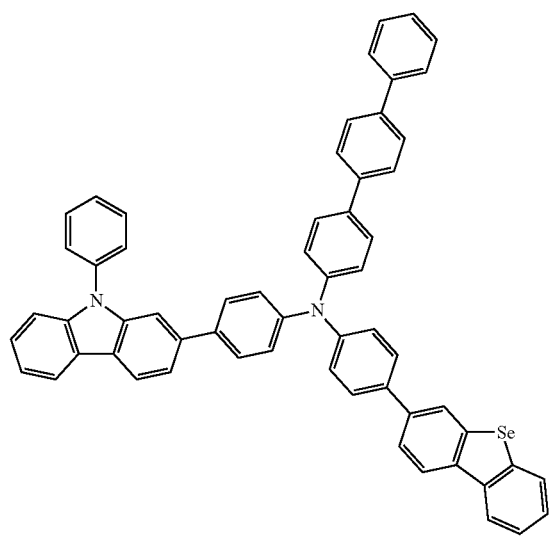
64
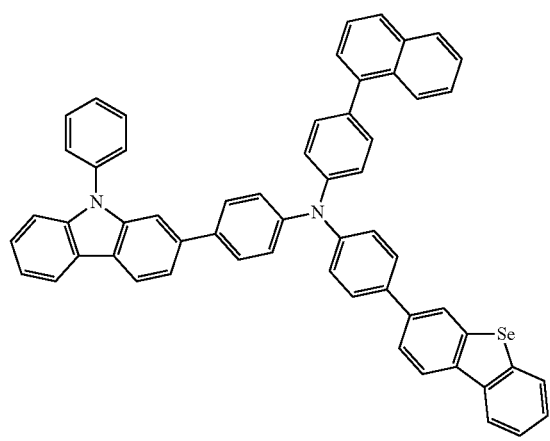
65
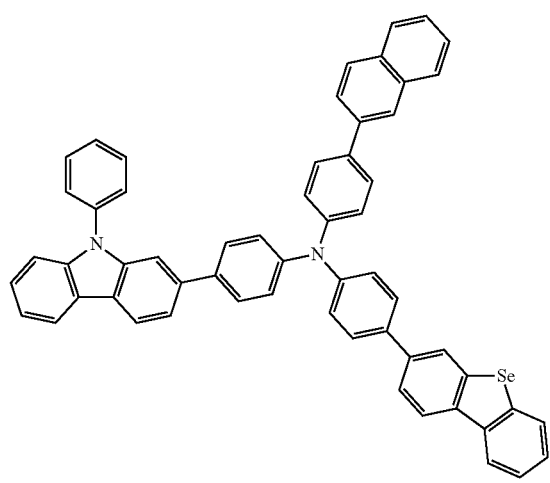
66
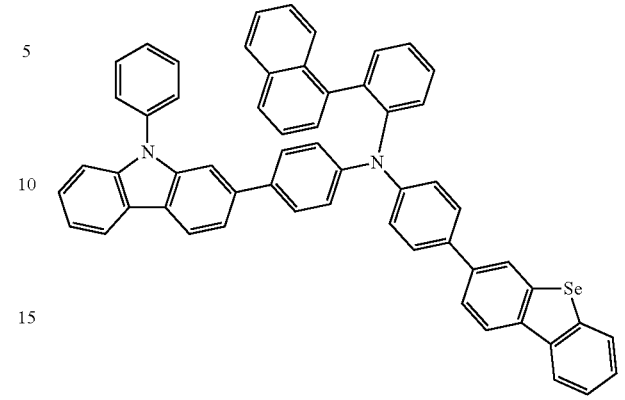
67
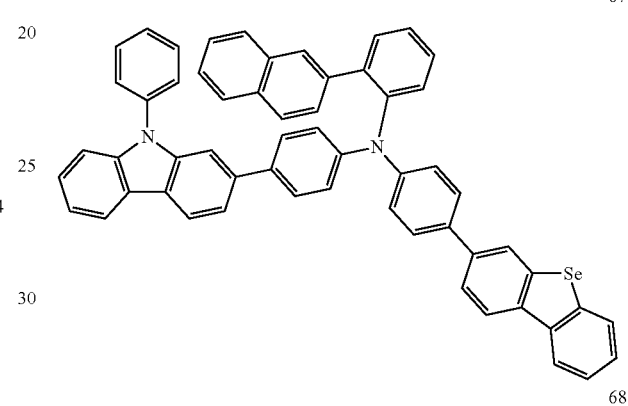
68
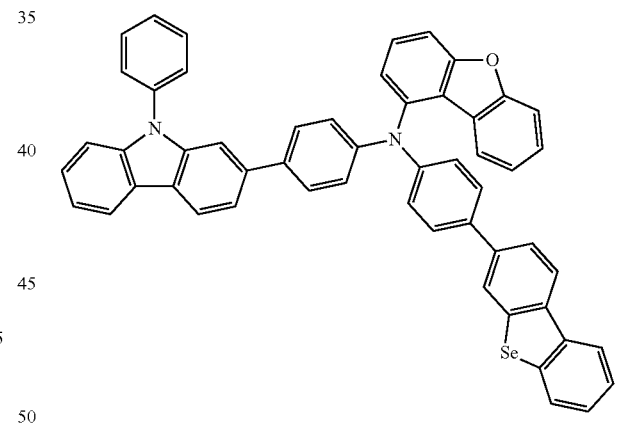
69
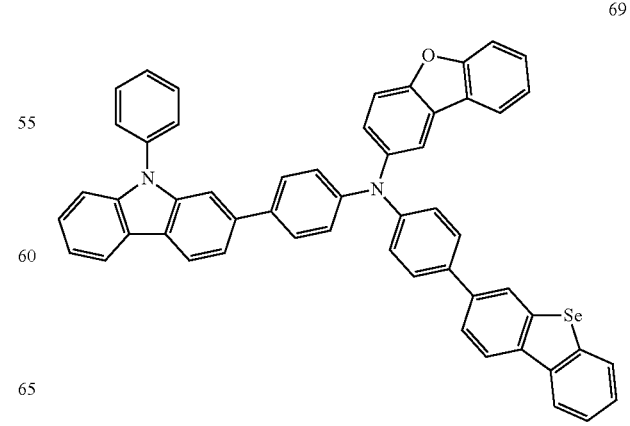

70
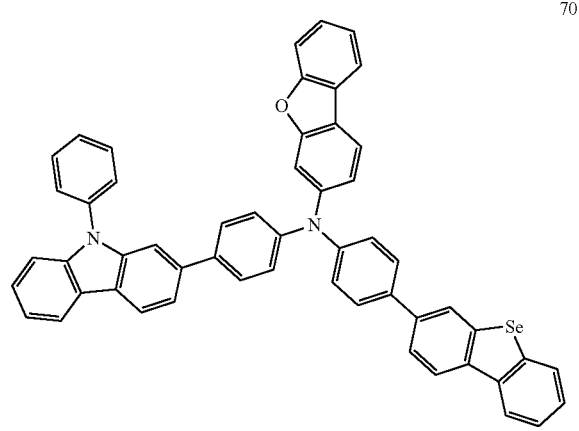
71
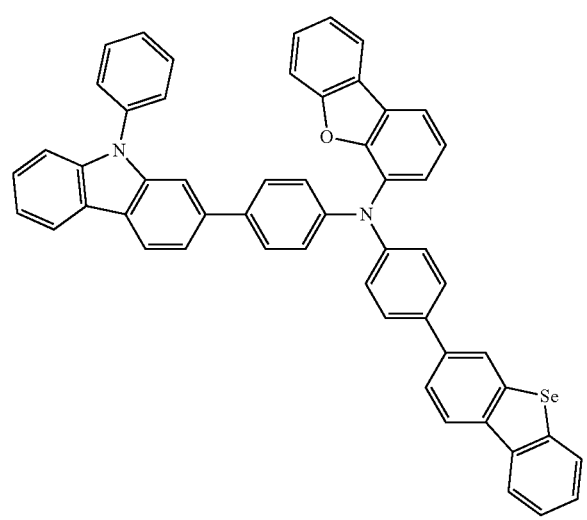
72
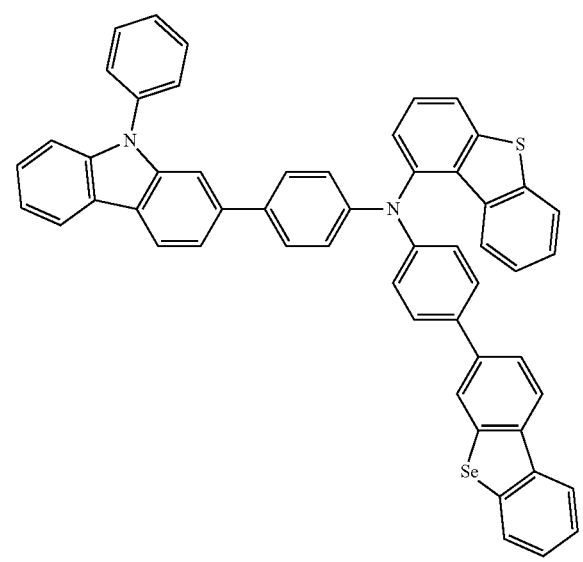
73
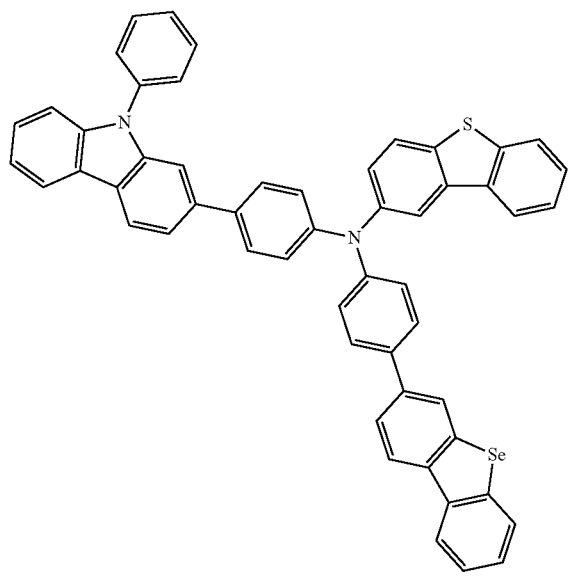
74
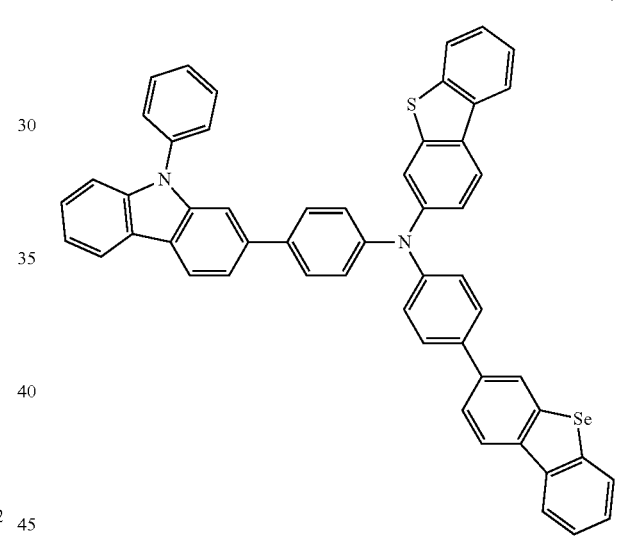
75
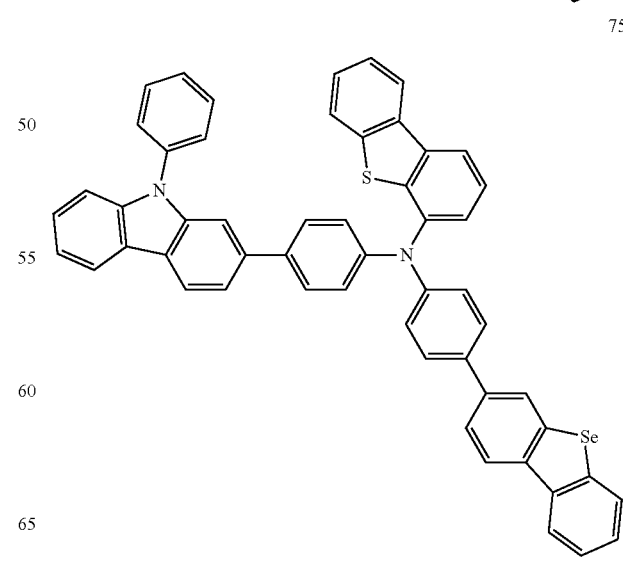

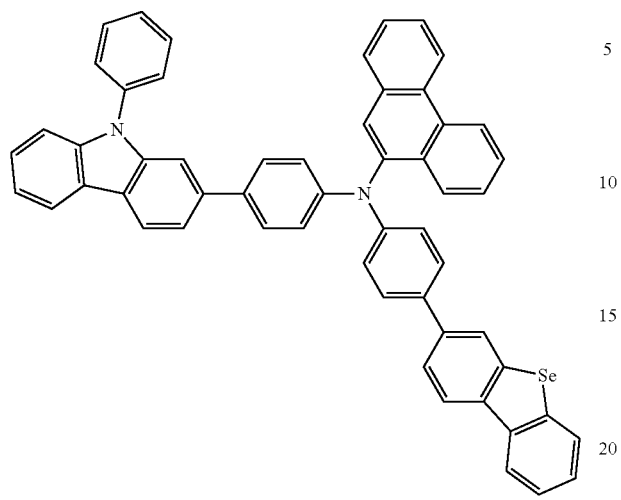
76
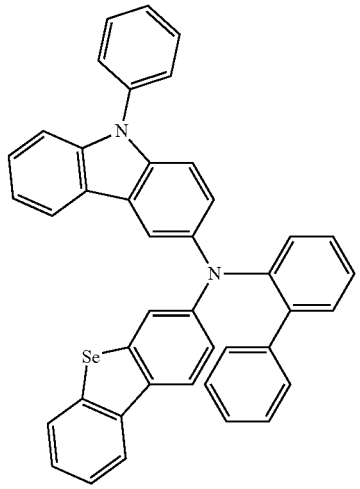
79
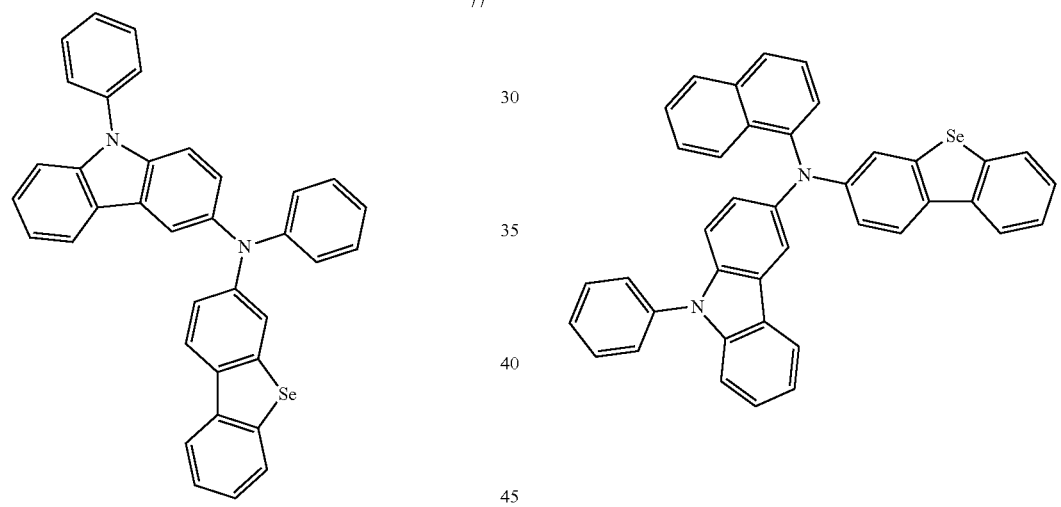
77
80
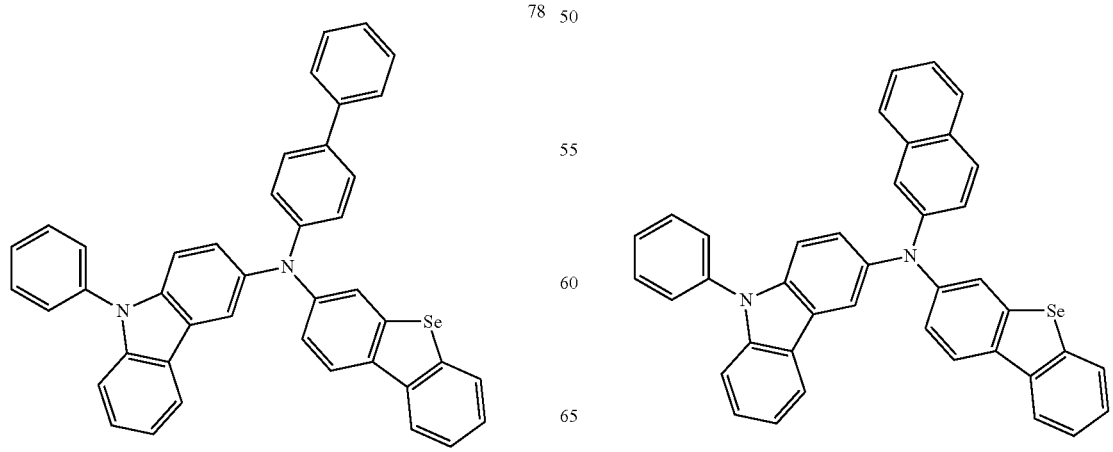
78
81

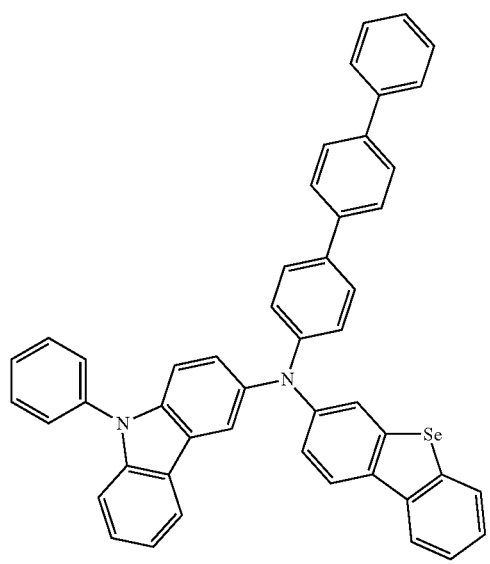
82
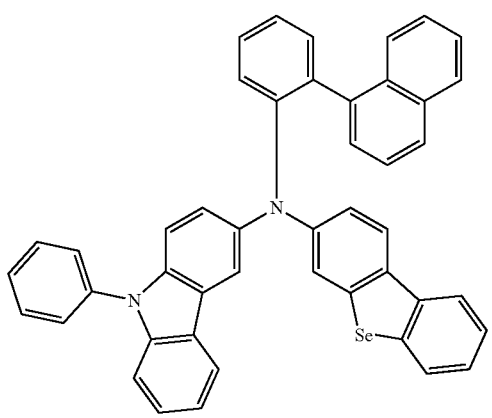
85
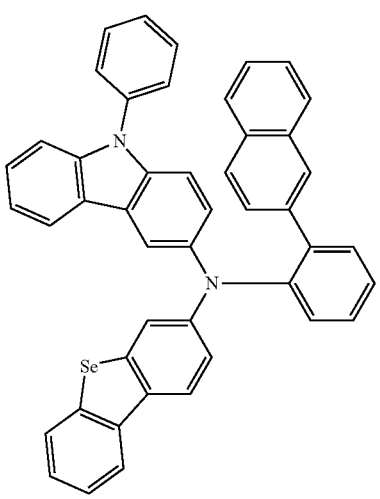
86
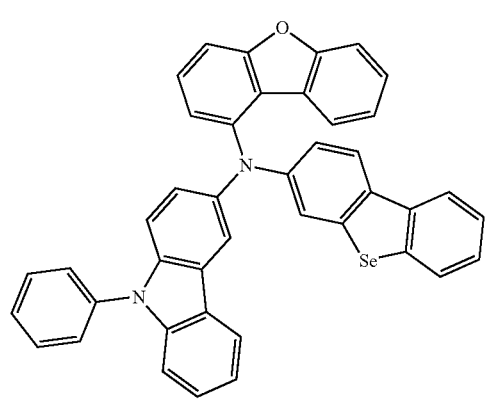
87

88
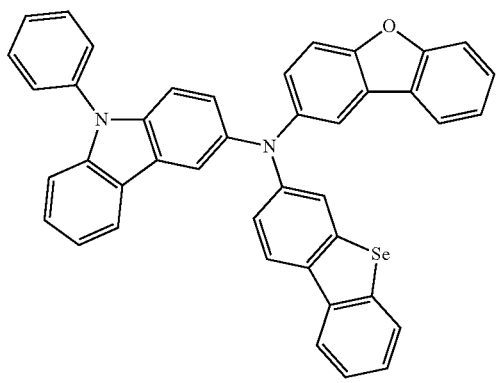
89
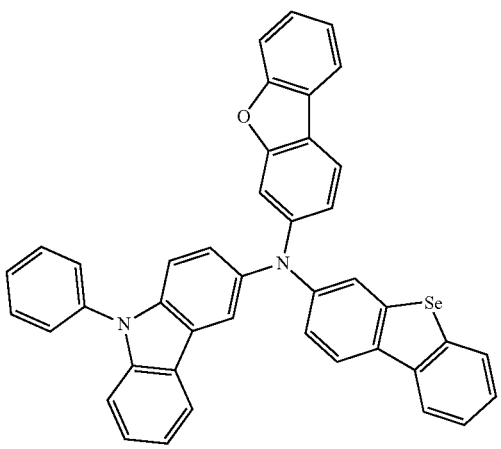
90
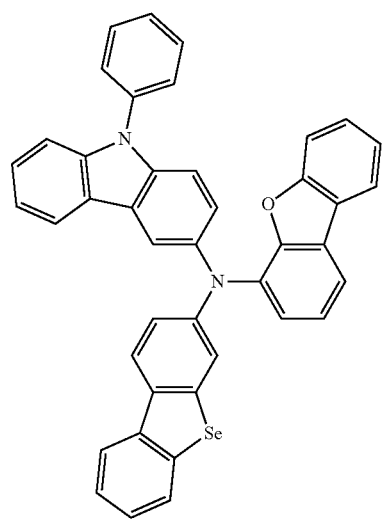
91
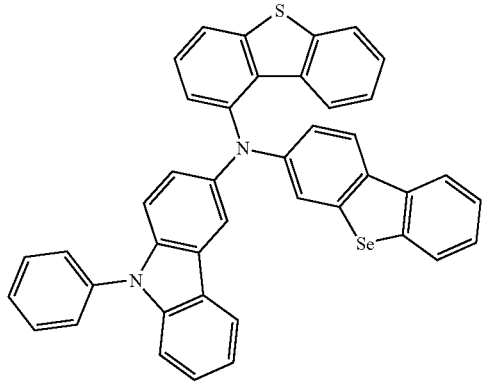
92
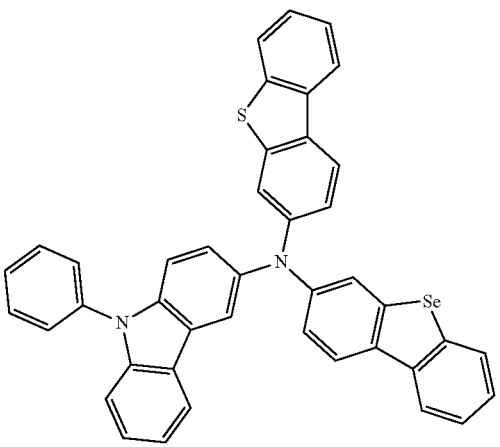
93

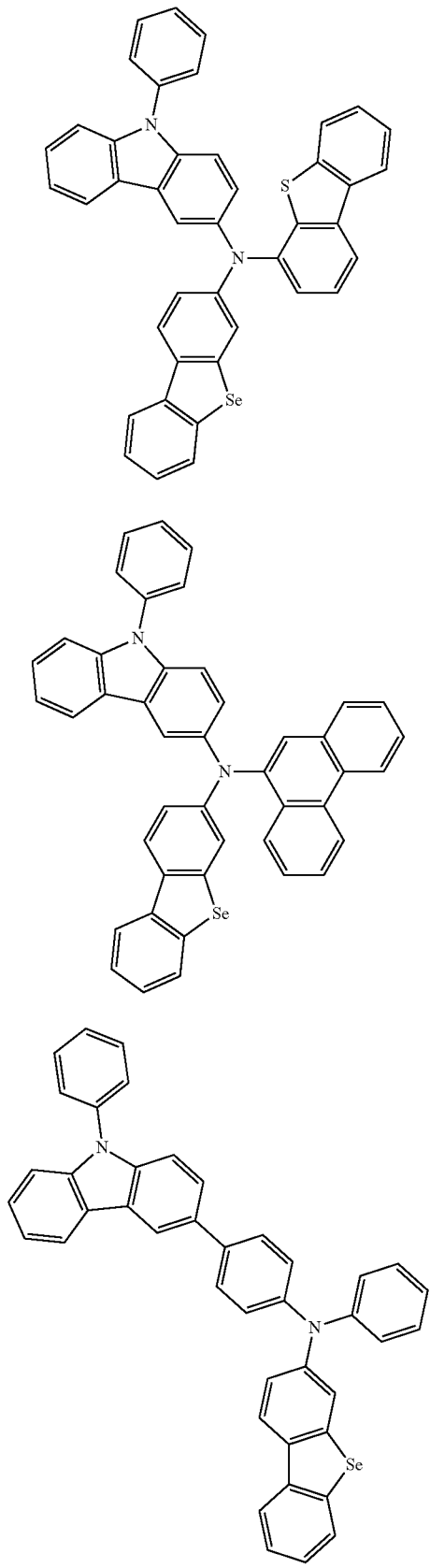
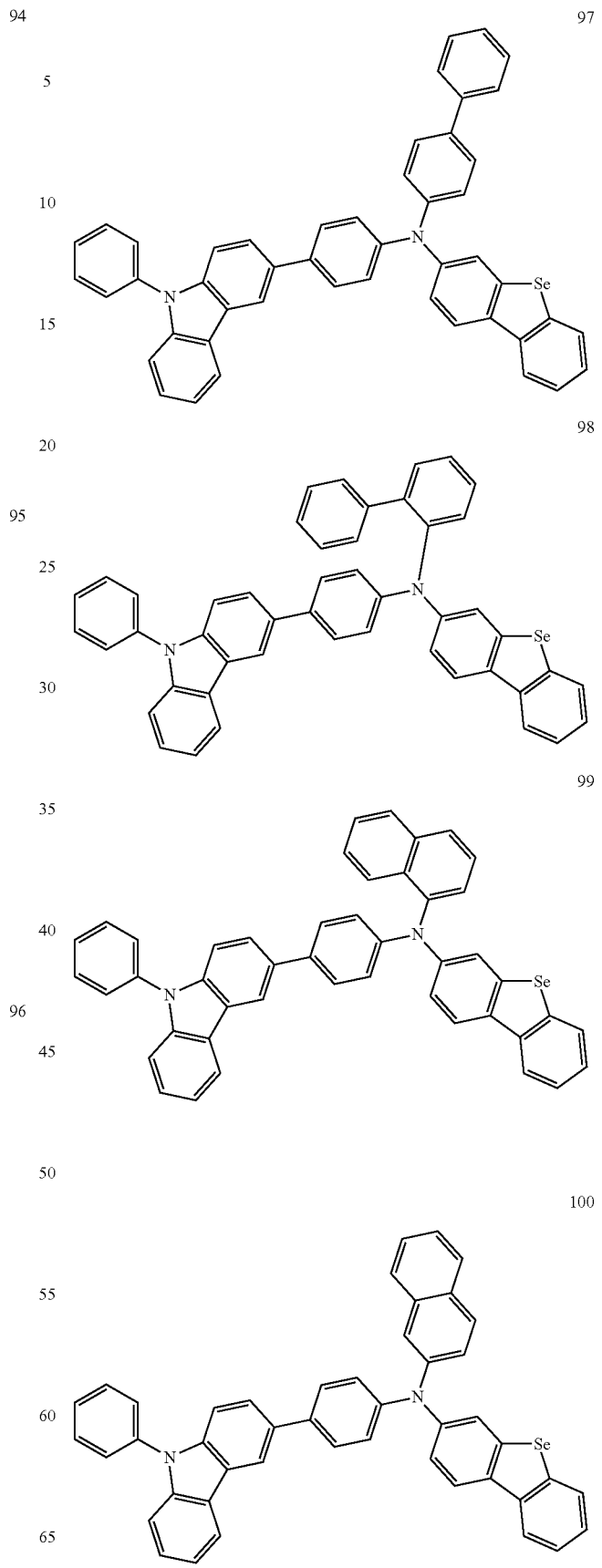

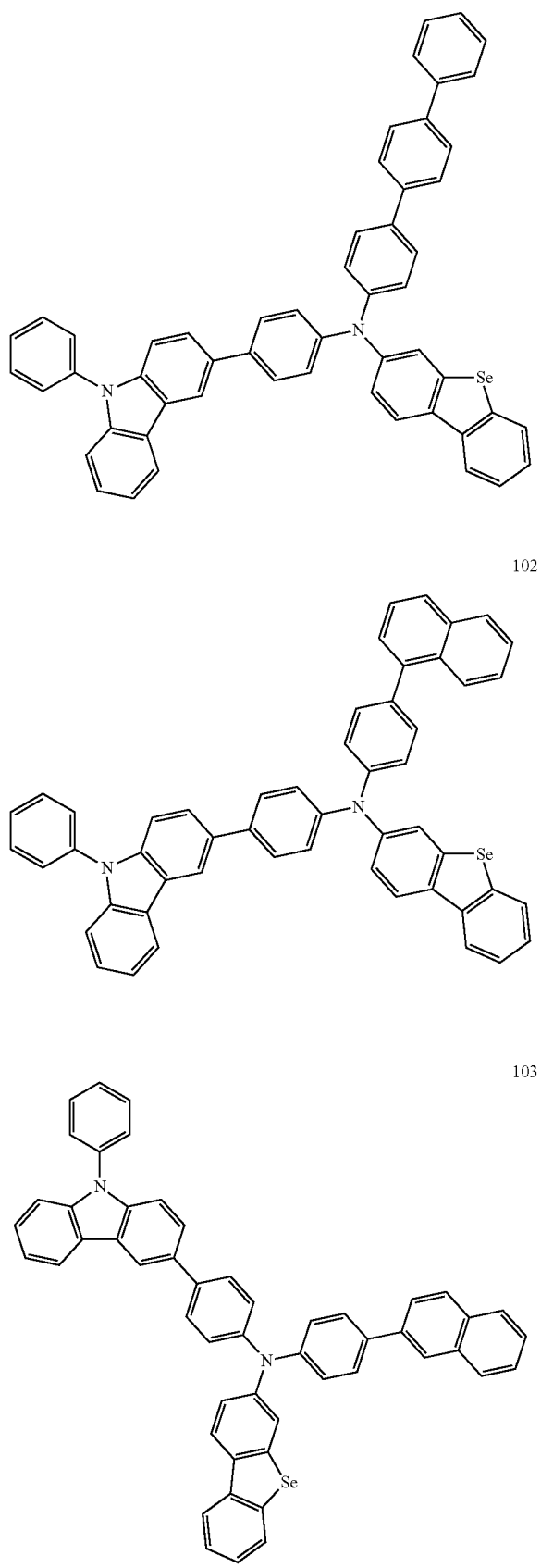
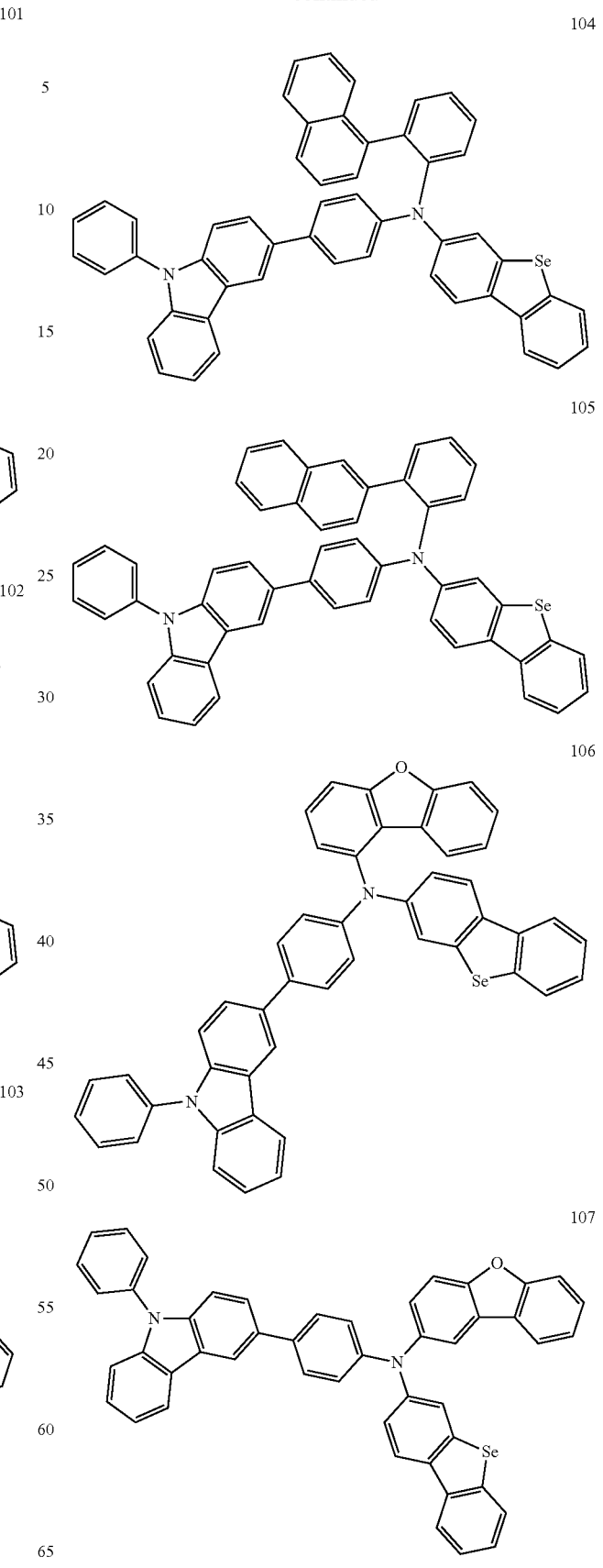

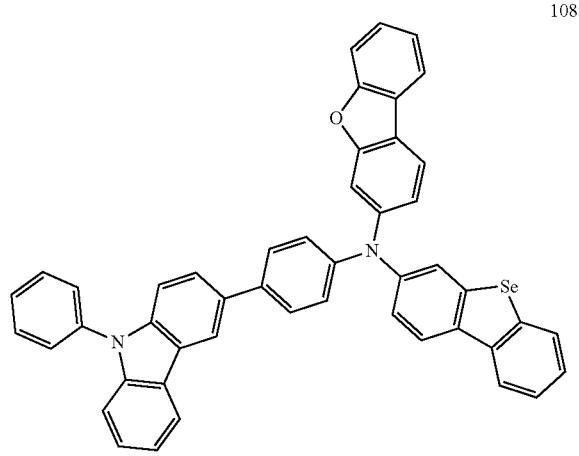
108
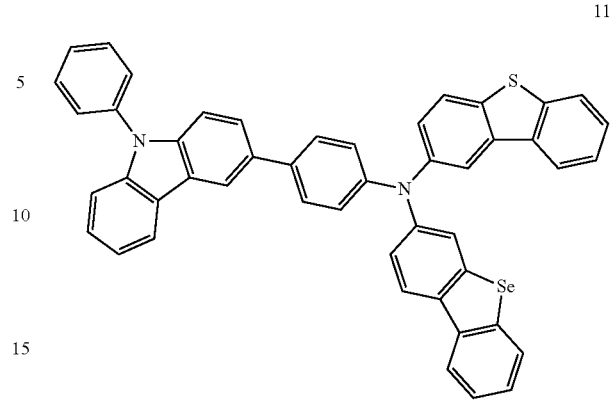
111
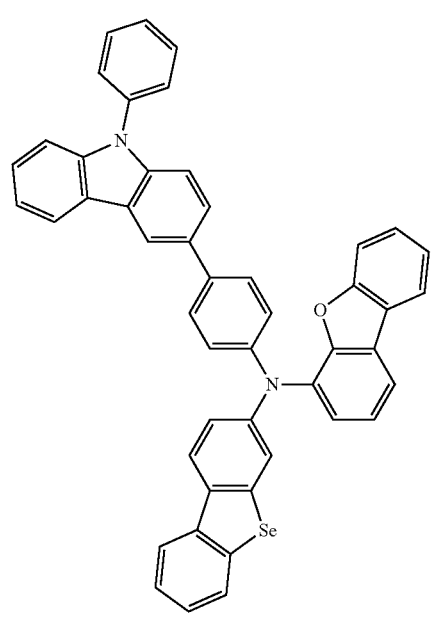
109
112
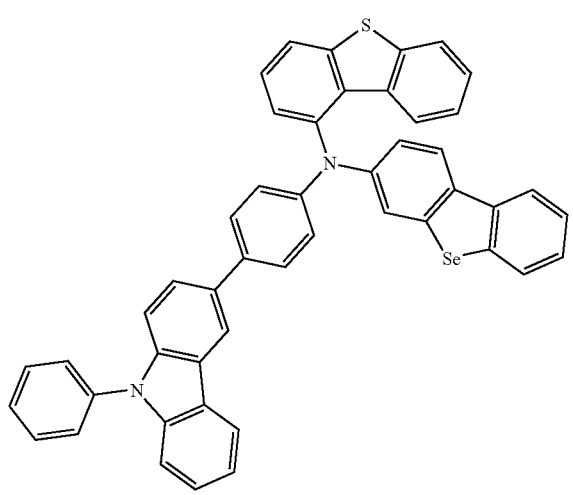
110
113

114
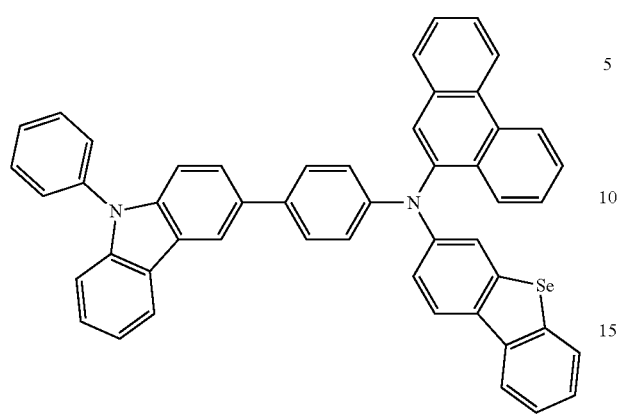
115
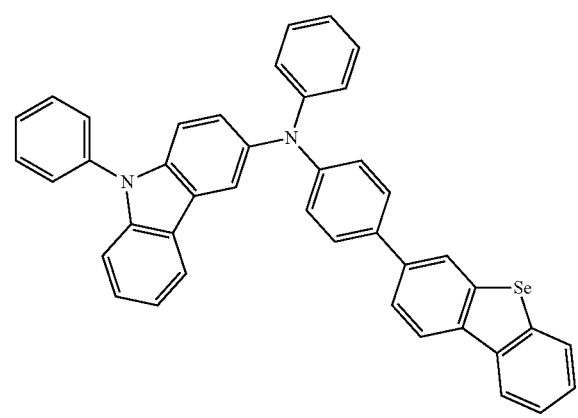
116
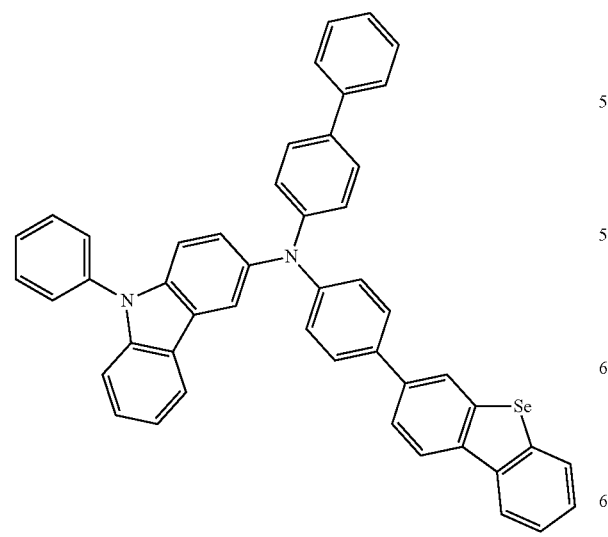
117
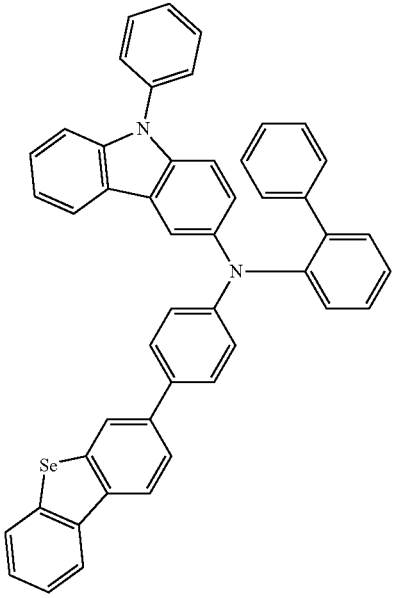
118
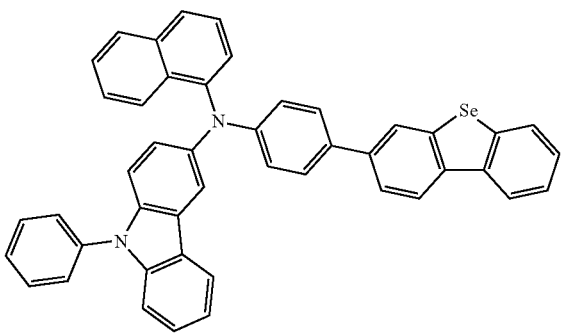
119
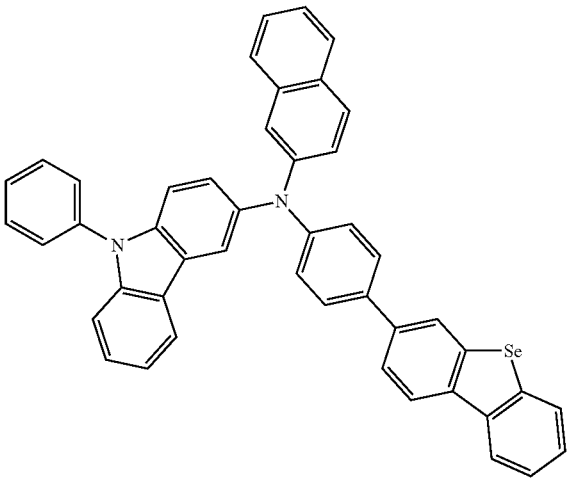

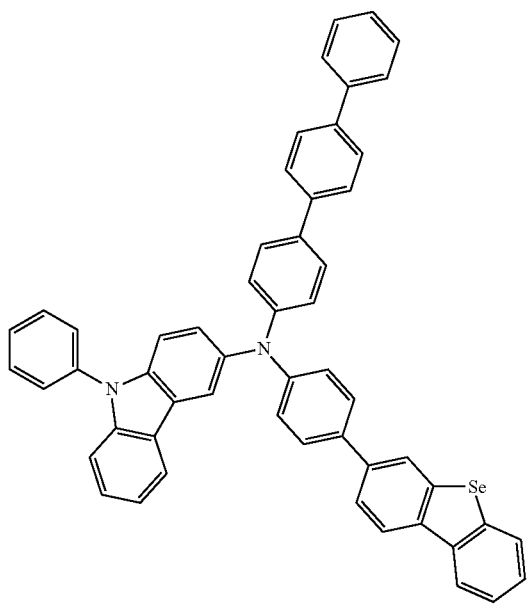
120
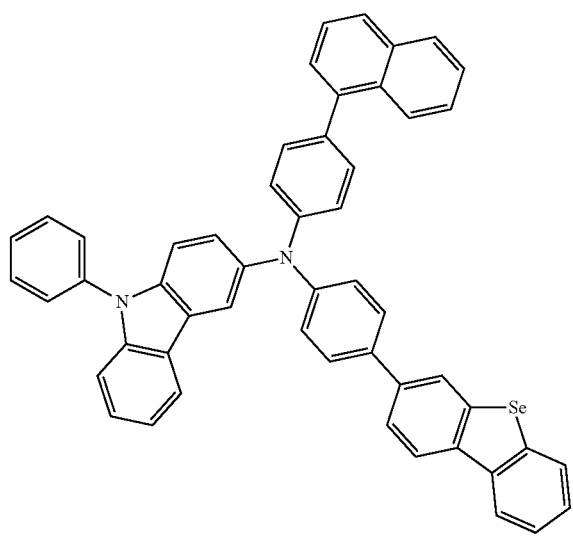
121
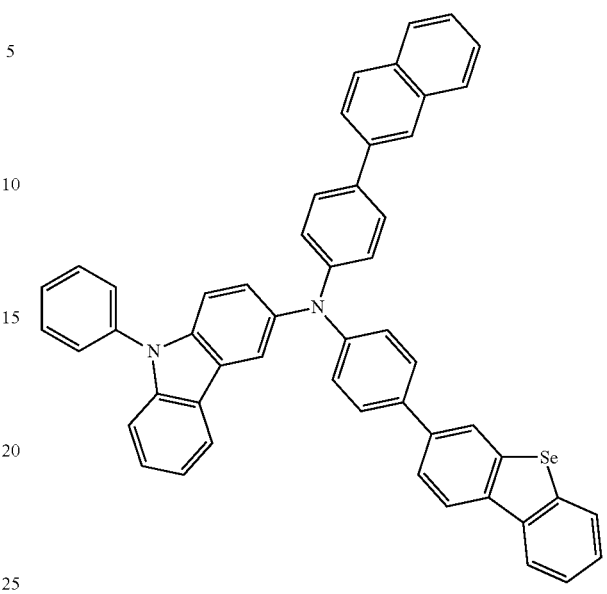
122
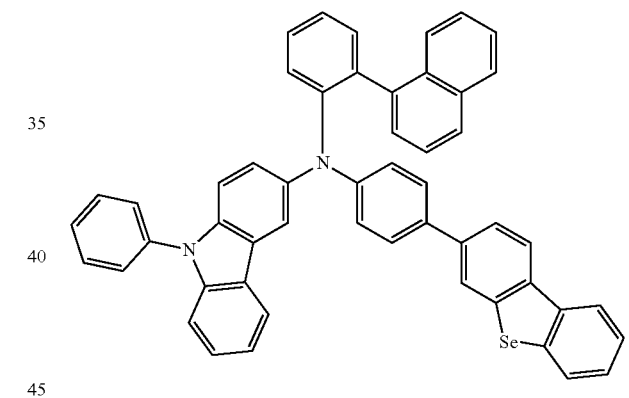
123
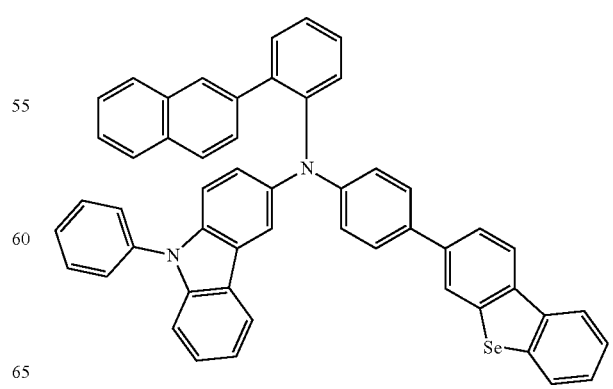
124

125
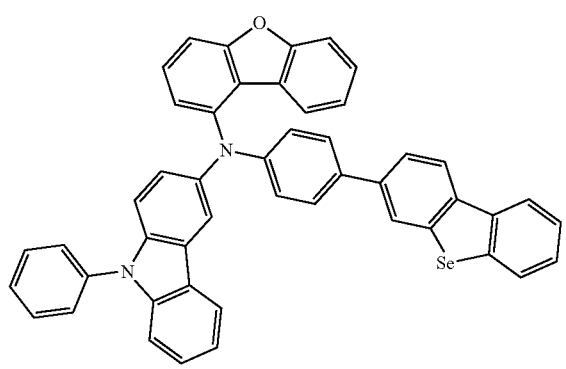
126
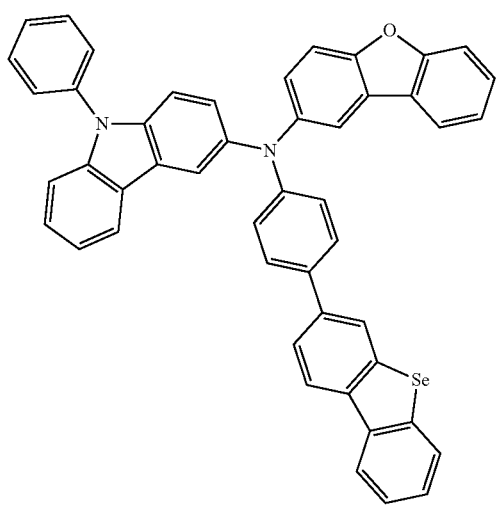
127
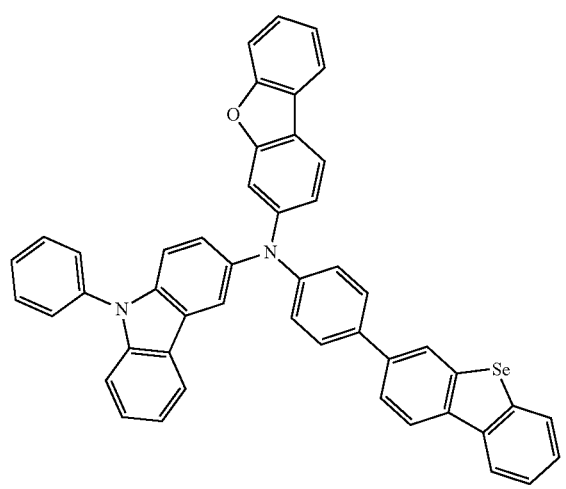
128
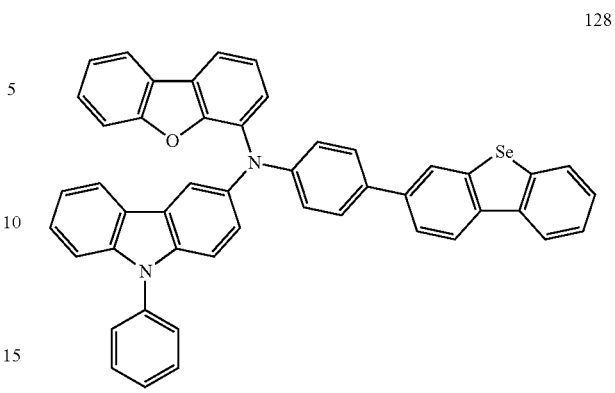
129
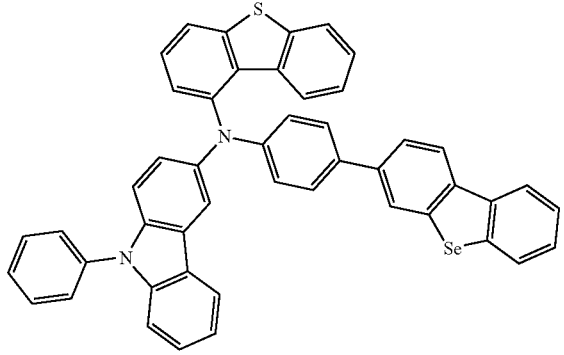
130
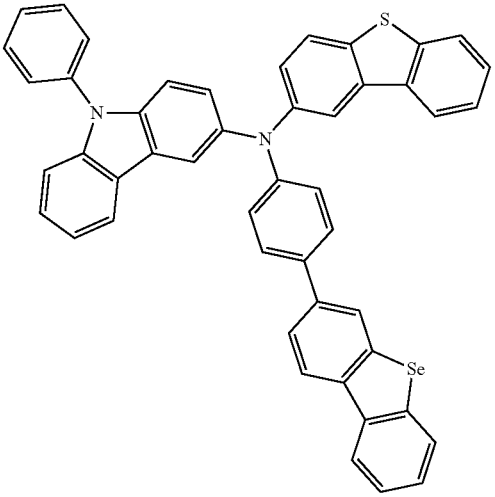

131
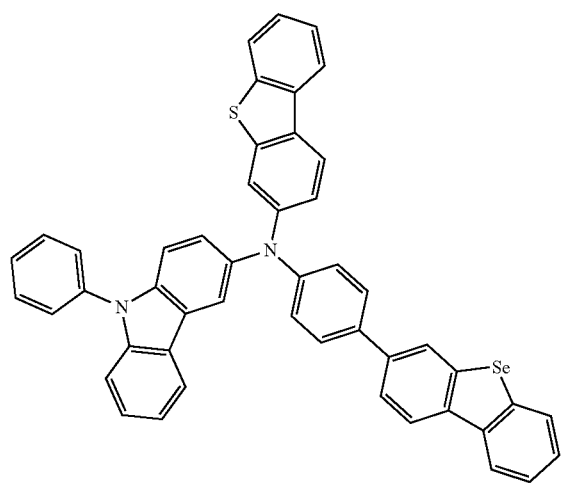
132
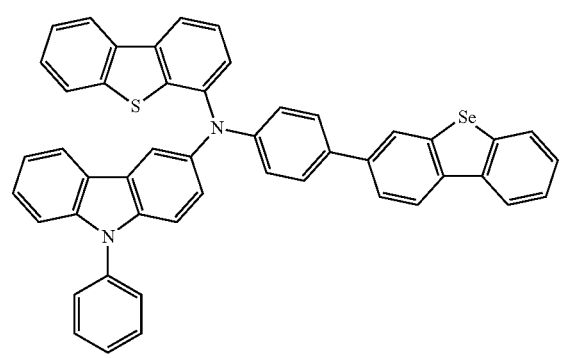
133
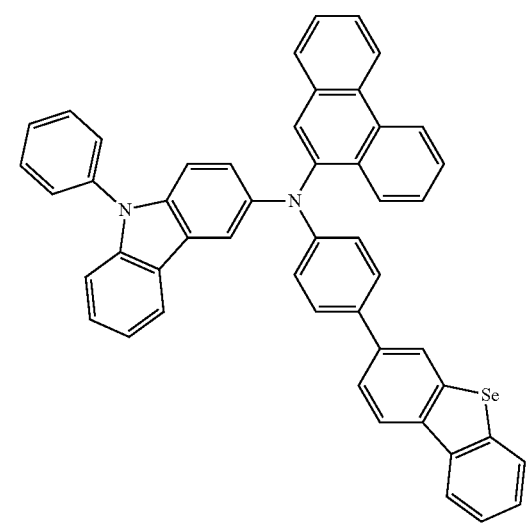
134
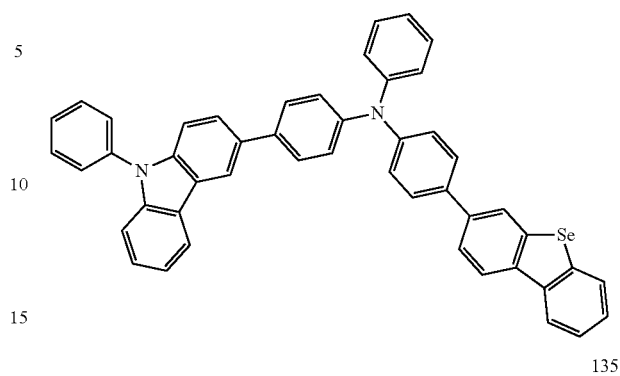
135
136
137
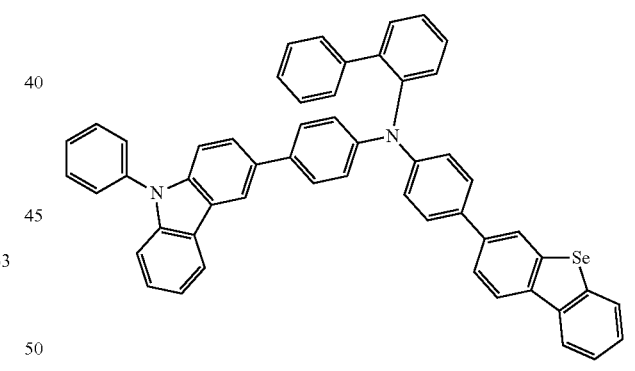

138
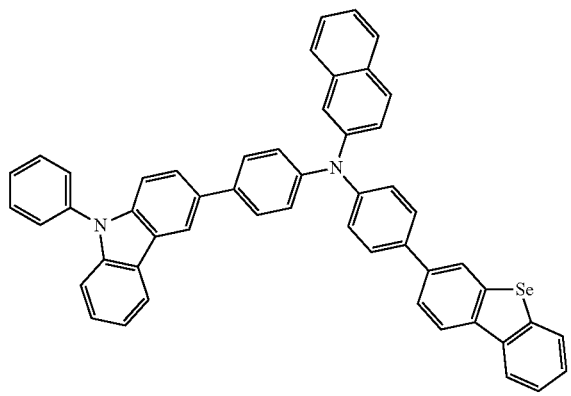
139
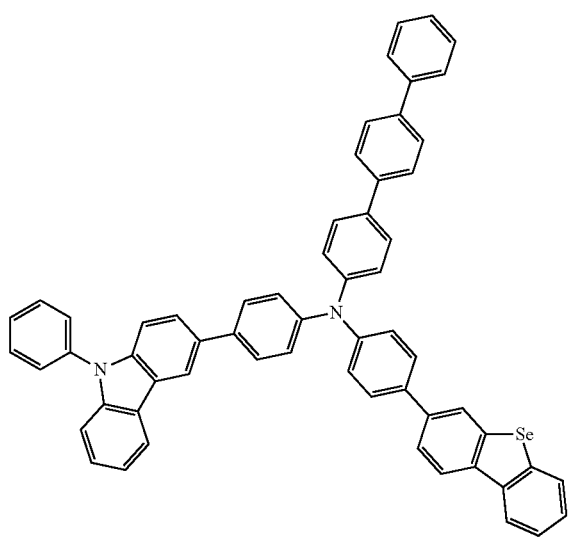
140
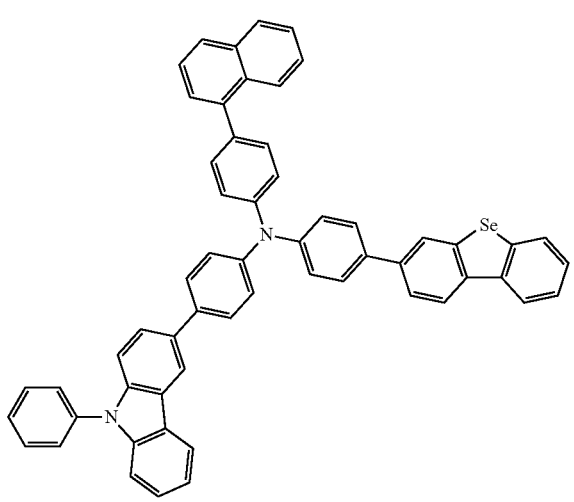
141
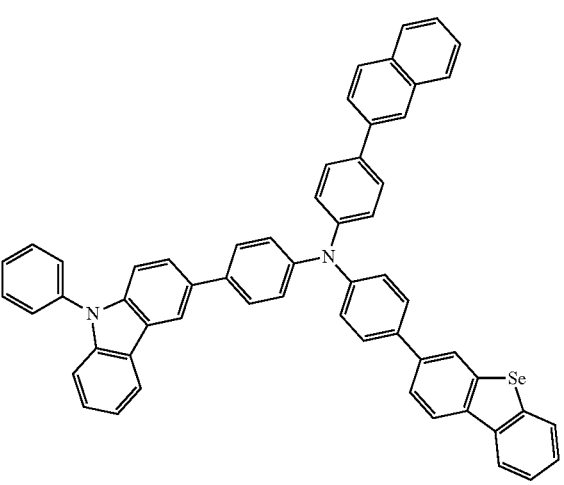
142
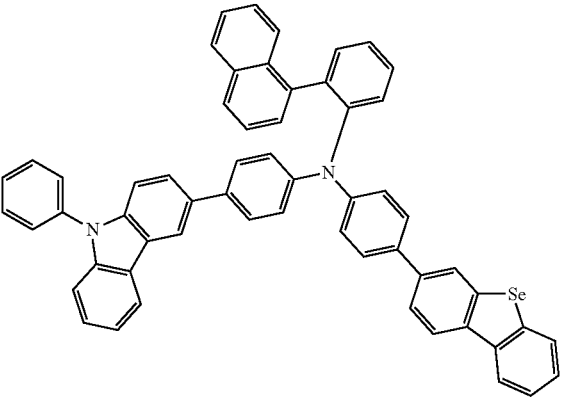
143
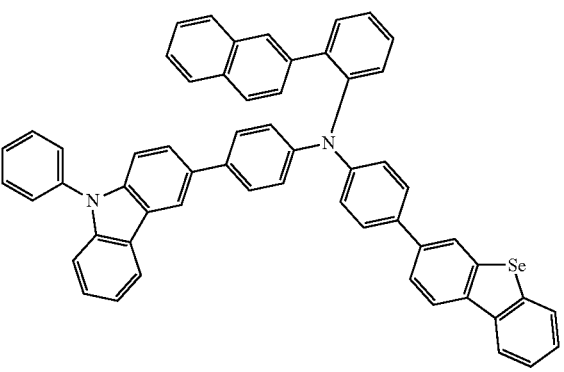

144
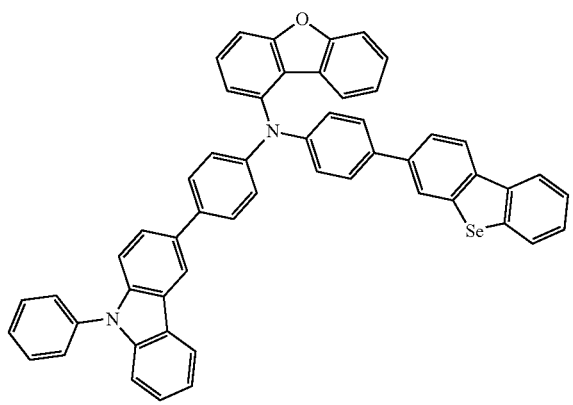
145
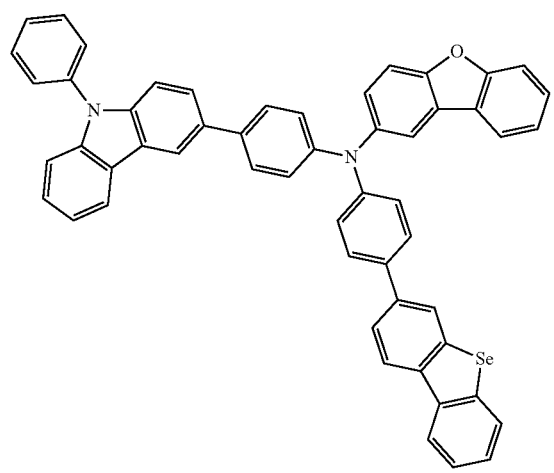
146
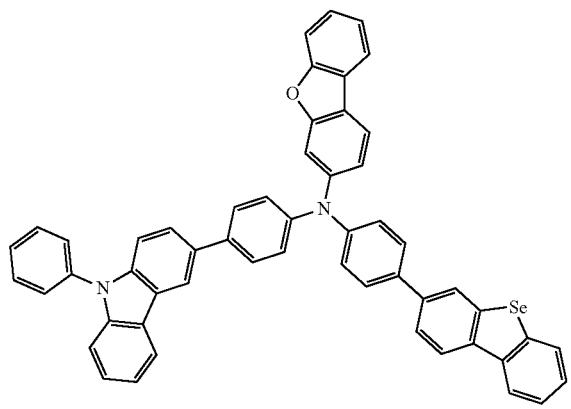
147
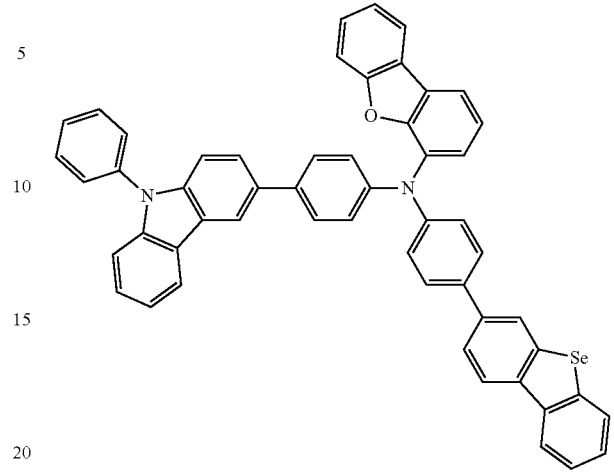
148
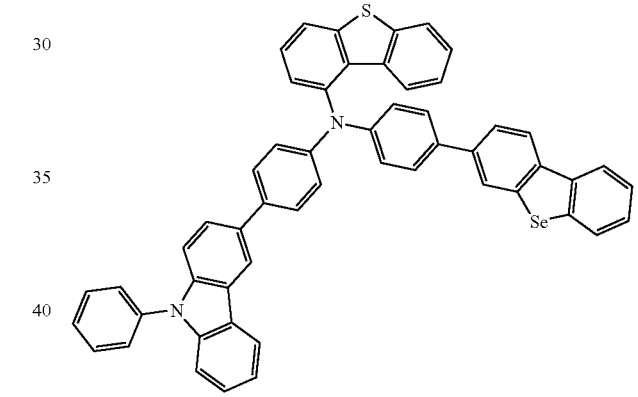
149
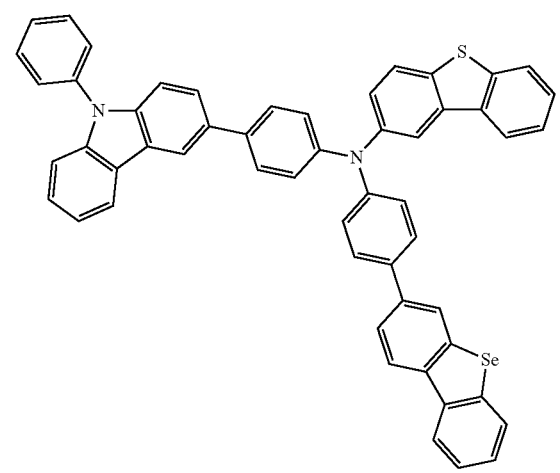

-continued
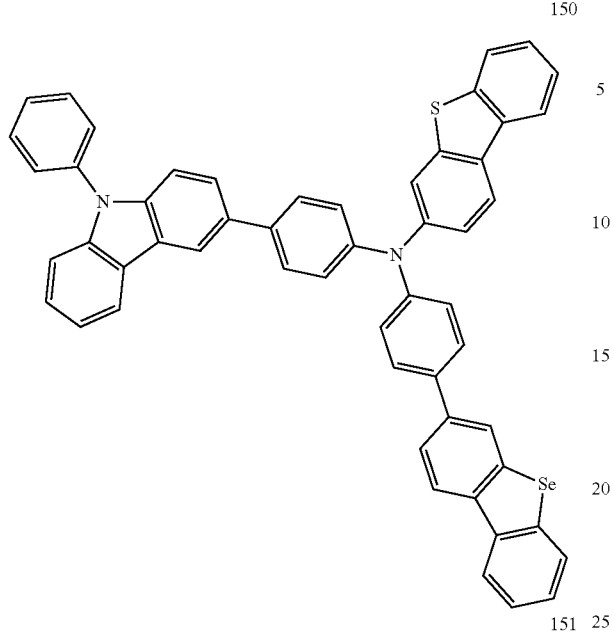
150
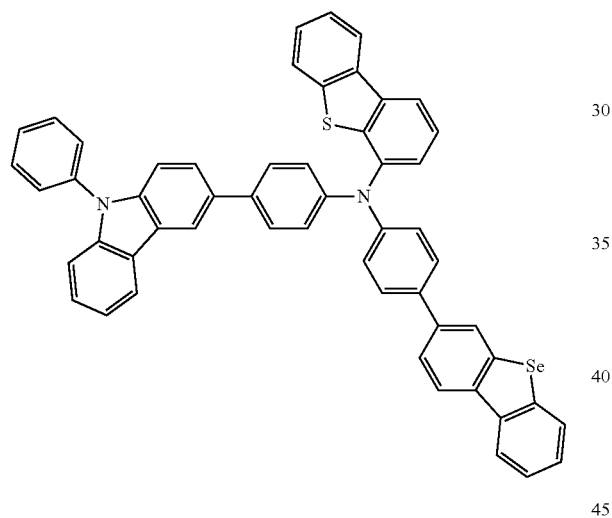
151
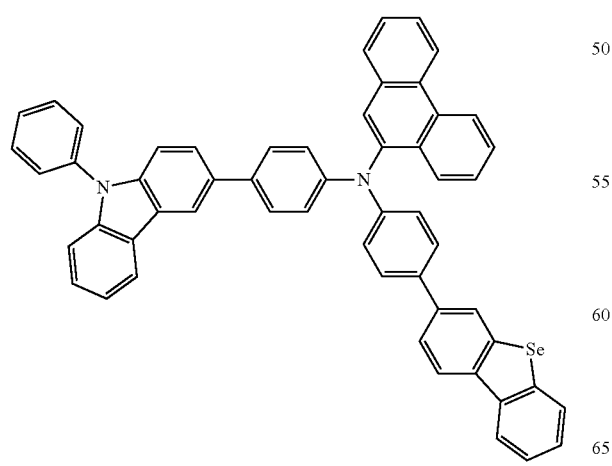
152
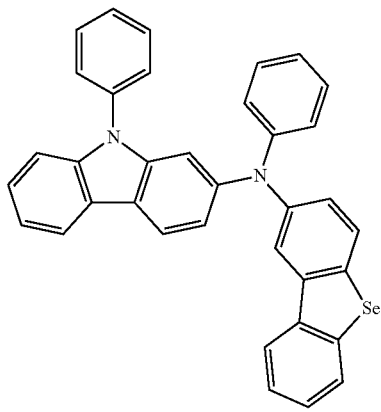
153
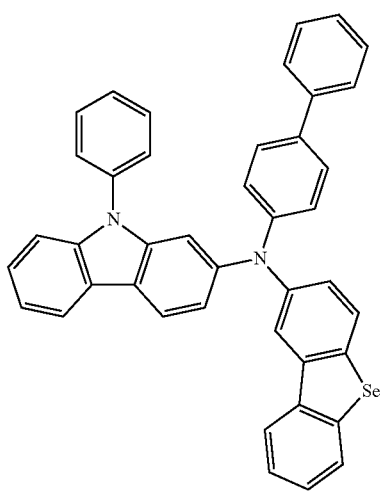
154
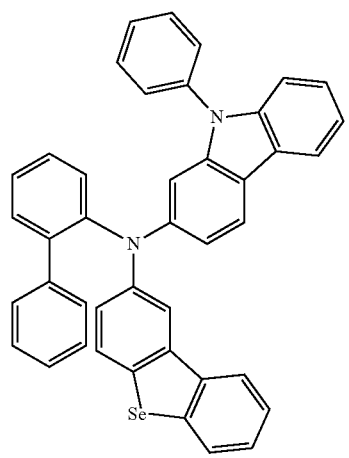
155

156
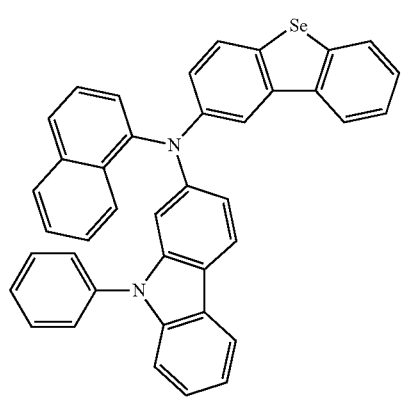
157
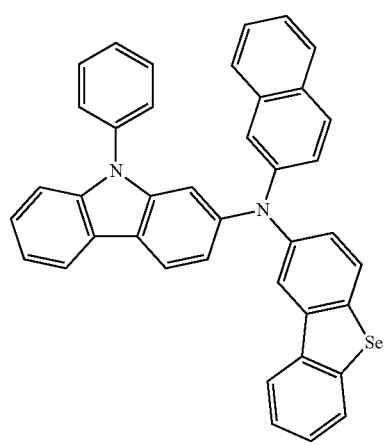
158
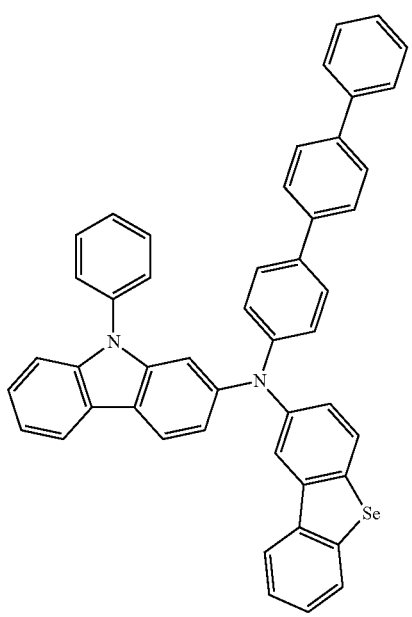
159
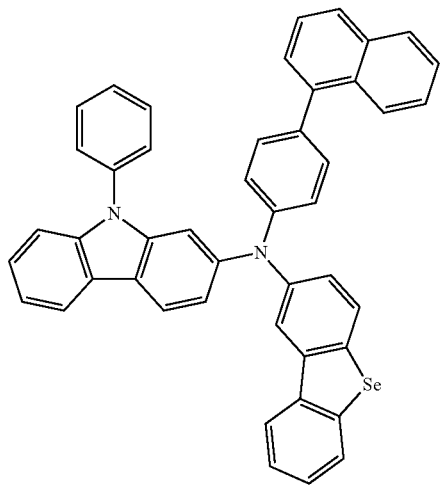
160
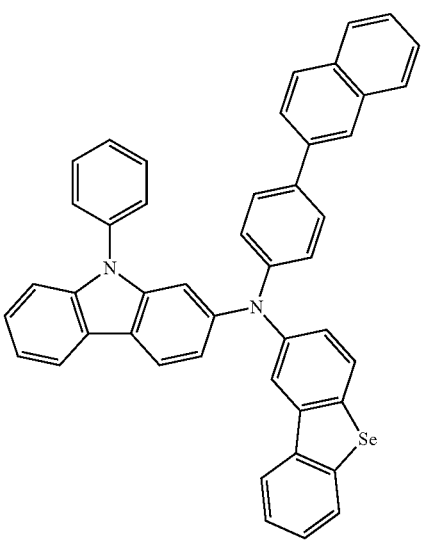
161
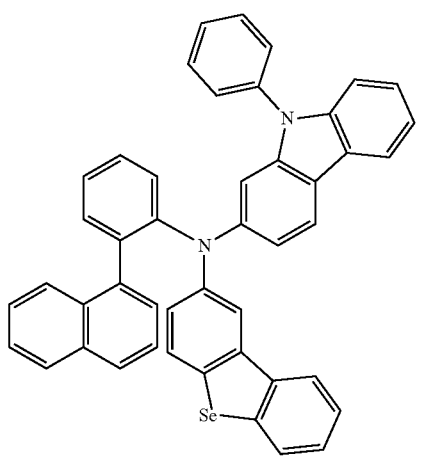

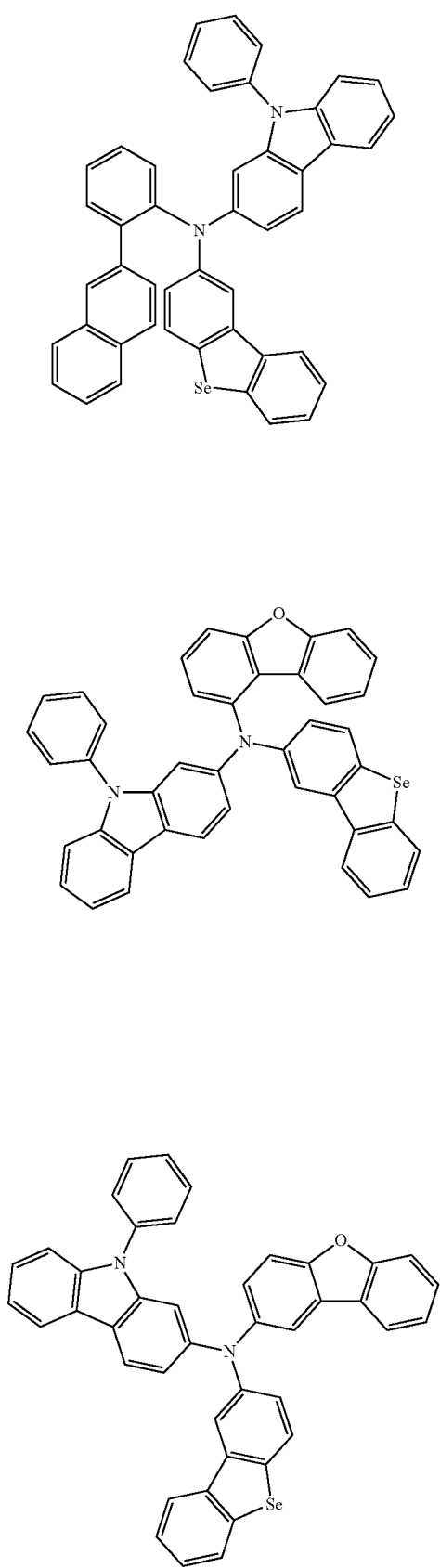

169
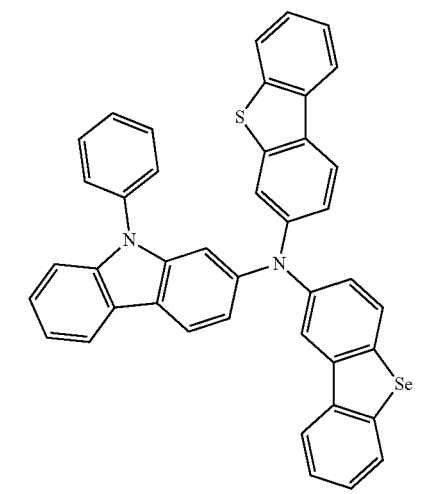
170
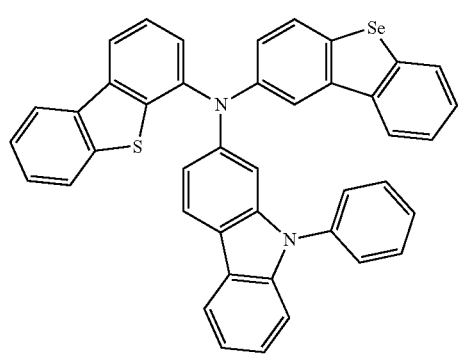
171
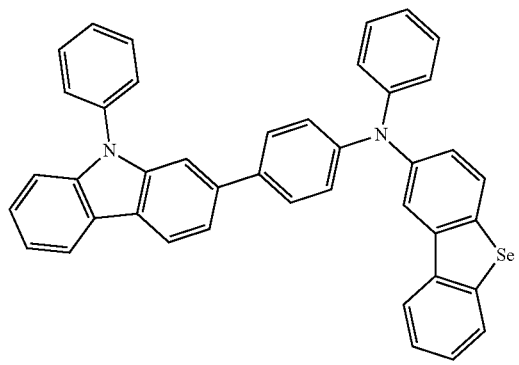
172
173
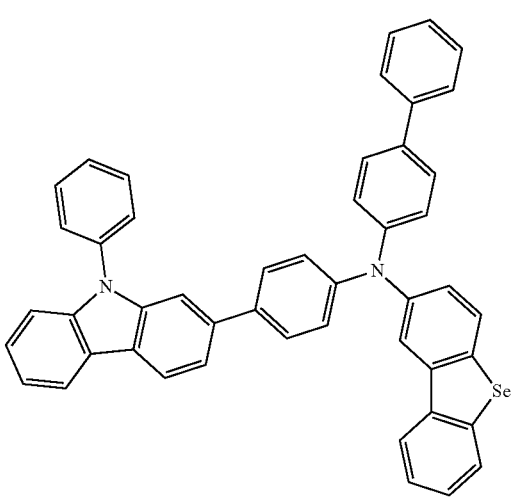
174
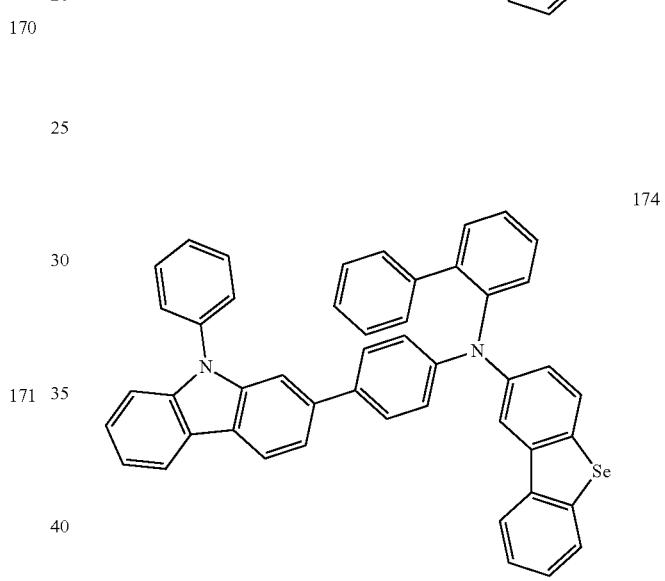
175
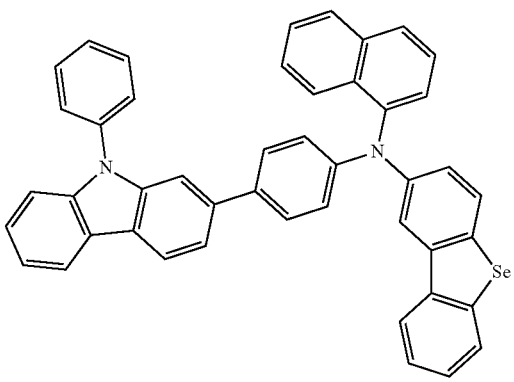

176
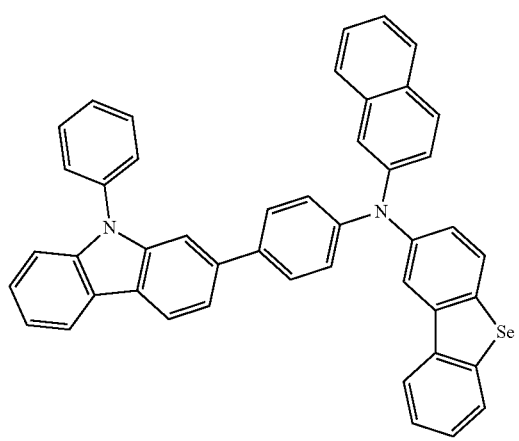
177
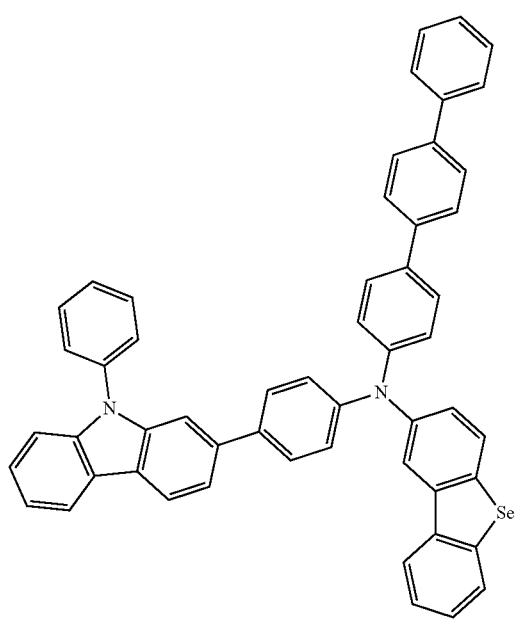
178
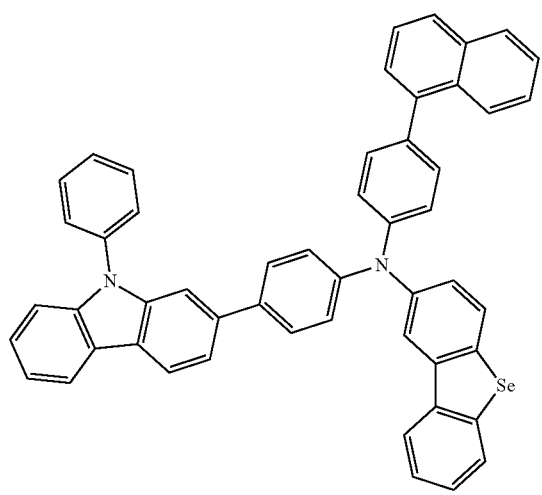
179
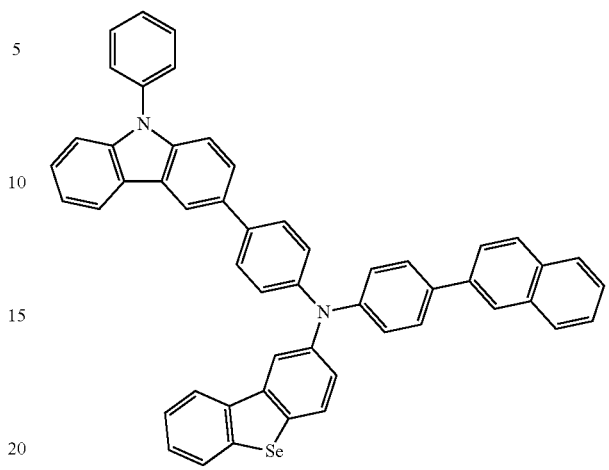
180
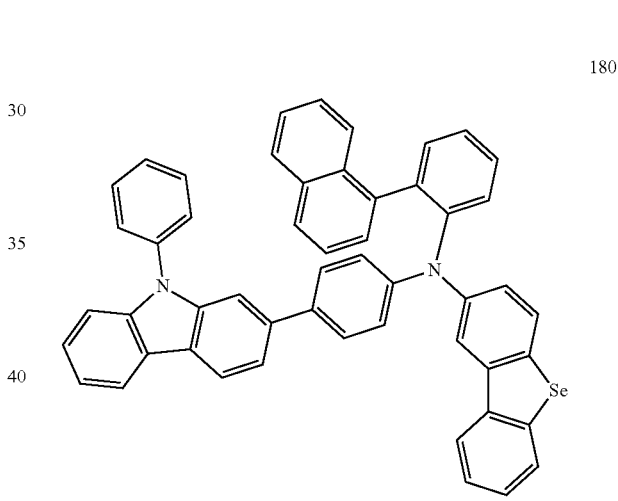
181
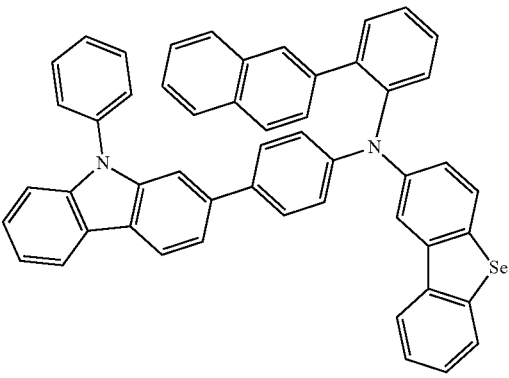

182
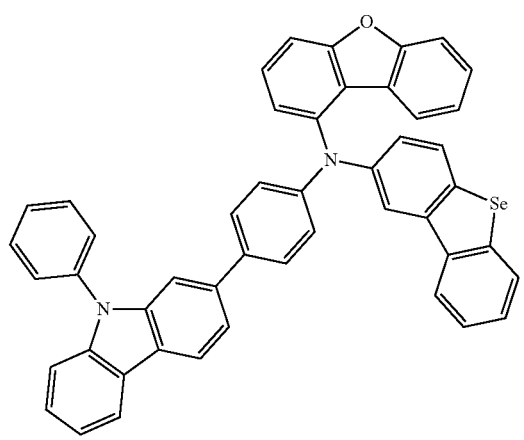
183
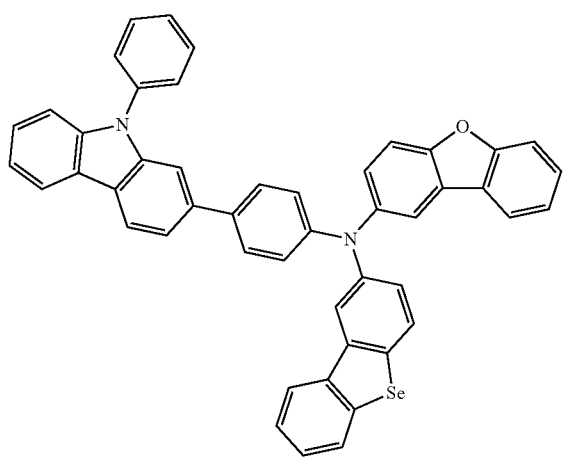
184
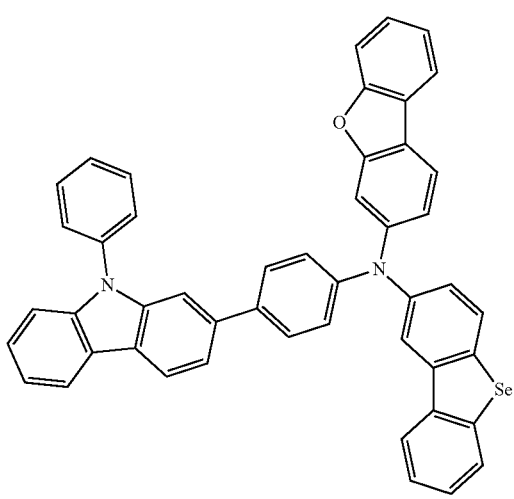
185
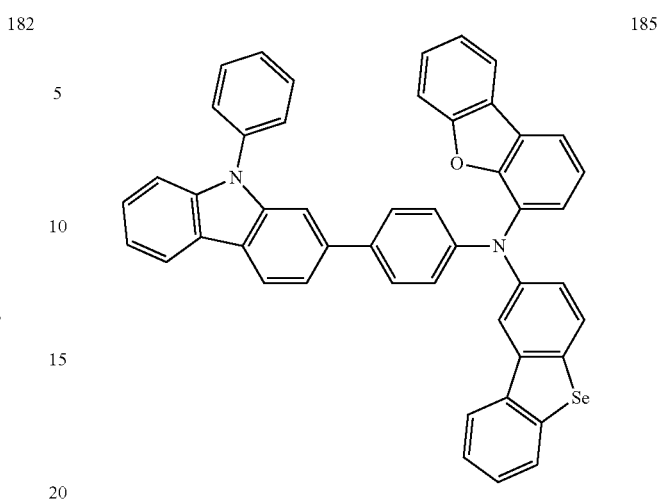
186
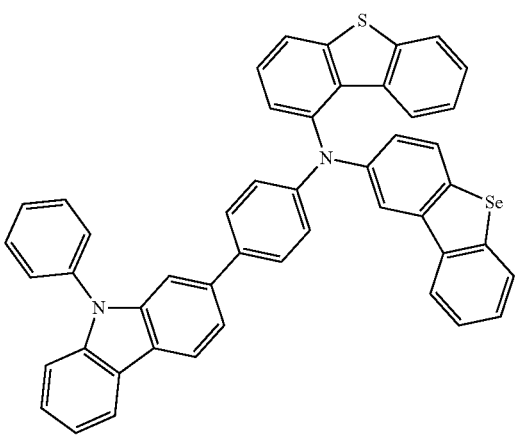
187
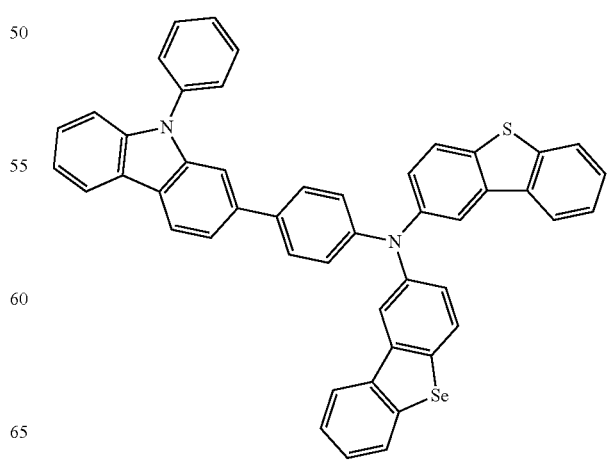

188
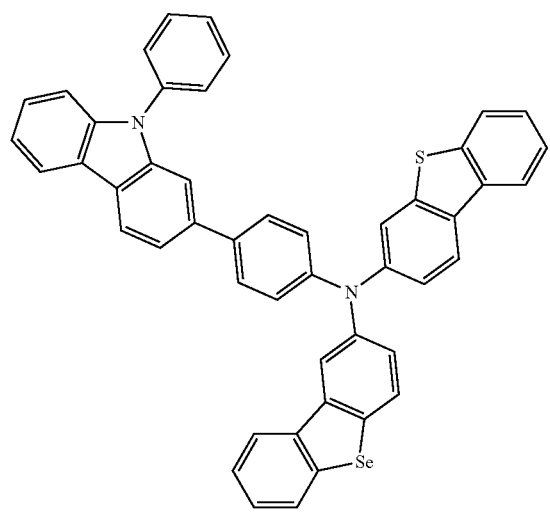
189
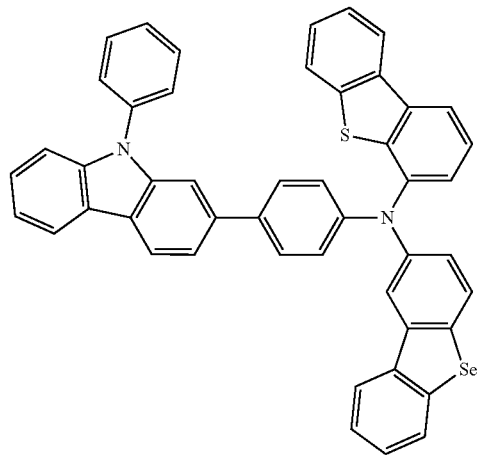
190
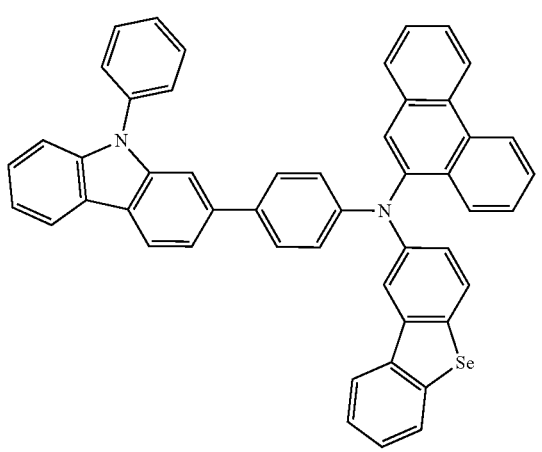
191
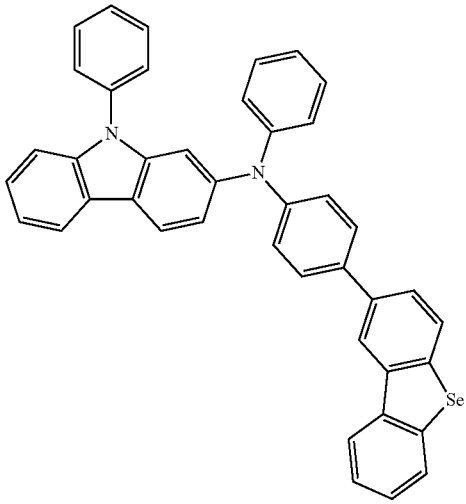
192
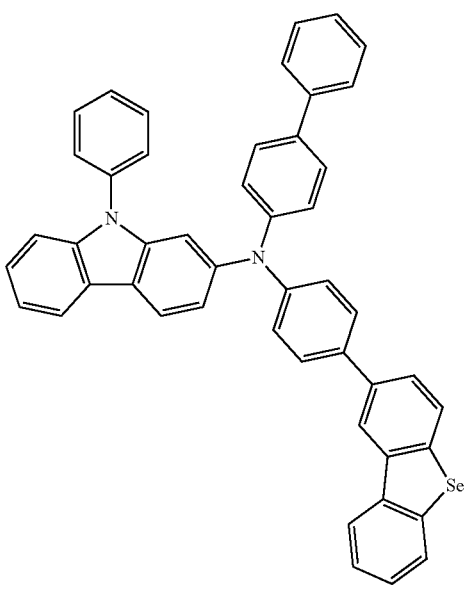
193
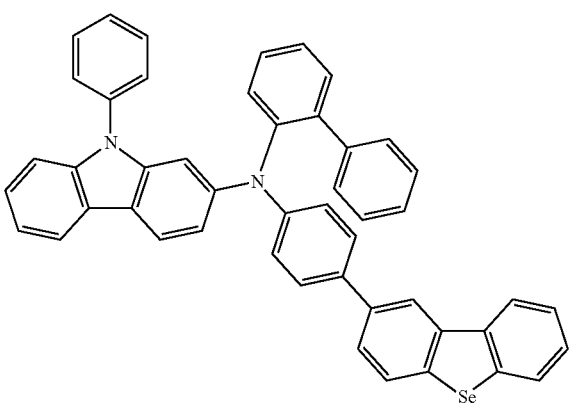

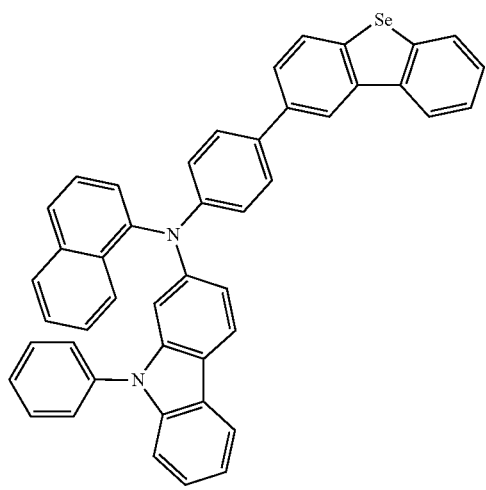
194
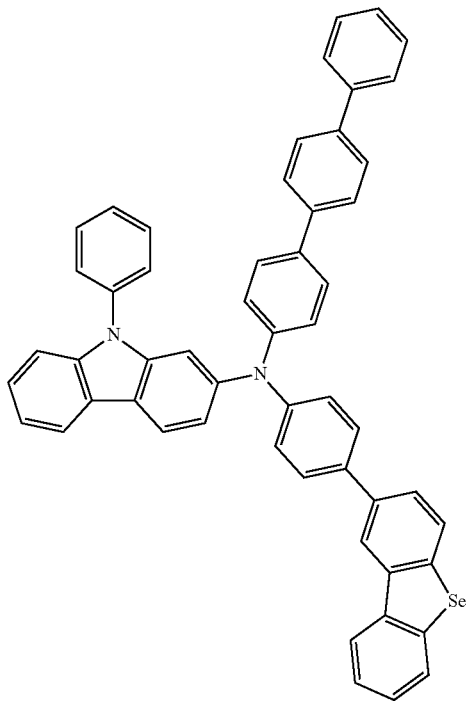
196
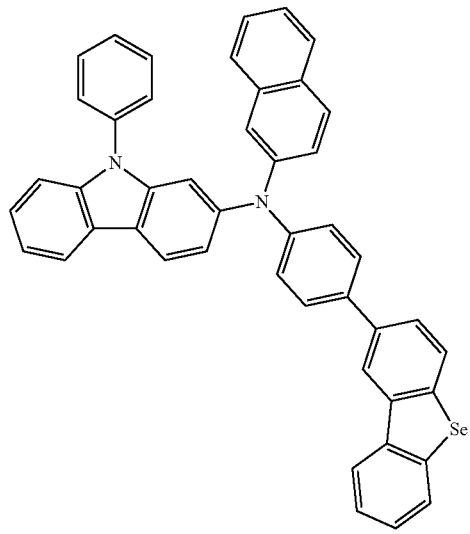
195
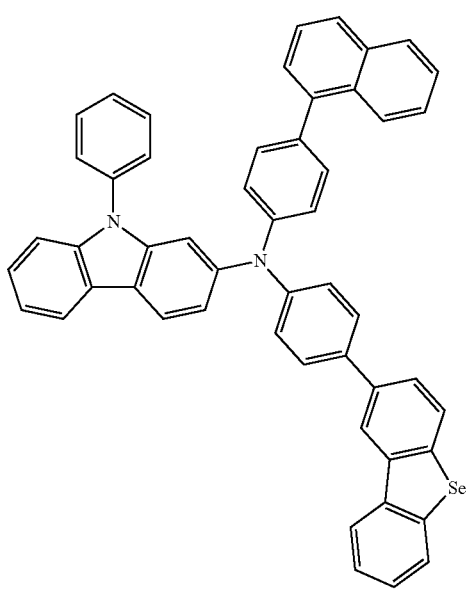
197

69
-continued
198
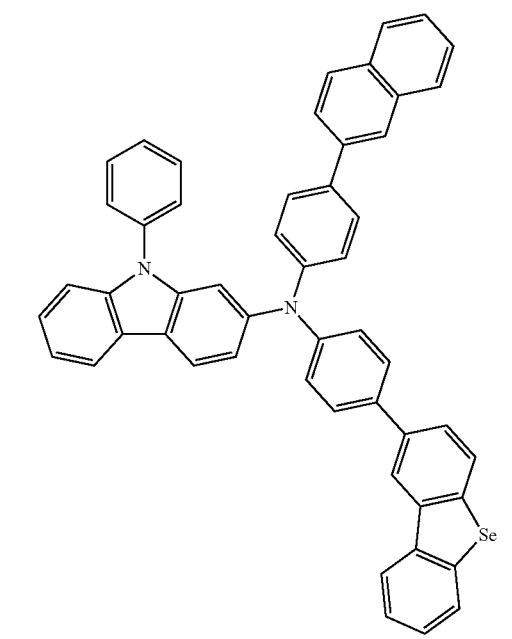
199
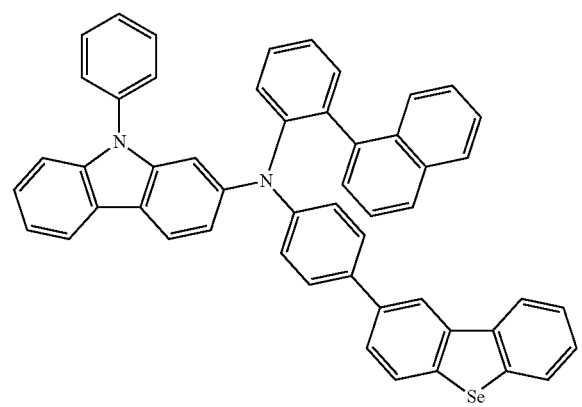
200
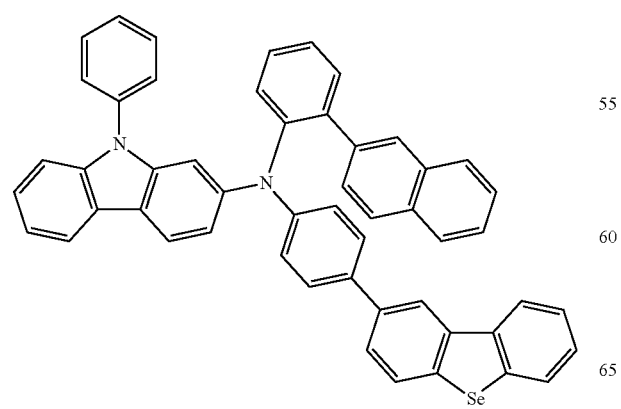
70
-continued
201
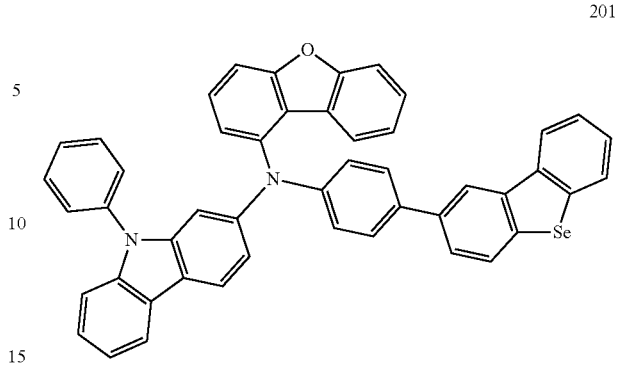
202
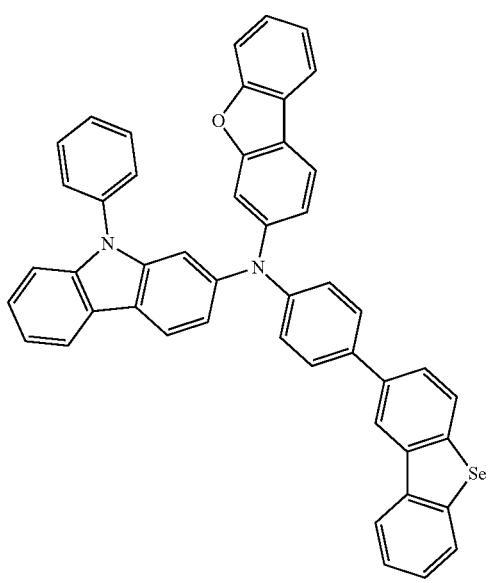
203

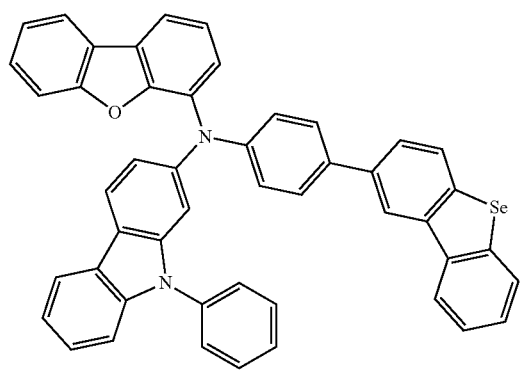
204
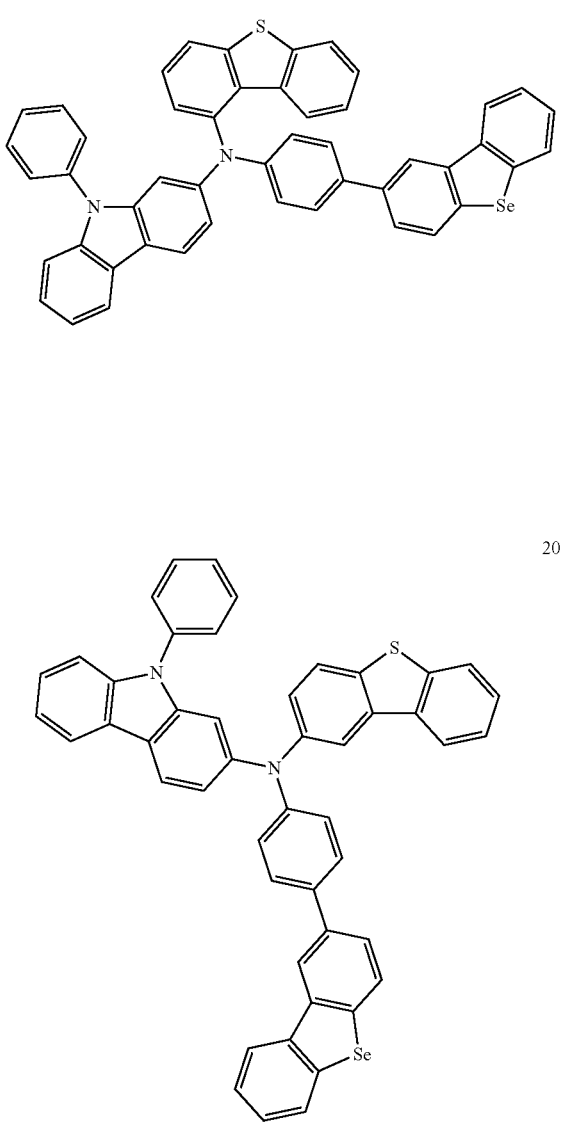
205
206
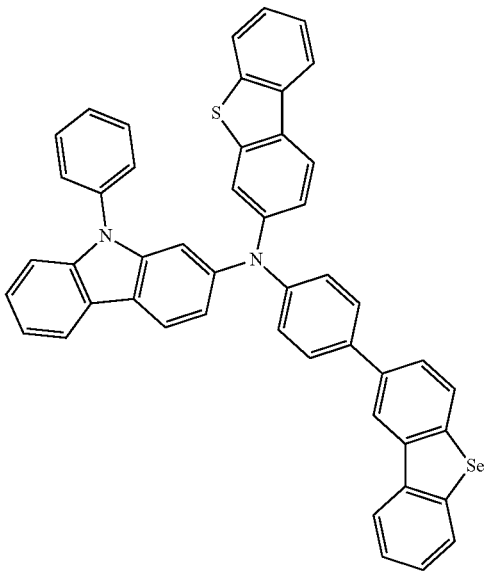
207
208
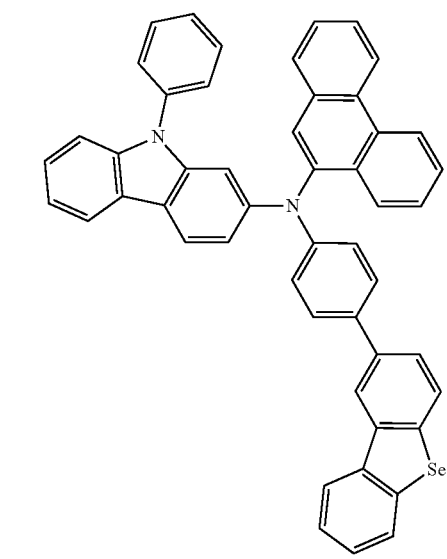
209

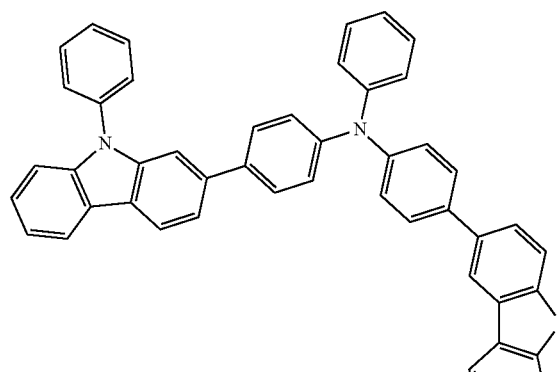
210
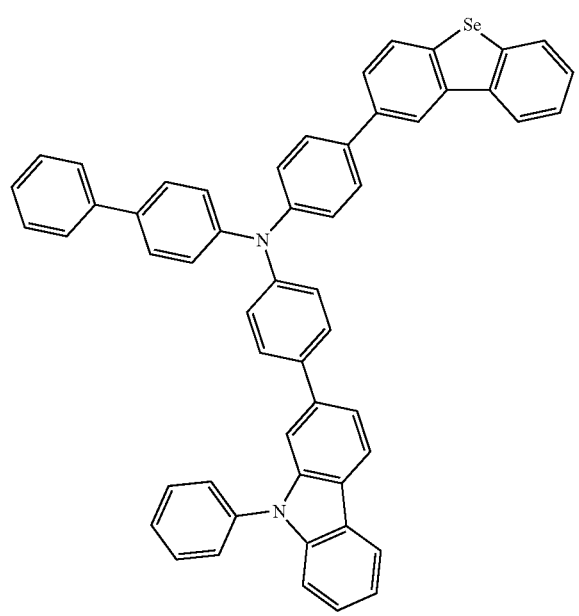
211
212
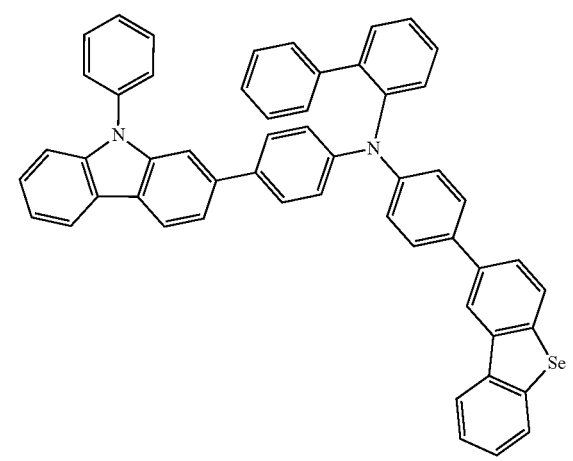
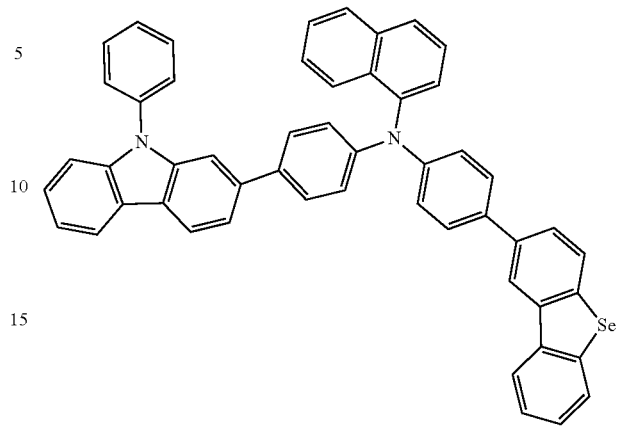
213
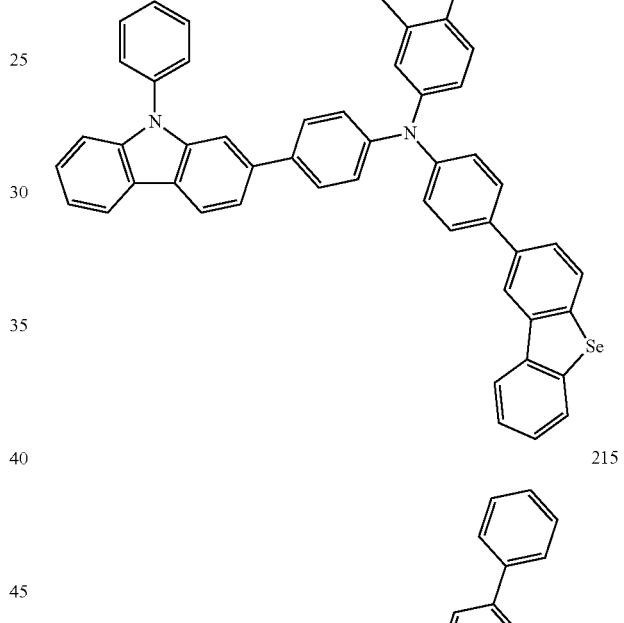
214
215
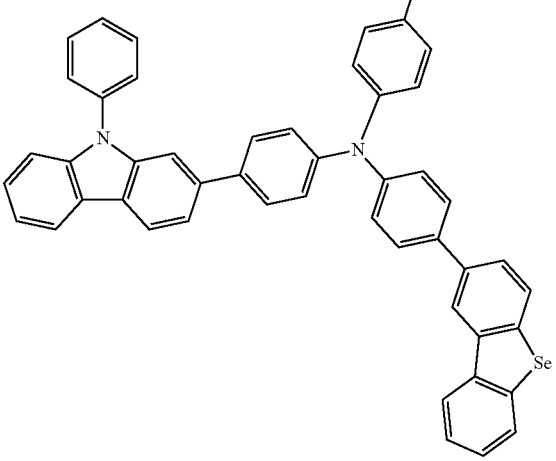

-continued
216
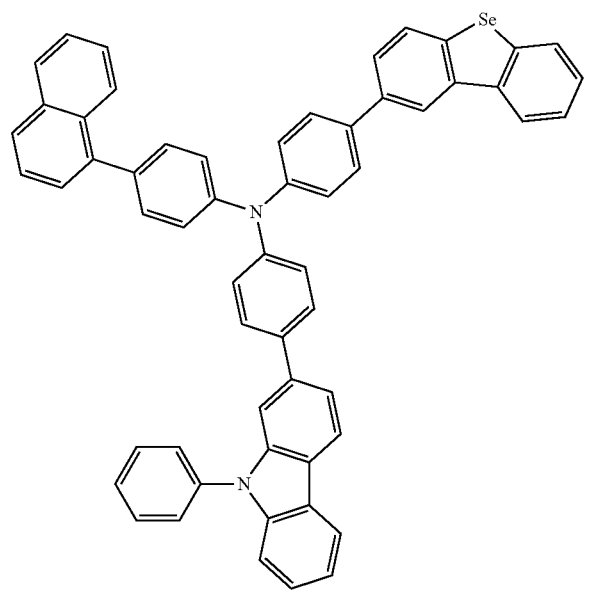
217
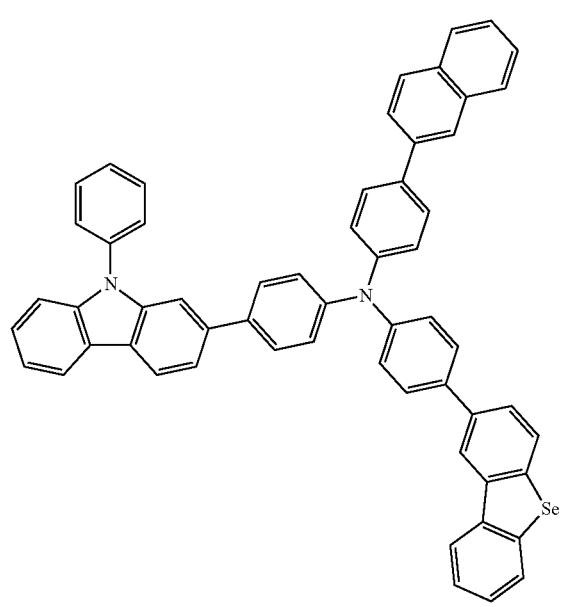
-continued
218
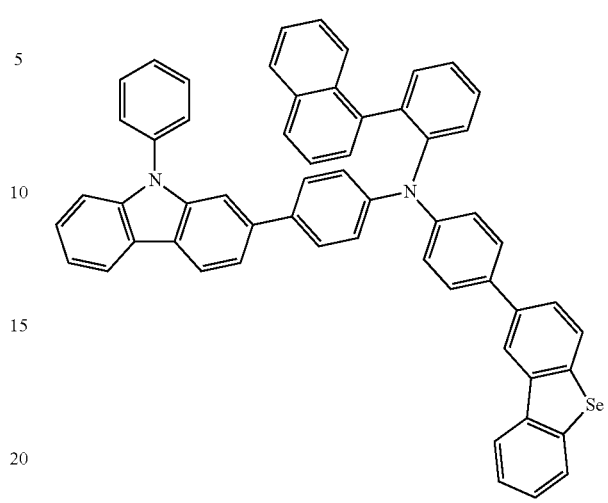
219
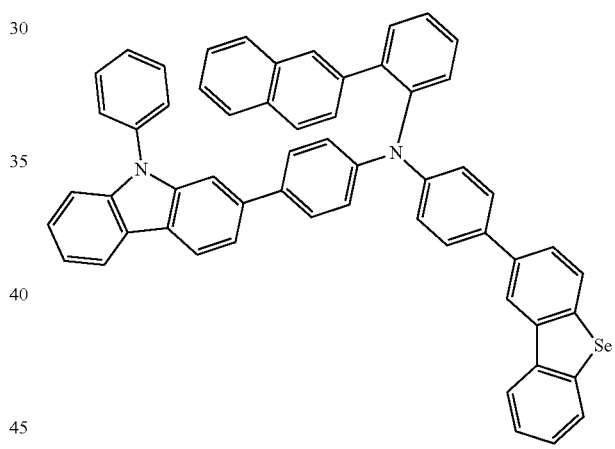
220
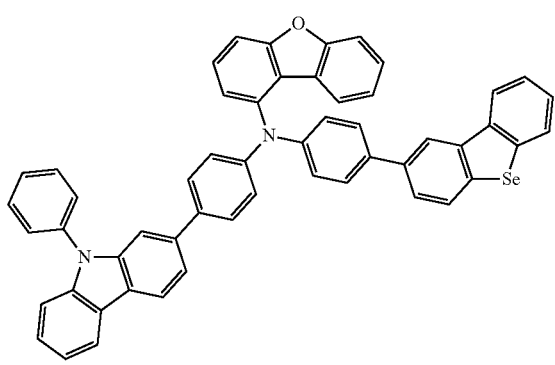

221
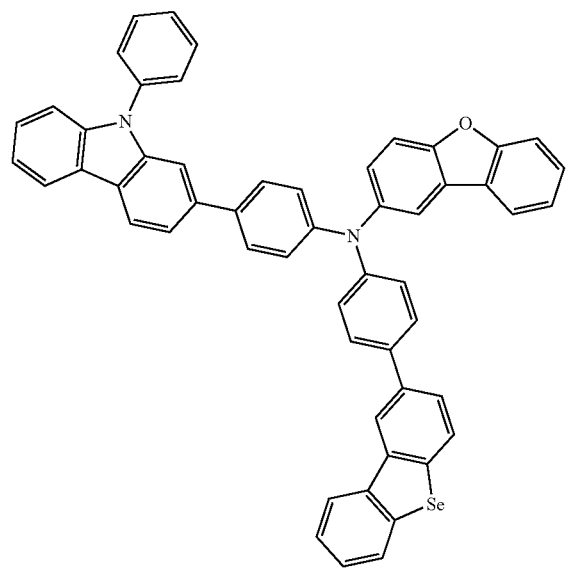
222
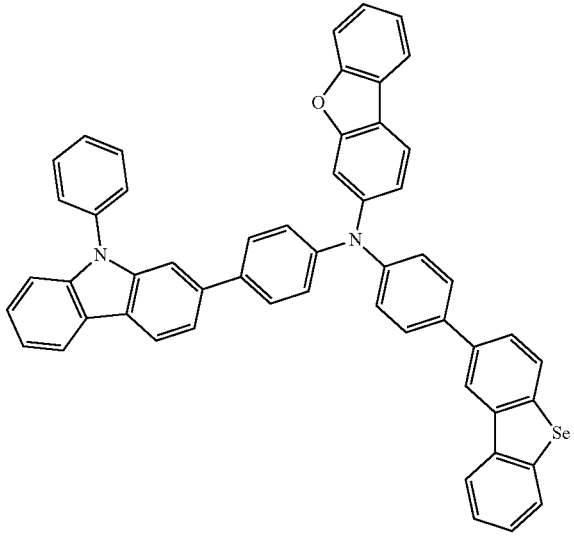
223
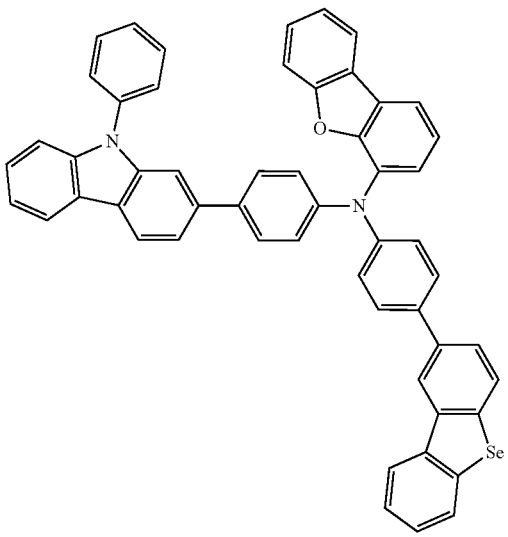
224
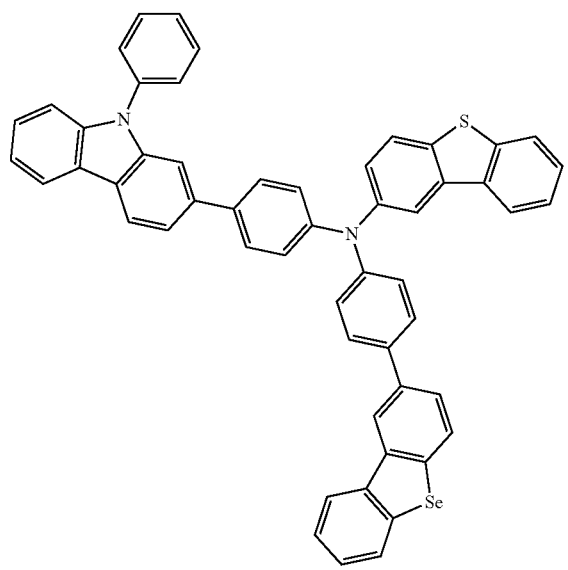
225

226
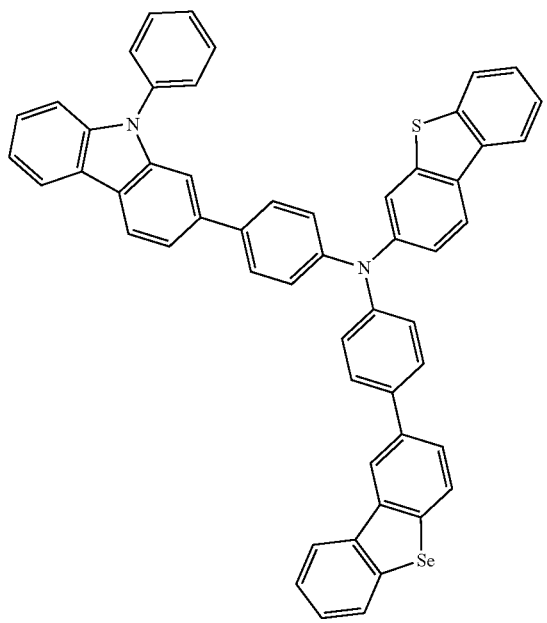
227
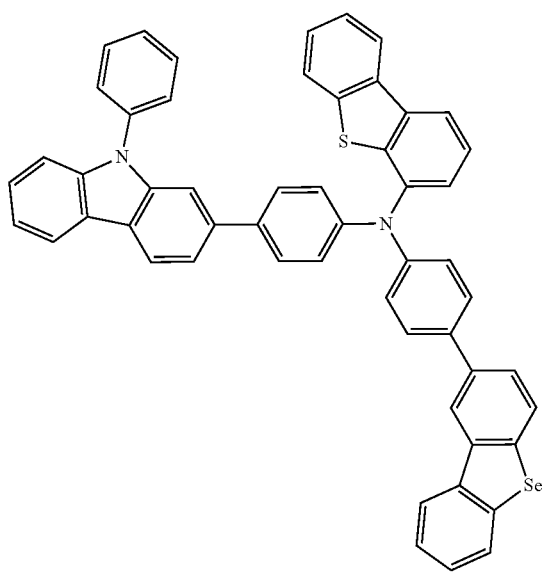
228
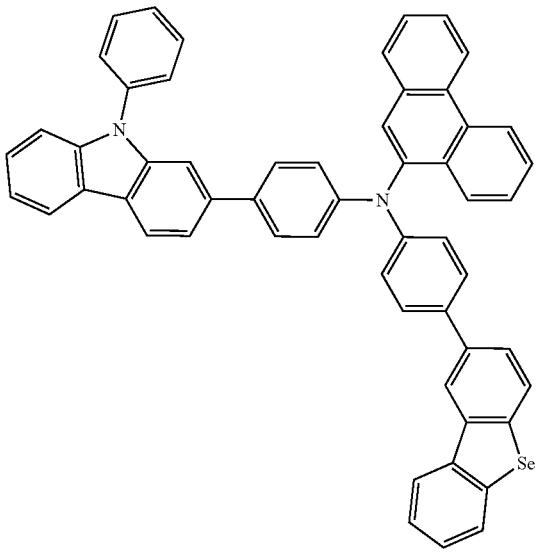
229
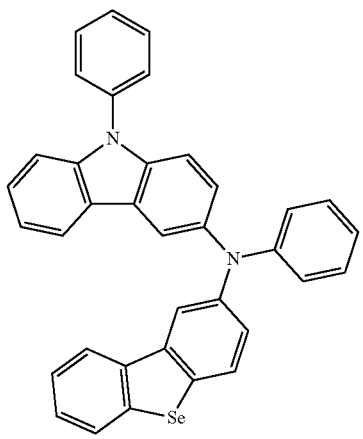
230
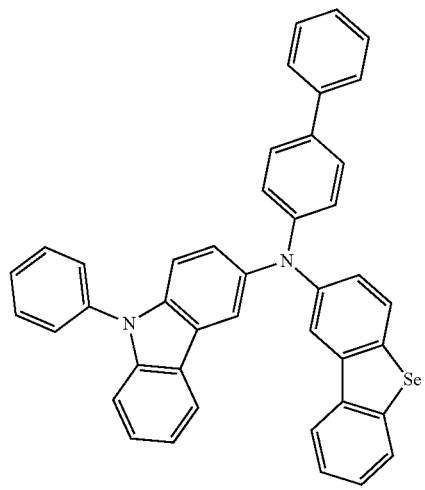

231
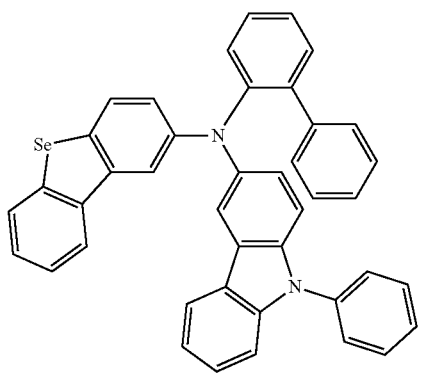
232
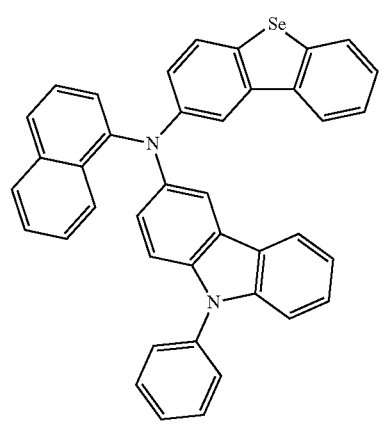
233
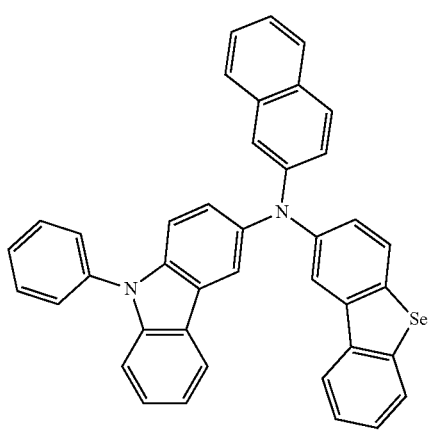
234
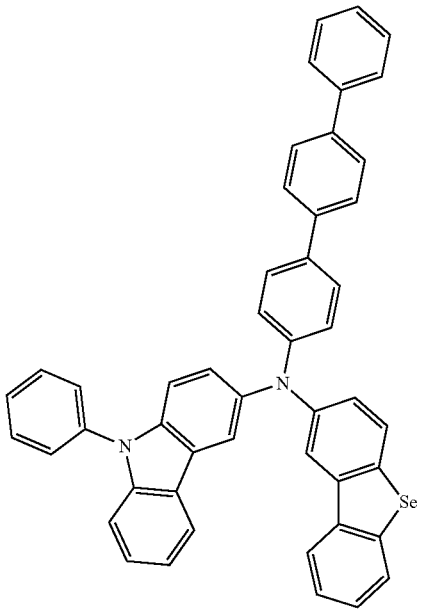
235
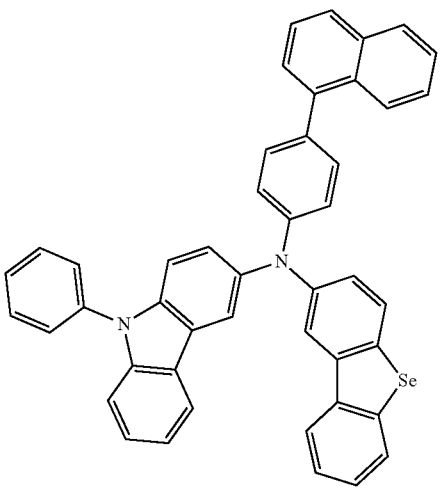
236
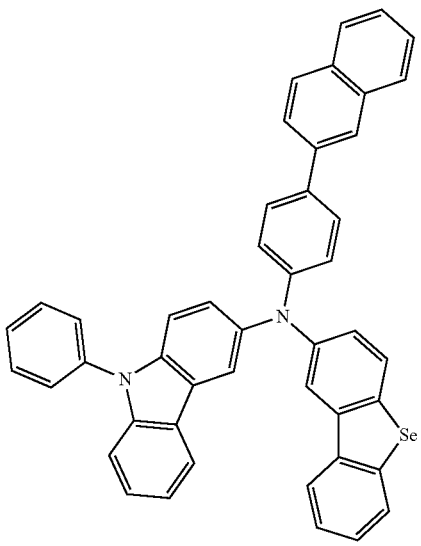

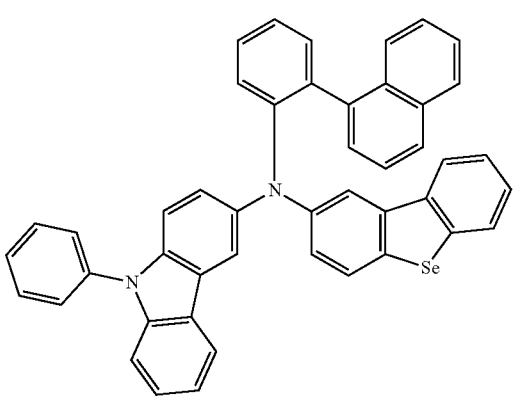 237
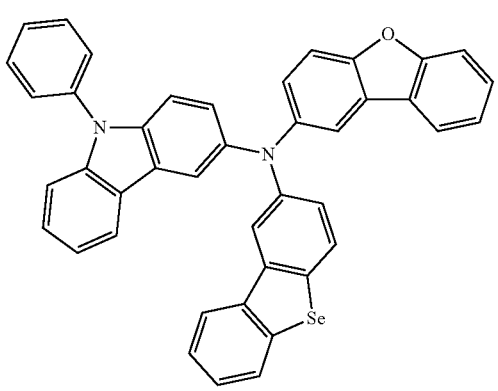 240
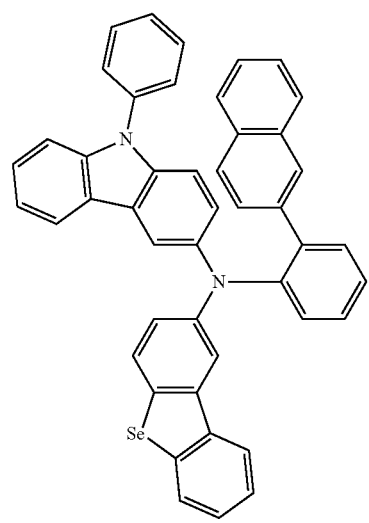 238
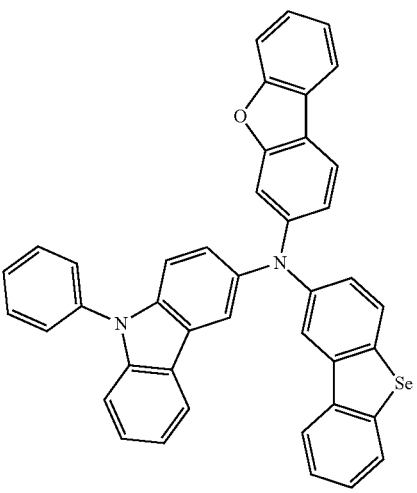 241
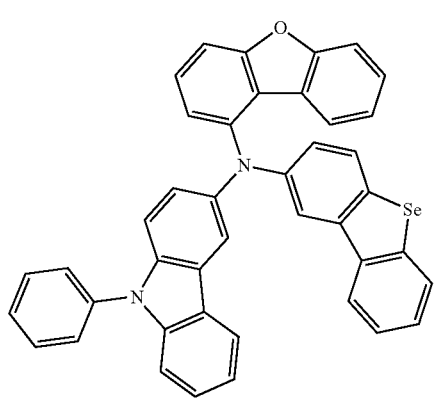 239
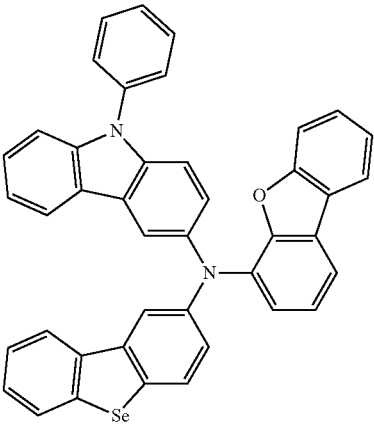 242

243
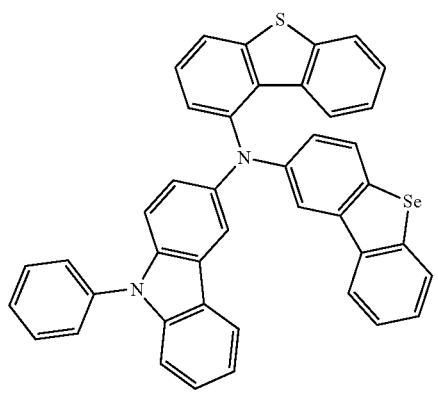
244
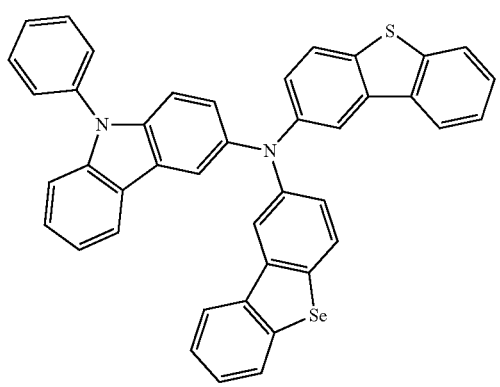
245
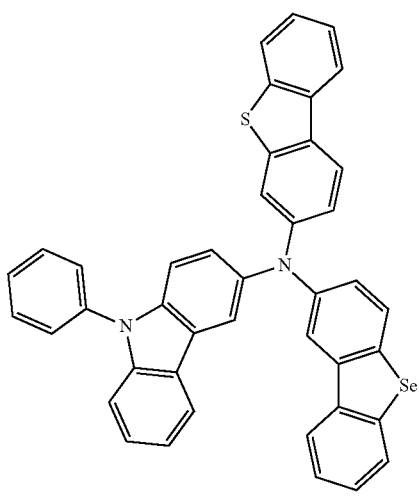
246
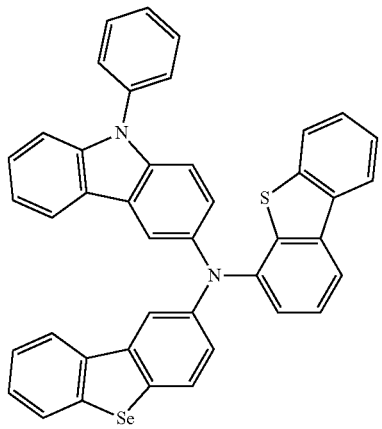
247
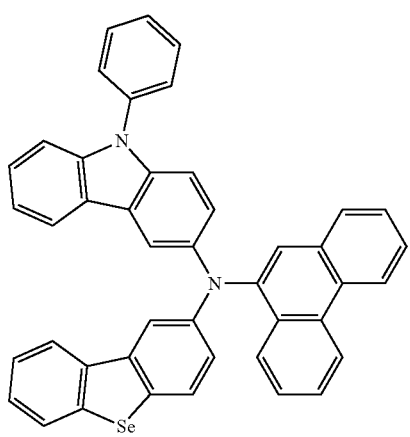
248
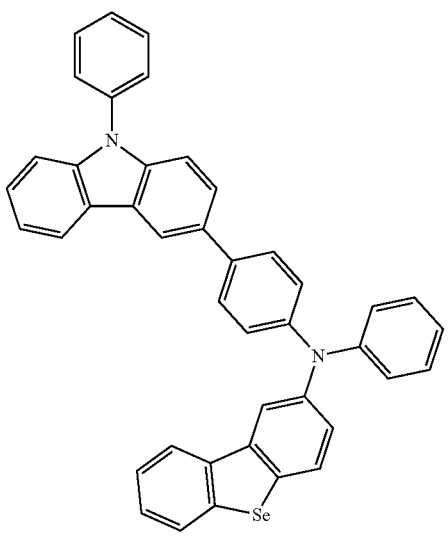

249
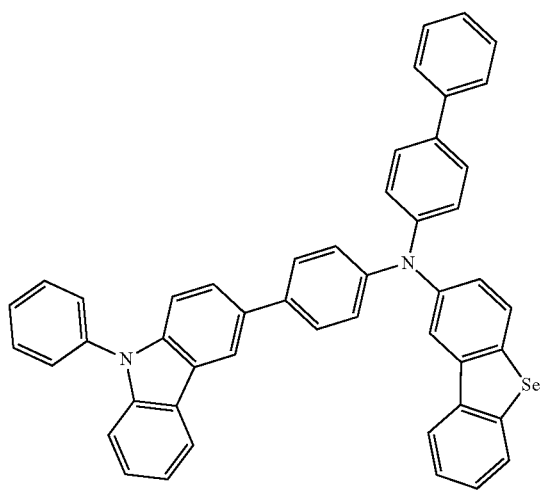
250
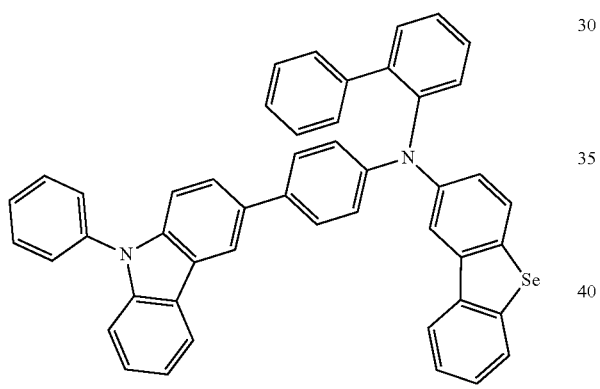
251
252
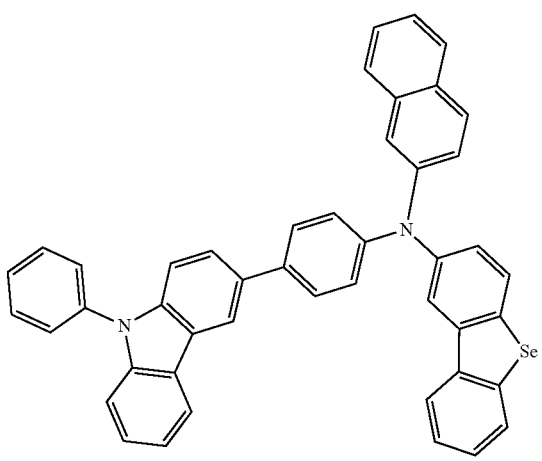
253
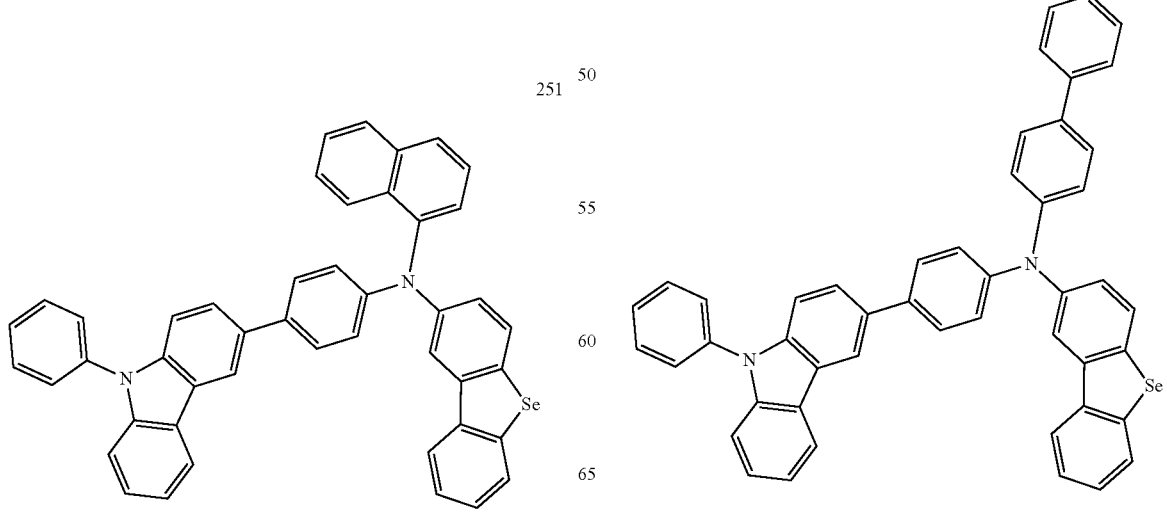

254
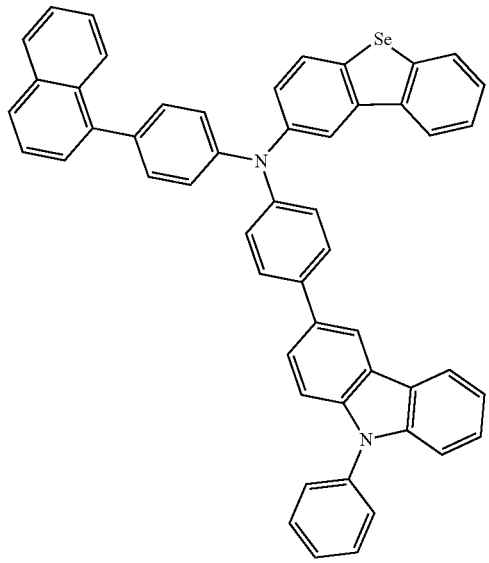
255
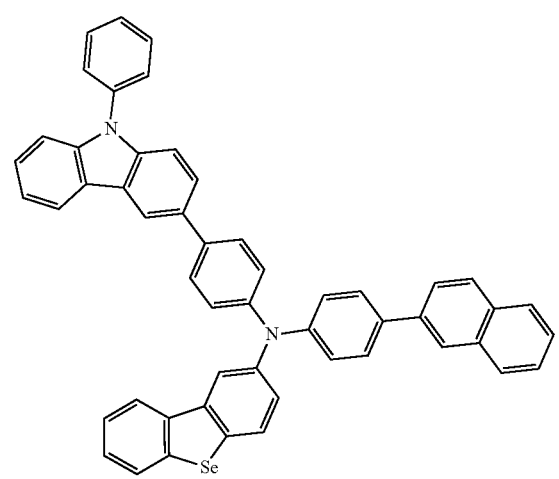
256
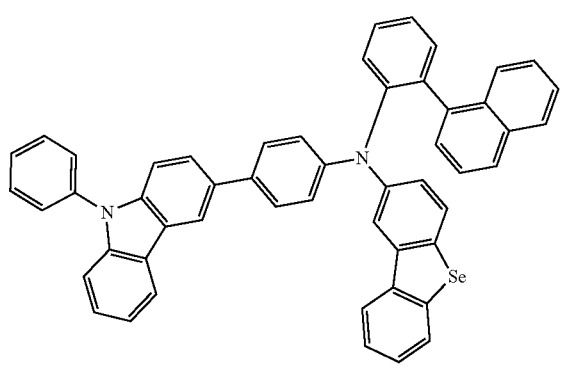
257
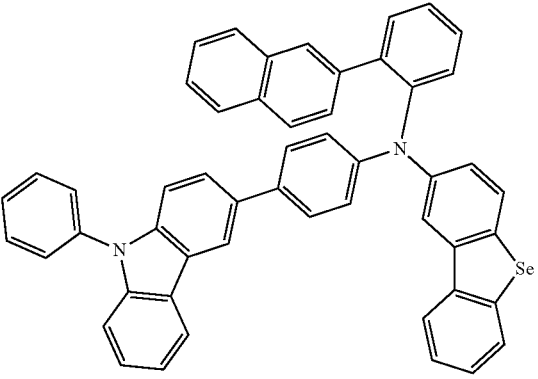
258
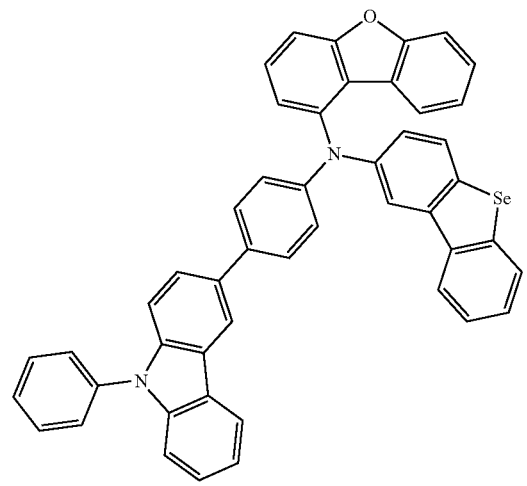
259
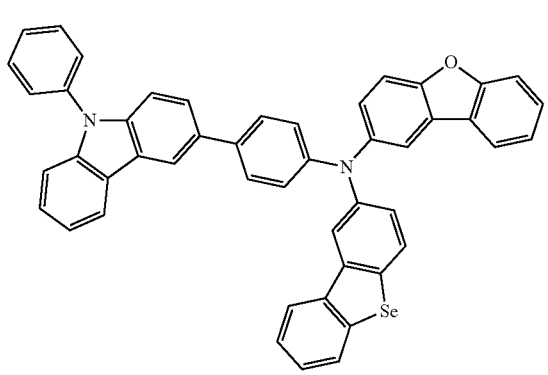

-continued
260
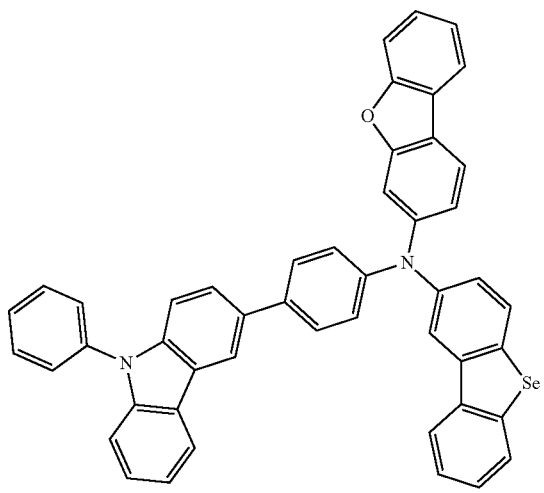
261
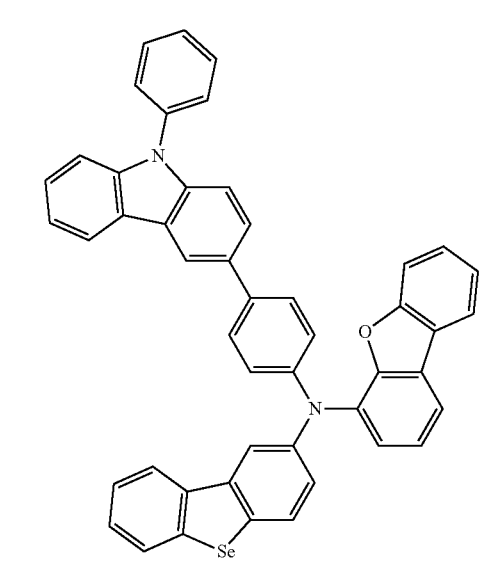
262
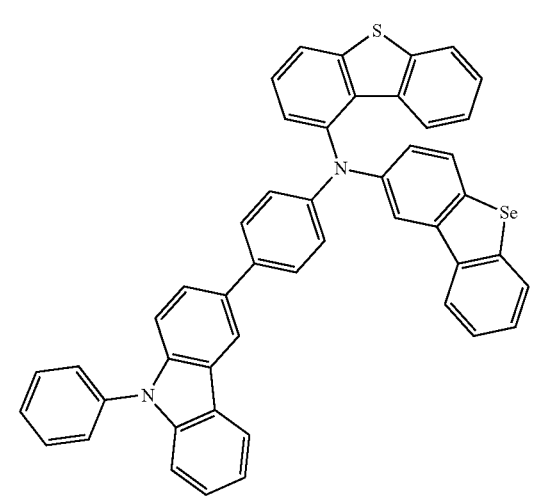
-continued
263
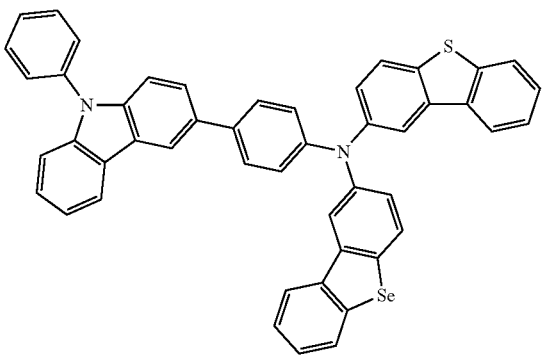
264
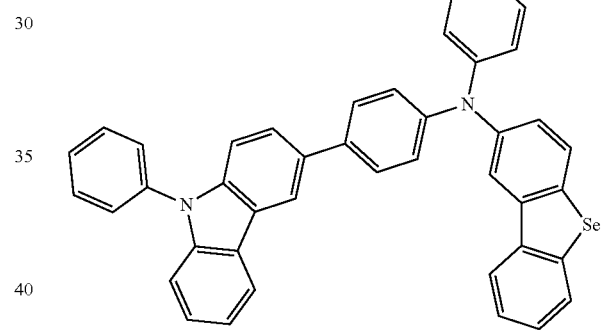
265
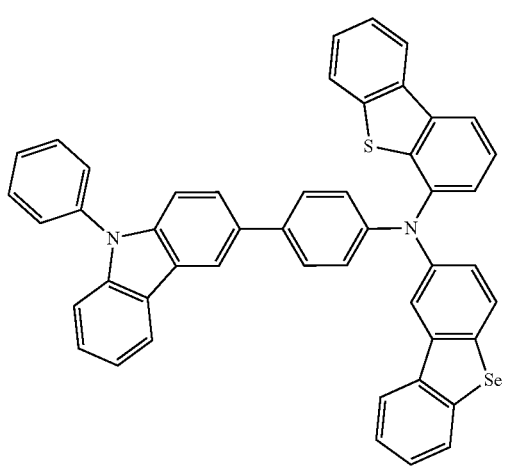

266
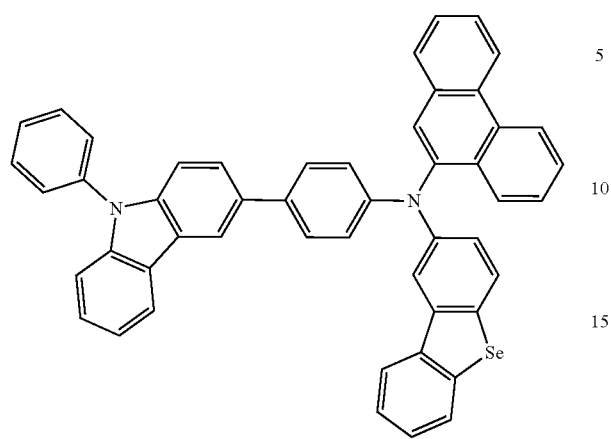
267
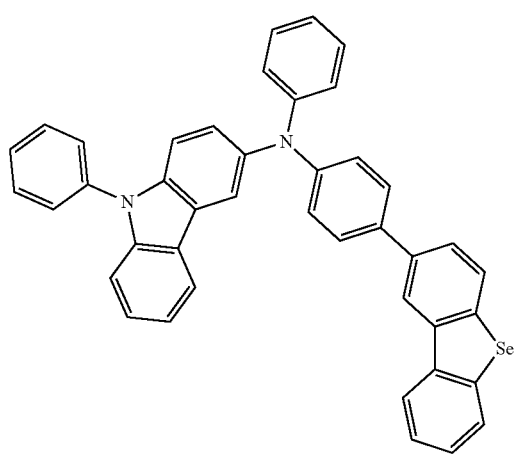
268
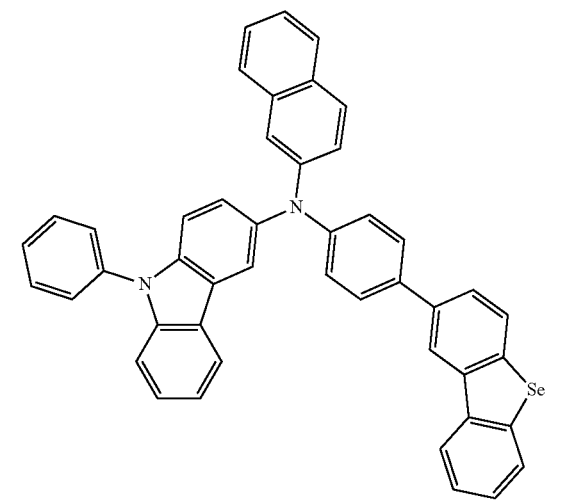
269
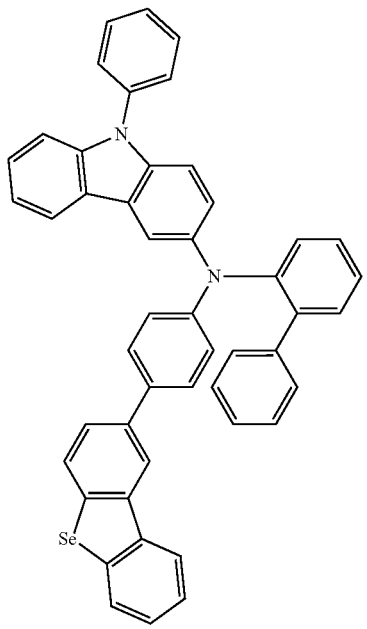
270
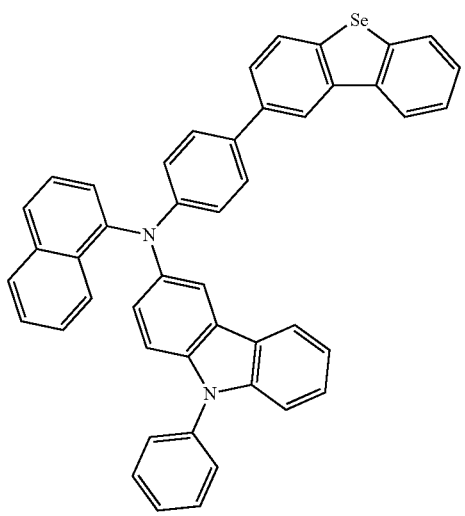
271
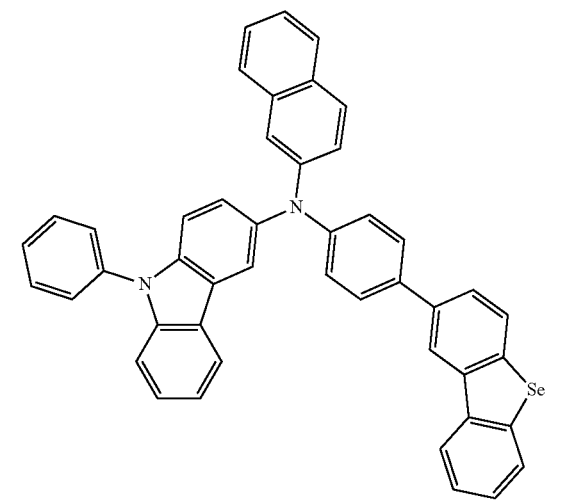

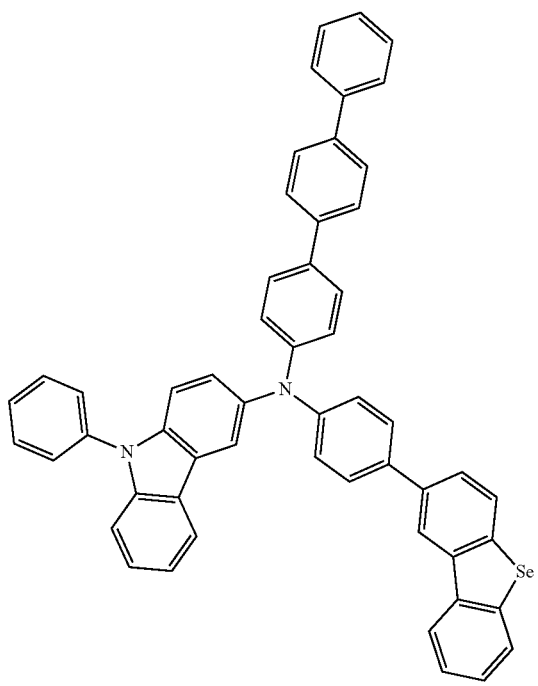
272
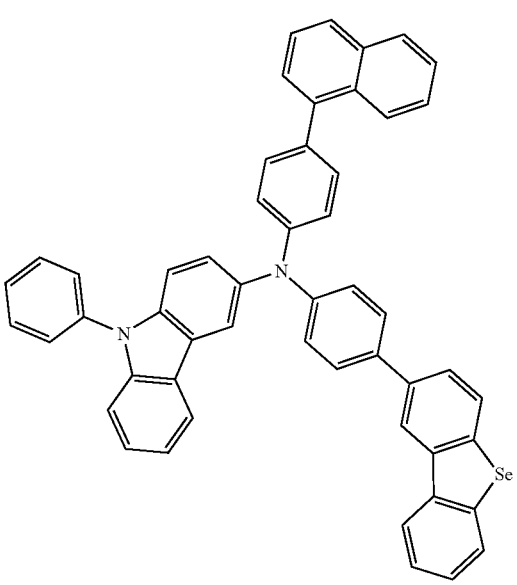
273
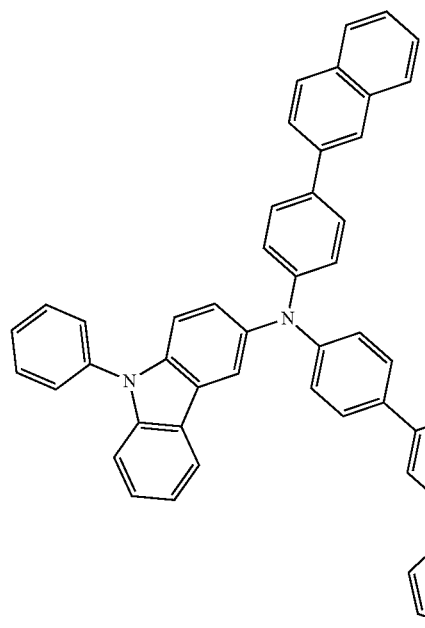
274
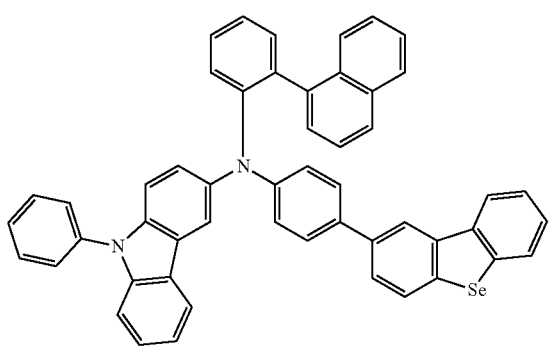
275
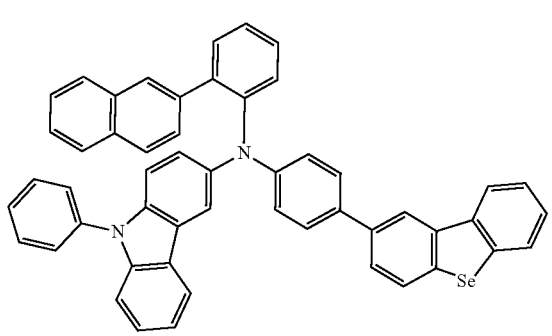
276

277
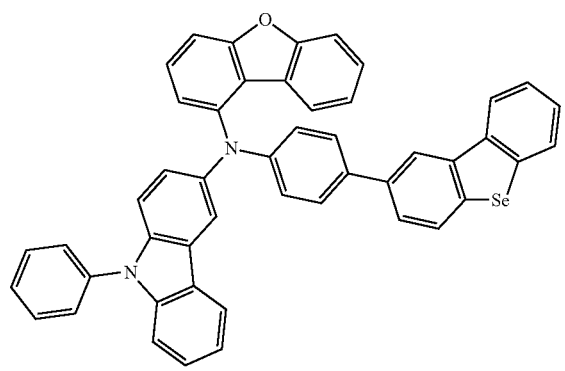
278
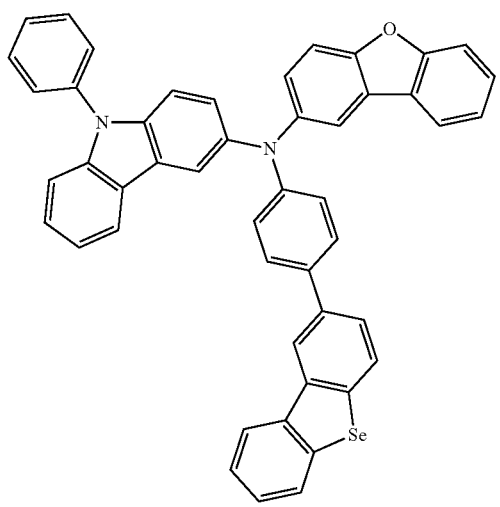
279
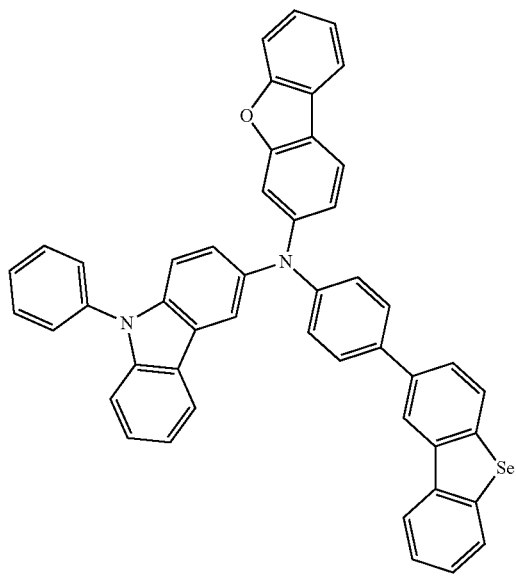
280
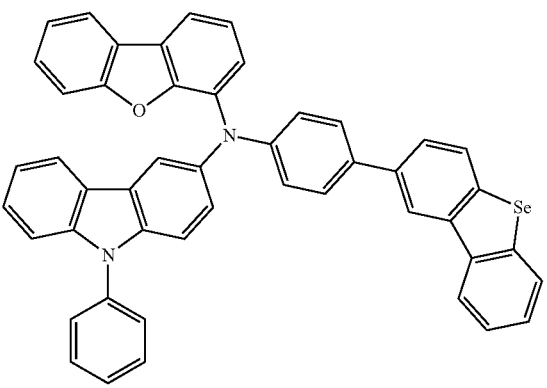
281
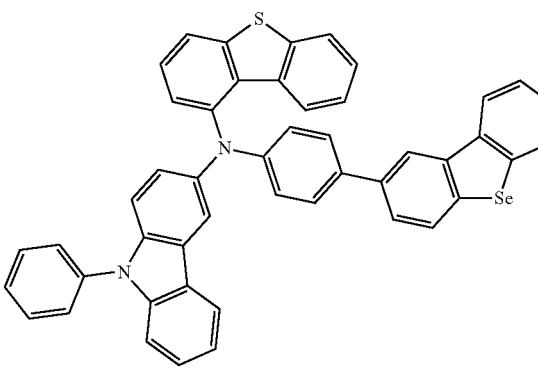
282
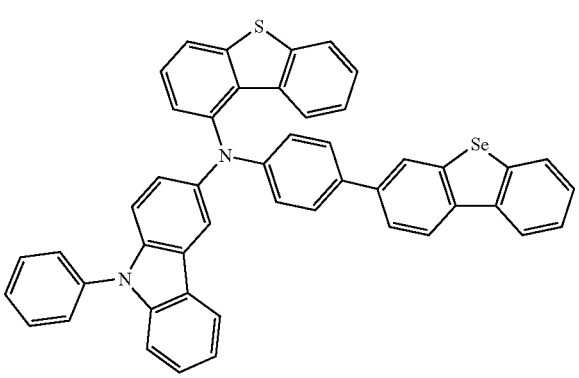

283
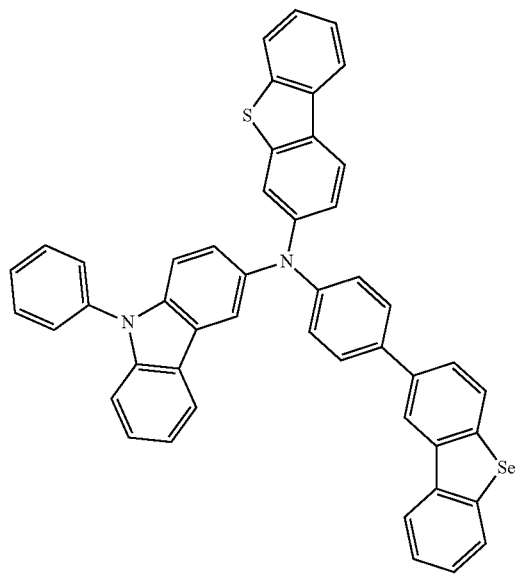
284
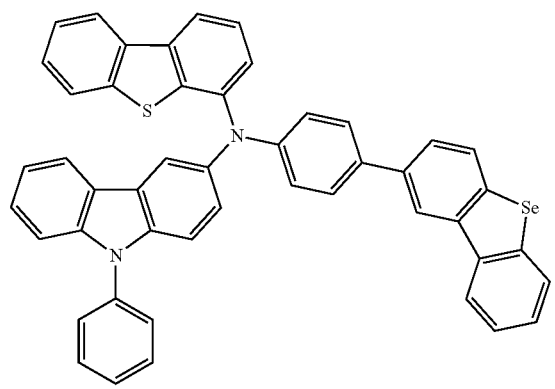
285
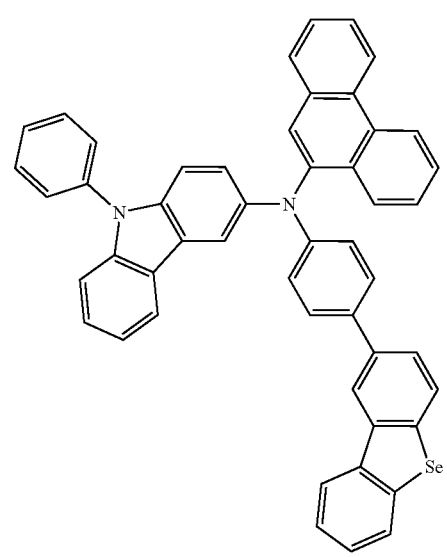
286
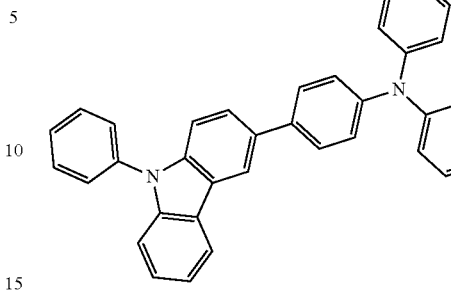
287
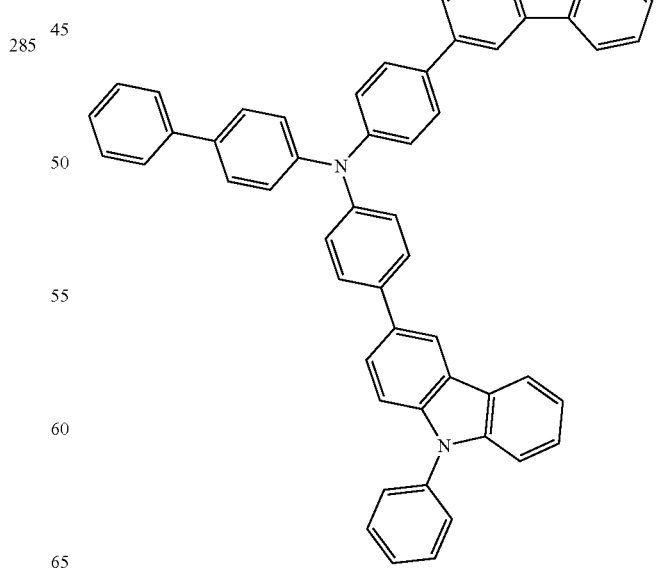

101
-continued
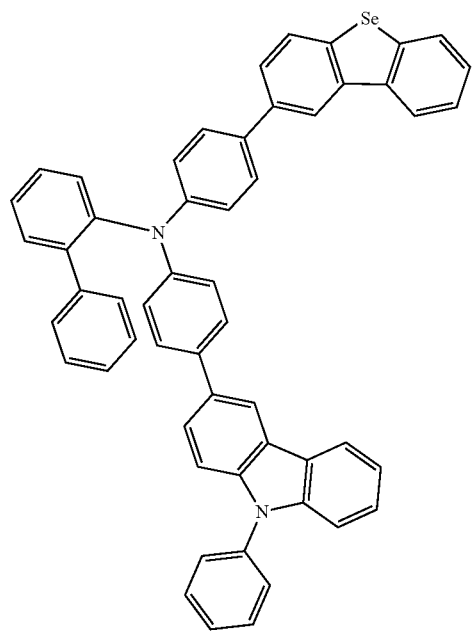
288
289
290
102
-continued
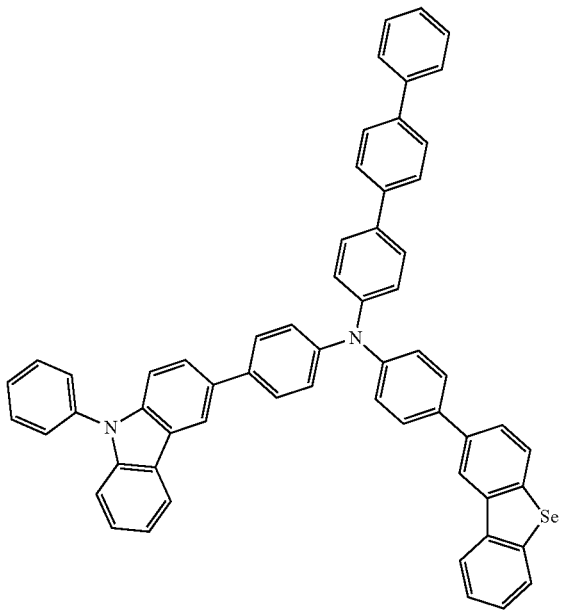
291
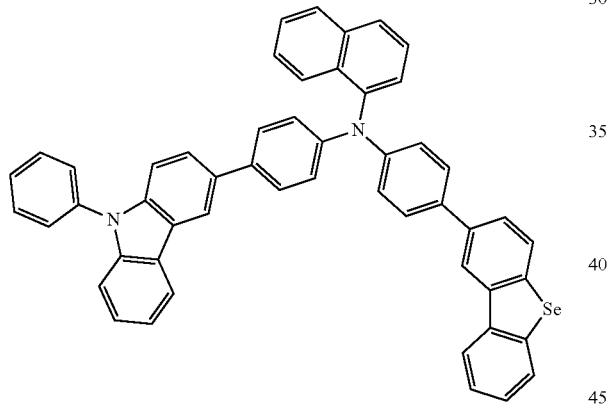
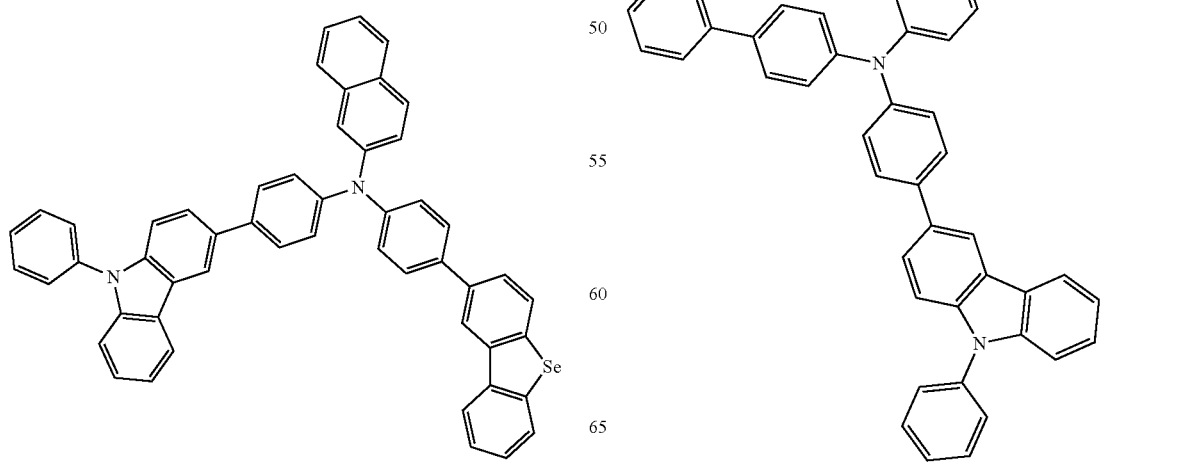
292

293
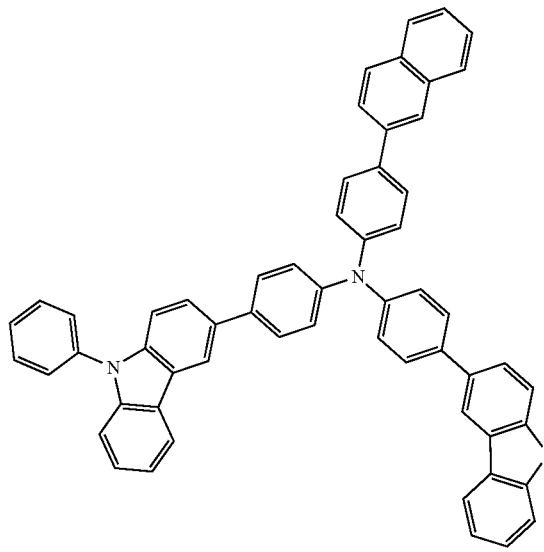
294
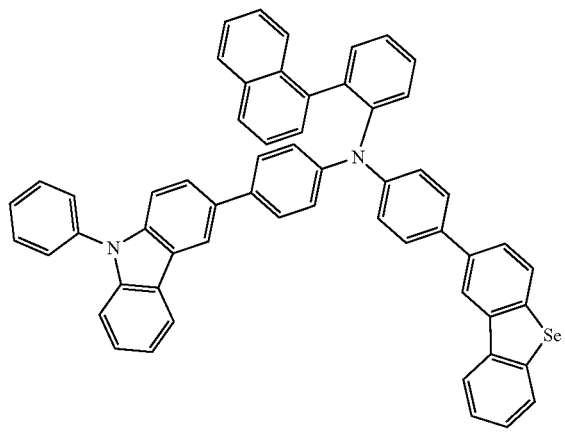
295
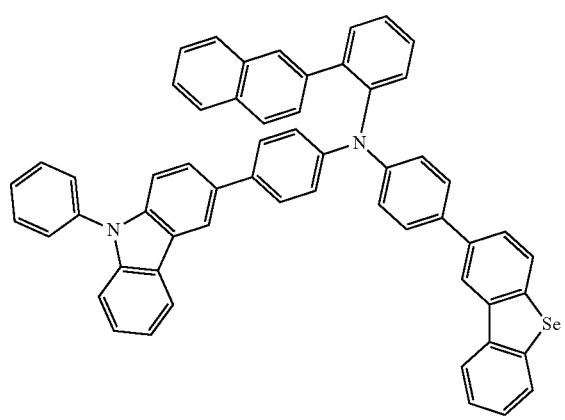
296
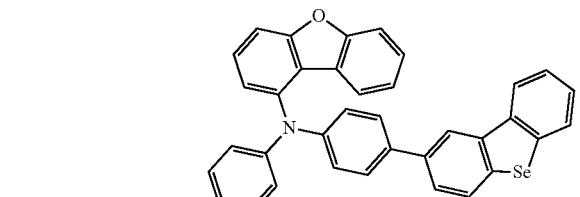
297
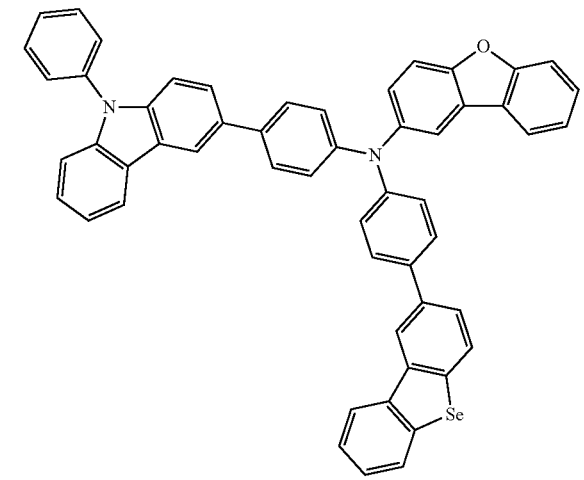
298
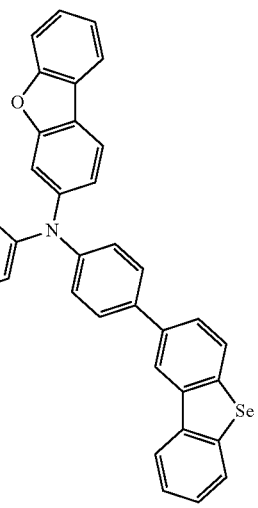

299
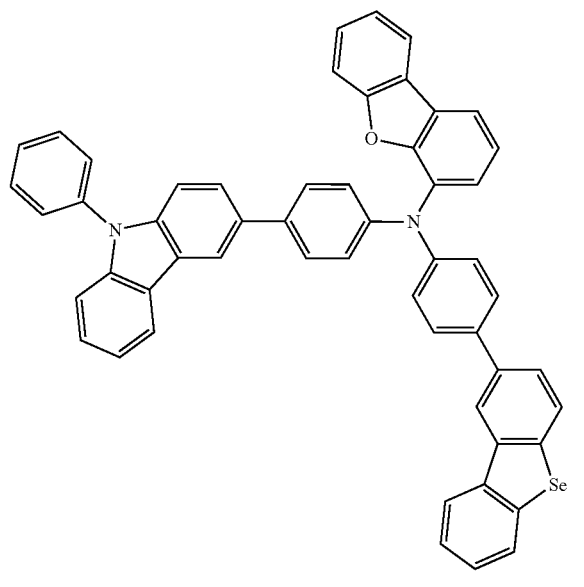
302
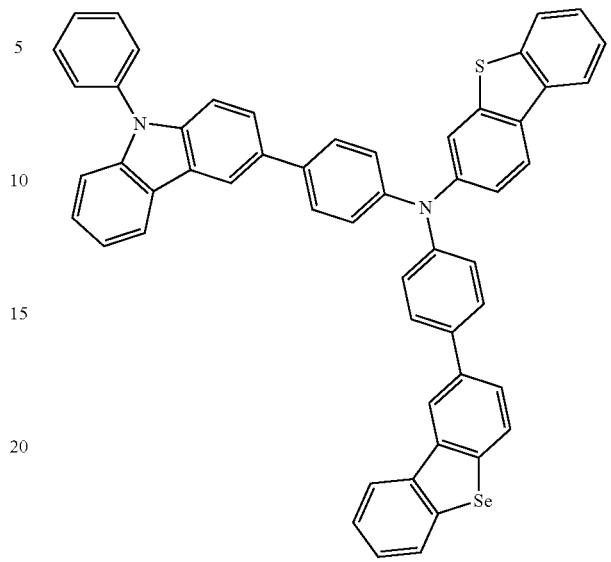
300
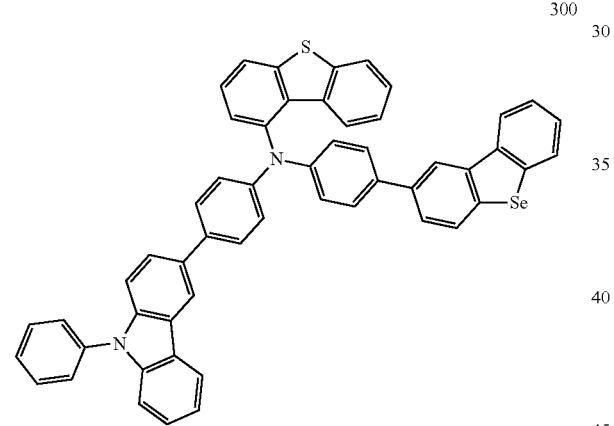
301
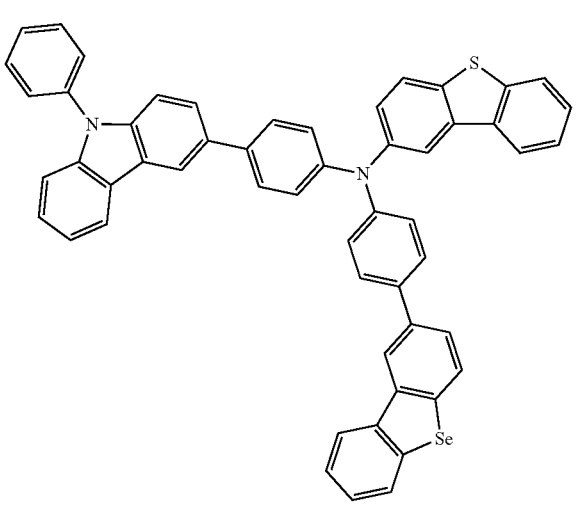
303
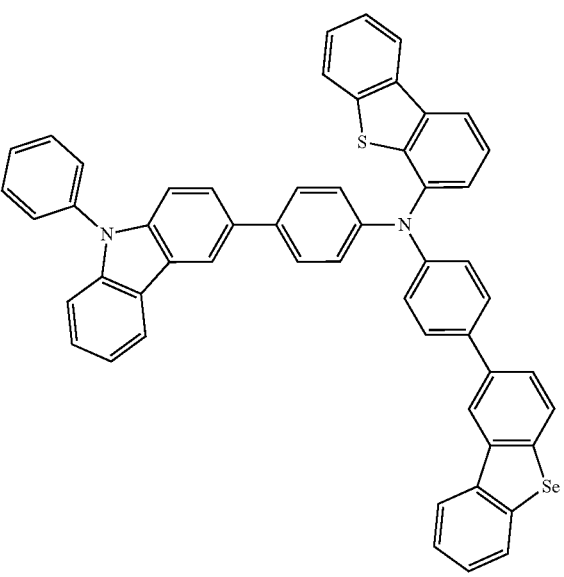

-continued

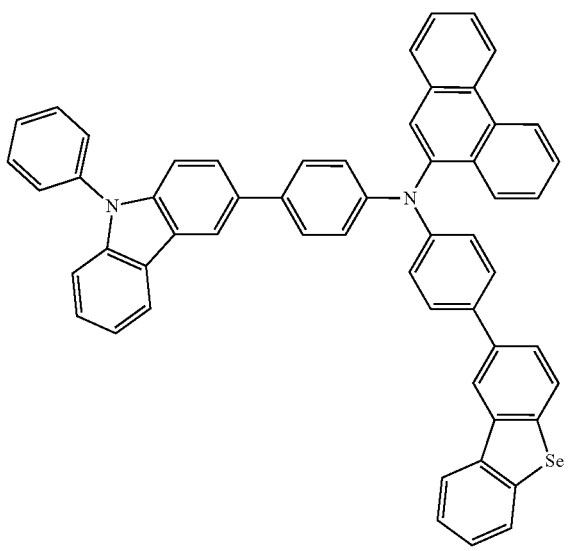

304

BRIEF DESCRIPTION OF THE DRAWINGS

The accompanying drawings are included to provide a further understanding of the present disclosure, and are incorporated in and constitute a part of this specification. The drawings illustrate example embodiments of the present disclosure and, together with the description, serve to explain principles of the present disclosure. In the drawings.

DETAILED DESCRIPTION

Figure 1:
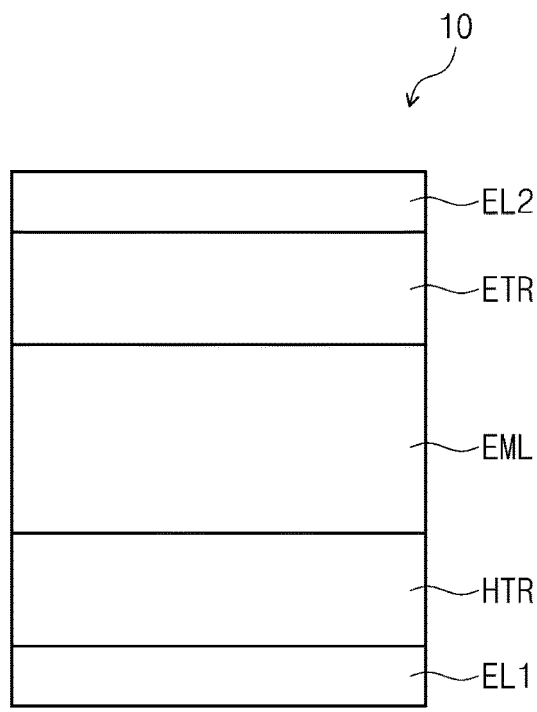
FIG. 1 is a cross-sectional view schematically illustrating an organic electroluminescence device according to an embodiment of the present disclosure.

The present disclosure may have various modifications and may be embodied in different forms, and example embodiments will be explained in more detail with reference to the accompany drawings. The present disclosure may, however, be embodied in different forms and should not be construed as limited to the embodiments set forth herein. Rather, all modifications, equivalents, and substituents which are included in the spirit and technical scope of the present disclosure should be included in the present disclosure.

In the drawings, like reference numerals refer to like elements throughout. The dimensions of structures are exaggerated for clarity of illustration. It will be understood that, although the terms first, second, etc. may be used herein to describe various elements, these elements should not be limited by these terms. These terms are only used to distinguish one element from another element. For example, a first element could be termed a second element without departing from the teachings of the present disclosure. Similarly, a second element could be termed a first element. As used herein, the singular forms are intended to include the plural forms as well, unless the context clearly indicates otherwise.

It will be further understood that the terms "comprises" and/or "comprising," when used in this specification, specify the presence of stated features, numerals, steps, operations, elements, parts, or the combination thereof, but do not preclude the presence or addition of one or more other features, numerals, steps, operations, elements, parts, or the combination thereof.

In the present disclosure, when a layer, a film, a region, a plate, etc. is referred to as being "on" or "above" another part, it can be directly on the other part (without any intervening layers therebetween), or one or more intervening layers may also be present. Similarly, it will be understood that when a layer, a film, a region, a plate, etc. is referred to as being "under" or "beneath" another part, it can be directly under the other part (without any intervening layers therebetween), or one or more intervening layers may also be present. In addition, it will also be understood that when a plate is referred to as being "on" another part, it can be above or beneath another part.

Hereinafter, an organic electroluminescence device and an amine compound according to an embodiment of the present disclosure will be described with reference to the drawings.

Figure 2:
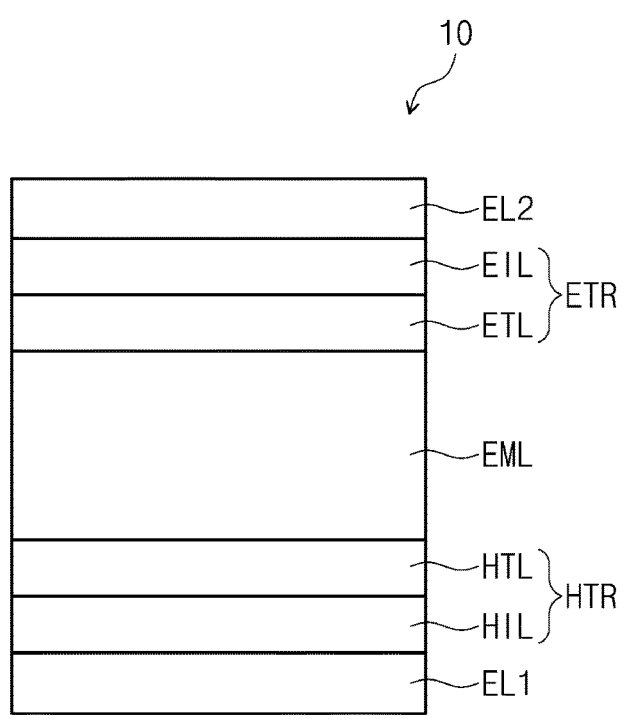
FIG. 2 is a cross-sectional view schematically illustrating an organic electroluminescence device according to an embodiment of the present disclosure.
Figure 3:
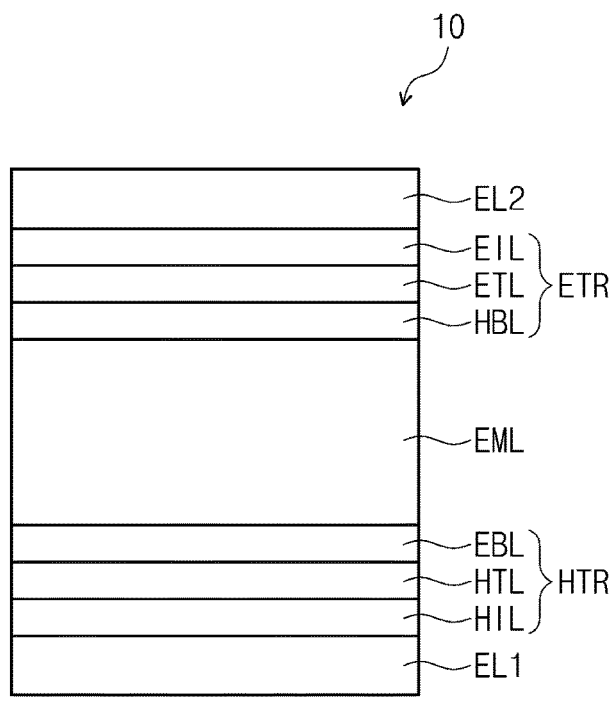
FIG. 3 is a cross-sectional view schematically illustrating an organic electroluminescence device according to an embodiment of the present disclosure.
Figure 4:
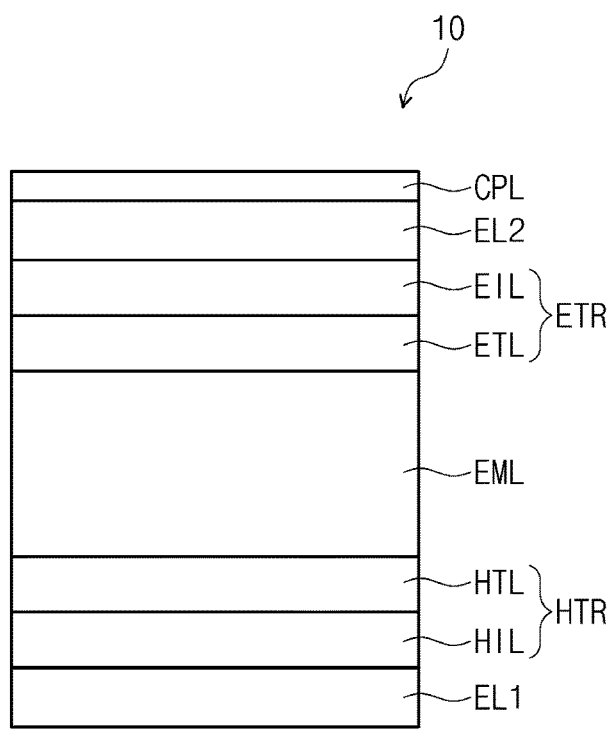
FIG. 4 is a cross-sectional view schematically illustrating an organic electroluminescence device according to an embodiment of the present disclosure.

FIGS. 1 to 4 are cross-sectional views schematically illustrating an organic electroluminescence device according to an embodiment of the present disclosure. Referring to FIGS. 1 to 4, in an organic electroluminescence device 10 according to an embodiment, a first electrode EL1 and a second electrode EL2 are positioned to face each other and an emission layer EML may be provided between the first electrode EL1 and the second electrode EL2.

The organic electroluminescence device 10 of an embodiment further includes a plurality of functional layers between the first electrode EL1 and the second electrode EL2, in addition to the emission layer EML. The plurality of functional layers may include a hole transport region HTR and an electron transport region ETR. For example, the organic electroluminescence device 10 according to an embodiment may include the first electrode EL1, the hole transport region HTR, the emission layer EML, the electron transport region ETR, and the second electrode EL2 that are sequentially stacked. In some embodiments, the organic electroluminescence device 10 of an embodiment may include a capping layer CPL on the second electrode EL2.

The organic electroluminescence device 10 of an embodiment may include a compound of an embodiment, which will be described in more detail hereinbelow, in the hole transport region HTR between the first electrode EL1 and the second electrode EL2. However, the embodiment is not limited thereto, and the organic electroluminescence device 10 of an embodiment may include the compound according to an embodiment not only in the hole transport region HTR, but also in the emission layer EML or electron transport region ETR (which is included in the plurality of functional layers between the first electrode EL1 and the second electrode EL2), or in the capping layer CPL on the second electrode EL2

The first electrode EL1 has conductivity. The first electrode EL1 may be formed of a metal alloy or any suitable conductive compound. The first electrode EL1 may be an anode. In some embodiments, the first electrode EL1 may be a pixel electrode. The first electrode EL1 may be a transmissive electrode, a transflective electrode, or a reflective electrode. When the first electrode EL1 is the transmissive electrode, the first electrode EL1 may include a transparent metal oxide such as indium tin oxide (ITO), indium zinc oxide (IZO), zinc oxide (ZnO), and/or indium tin zinc oxide (ITZO). When the first electrode EL1 is the transflective electrode or the reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). In some embodiments, the first electrode EL1 may have a multilayer structure including a reflective film or a transflective film, and a transparent conductive film formed of indium tin oxide (ITO), indium zinc oxide (IZO), zinc oxide (ZnO), indium tin zinc oxide (ITZO), etc. For example, the first electrode EL1 may have a three-layer structure of ITO/Ag/ITO, but is not limited thereto. The thickness of the first electrode EL1 may be from about 1,000 Å to about 10,000 Å, for example, from about 1,000 Å to about 3,000 Å.

The hole transport region HTR is provided on the first electrode EL1. The hole transport region HTR may include at least one of a hole injection layer HIL, a hole transport layer HTL, a hole buffer layer, or an electron blocking layer EBL. The thickness of the hole transport region HTR may be, for example, from about 50 Å to about 15,000 Å.

The hole transport region HTR may have a single layer formed of a single material, a single layer formed of a plurality of different materials, or a multilayer structure including a plurality of layers formed of a plurality of different materials.

For example, the hole transport region HTR may have a single layer structure of a hole injection layer HIL or a hole transport layer HTL, and may have a single layer structure formed of a hole injection material and a hole transport material. In some embodiments, the hole transport region HTR may have a single layer structure formed of a plurality of different materials, or a structure in which a hole injection layer HIL/hole transport layer HTL, a hole injection layer HIL/hole transport layer HTL/hole buffer layer, a hole injection layer HIL/hole buffer layer, a hole transport layer HTL/hole buffer layer, or a hole injection layer HIL/hole transport layer HTL/electron blocking layer EBL are stacked in order from the first electrode EL1, but the embodiment is not limited thereto.

The hole transport region HTR may be formed using one or more suitable methods such as a vacuum deposition method, a spin coating method, a cast method, a Langmuir-Blodgett (LB) method, an inkjet printing method, a laser printing method, and/or a laser induced thermal imaging (LITI) method.

In the organic electroluminescence device 10 of an embodiment, the hole transport region HTR includes an amine compound of an embodiment. The amine compound of an embodiment includes a central nitrogen atom, a carbazole group substituted to (on) the central nitrogen atom, and a dibenzoselenophene group substituted to (on) the central nitrogen atom.

The amine compound of an embodiment may further include a substituted or unsubstituted aryl group or a substituted or unsubstituted heteroaryl group substituted to (on) the central nitrogen atom. For example, the amine compound may further include a substituted or unsubstituted aryl group having 6 to 60 ring-forming carbon atoms or a substituted or unsubstituted heteroaryl group having 3 to 60 ring-forming carbon atoms, substituted to (on) the central nitrogen atom.

In some embodiments, the amine compound of an embodiment may be a tertiary amine compound. The amine compound may include three aromatic rings (e.g., aromatic cyclic groups) substituted to the central nitrogen atom. For example, the amine compound may include a central nitrogen atom, a carbazole group substituted to the central nitrogen atom, a dibenzoselenophene group substituted to the central nitrogen atom, and a substituted or unsubstituted aryl group or a substituted or unsubstituted heteroaryl group substituted to the central nitrogen atom.

The carbazole group may be substituted or unsubstituted. In an embodiment, a substituted or unsubstituted aryl group or a substituted or unsubstituted heteroaryl group may be substituted to a nitrogen atom of the carbazole group. A substituted or unsubstituted aryl group or a substituted or unsubstituted heteroaryl group may be substituted directly to the nitrogen atom (e.g., may be directed connected to the nitrogen atom) or may be linked to the nitrogen atom by a linker.

In an embodiment, the linker may be a substituted or unsubstituted arylene group having 6 to 60 ring-forming carbon atoms, or a substituted or unsubstituted heteroarylene group having 3 to 60 ring-forming carbon atoms. However, the embodiment is not limited thereto.

The dibenzoselenophene group may be substituted or unsubstituted. In an embodiment, the dibenzoselenophene group may be unsubstituted. However, the embodiment is not limited thereto.

In an embodiment, the amine compound may include a linker between the central nitrogen atom and the carbazole group. The amine compound may include a linker between the central nitrogen atom and the dibenzoselenophene group. The amine compound may include a linker between the central nitrogen atom and a substituted or unsubstituted aryl group or a substituted or unsubstituted heteroaryl group attached to the central nitrogen atom.

For example, the linker may be a substituted or unsubstituted arylene group having 6 to 60 ring-forming carbon atoms or a substituted or unsubstituted heteroarylene group having 3 to 60 ring-forming carbon atoms. However, the embodiment is not limited thereto. The amine compound may be formed with a direct linkage between the central nitrogen atom and the carbazole group, between the central nitrogen atom and dibenzoselenophene, and between the central nitrogen atom and a substituted or unsubstituted aryl group or a substituted or unsubstituted heteroaryl group.

In the description of an embodiment, the term "substituted or unsubstituted" may indicate a group that is unsubstituted or is substituted with at least one substituent selected from the group consisting of a deuterium atom, a halogen atom, a cyano group, a nitro group, an amino group, a silyl group, oxy group, thio group, sulfinyl group, sulfonyl group, carbonyl group, a boron group, a phosphine oxide group, a phosphine sulfide group, an alkyl group, an alkenyl group, an alkoxy group, a hydrocarbon ring group, an aryl group, and a heterocyclic group. In addition, each of the substituents exemplified above may be substituted or unsubstituted. For example, a biphenyl group may be interpreted as an aryl group or a phenyl group substituted to a phenyl group.

In the description, the term "bonded to an adjacent group to form a ring" may indicate a group that is bonded to an adjacent group to form a substituted or unsubstituted hydrocarbon ring, or a substituted or unsubstituted heterocycle. The hydrocarbon ring includes an aliphatic hydrocarbon ring and an aromatic hydrocarbon ring. The heterocycle includes an aliphatic heterocycle and an aromatic heterocycle. The hydrocarbon ring and heterocycle may each independently be monocyclic or polycyclic. In some embodiments, the rings formed by being bonded to each other may be connected to another ring to form a spiro structure.

In the description, the term "an adjacent group" may refer to a pair of substituent groups where the first substituent is connected to an atom which is directly connected to another atom substituted with the second substituent; a pair of substituent groups connected to the same atom; or a pair of substituent groups where the first substituent is sterically positioned at the nearest position to the second substituent. For example, two methyl groups in 1,2-dimethylbenzene may be interpreted as mutually "adjacent groups" and two ethyl groups in 1,1-diethylcyclopentane may be interpreted as mutually "adjacent groups".

In the description, examples of a halogen atom may include a fluorine atom, a chlorine atom, a bromine atom and an iodine atom.

In the description, an alkyl group may be a linear, branched or cyclic saturated hydrocarbon group. The number of carbon atoms in the alkyl group is 1 to 50, 1 to 30, 1 to 20, 1 to 10, or 1 to 6. Examples of the alkyl group may include methyl group, ethyl group, n-propyl group, isopropyl group, n-butyl group, s-butyl group, t-butyl group, i-butyl group, 2-ethylbutyl group, 3,3-dimethylbutyl group, n-pentyl group, i-pentyl group, neopentyl group, t-pentyl group, cyclopentyl group, 1-methylpentyl group, 3-methylpentyl group, 2-ethylpentyl group, 4-methyl-2-pentyl group, n-hexyl group, 1-methylhexyl group, 2-ethylhexyl group, 2-butylhexyl group, cyclohexyl group, 4-methylcyclohexyl group, 4-t-butylcyclohexyl group, n-heptyl group, 1-methylheptyl group, 2,2-dimethylheptyl group, 2-ethylheptyl group, 2-butylheptyl group, n-octyl group, t-octyl group, 2-ethyloctyl group, 2-butyloctyl group, 2-hexyloctyl group, 3,7-dimethyloctyl group, cyclooctyl group, n-nonyl group, n-decyl group, adamantyl group, 2-ethyldecyl group, 2-butyldecyl group, 2-hexyldecyl group, 2-octyldecyl group, n-undecyl group, n-dodecyl group, 2-ethyldodecyl group, 2-butyldodecyl group, 2-hexyldocecyl group, 2-octyldodecyl group, n-tridecyl group, n-tetradecyl group, n-pentadecyl group, n-hexadecyl group, 2-ethylhexadecyl group, 2-butylhexadecyl group, 2-hexylhexadecyl group, 2-octylhexadecyl group, n-heptadecyl group, n-octadecyl group, n-nonadecyl group, n-eicosyl group, 2-ethyleicosyl group, 2-butyleicosyl group, 2-hexyleicosyl group, 2-octyleicosyl group, n-henicosyl group, n-docosyl group, n-tricosyl group, n-tetracosyl group, n-pentacosyl group, n-hexacosyl group, n-heptacosyl group, n-octacosyl group, n-nonacosyl group, n-triacontyl group, etc., but are not limited thereto.

In the description, a hydrocarbon ring group may be an any functional group or substituent derived from an aliphatic hydrocarbon ring. The hydrocarbon ring group may be a saturated hydrocarbon ring group having 5 to 20 ring-forming carbon atoms.

In the description, an aryl group may be any functional group or substituent derived from an aromatic hydrocarbon ring. The aryl group may be a monocyclic aryl group or a polycyclic aryl group. The number of ring-forming carbon atoms in the aryl group may be 6 to 30, 6 to 20, or 6 to 15. Examples of the aryl group may include a phenyl group, a naphthyl group, a fluorenyl group, an anthracenyl group, a phenanthryl group, a biphenyl group, a terphenyl group, a quaterphenyl group, a quinquephenyl group, a sexaphenyl group, a triphenylenyl group, a pyrenyl group, a benzofluoranthenyl group, a chrysenyl group, etc., but are not limited thereto.

In the description, a fluorenyl group may be substituted, and two substituents may be bonded to each other to form a spiro structure. Example of the substituted fluorenyl group are as follows. However, the embodiment is not limited thereto:

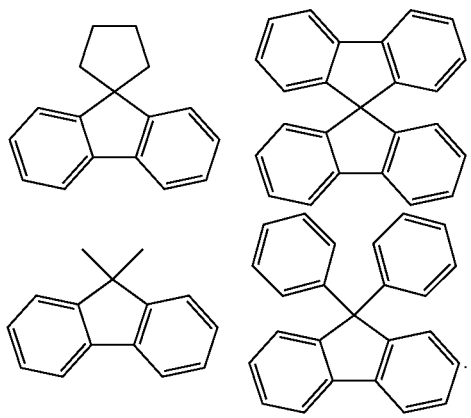

In the description, a heterocyclic group may be any functional group or substituent derived from a ring containing at least one of B, O, N, P, Si, S or Se as a ring-forming hetero atom. The heterocyclic group includes an aliphatic heterocyclic group and an aromatic heterocyclic group. The aromatic heterocyclic group may be a heteroaryl group. The aliphatic heterocycle (e.g., aliphatic heterocyclic group) and aromatic heterocycle (e.g., aromatic heterocyclic group) may each independently be monocyclic or polycyclic.

When the heterocyclic group contains two or more hetero atoms, the two or more hetero atoms may be the same as or different from each other. The heterocyclic group may be a monocyclic heterocyclic group or a polycyclic heterocyclic group, and may include a heteroaryl group. The number of ring-forming carbon atoms in the heterocyclic group may be 2 to 30, 2 to 20, or 2 to 10.

The number of ring-forming carbon atoms in the aliphatic heterocyclic group may be 2 to 30, 2 to 20, or 2 to 10. Examples of the aliphatic heterocyclic group include an oxirane group, a pyran group, a pyrrolidine group, a piperidine group, a tetrahydrofuran group, a tetrahydrothiophene group, a thiane group, a tetrahydropyran group, a 1,4-dioxane group, etc., but are not limited to thereto.

When the heteroaryl group contains two or more hetero atoms, the two or more hetero atoms may be the same as or different from each other. The heteroaryl group may be a monocyclic heteroaryl group or a polycyclic heteroaryl group. The number of ring-forming carbon atoms in the heteroaryl group may be 2 to 30, 2 to 20, or 2 to 10. Examples of the heteroaryl group may include thiophene, furan, pyrrole, imidazole, thiazole, oxazole, oxadiazole, triazole, pyridine, bipyridine, pyrimidine, triazine, triazole, acridine, pyridazine, pyrazine, quinoline, quinazoline, quinoxaline, phenoxazole, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophene, thienothiophene, benzofuran, phenanthroline, thiazole, isooxazole, oxadiazole, thiadiazole, phenothiazole, phenothiazine, dibenzosilole, dibenzofuranyl, etc., but are not limited thereto.

In the description, the above description on the aryl group may be applied to an arylene group, except that the arylene group is a divalent group. The above description on the heteroaryl group may be applied to a heteroarylene group, except that the heteroarylene group is a divalent group.

In the description, the number of carbon atoms in an amino group is not particularly limited, but may be 1 to 30. The amino group may include an alkyl amino group, an aryl amino group, or a heteroaryl amino group. Examples of the amino group include a methylamino group, a dimethylamino group, a phenylamino group, a diphenylamino group, a naphthylamino group, a 9-methyl-anthracenylamino group, a triphenylamino group, etc., but are not limited thereto.

In the description, an alkenyl group may be a linear or branched hydrocarbon group with at least one carbon-carbon double bond with the chain. Although the number of carbon atoms is not specifically limited, it may be 2 to 30, 2 to 20, or 2 to 10. Examples of the alkenyl group include a vinyl group, a 1-butenyl group, a 1-pentenyl group, a 1,3-butadienyl aryl group, a styrenyl group, a styryl vinyl group, etc., but are not limited thereto.

In the description, the number of carbon atoms in an amine group is not particularly limited, but may be 1 to 30. The amine group may include an alkyl amine group and an aryl amine group. Examples of the amine group include a methylamine group, a dimethylamine group, a phenylamine group, a diphenylamine group, a naphthylamine group, a 9-methyl-anthracenylamine group, a triphenylamine group, etc., but are not limited thereto.

In the description, the alkyl group in the alkyl amine group is the same as the examples of the alkyl group described above.

In the description, the aryl group in the aryl amine group is the same as the examples of the aryl group described above.

In the description, a direct linkage may refer to a single linkage (e.g., a single bond).

Meanwhile, in the description, "-*" refers to a position to be connected (e.g., a binding site).

An amine compound of an embodiment may be represented by Formula 1 below.

60 ring-forming carbon atoms, or a substituted or unsubstituted heteroaryl group having 3 to 60 ring-forming carbon atoms. For example, $Ar_1$ may be a substituted or unsubstituted aryl group. In some embodiments, $Ar_1$ may be a phenyl group. For example, $Ar_2$ may be a substituted or unsubstituted phenyl group, a substituted or unsubstituted naphthyl group, a substituted or unsubstituted phenanthrene group, a substituted or unsubstituted dibenzofuran group, or a substituted or unsubstituted dibenzothiophenyl group. In some embodiments, $Ar_2$ may be an unsubstituted phenyl group, an unsubstituted naphthyl group, an unsubstituted phenanthrene group, an unsubstituted dibenzofuran group or an unsubstituted dibenzothiophenyl group. However, the embodiment is not limited thereto.

$L_1$ to $L_4$ may be each independently a direct linkage, a substituted or unsubstituted arylene group having 6 to 60 ring-forming carbon atoms, or a substituted or unsubstituted heteroarylene group having 3 to 60 ring-forming carbon atoms. For example, $L_1$ may be a direct linkage. For example, $L_2$ to $L_4$ may be a substituted or unsubstituted arylene group having 6 to 60 ring-forming carbon atoms. In some embodiments, $L_2$ to $L_4$ may be an unsubstituted phenylene group. However, the embodiment is not limited thereto.

$R_1$ to $R_4$ may be each independently a hydrogen atom, a deuterium atom, a halogen atom, a substituted or unsubstituted alkyl group having 1 to 20 carbon atoms, a substituted or unsubstituted aryl group having 6 to 60 ring-forming carbon atoms, or a substituted or unsubstituted heteroaryl group having 3 to 60 ring-forming carbon atoms. For example, each of $R_1$ to $R_4$ may be a hydrogen atom. However, the embodiment is not limited thereto.

$m_1$ to $m_4$ may be each independently an integer of 0 to 4. When each of $m_1$ to $m_4$ is an integer of 2 or more, each of a plurality of $R_1$ to $R_4$ may be the same as or different from each other.

$n_1$ to $n_4$ may be each independently an integer of 0 to 1. For example, $n_1$ may be 0. When $n_1$ is 0, it may be the same as when $n_1$ is 1 and $L_1$ is a direct linkage. However, the embodiment is not limited thereto.

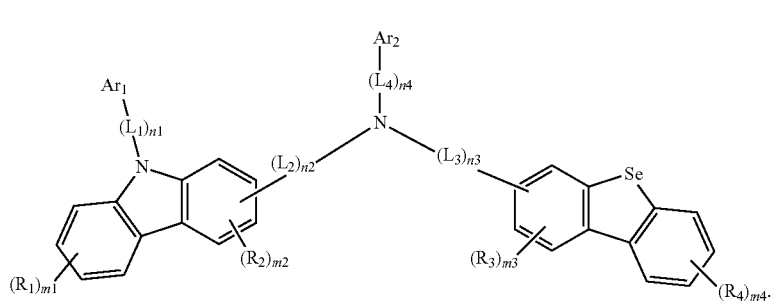

Formula 1

In Formula 1 above, $Ar_1$ and $Ar_2$ may be each independently a substituted or unsubstituted aryl group having 6 to In an embodiment, the amine compound represented by Formula 1 may be represented by Formula 1-1 below.

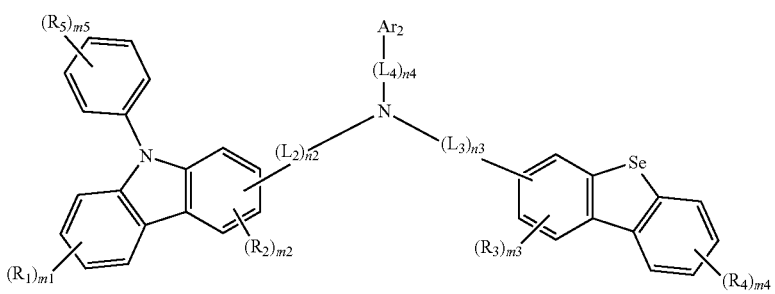

Formula 1-1

Formula 1-1 above may represent a case where $n_1$ is 0 and $Ar_1$ is a substituted or unsubstituted phenyl group in Formula 1.

In Formula 1-1 above, $R_5$ may be a hydrogen atom, a deuterium atom, a halogen atom, a substituted or unsubstituted alkyl group having 1 to 20 carbon atoms, a substituted or unsubstituted aryl group having 6 to 60 ring-forming carbon atoms, or a substituted or unsubstituted heteroaryl group having 3 to 60 ring-forming carbon atoms. For example, $R_5$ may be a hydrogen atom. However, the embodiment is not limited thereto.

$m_5$ may be an integer of 0 to 5. When $m_5$ is an integer of 2 or more, a plurality of $R_5$'s may be the same as or different from each other.

In Formula 1-1, $Ar_2$, $L_2$ to $L_4$, $R_1$ to $R_4$, $m_1$ to $m_4$, and $n_2$ to $n_4$ may be the same as those described in Formula 1 above.

In an embodiment, the amine compound represented by Formula 1 may be represented by any one of Formulae 2-1 to 2-4 below.

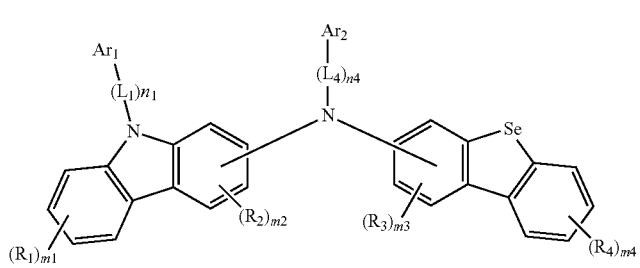

Formula 2-1

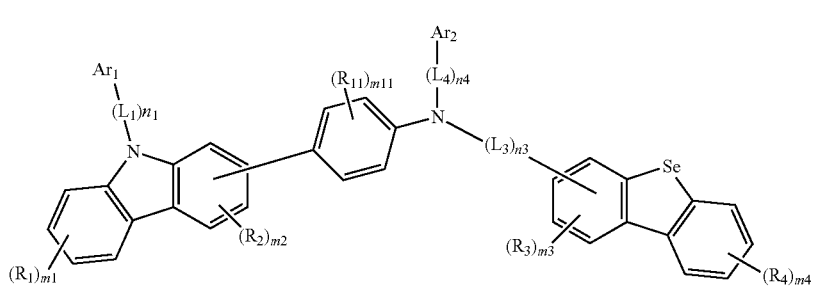

Formula 2-2

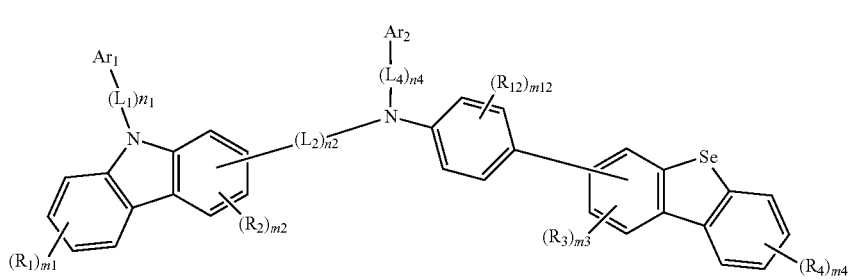

Formula 2-3

Formula 2-4

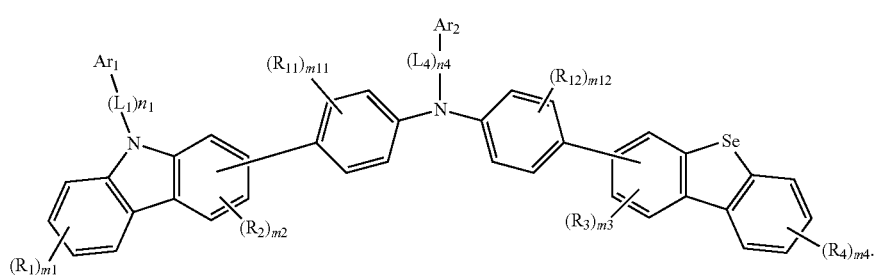

Formulae 2-1 to 2-4 above are examples of $L_2$ and/or $L_3$ of the amine compound represented by Formula 1 above being defined. Formula 2-1 above may represent a case where a carbazole group and a dibenzoselenophene group are directly bonded to a central nitrogen atom in Formula 1. Formula 2-2 above may represent a case where a substituted or unsubstituted phenylene group is linked between the central nitrogen atom and the carbazole group, and the dibenzoselenophene group is directly bonded to the central nitrogen atom. Formula 2-3 above may represent a case where a substituted or unsubstituted phenylene group is linked between the central nitrogen atom and the dibenzoselenophene group, and the carbazole group is directly bonded to the central nitrogen atom in Formula 1 above. Formula 2-4 above may represent a case where a substituted or unsubstituted phenylene group is linked between each of the central nitrogen atom, and the dibenzoselenophene group, and the carbazole group in Formula 1 above.

In Formulae 2-1 to 2-4 above, $R_{11}$ and $R_{12}$ may be each independently a hydrogen atom, a deuterium atom, a halogen atom, a substituted or unsubstituted alkyl group having 1 to 20 carbon atoms, a substituted or unsubstituted aryl group having 6 to 60 ring-forming carbon atoms, or a substituted or unsubstituted heteroaryl group having 3 to 60 ring-forming carbon atoms. For example, each of $R_{11}$ and $R_{12}$ may be a hydrogen atom. However, the embodiment is not limited thereto.

$m_{11}$ and $m_{12}$ may be each independently an integer of 0 to 4. When $m_{11}$ and $m_{12}$ are integers of 2 or more, each of the plurality of $R_{11}$ and $R_{12}$ may be the same as or different from each other.

In Formulae 2-1 to 2-4, $Ar_1$, $Ar_2$, $L_1$ to $L_4$, $R_1$ to $R_4$, $m_1$ to $m_4$, and $n_1$ to $n_4$ may be the same as those described in Formula 1 above.

In an embodiment, the amine compound represented by Formula 1 may be represented by any one of Formulae 3-1 to 3-4 below.

Formula 3-1

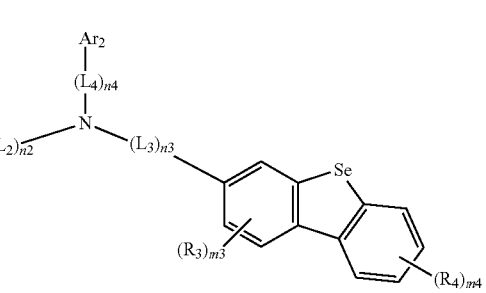

Formula 3-2

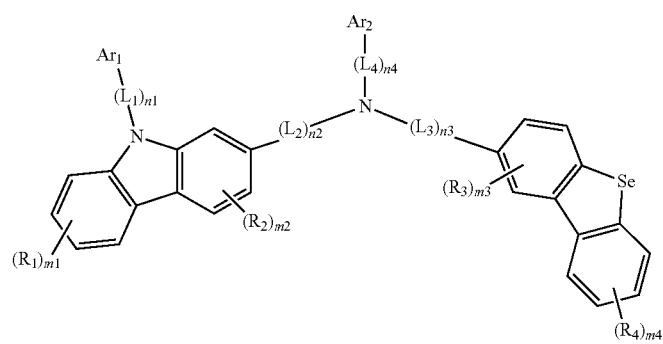

-continued

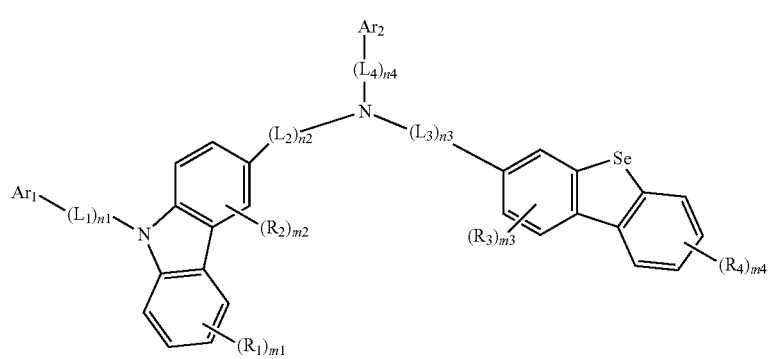

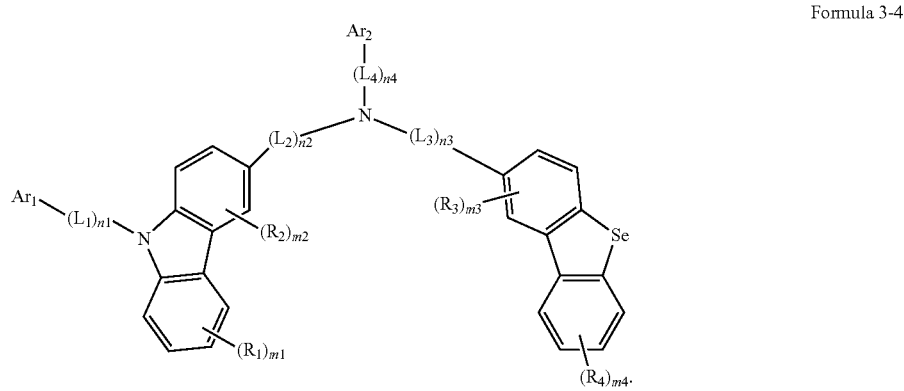

Formulae 3-1 to 3-4 above are examples showing set substitution positions of the carbazole group and the dibenzoselenophene group in Formula 1 above. Formula 3-1 above may represent a case where the carbazole group is attached to the central atom at the no. 2 carbon position, and the dibenzoselenophene group is attached to the central atom at the no. 3 carbon position in Formula 1 above. Formula 3-2 above may represent a case where each of the carbazole group and the dibenzoselenophene group is attached to the central atom at the no. 2 carbon in Formula 1 above. Formula 3-3 above may represent a case where each of the carbazole group and the dibenzoselenophene group is attached to the central atom at the no. 3 carbon in Formula 1 above. Formula 3-4 above may represent a case where the carbazole group is attached at the no. 3 carbon position, and the dibenzoselenophene group is attached at the no. 2 carbon position in Formula 1 above.

In Formulae 3-1 to 3-4 above, $Ar_1$, $Ar_2$, $L_1$ to $L_4$, $R_1$ to $R_4$, $m_1$ to $m_4$, and $n_1$ to $n_4$ are the same as those described in Formula 1 above.

In an embodiment, the amine compound represented by Formula 1 may be any one of the compounds represented by Compound Group 1 below.

Compound Group 1

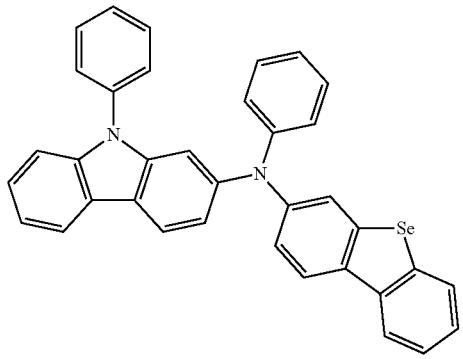

1

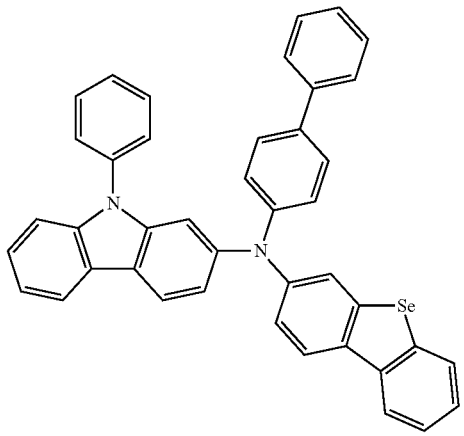

2

121
-continued
3
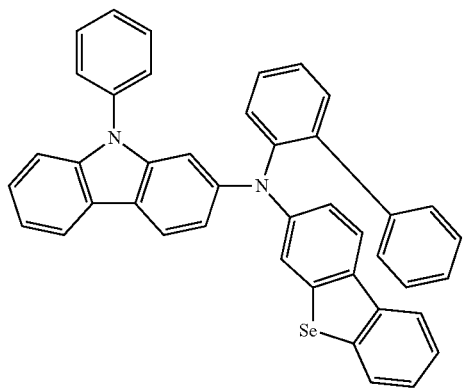
4
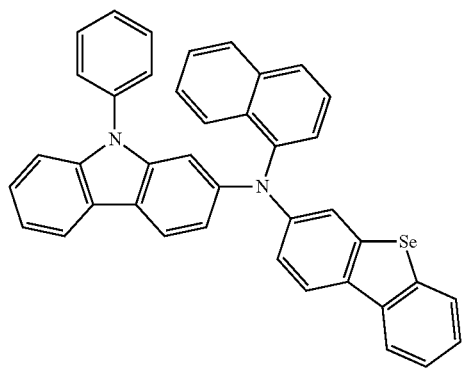
5
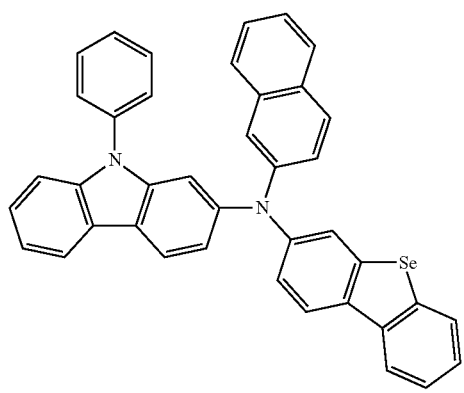
122
-continued
6
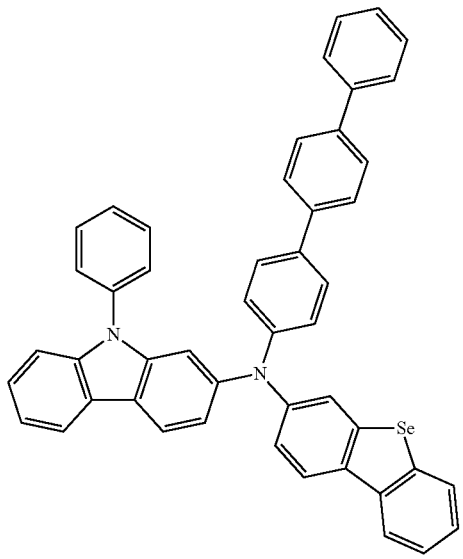
7
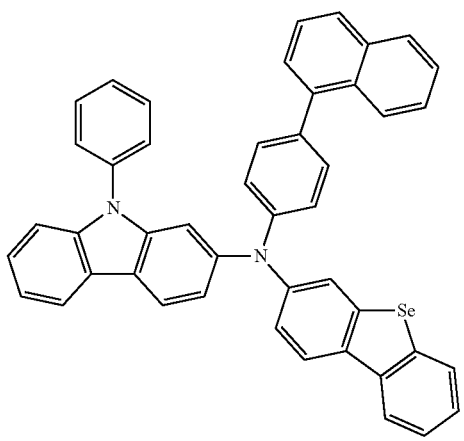
8
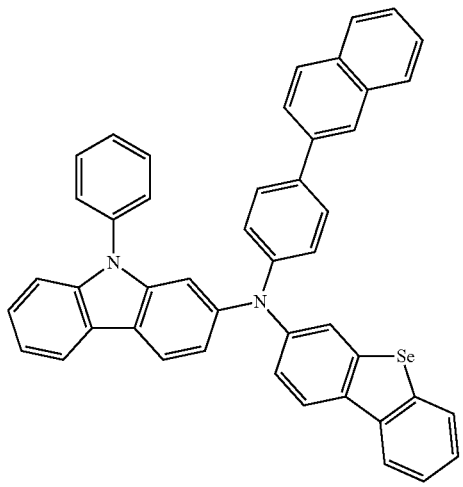

9
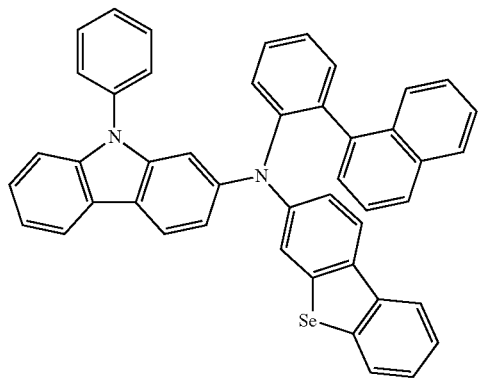
10
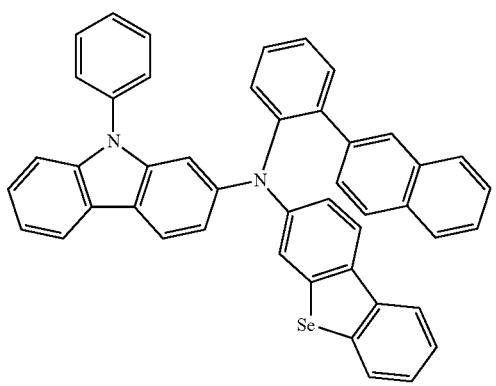
11
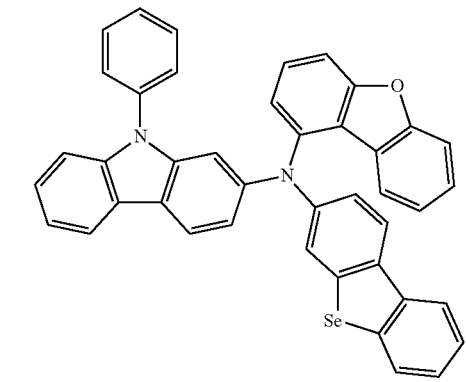
12
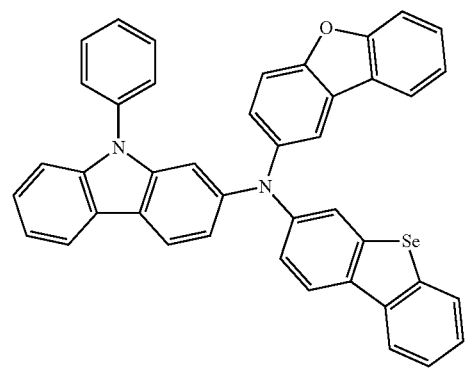
13
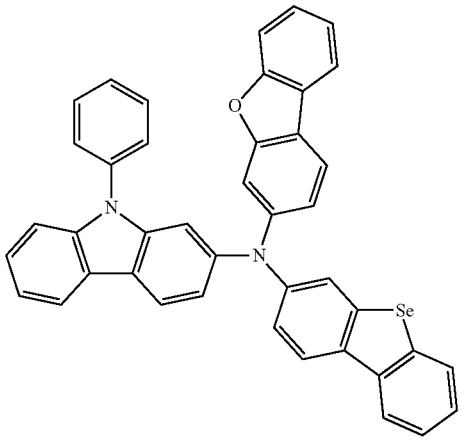
14
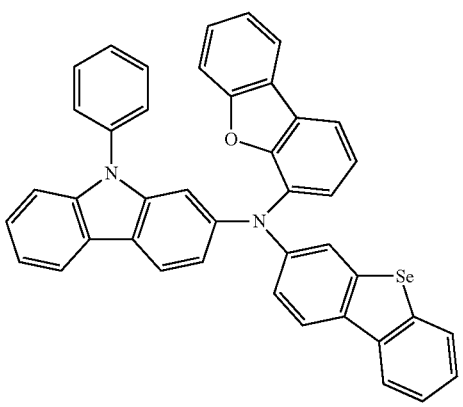
15
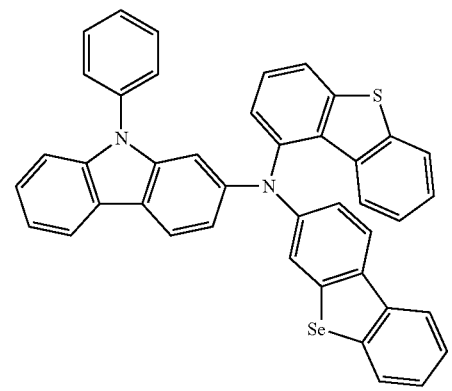
16
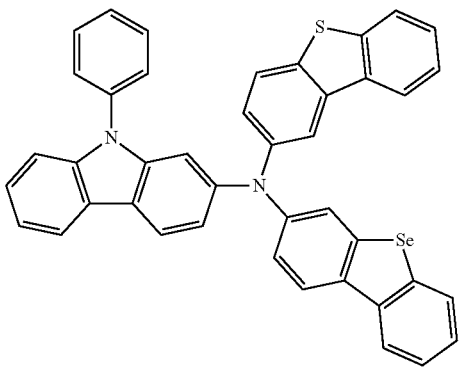

| 17 | 21 |
|---|---|
| 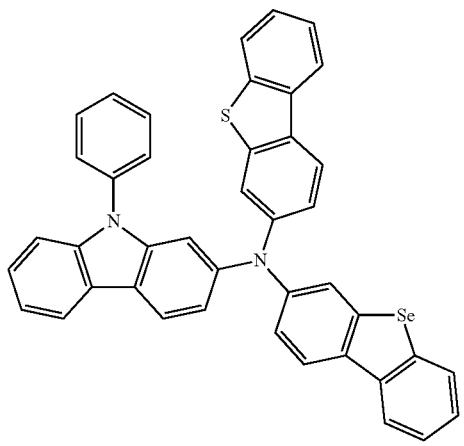 | 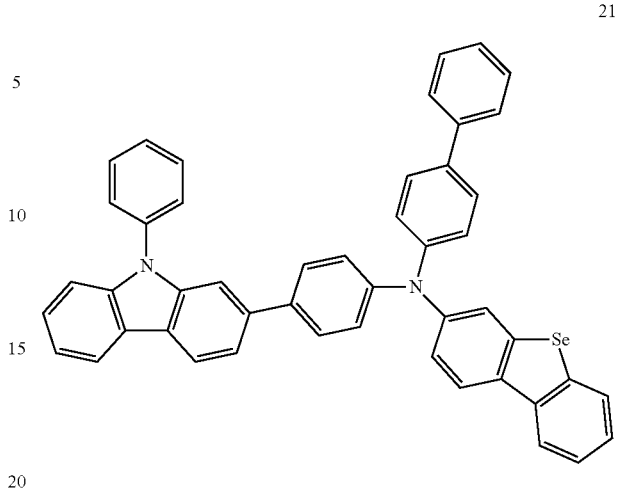 |
| 18 | 22 |
| 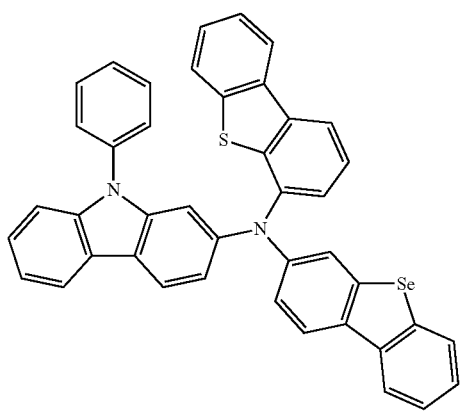 | 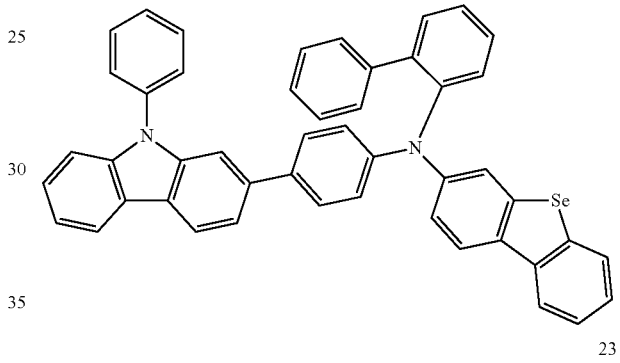 |
| 19 | 23 |
| 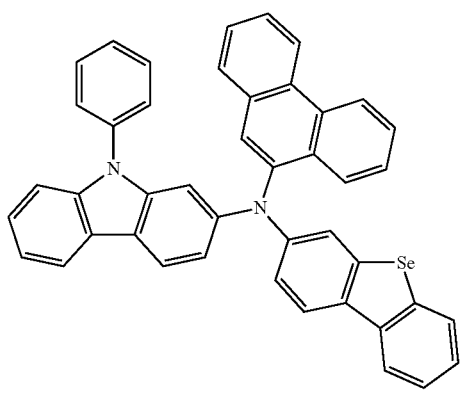 | 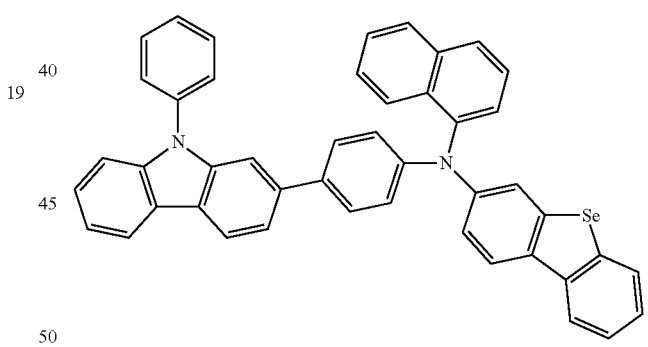 |
| 20 | 24 |
| 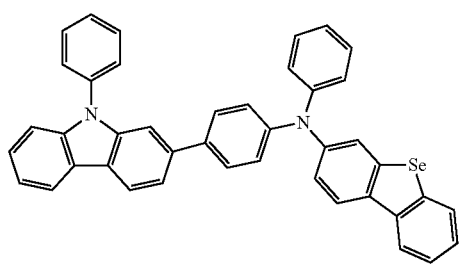 | 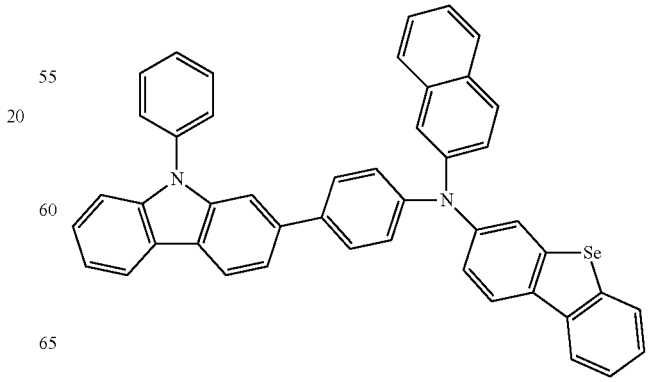 |

25
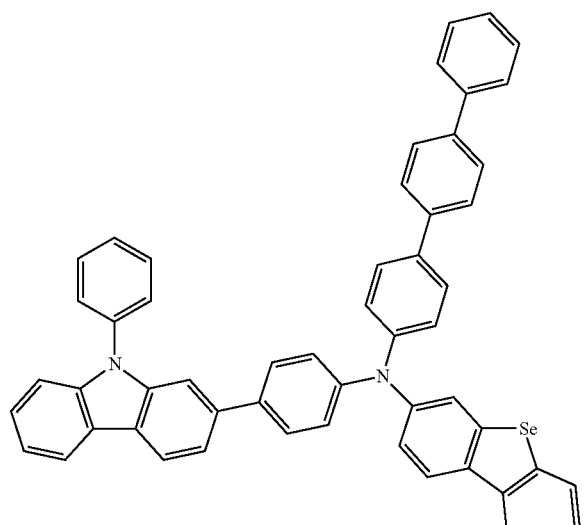
26
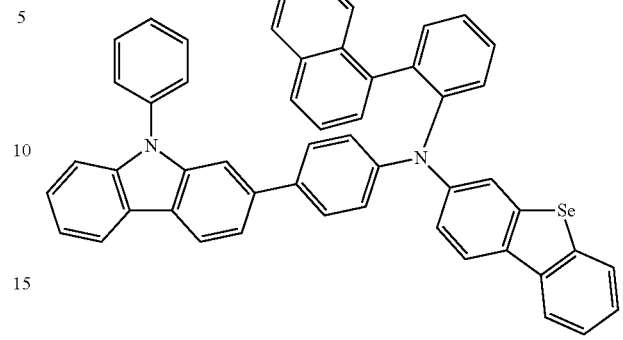
27
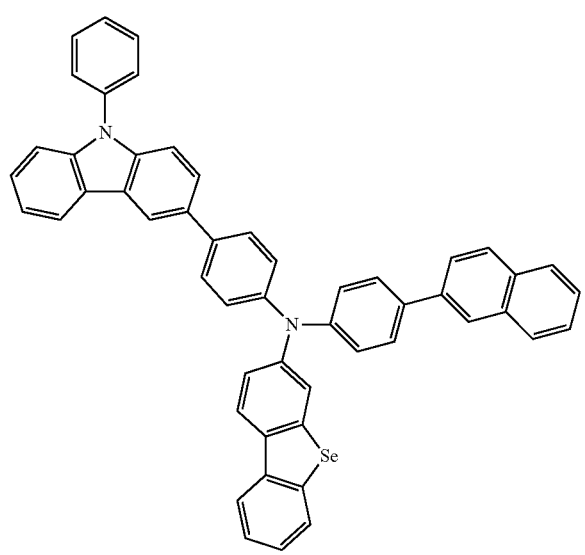
28
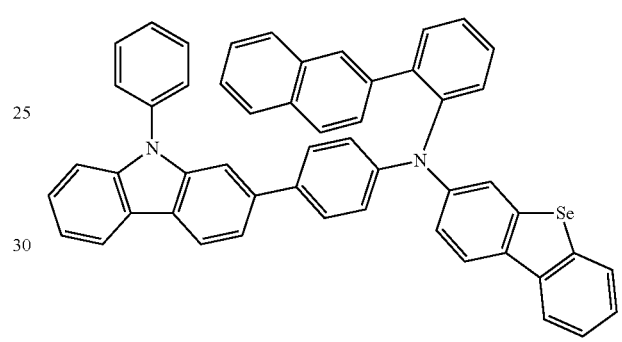
29
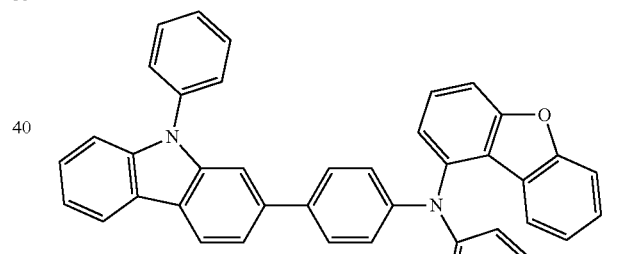
30
31
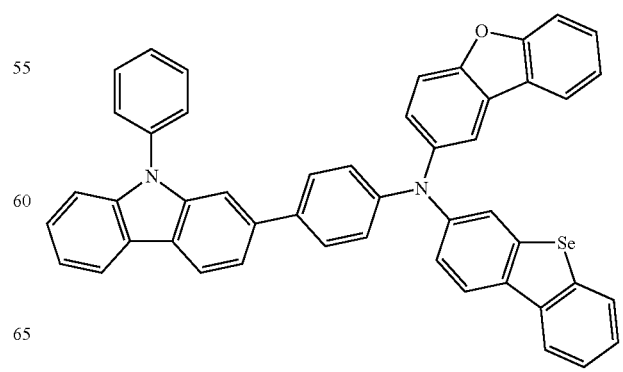

129
-continued
32
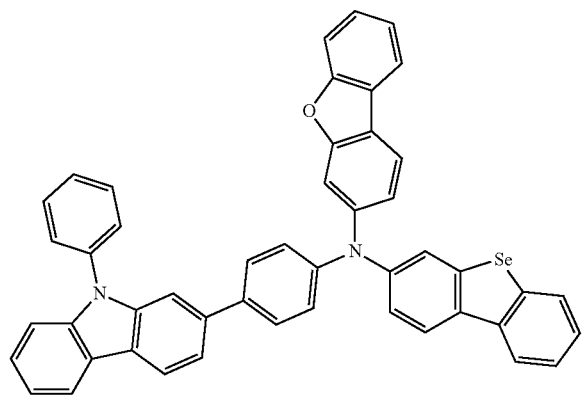
33
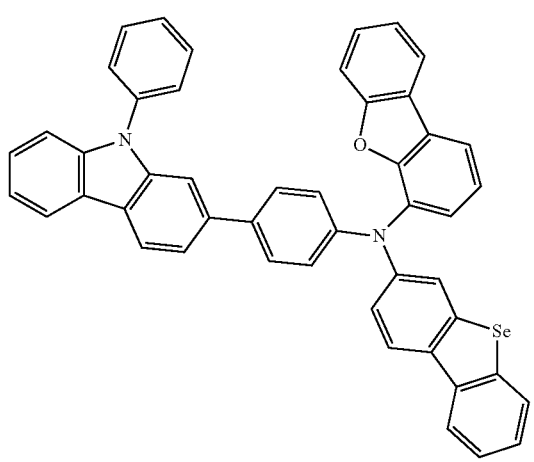
34
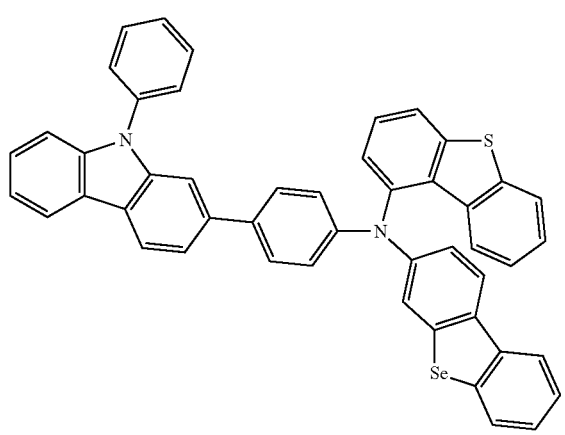
130
-continued
35
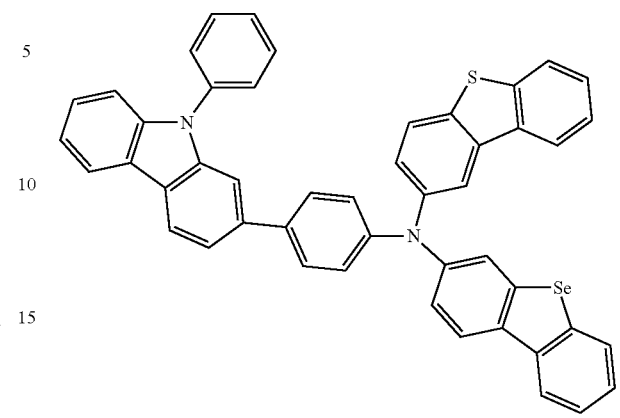
36
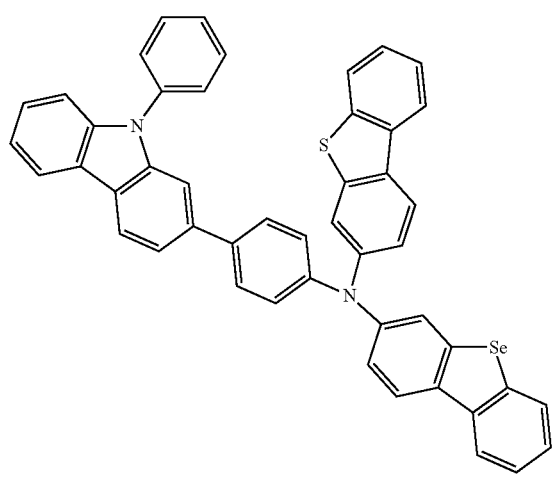
37
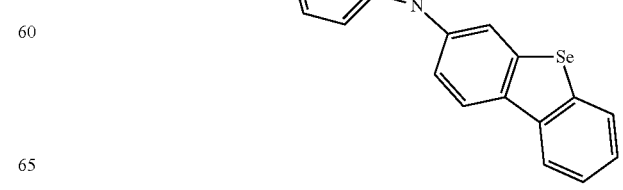

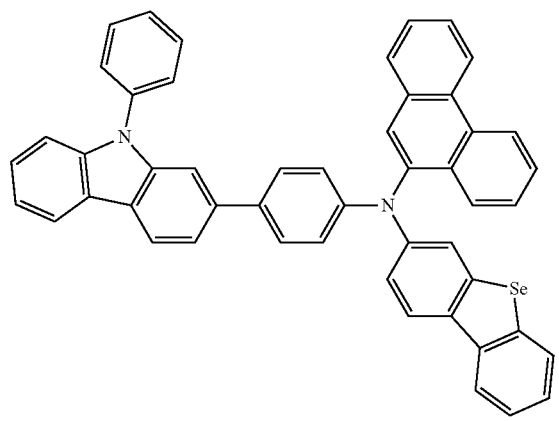
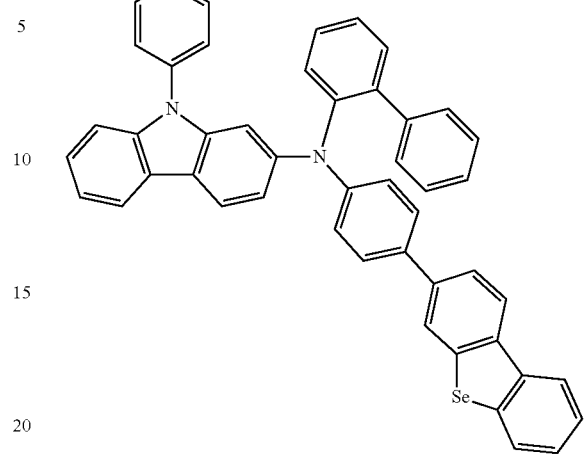
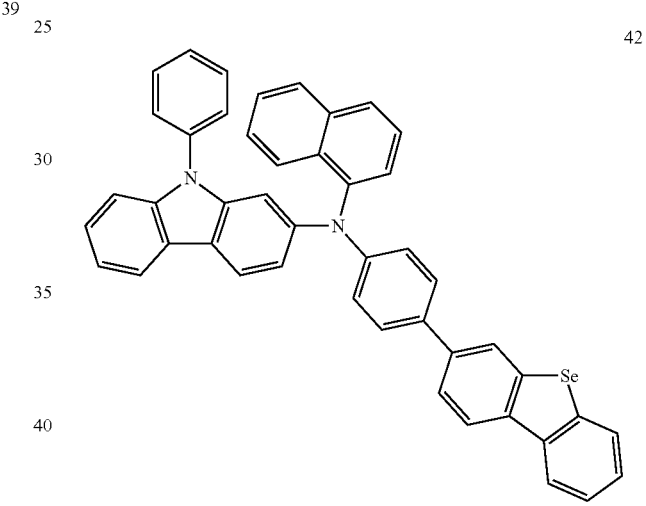
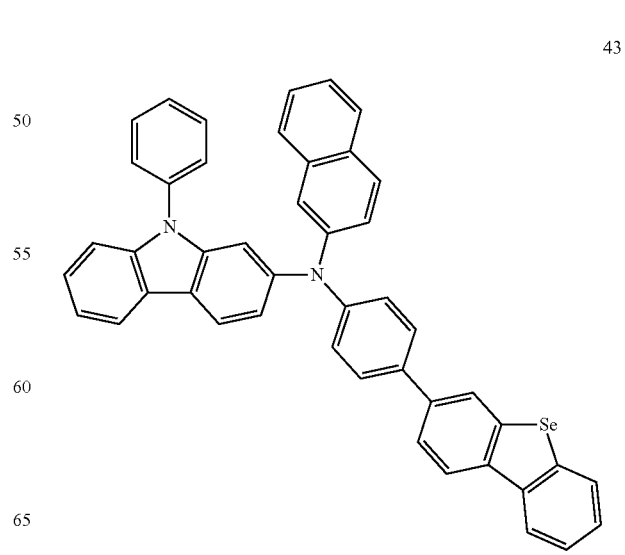

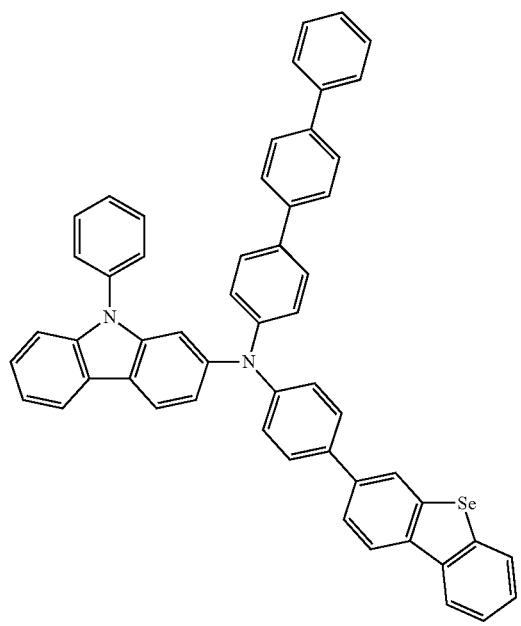
44
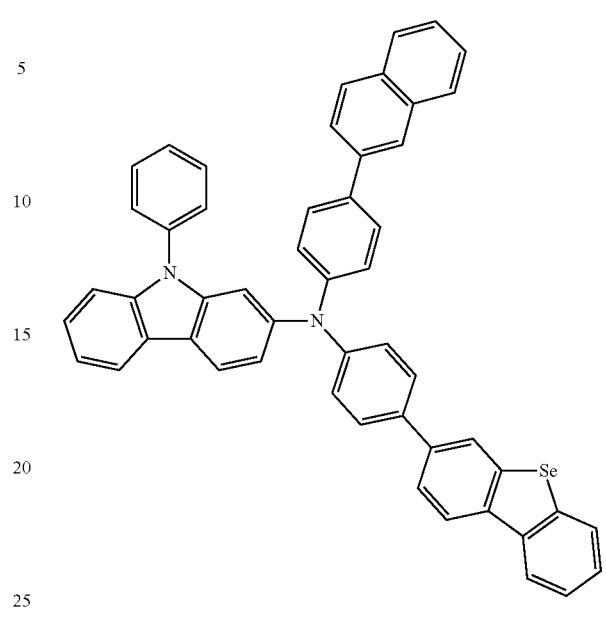
46
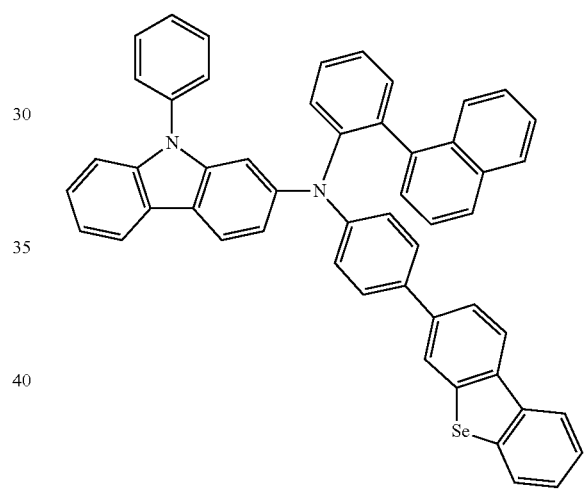
47
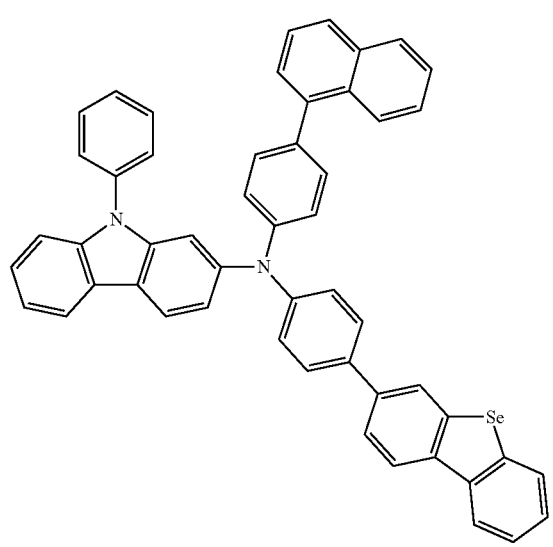
45
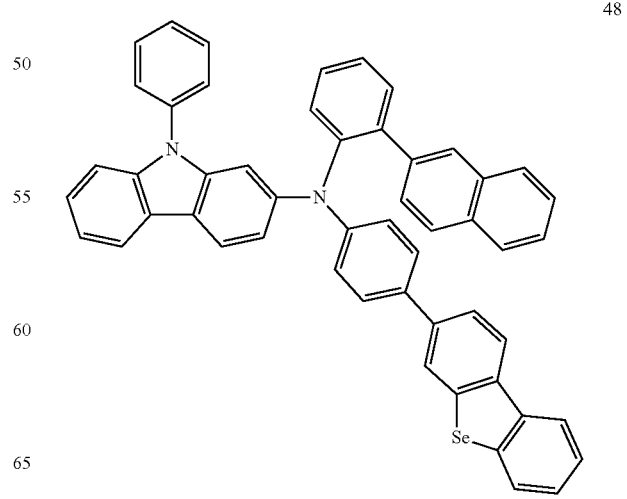
48

49
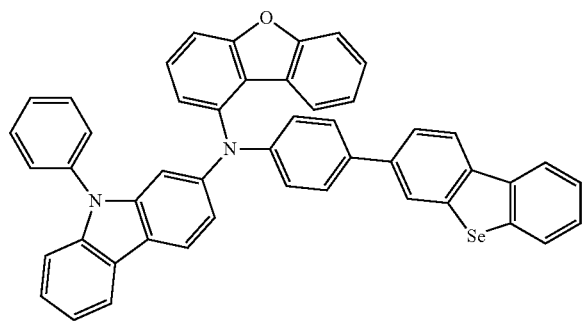
50
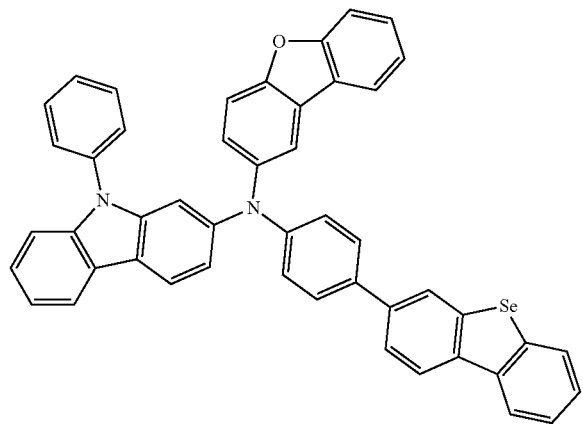
51
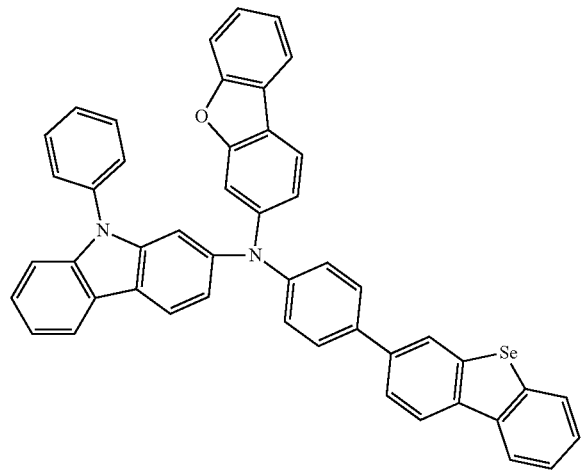
52
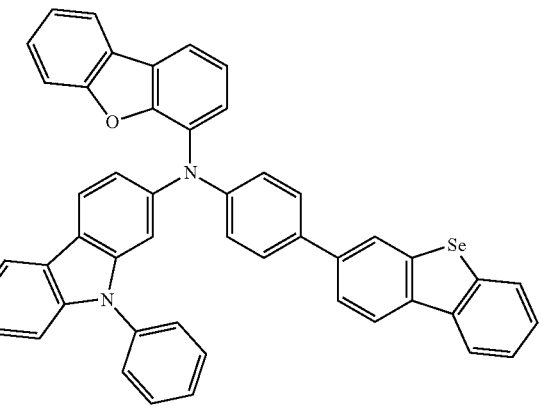
53
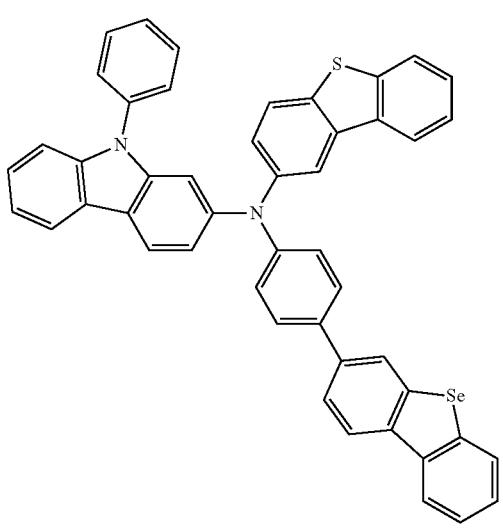
54

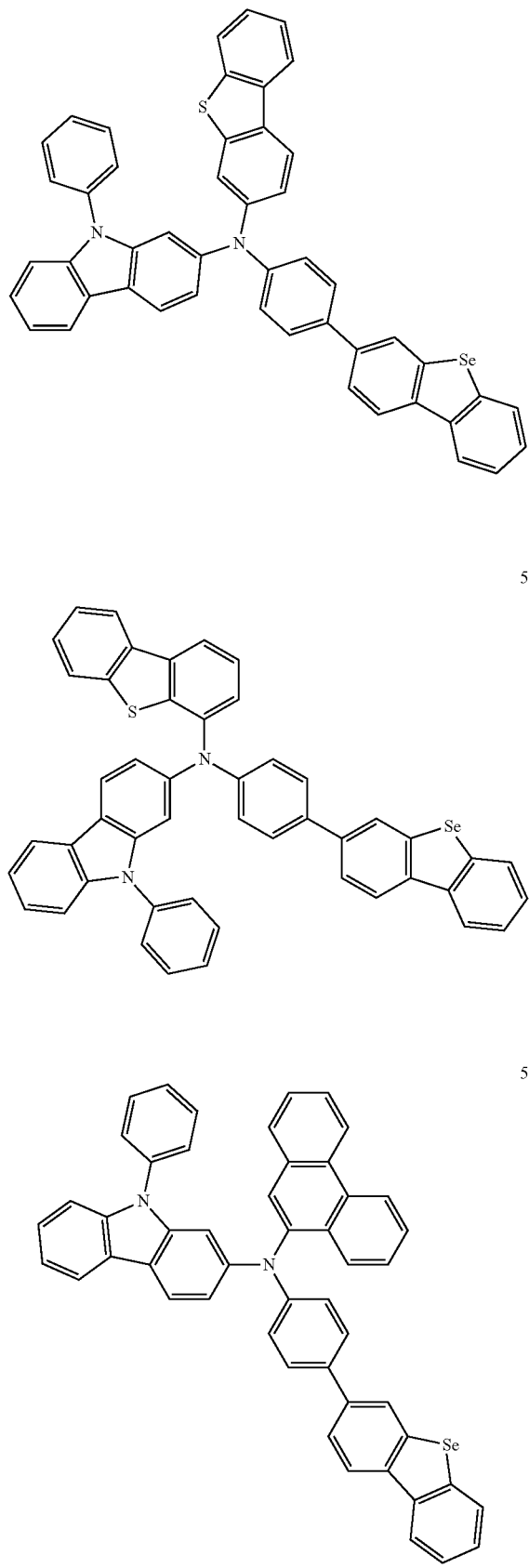
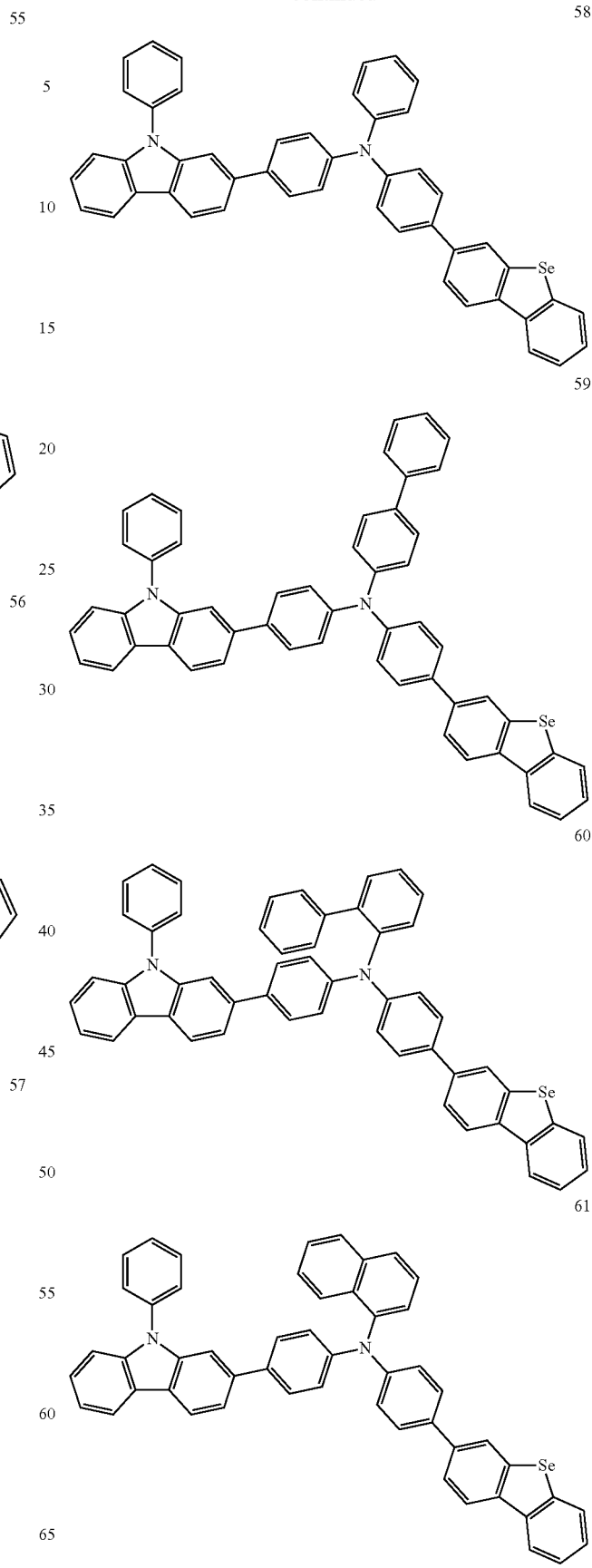

62
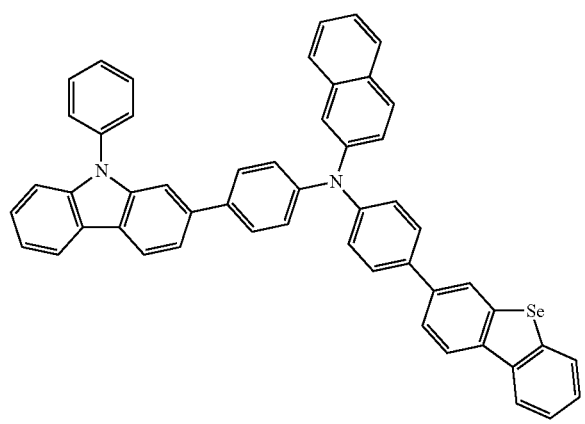
63
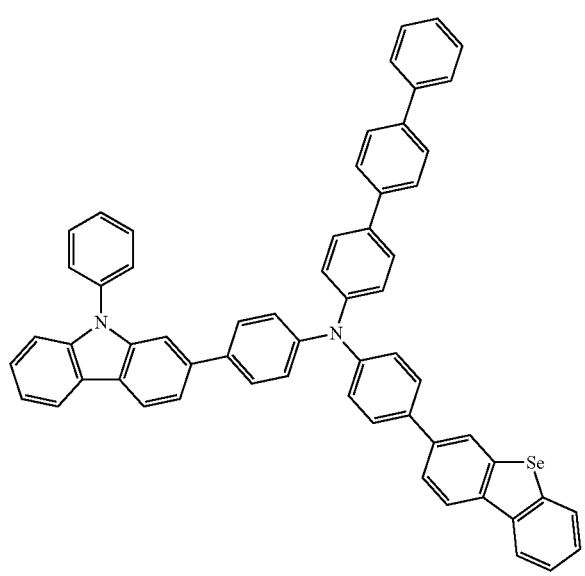
64
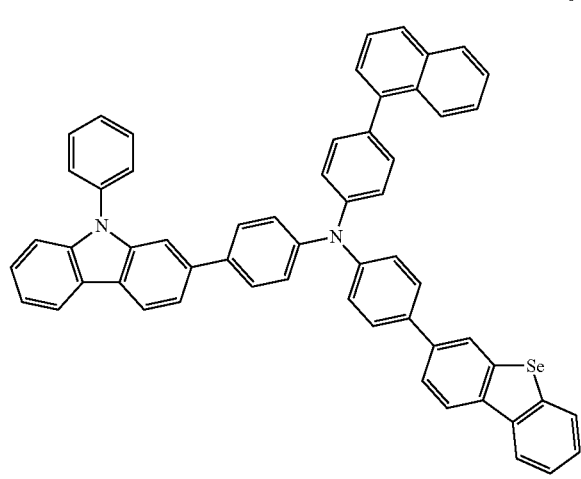
65
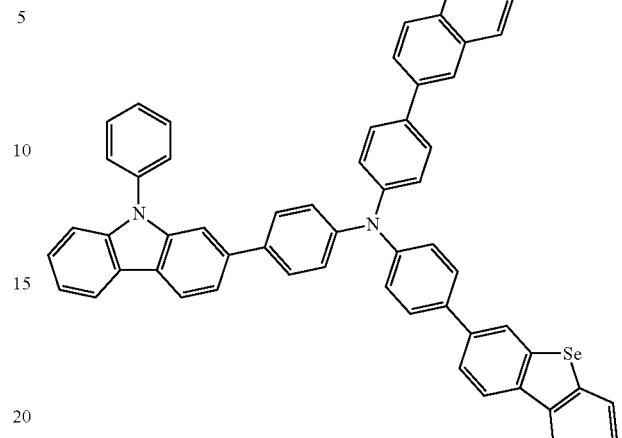
66
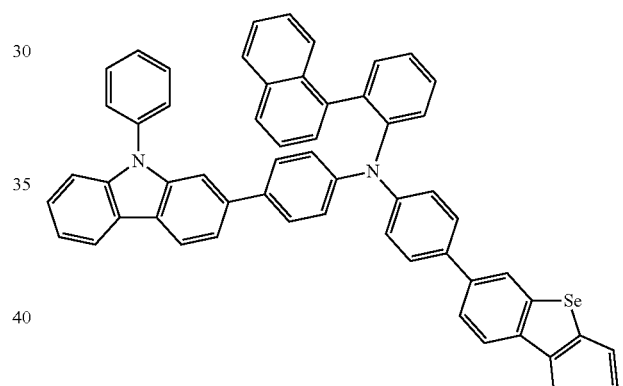
67
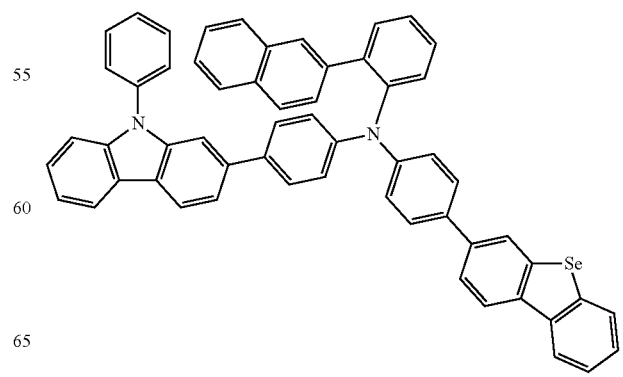

68
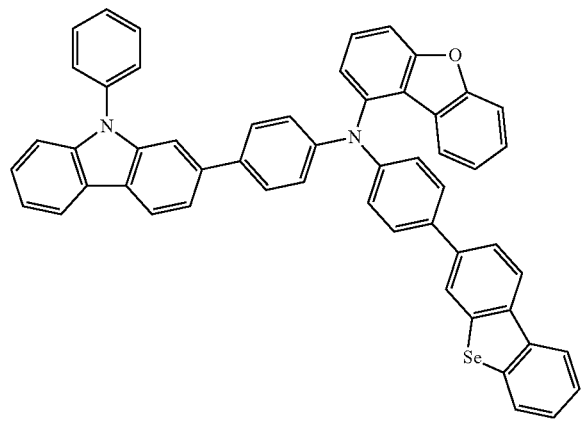
69
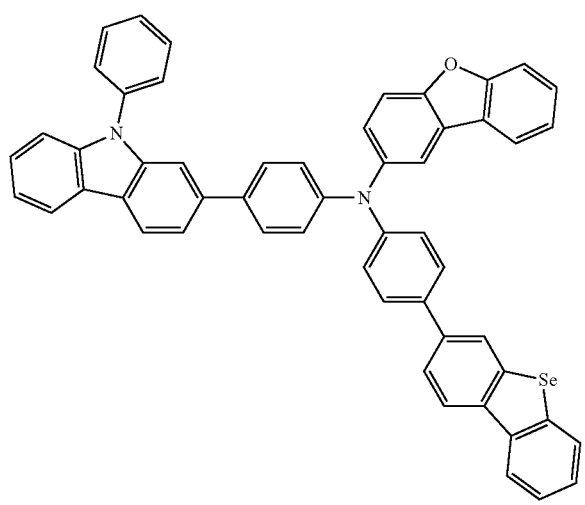
70
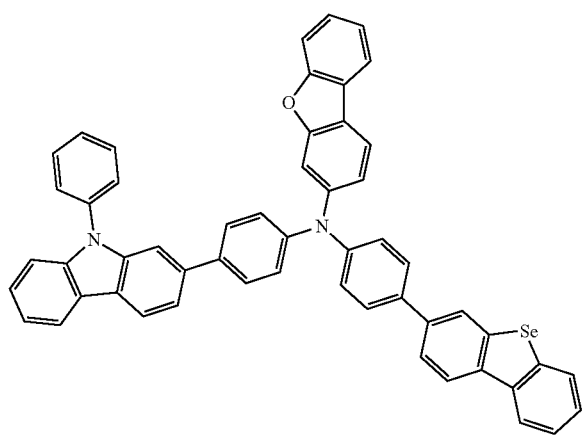
71
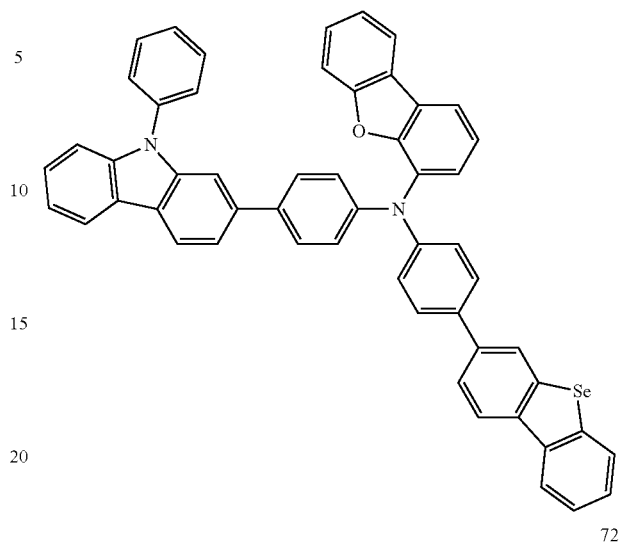
72
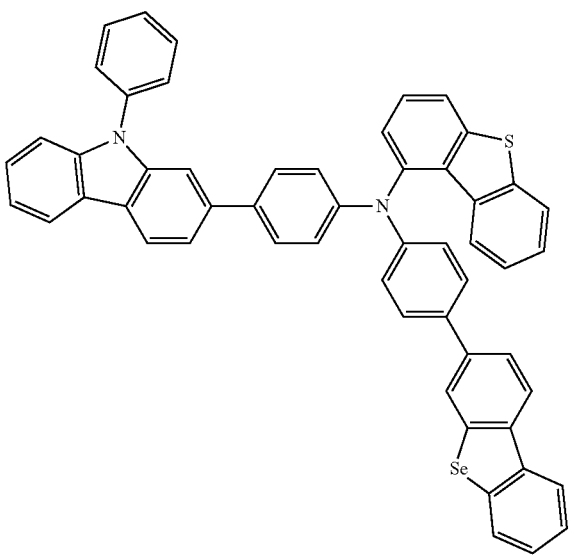
73
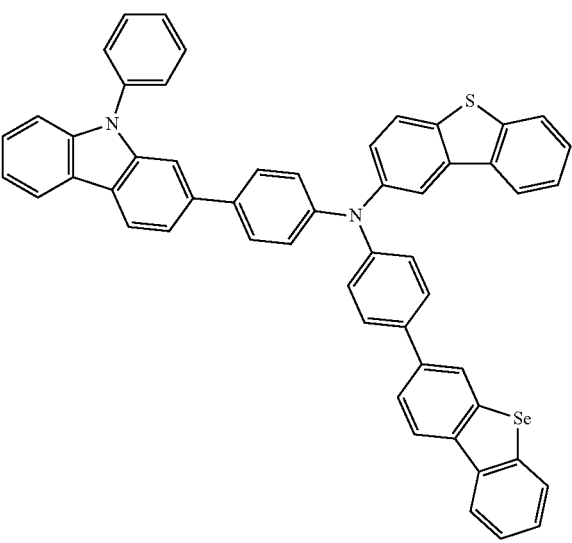

74
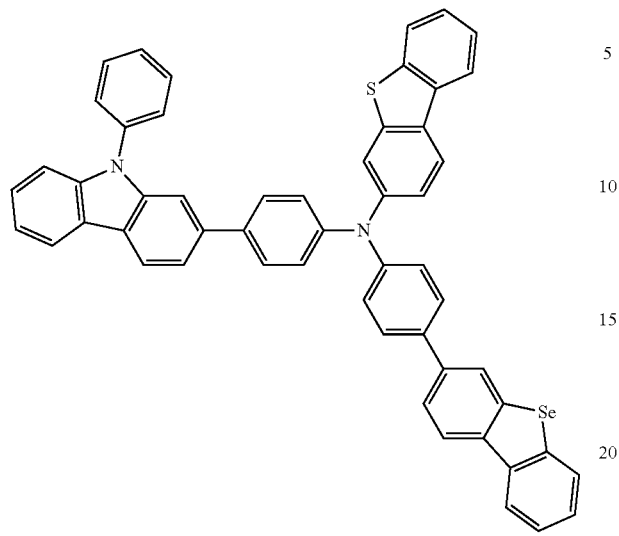
77
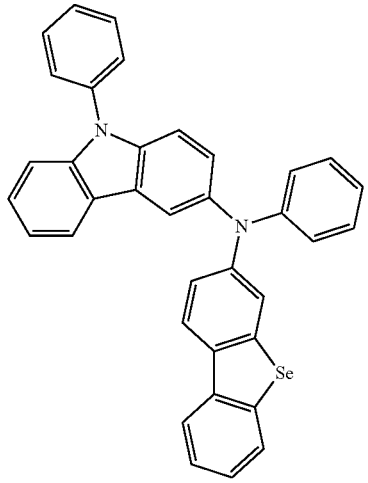
75
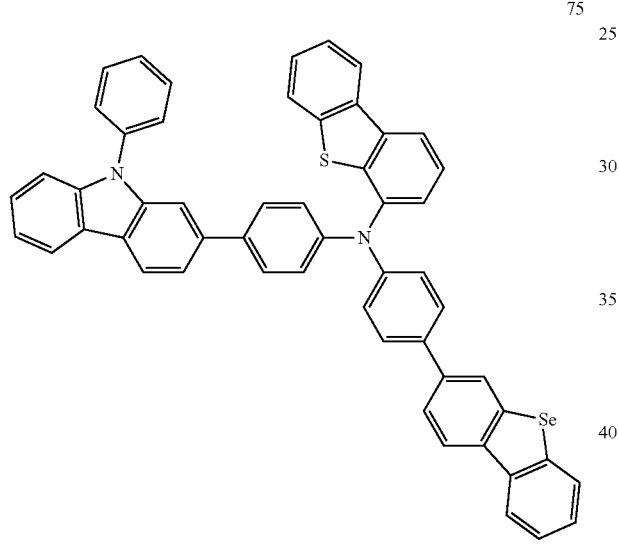
78
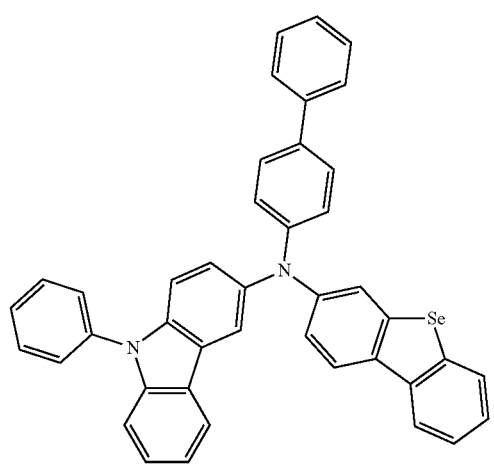
76
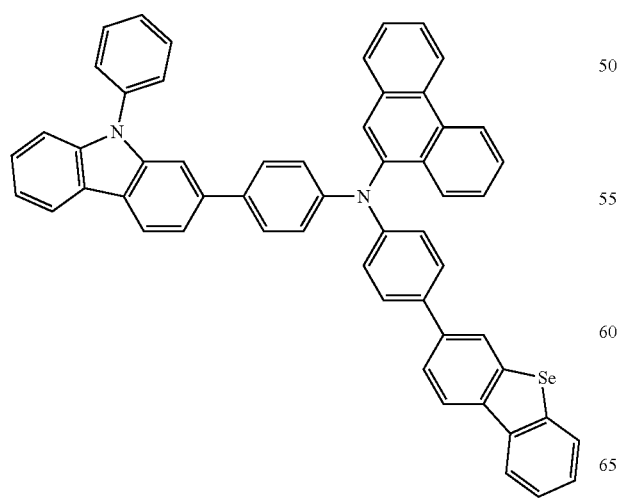
79
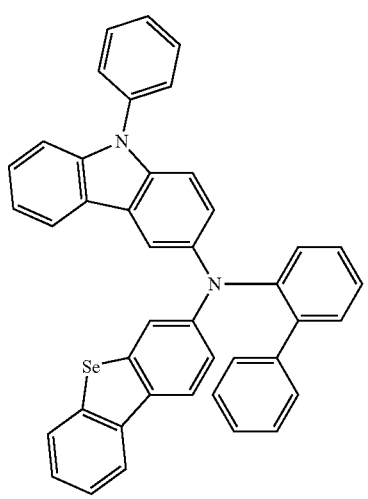

80
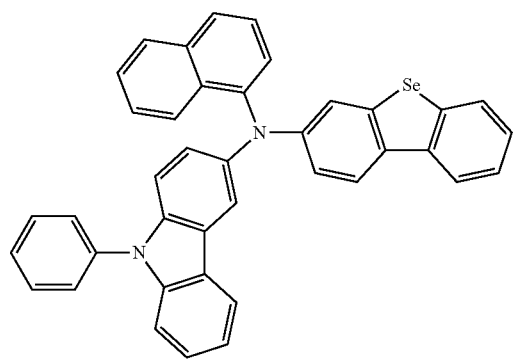
81
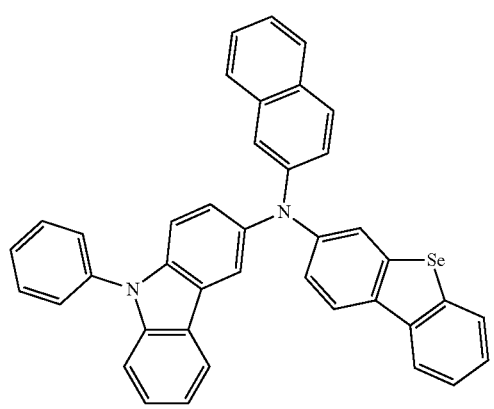
82
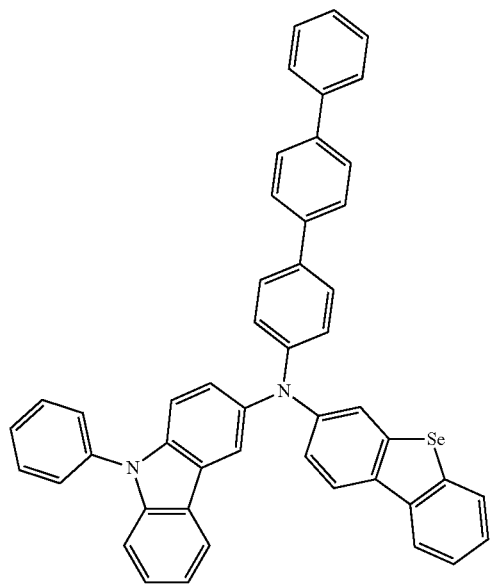
83
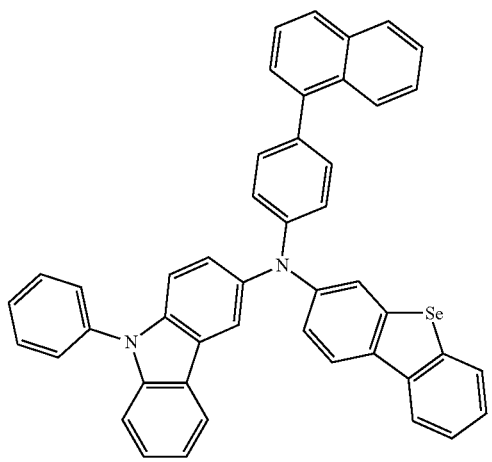
84
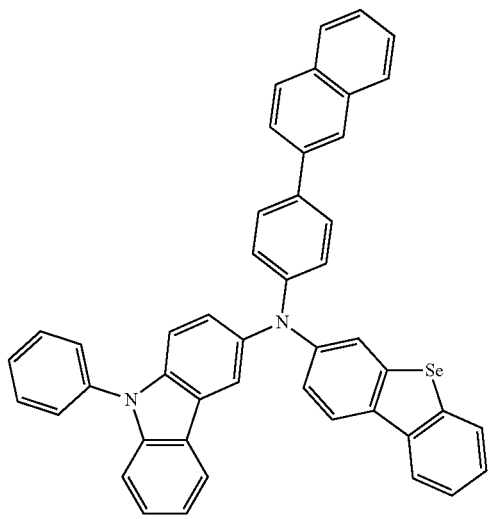
85
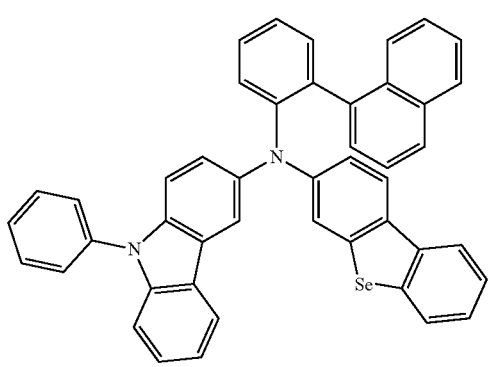

86
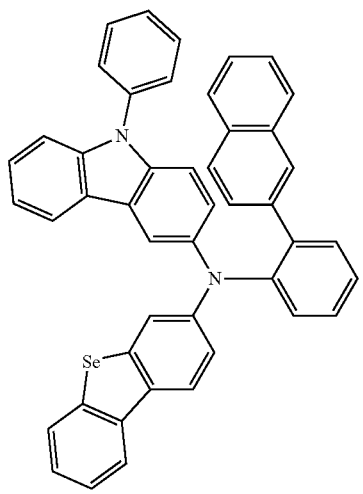
87
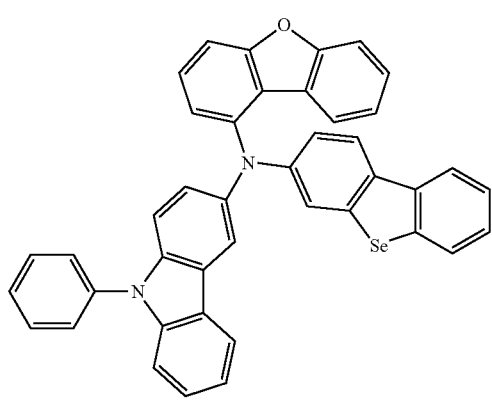
88
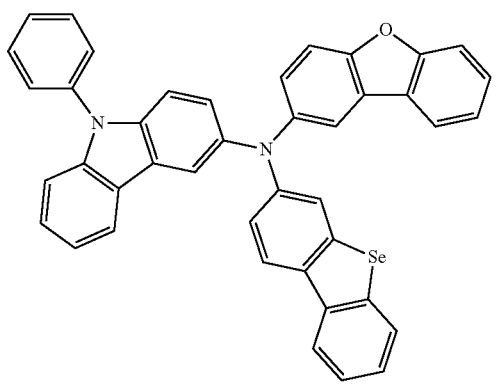
89
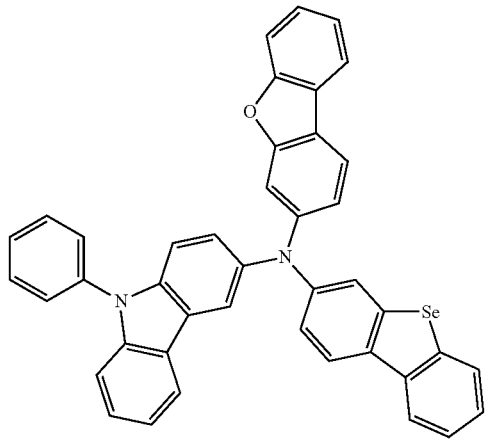
90
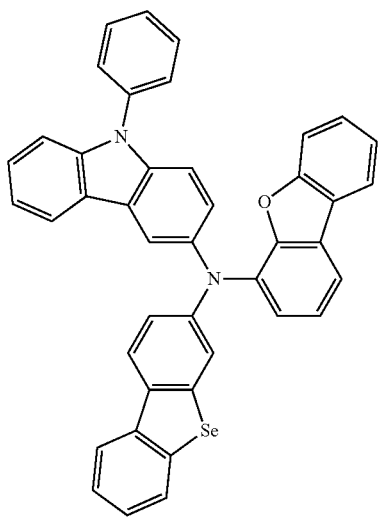
91
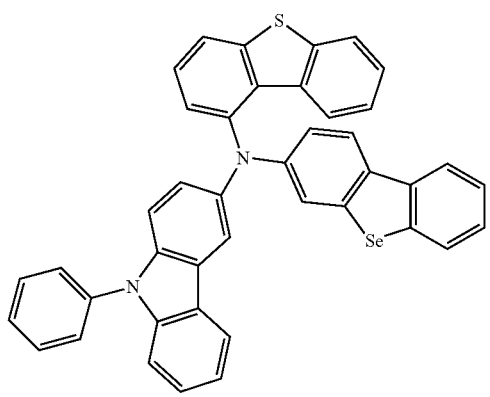

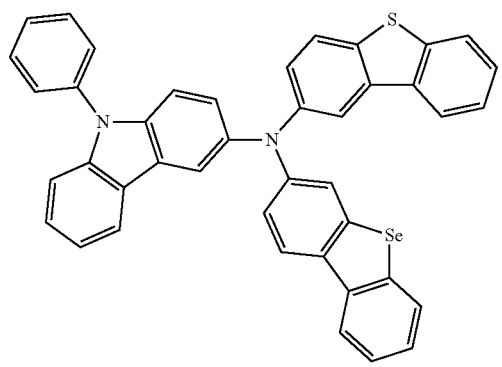
92
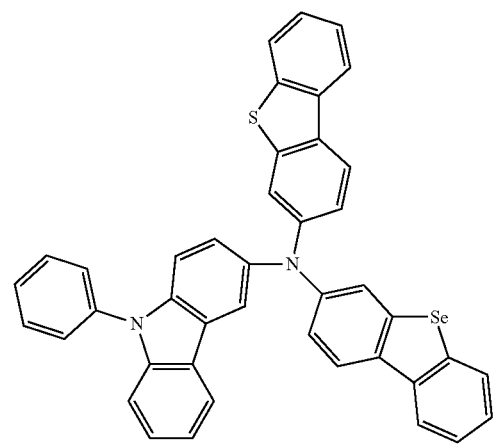
93
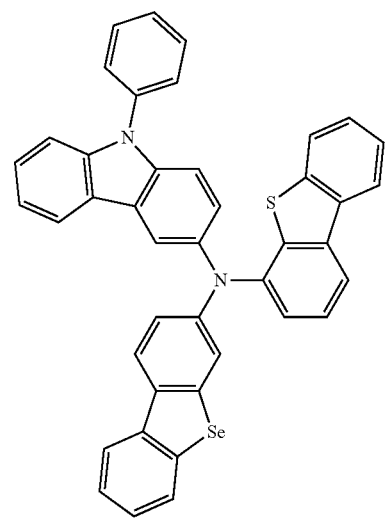
94
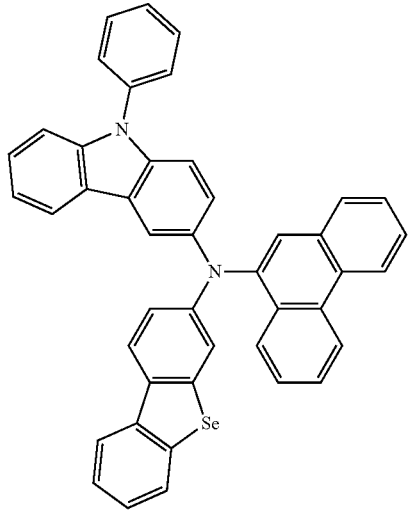
95
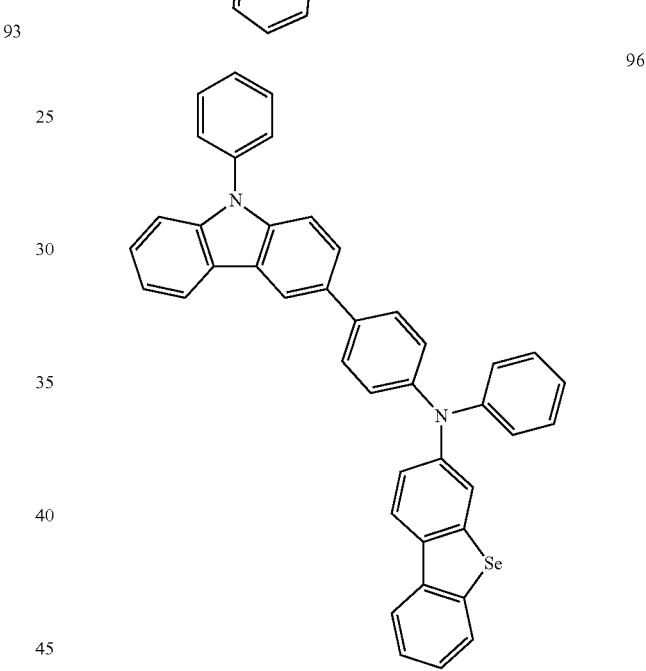
96
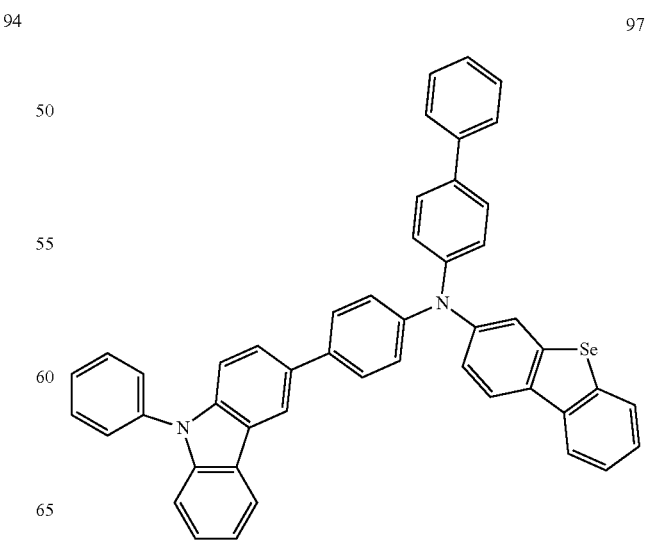
97

-continued
98
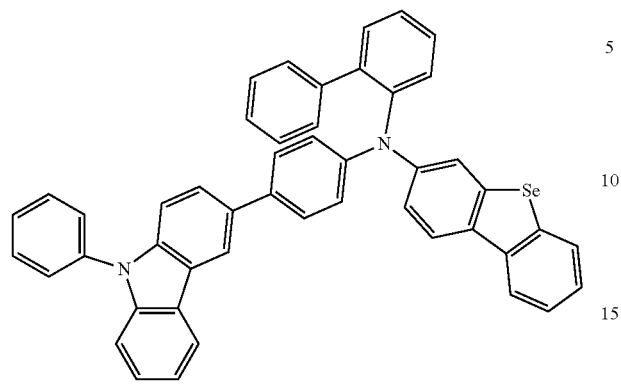
99
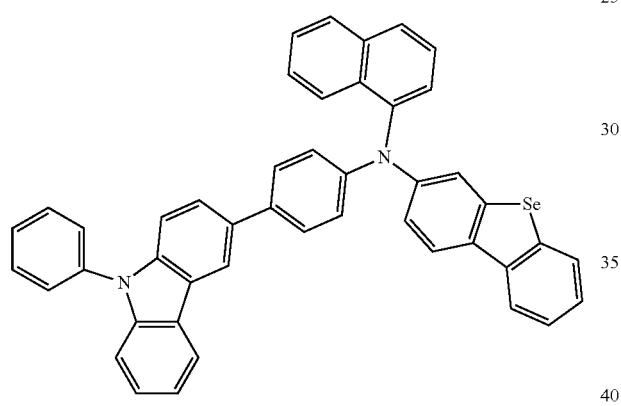
100
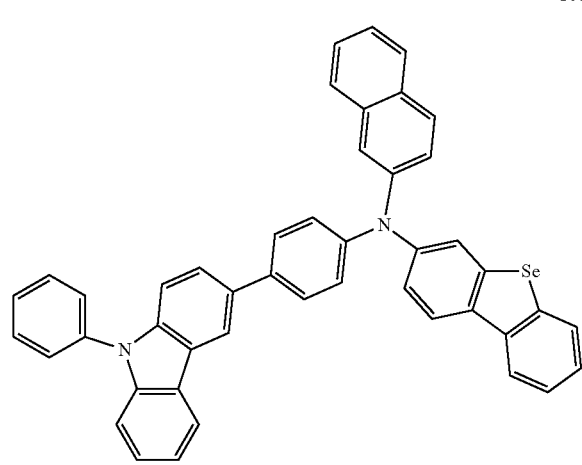
-continued
101
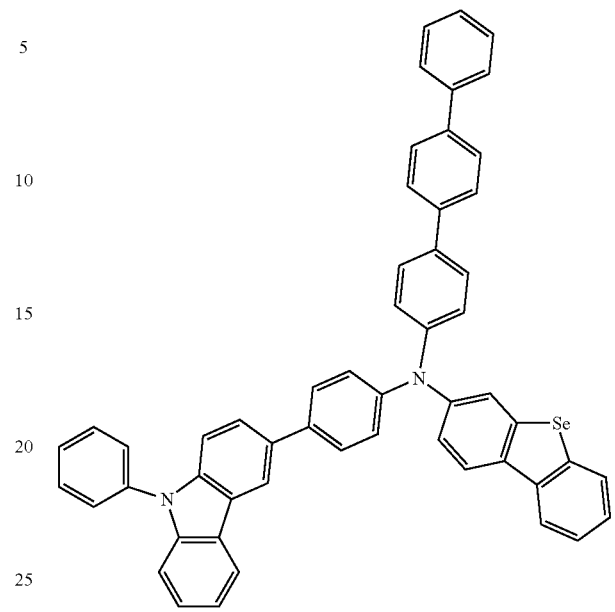
102
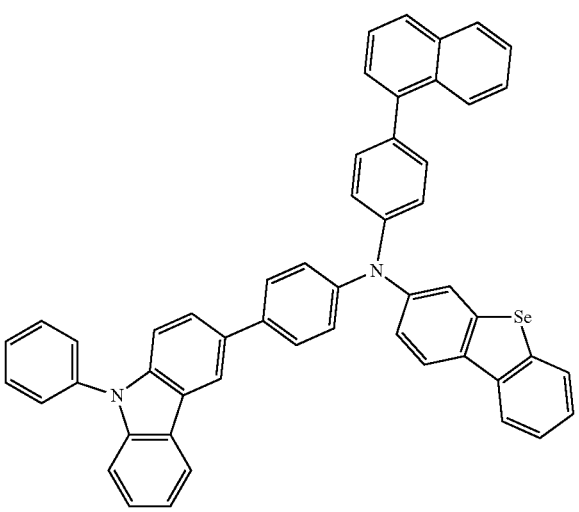

103
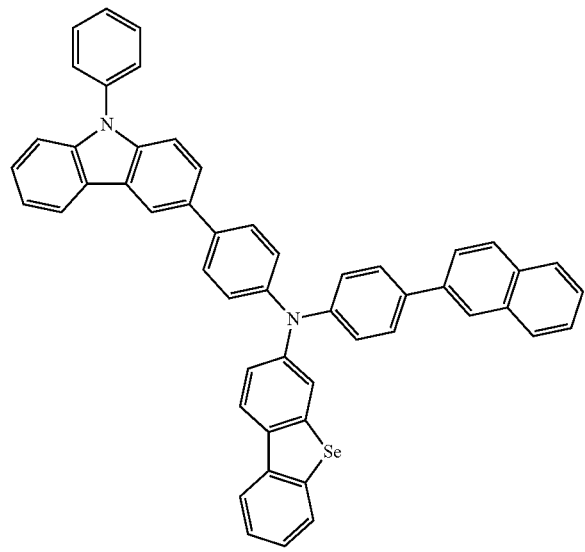
104
106
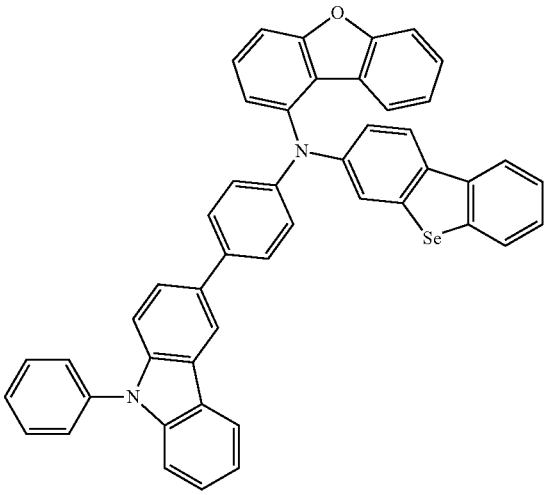
107
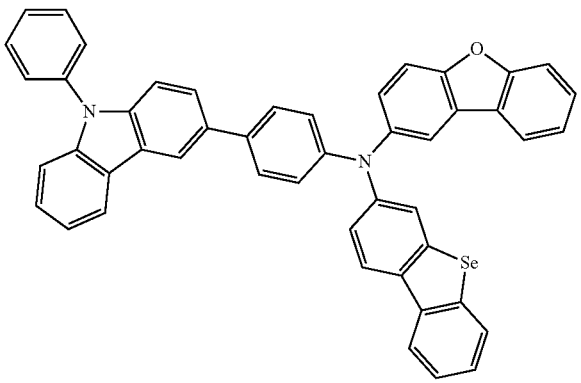
105
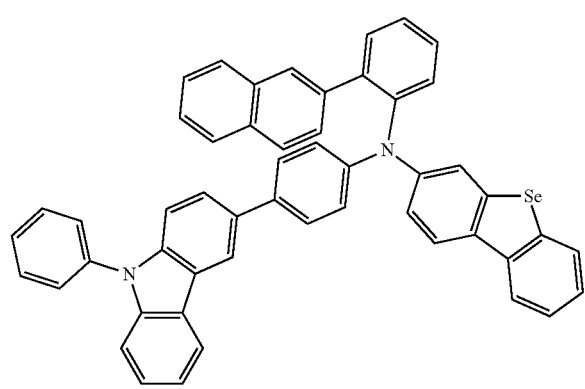
108
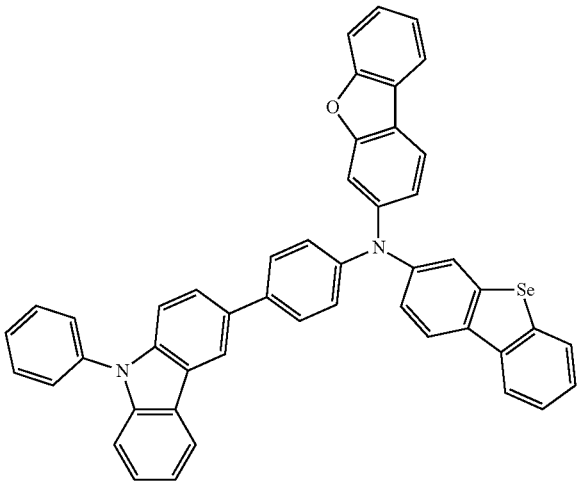

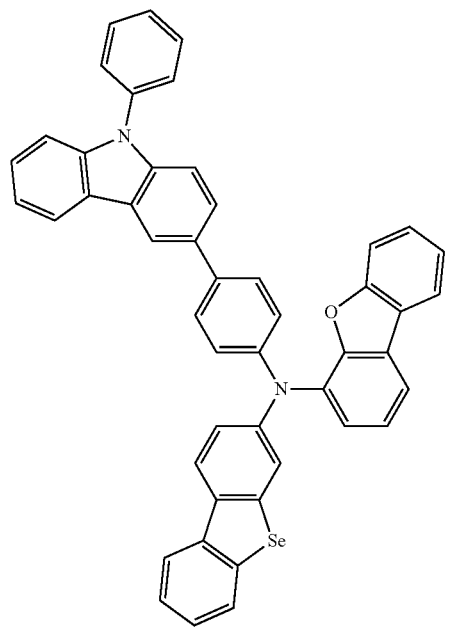
109
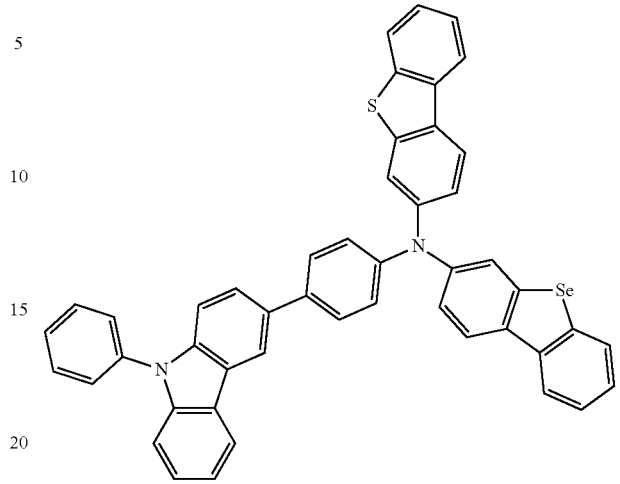
112
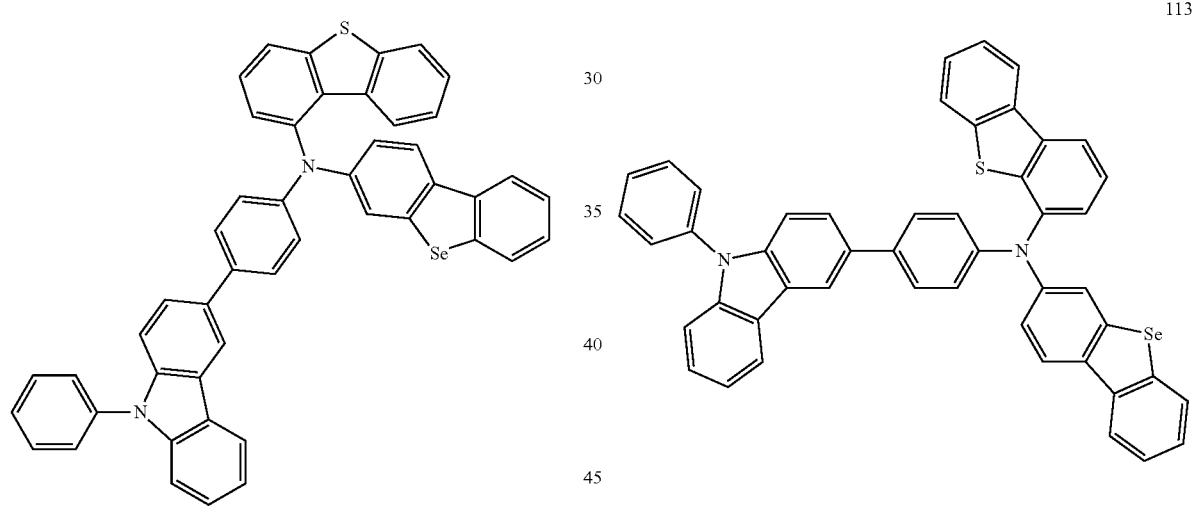
110
113
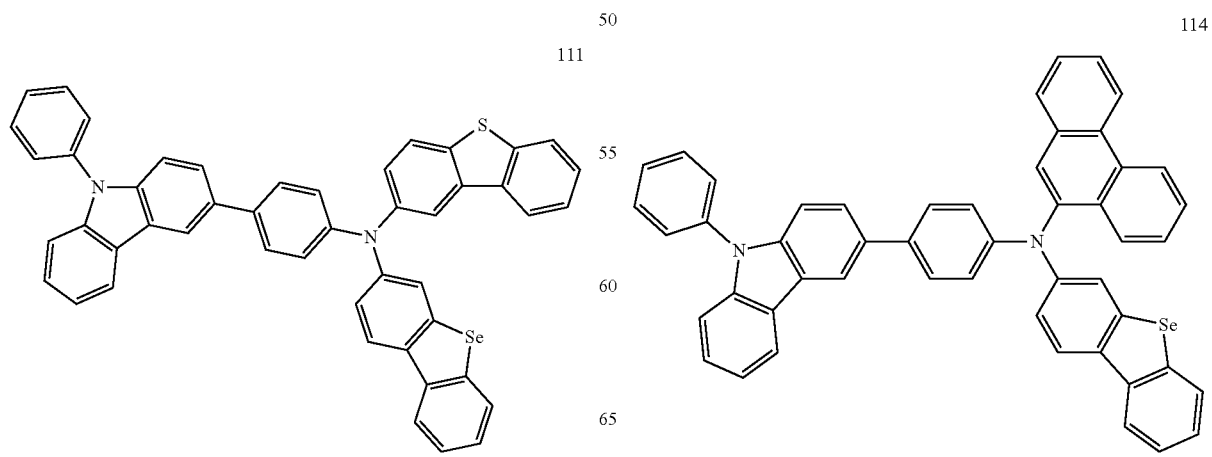
111
114

115
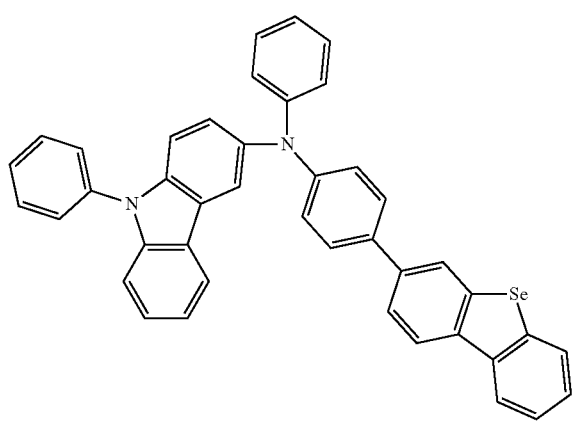
116
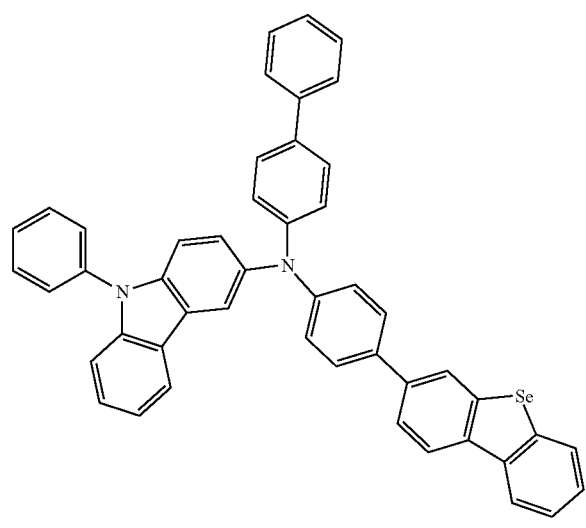
117
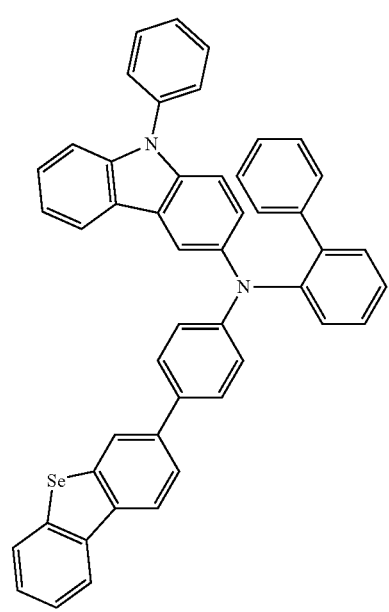
118
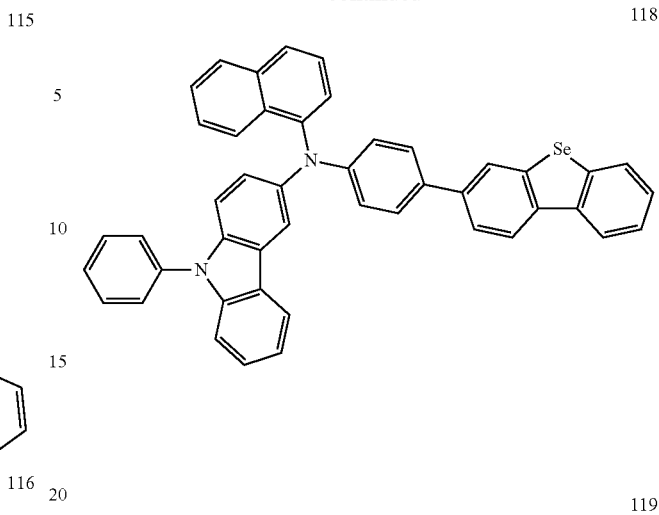
119
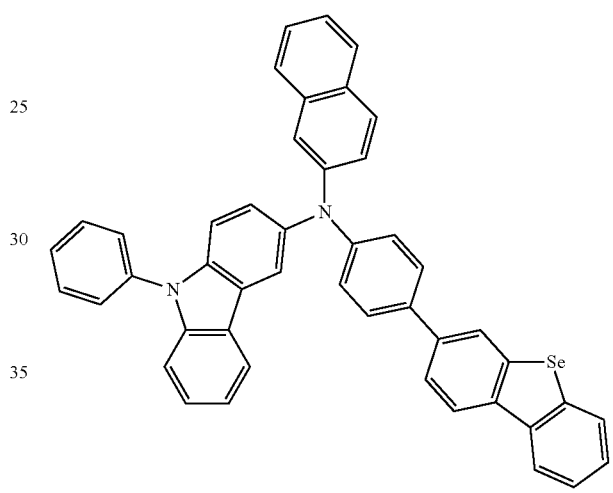
120
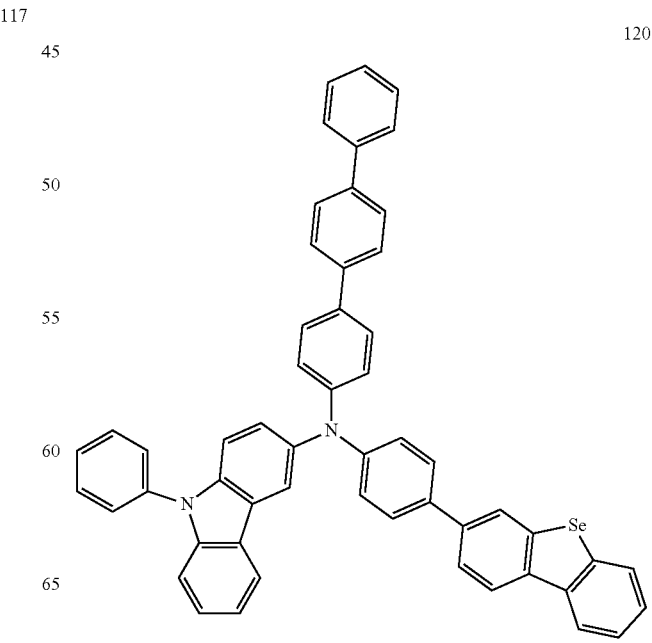

159
-continued
121
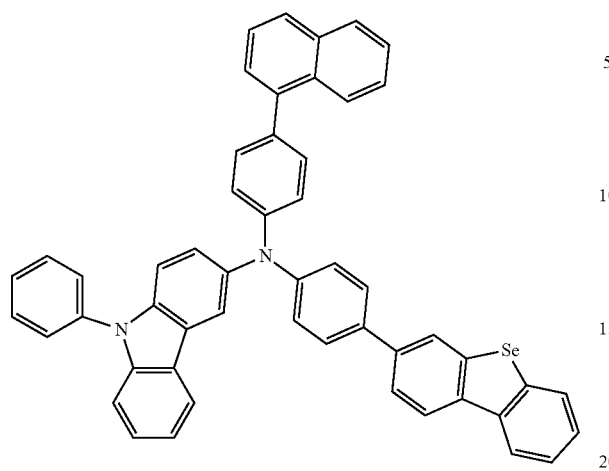
122
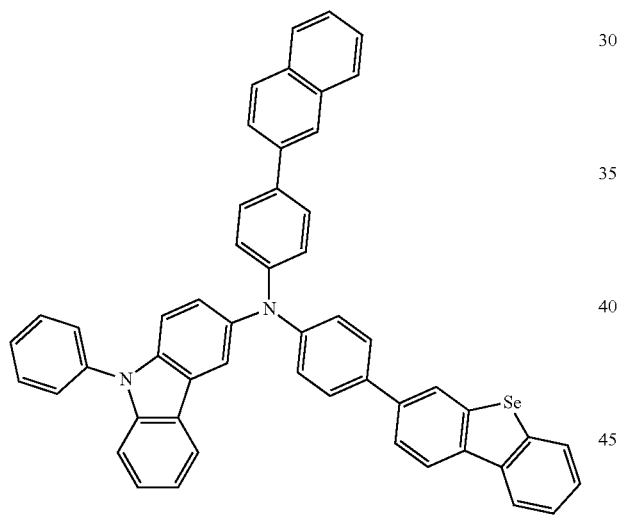
123
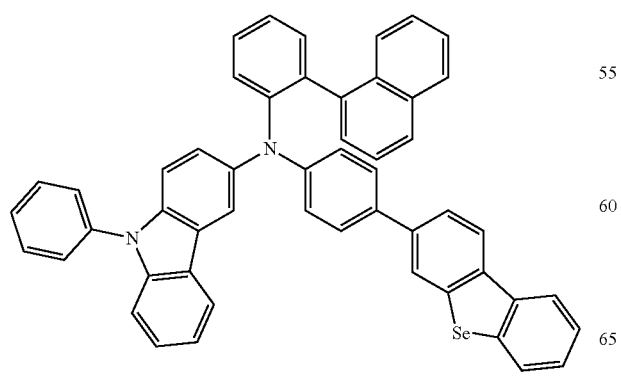
160
-continued
124
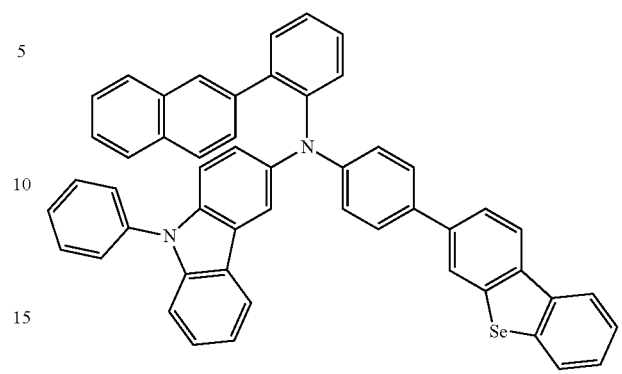
125
126

127
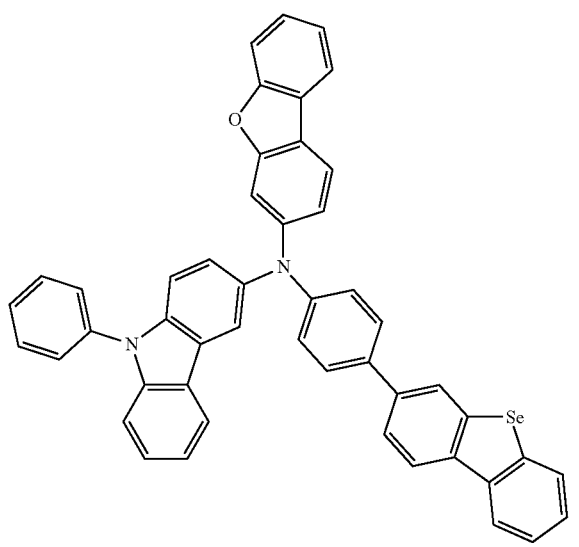
130
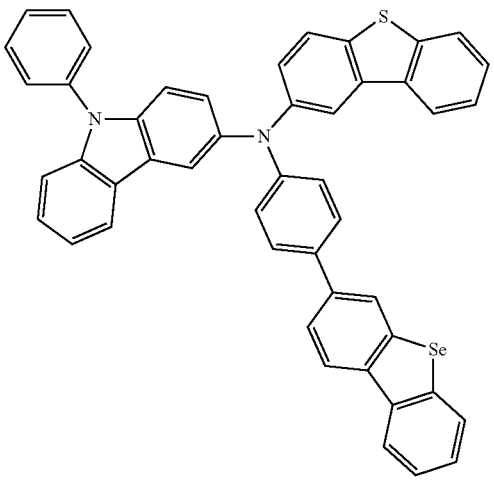
128
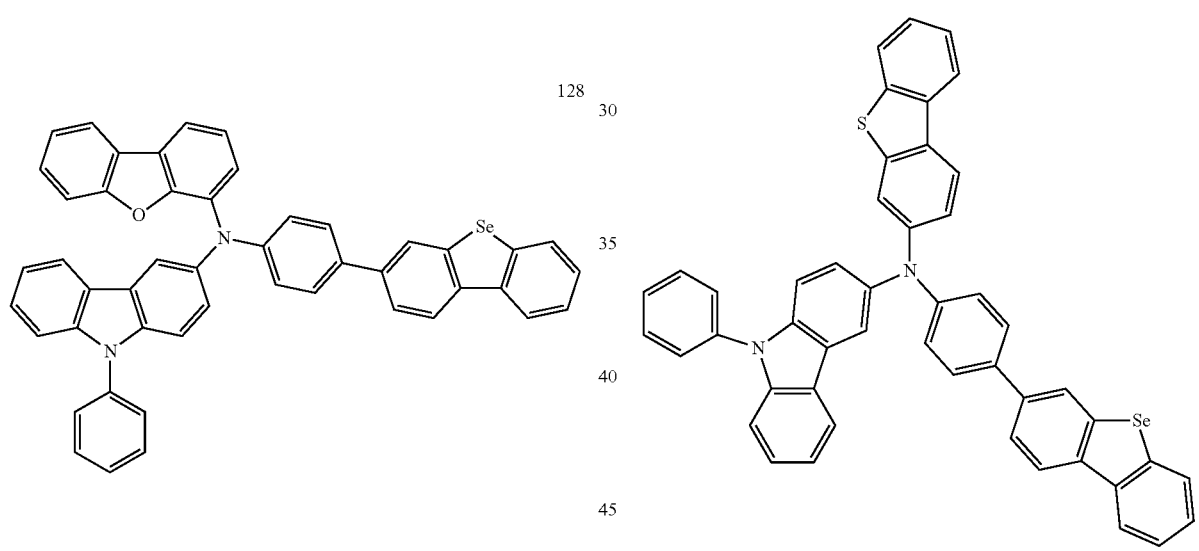
131
129
132
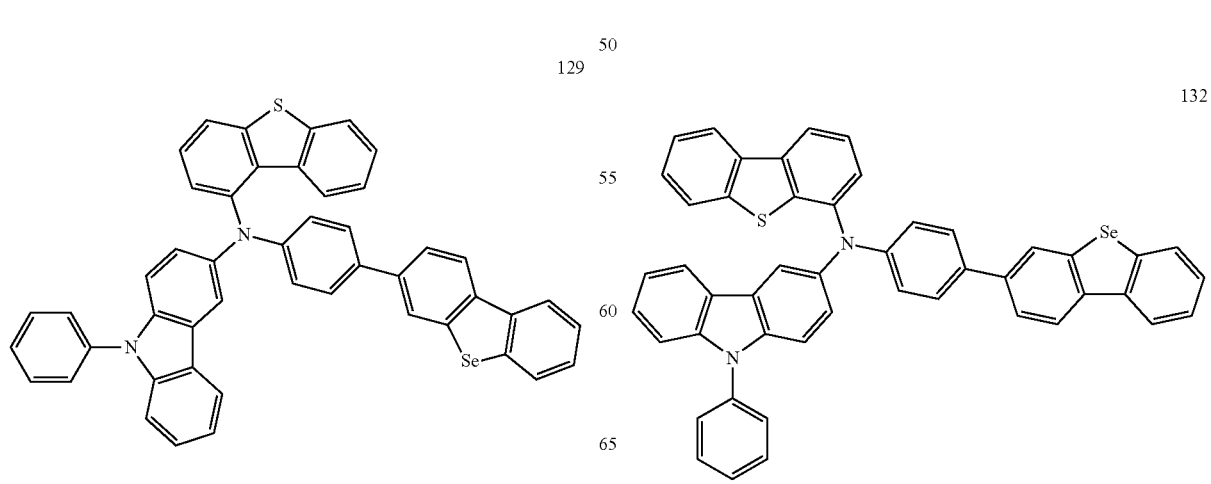

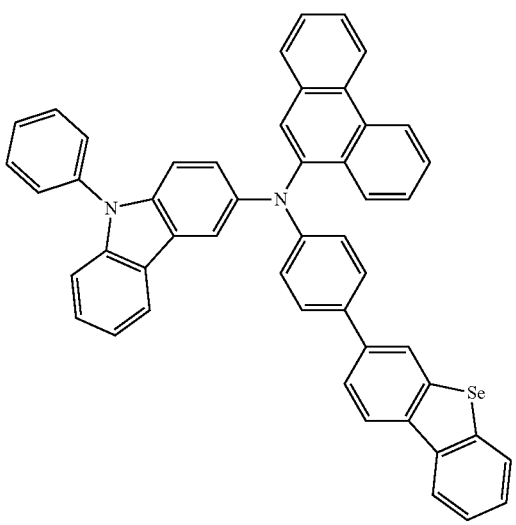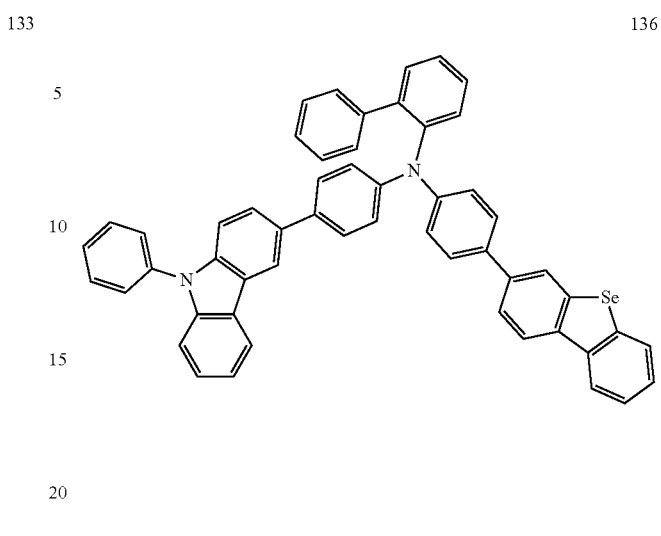

139
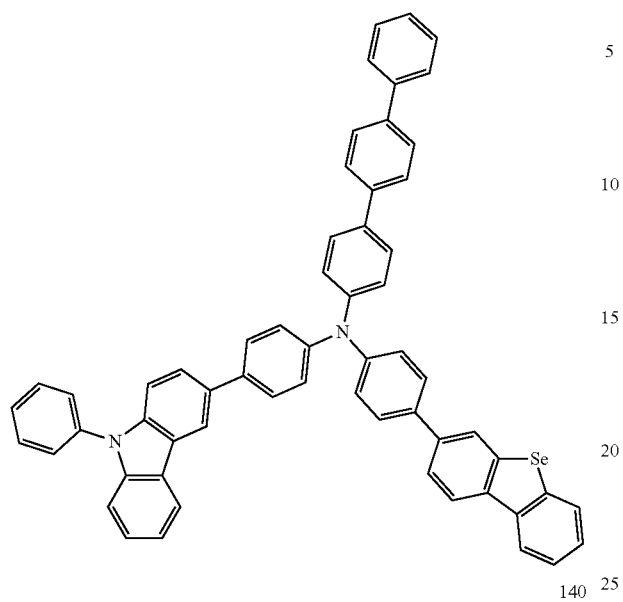
140
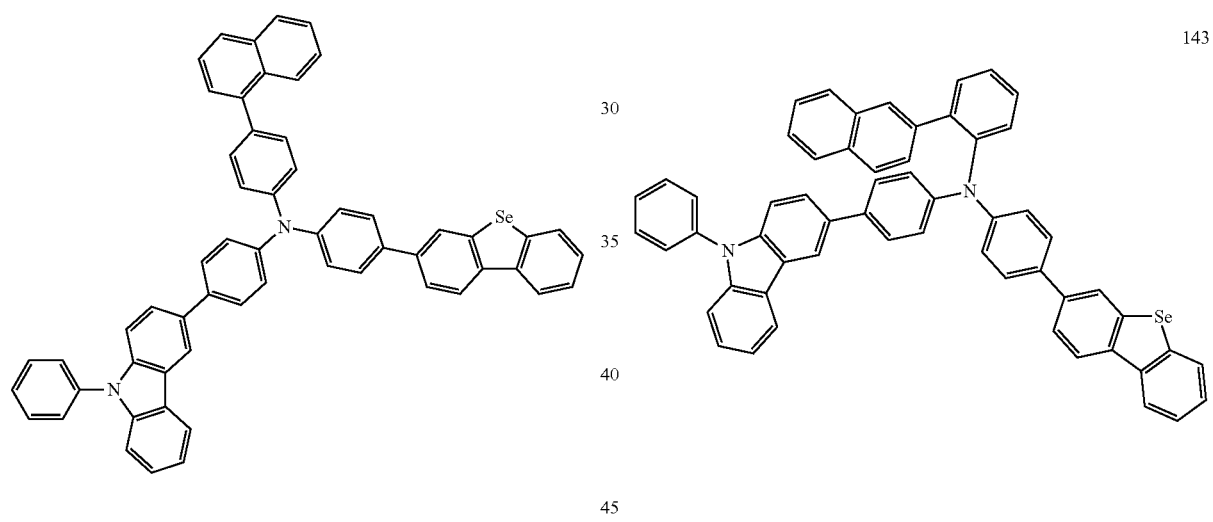
141
142
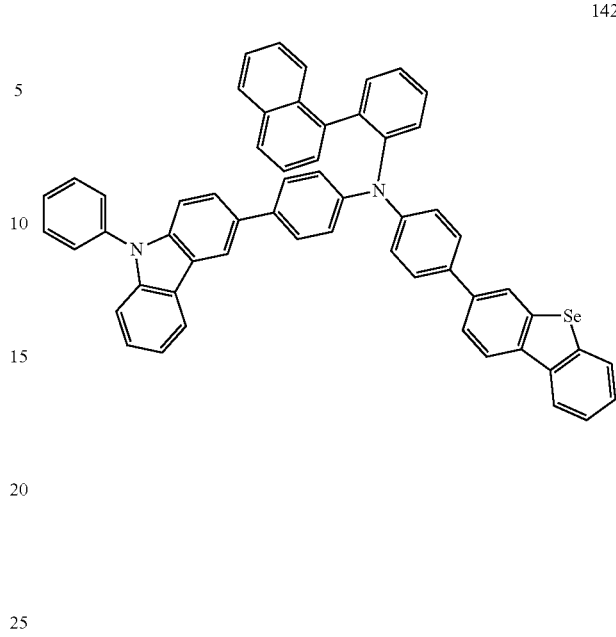
143
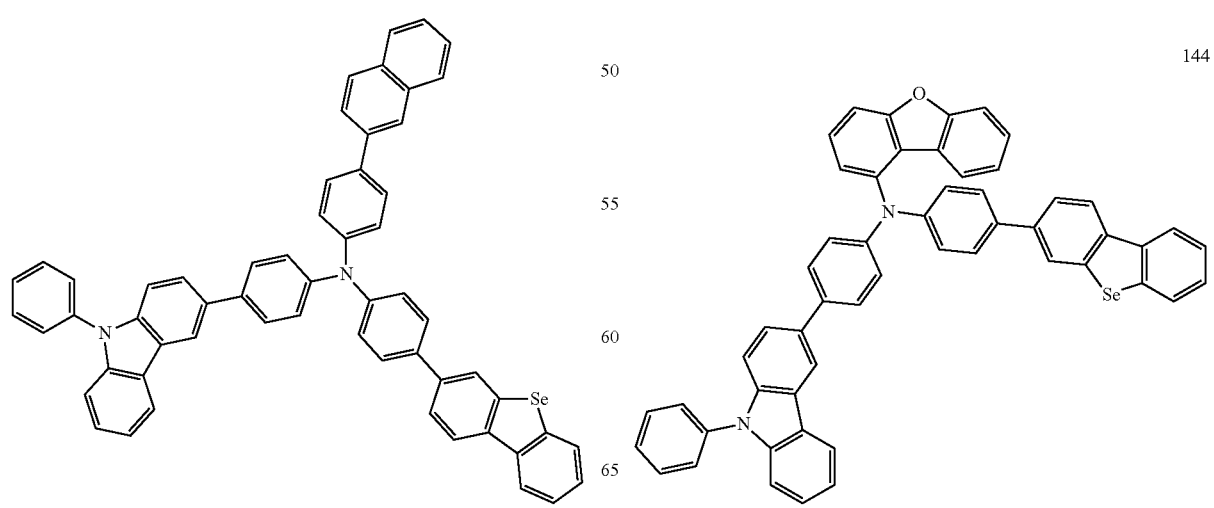
144

-continued
145
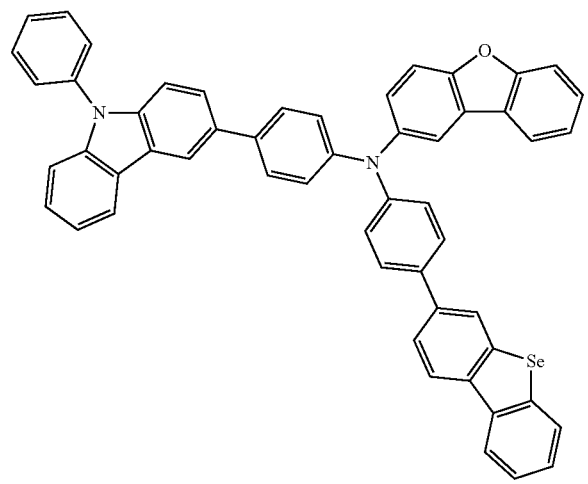
146
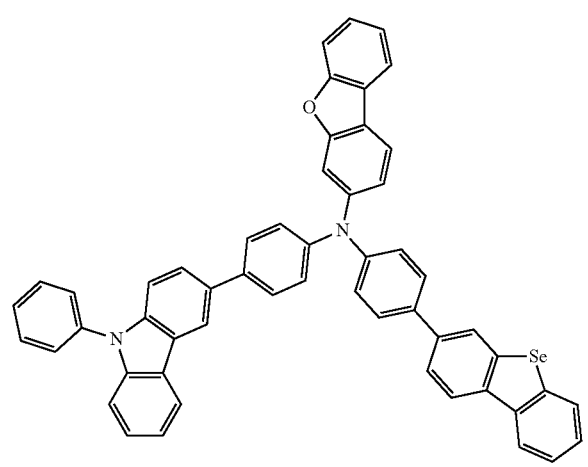
147
-continued
148
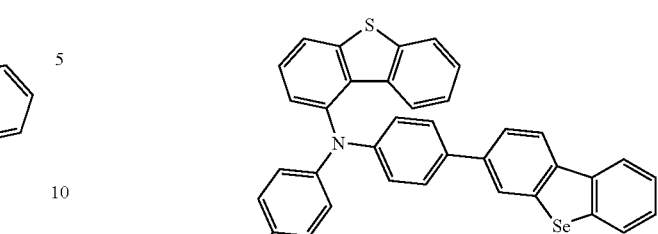
149
150
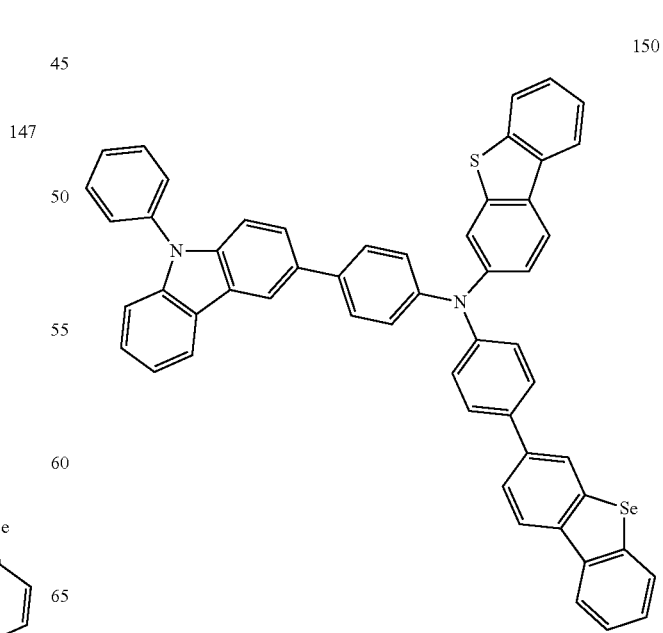

-continued
151
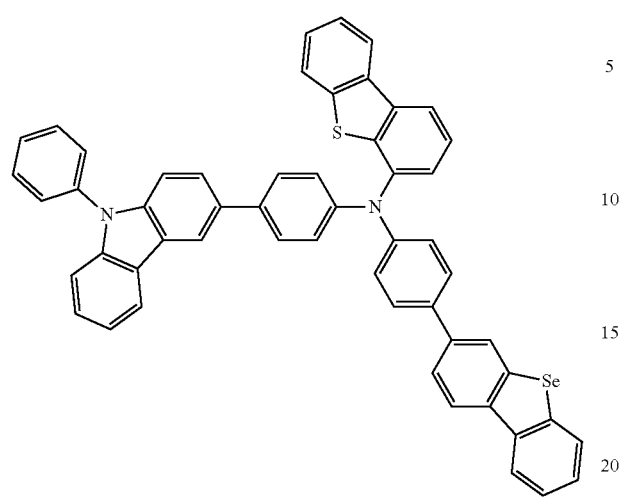
152
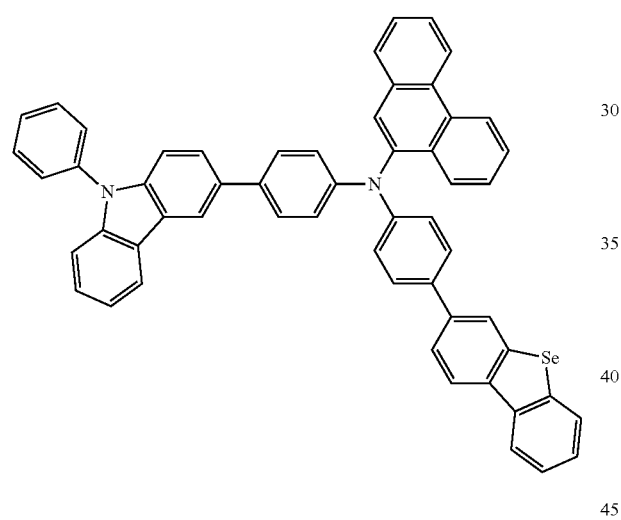
153
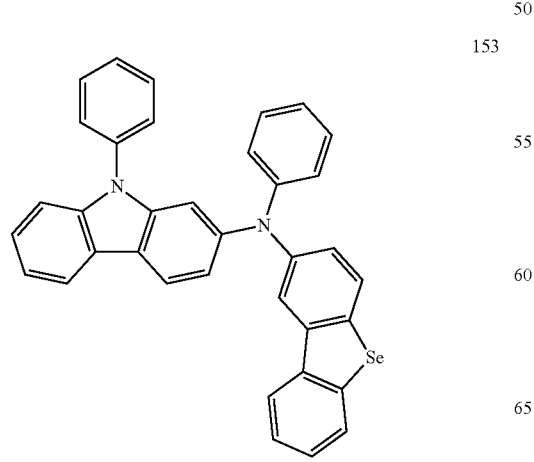
-continued
154
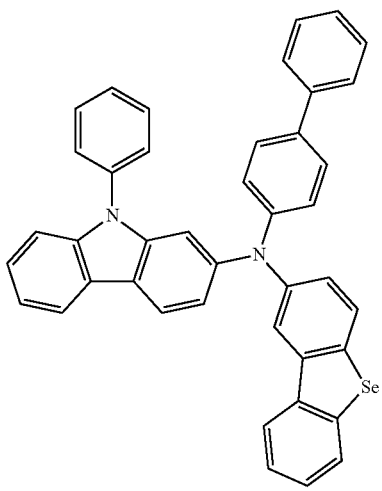
155
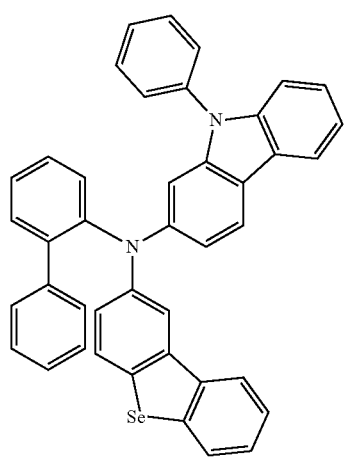
156
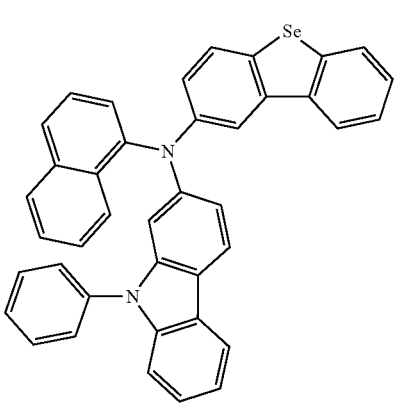

157
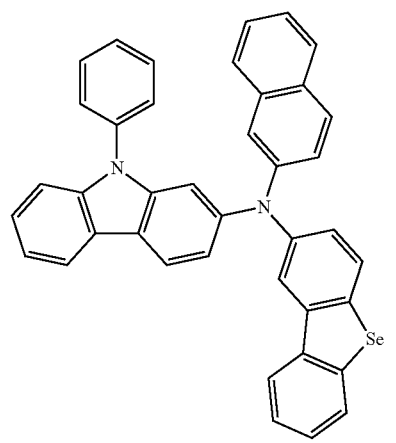
158
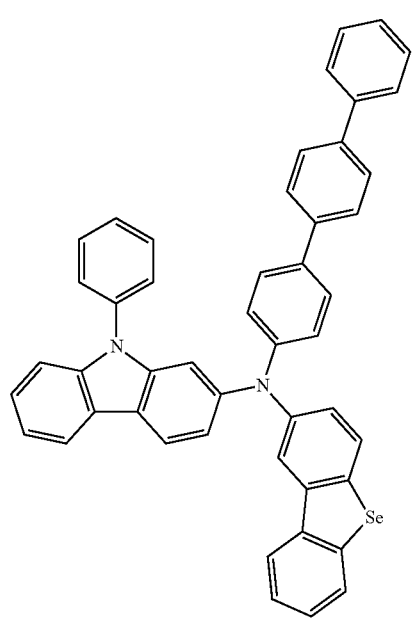
159
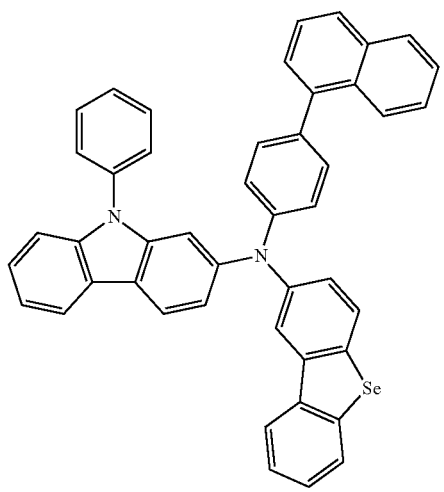
160
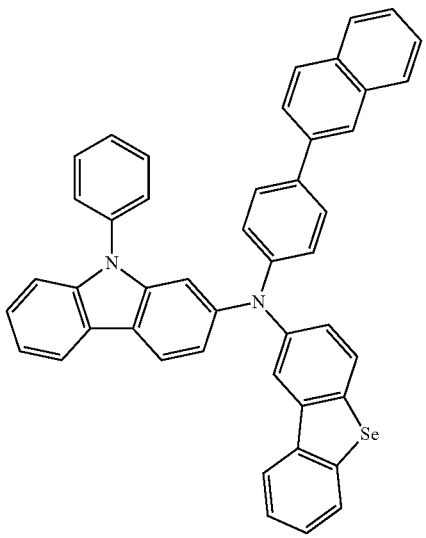
161
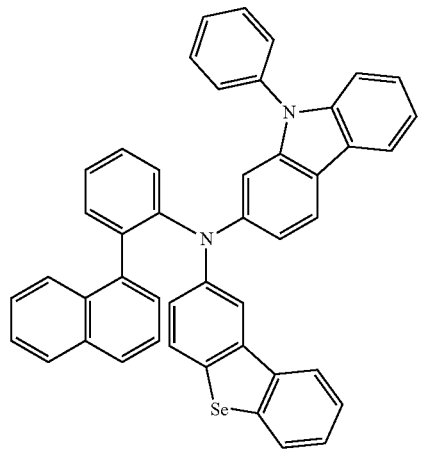
162
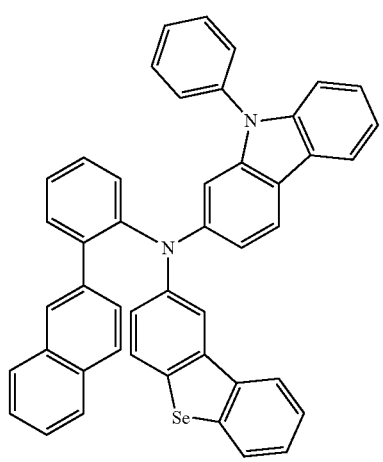

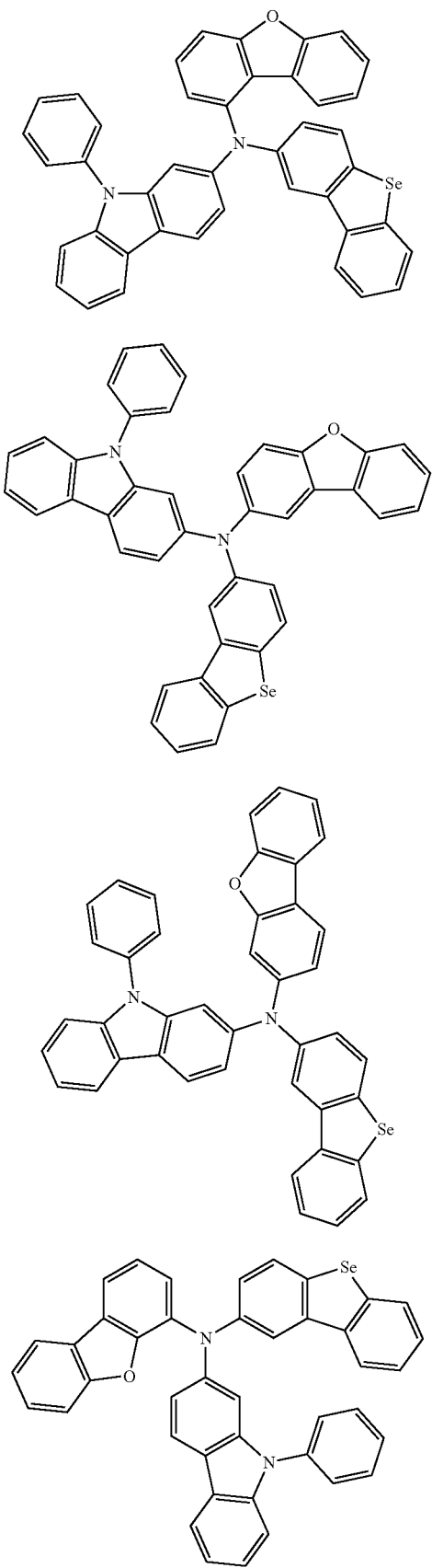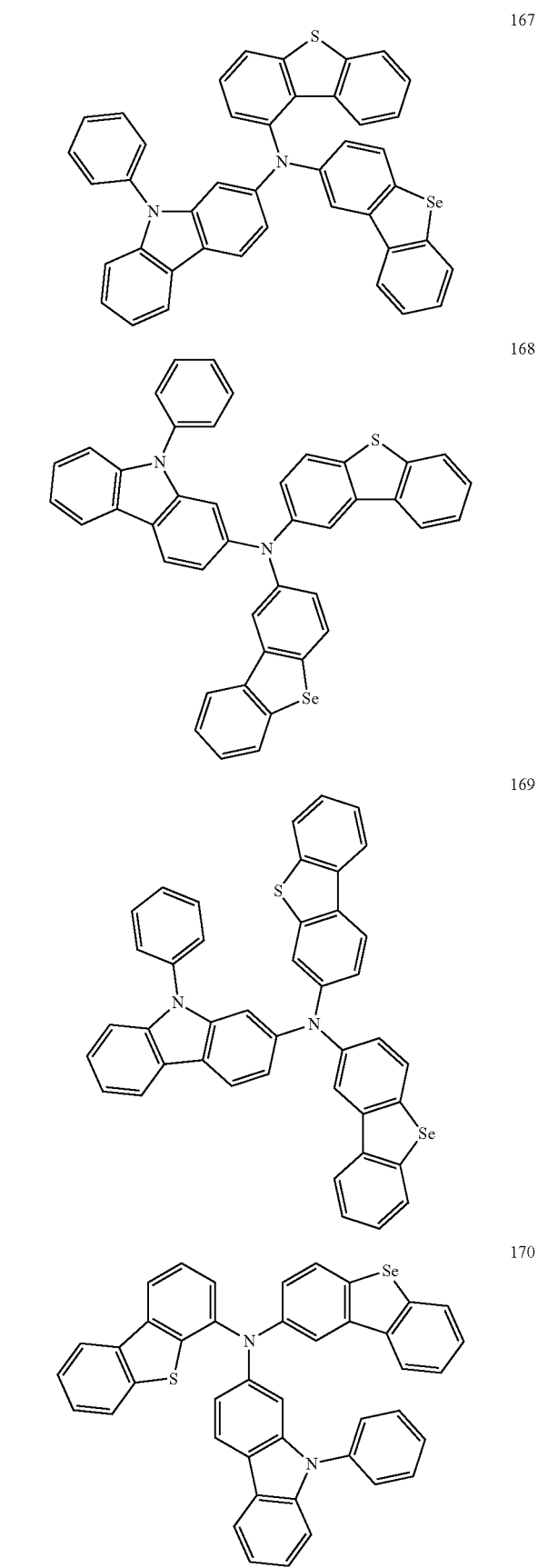

-continued
171
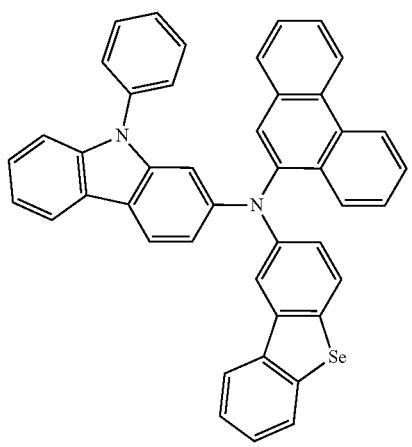
172
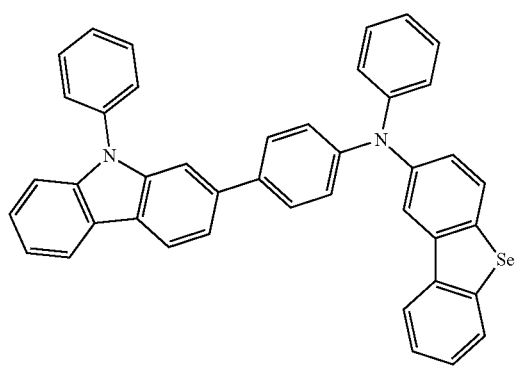
173
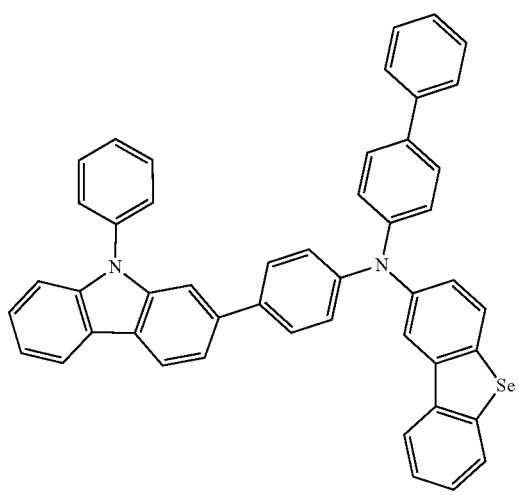
-continued
174
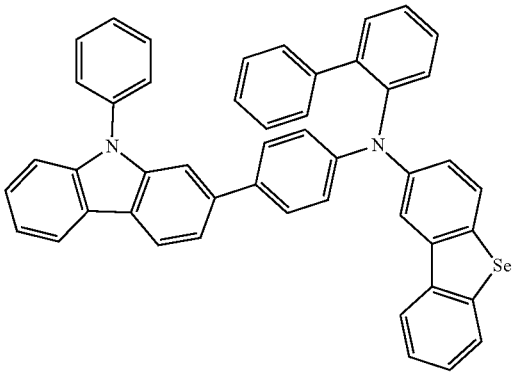
175
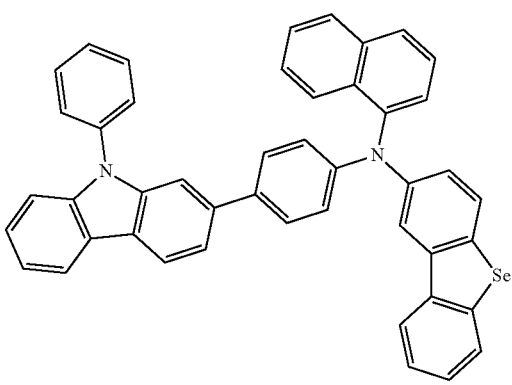
176
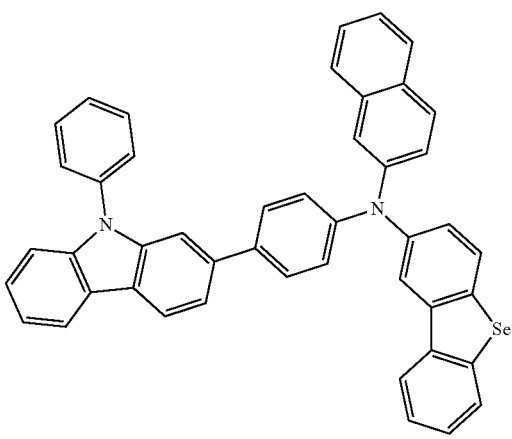

177
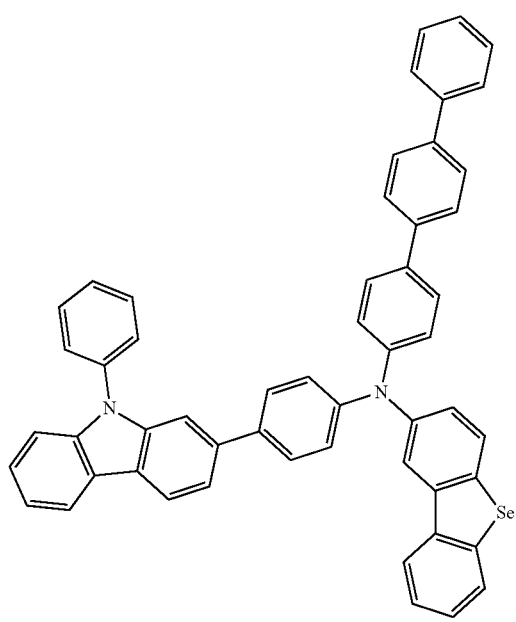
178
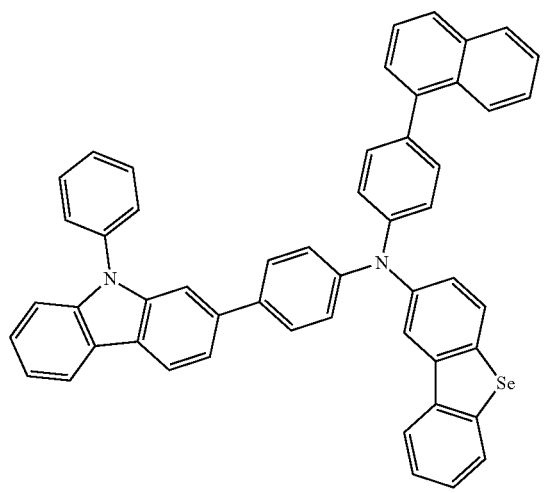
179
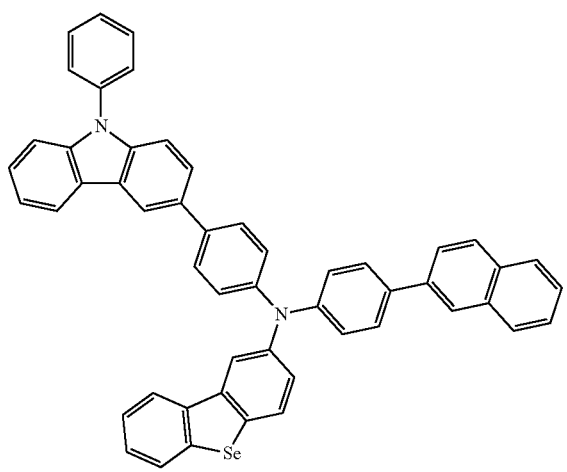
180
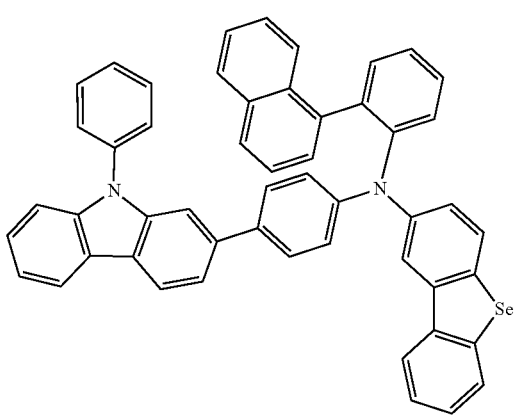
181
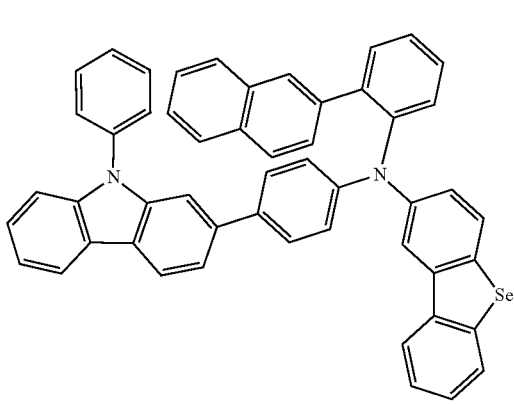
182
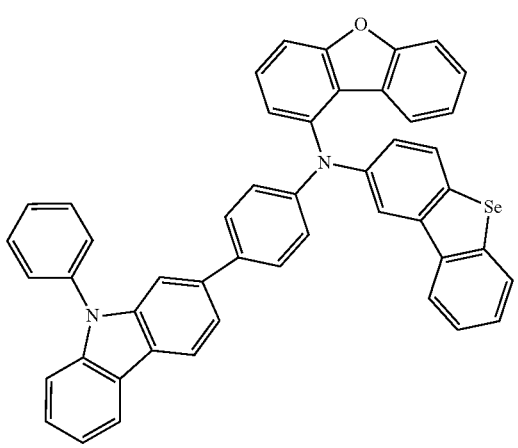

183
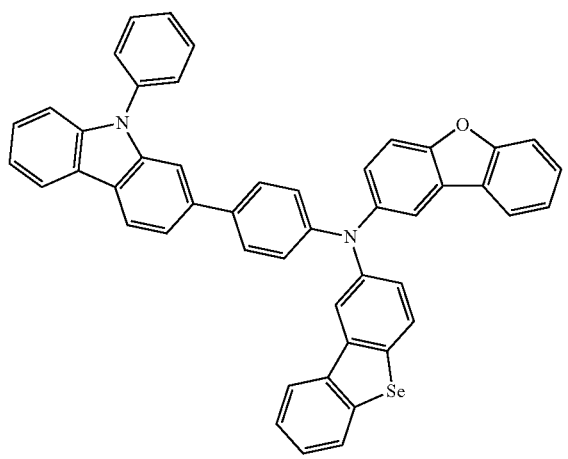
184
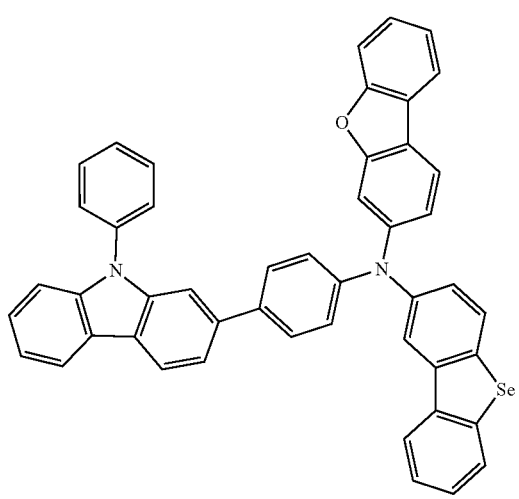
185
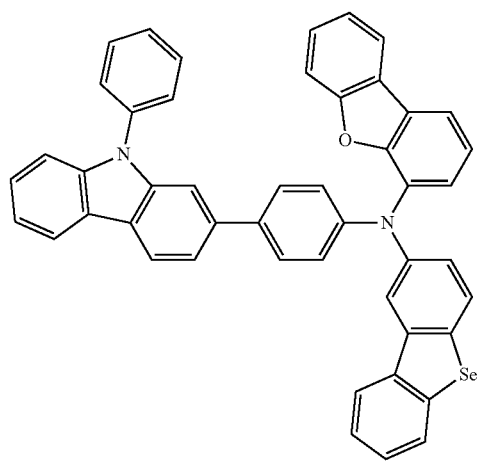
186
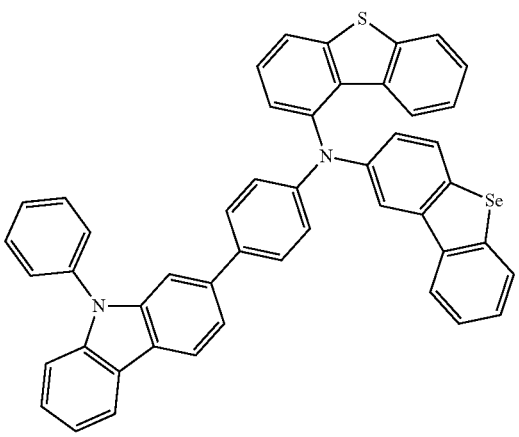
187
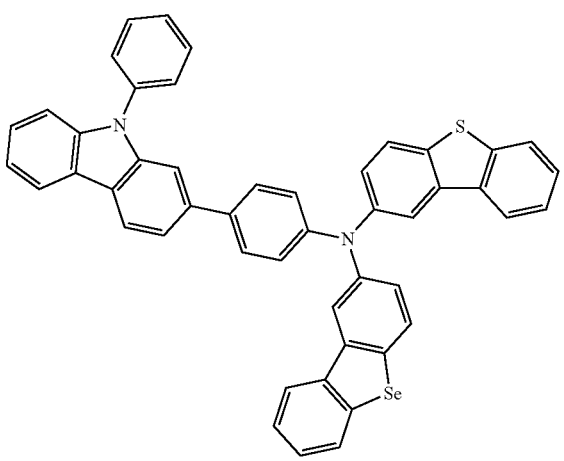
188
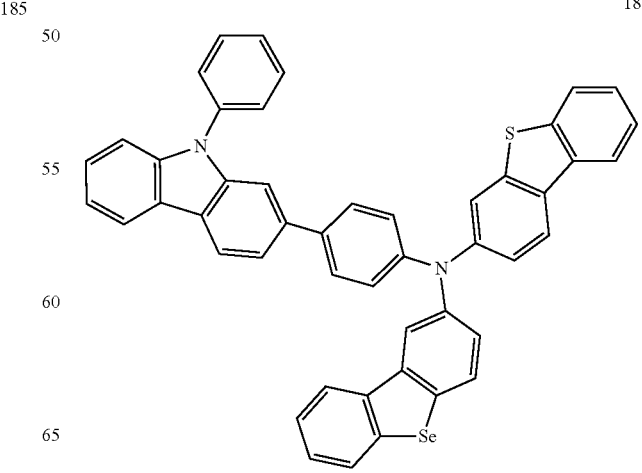

189
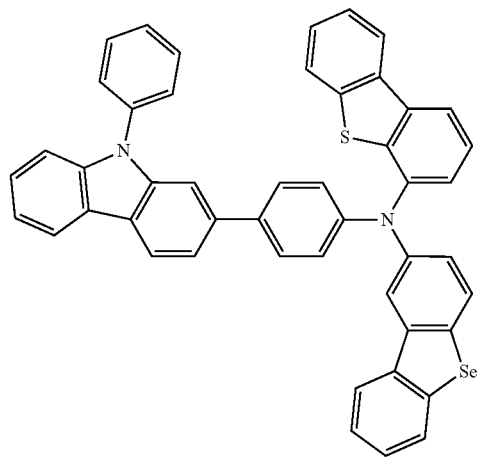
190
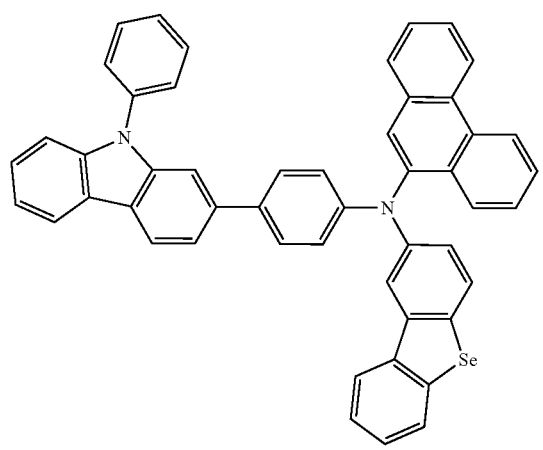
191
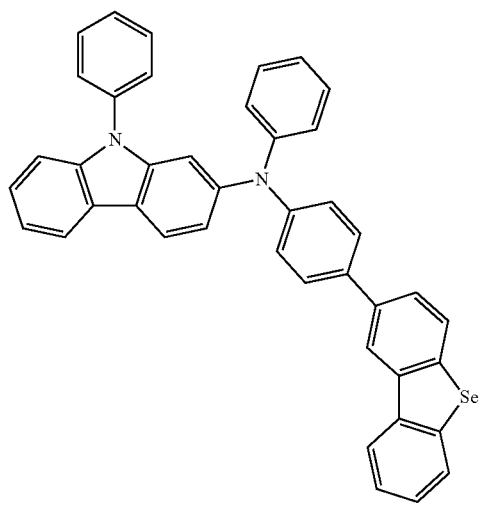
192
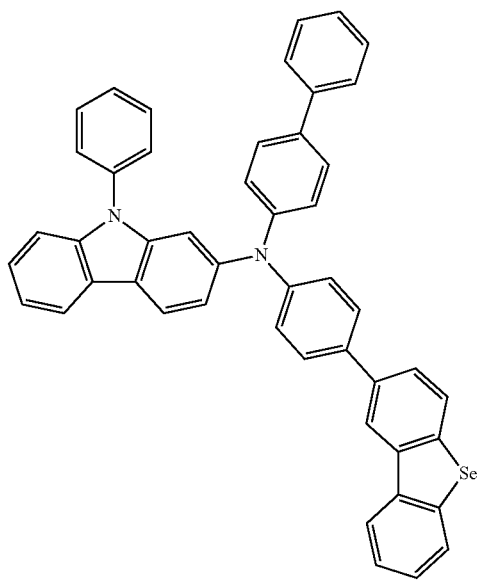
193
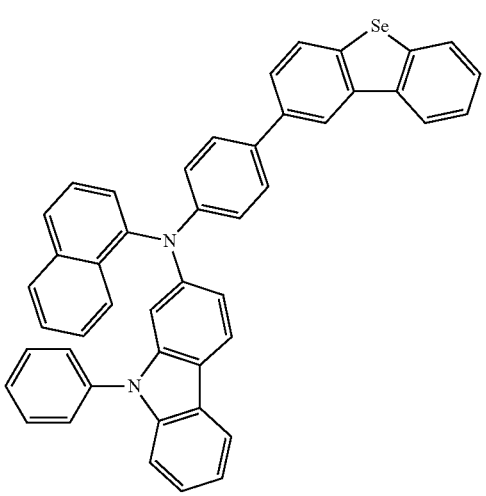
194

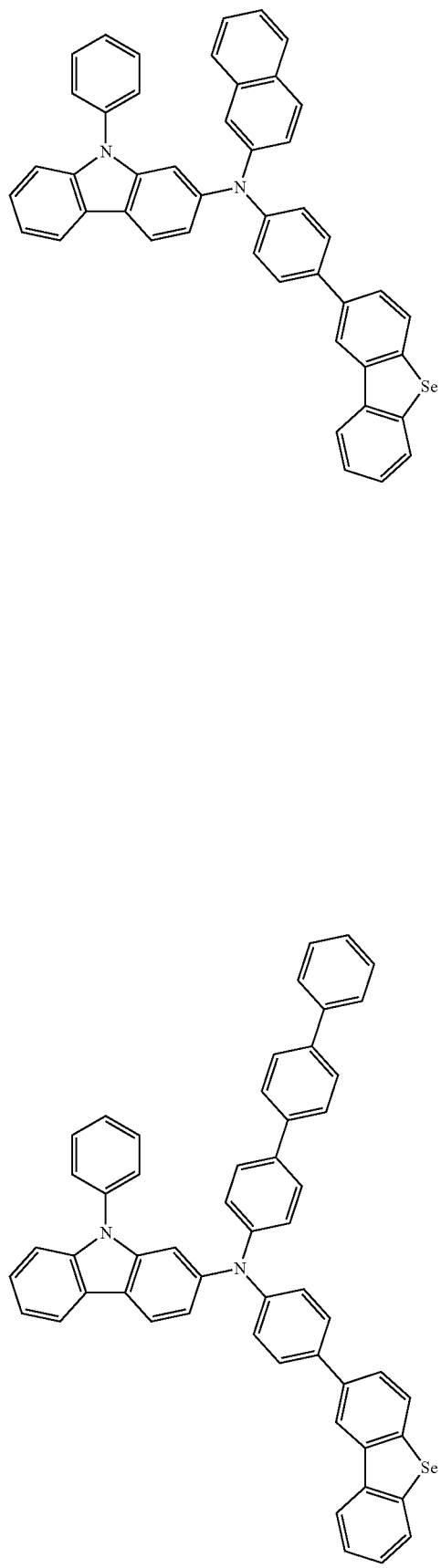
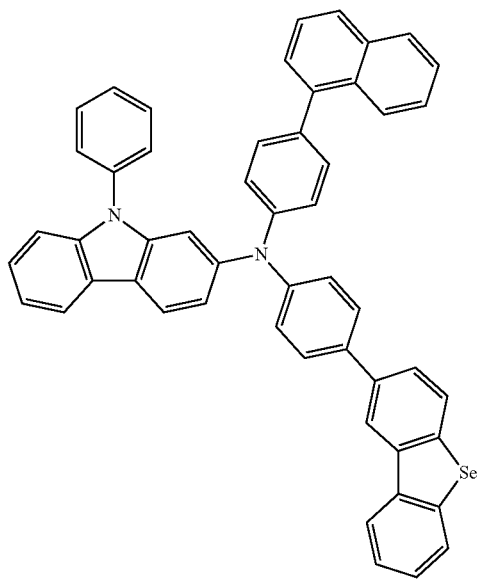
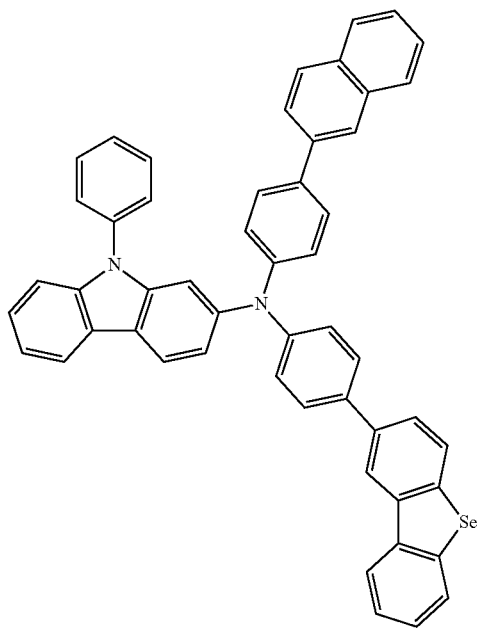
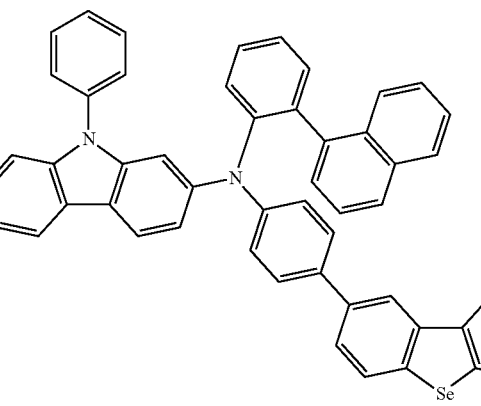

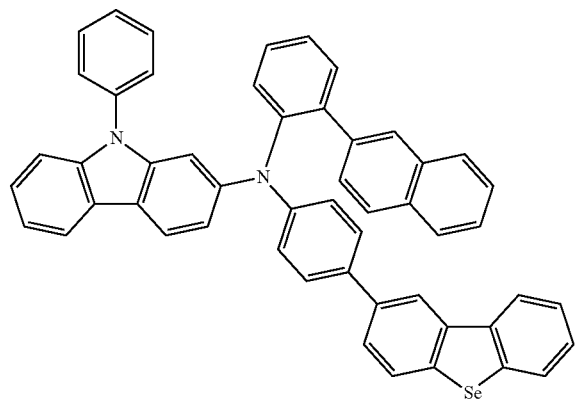
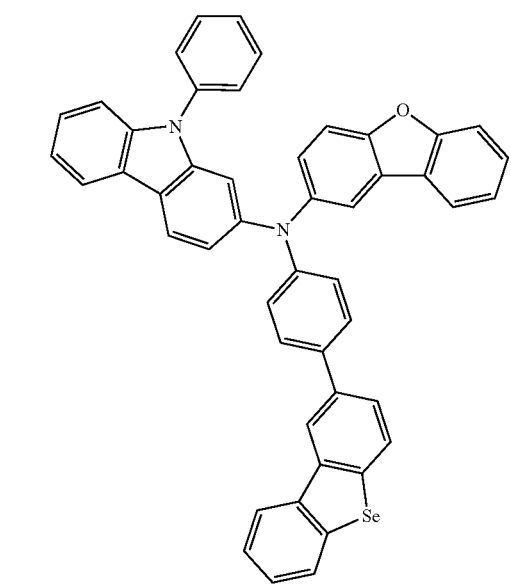
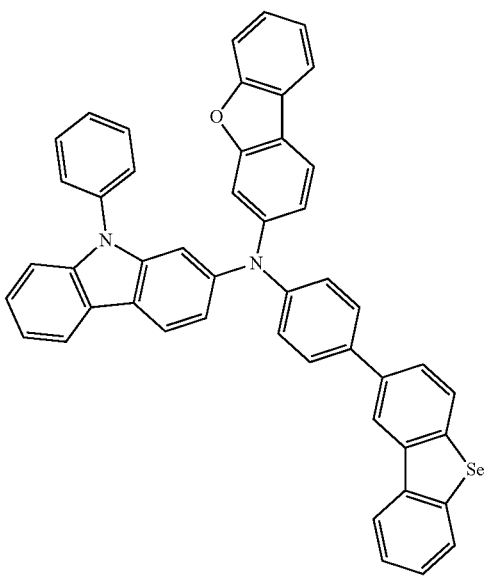

187
-continued
206
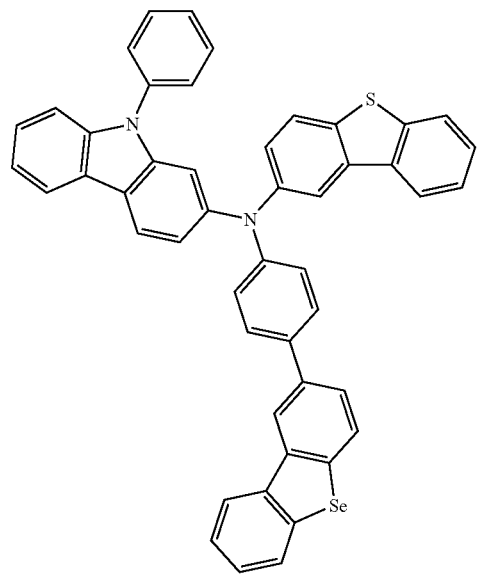
207
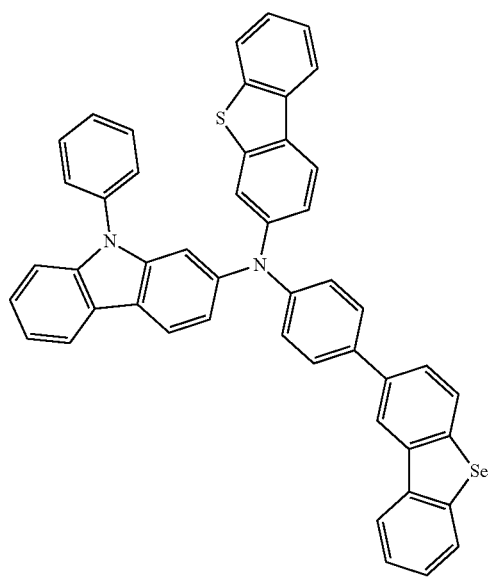
208
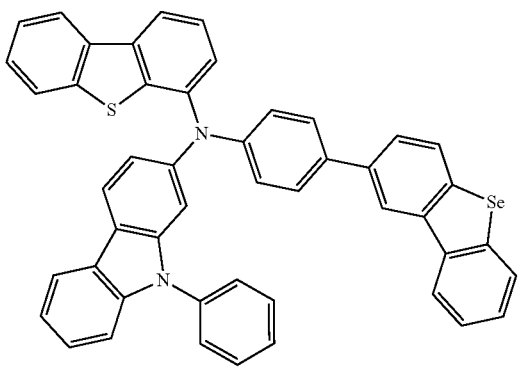
188
-continued
209
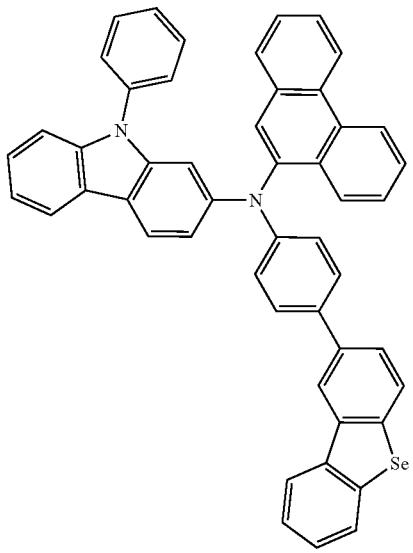
210
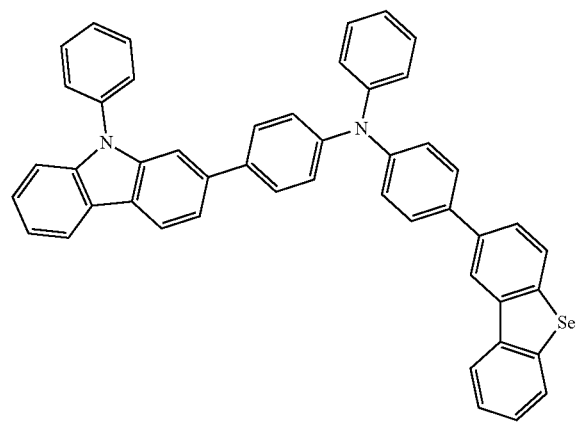
211
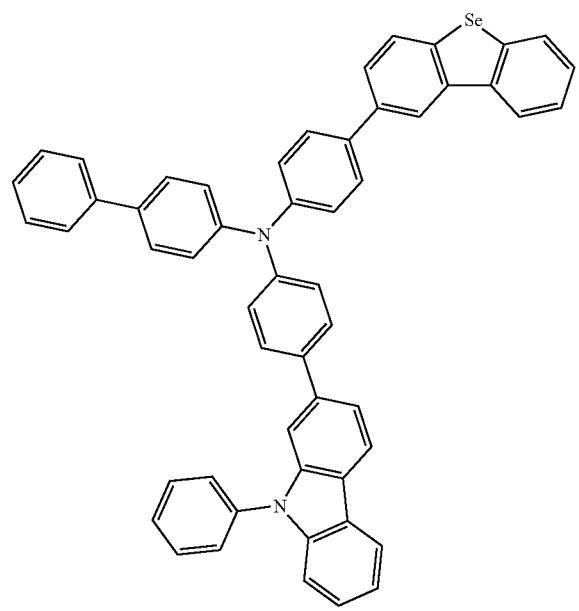

-continued
212
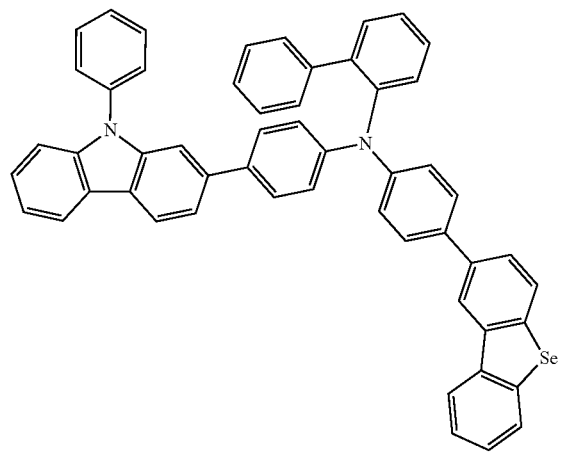
213
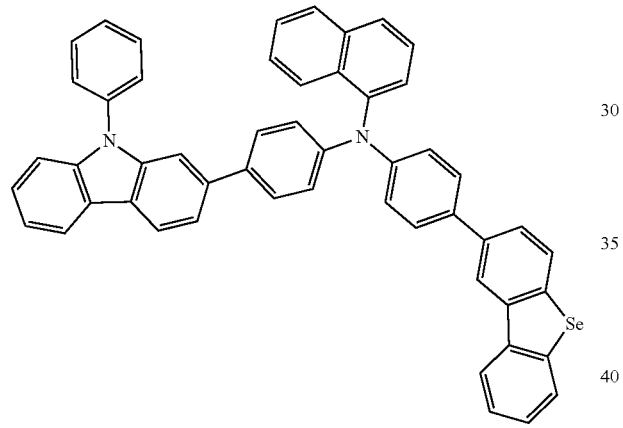
214
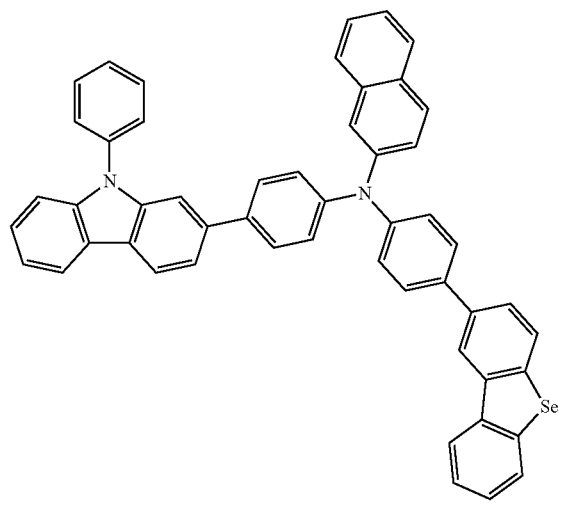
-continued
215
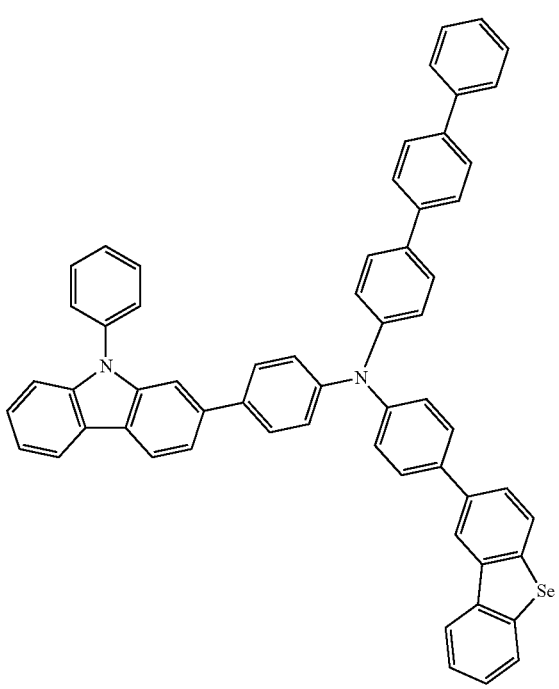
216
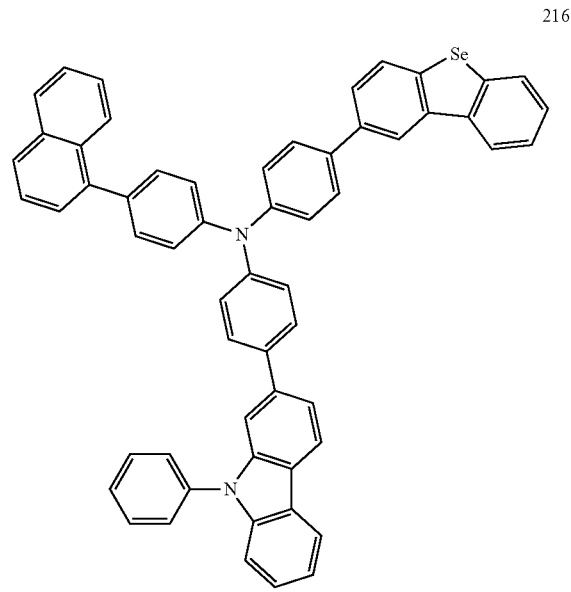

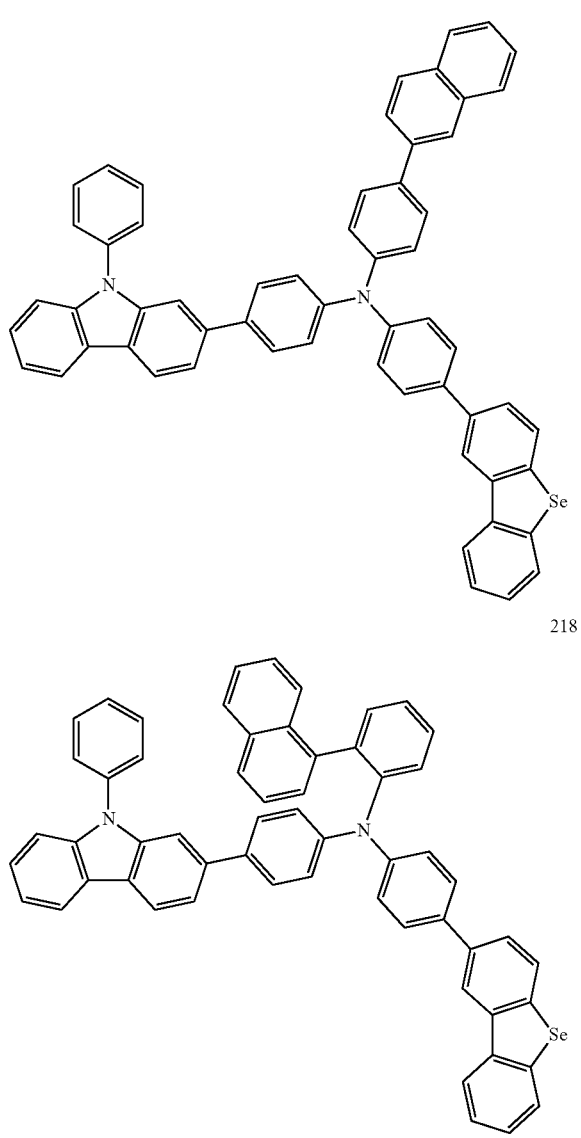
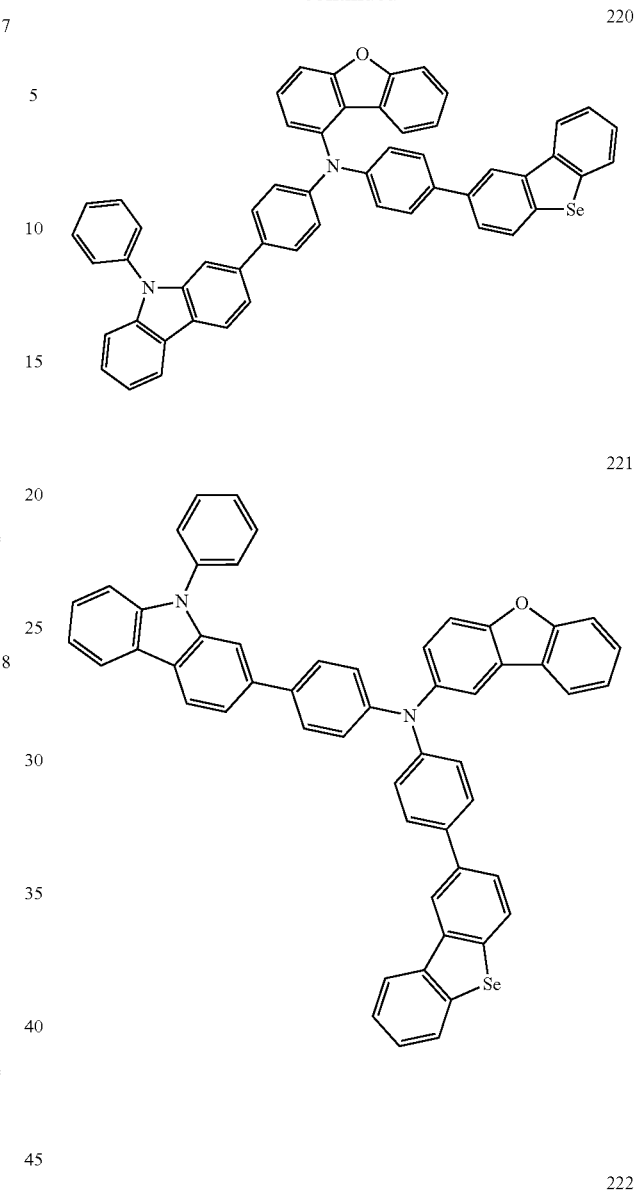
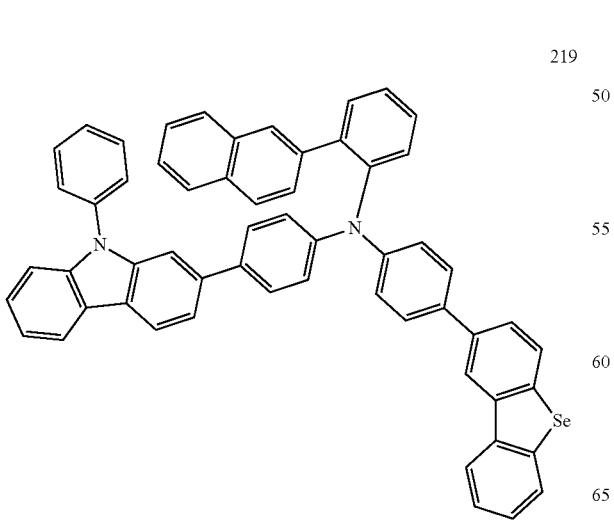

193
-continued
223
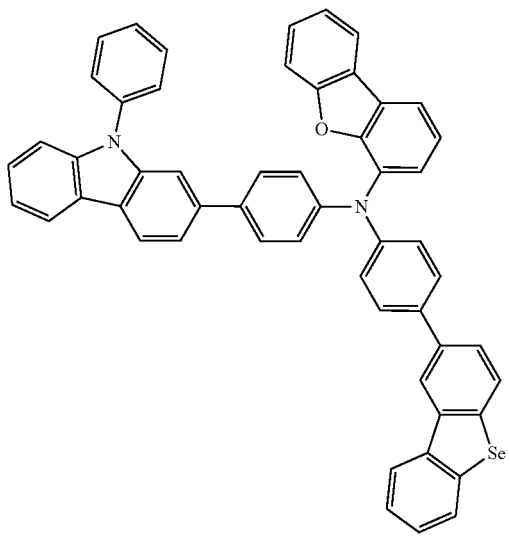
224
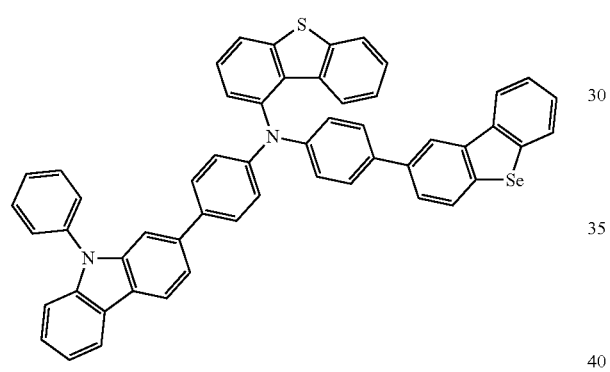
225
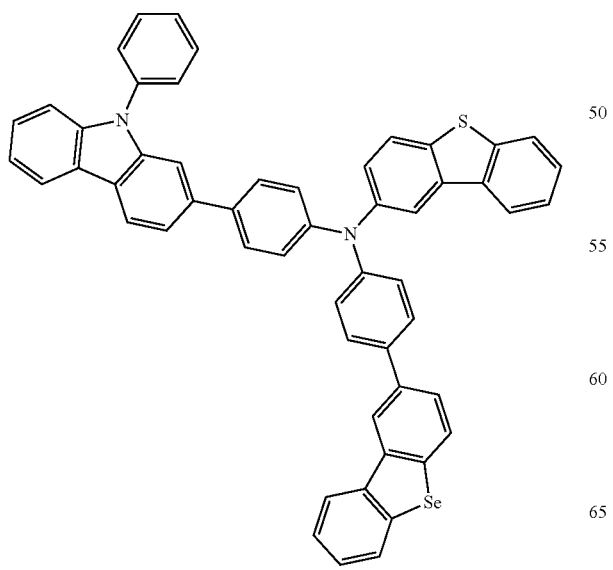
194
-continued
226
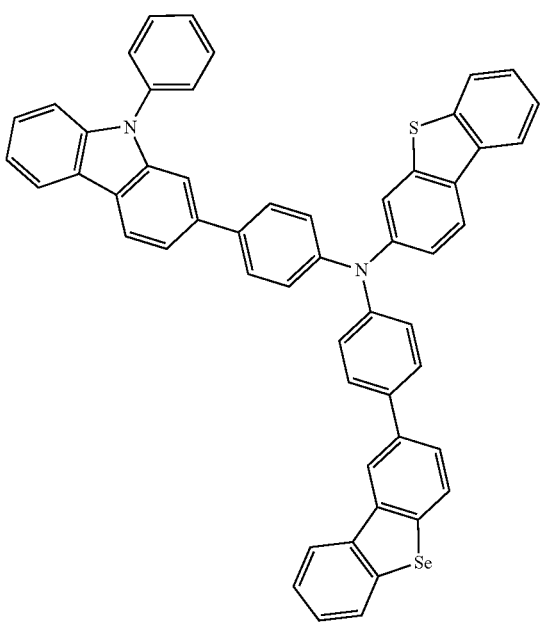
227
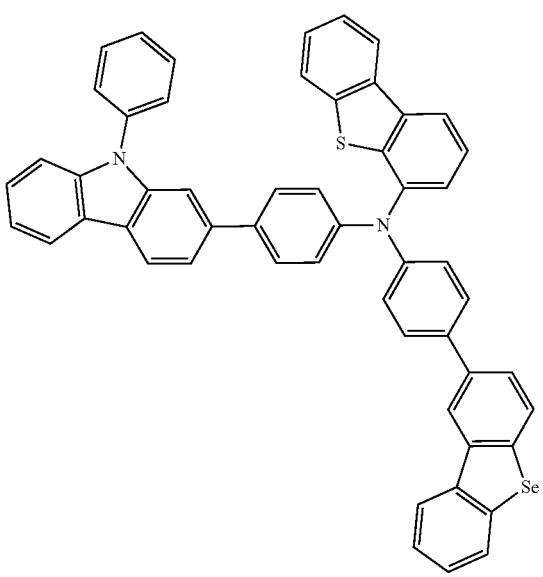

-continued
228
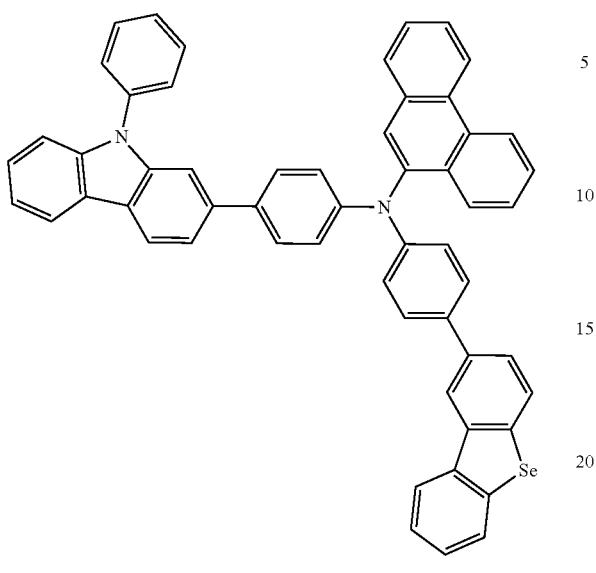
229
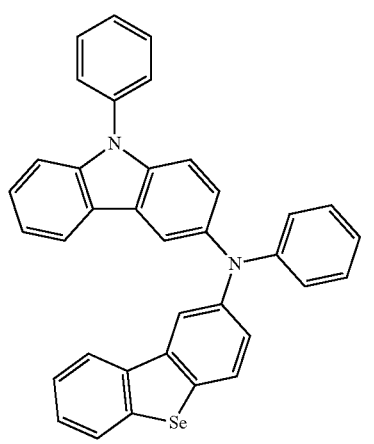
230
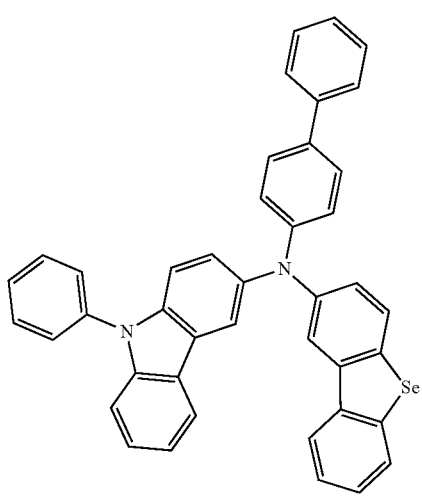
-continued
231
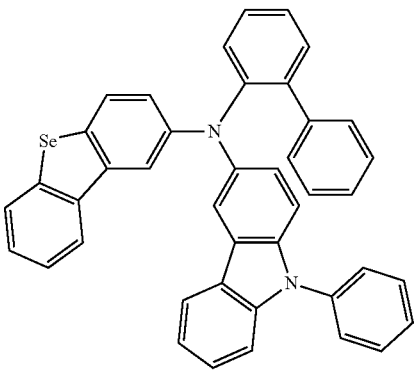
232
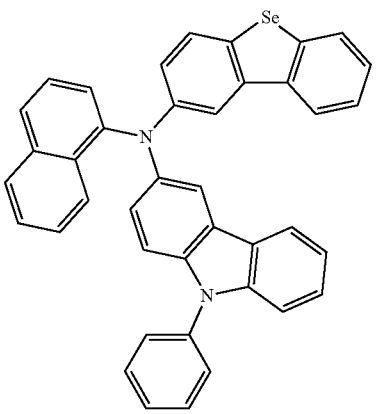
233
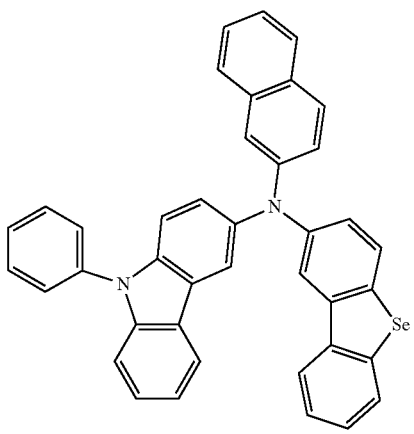

234
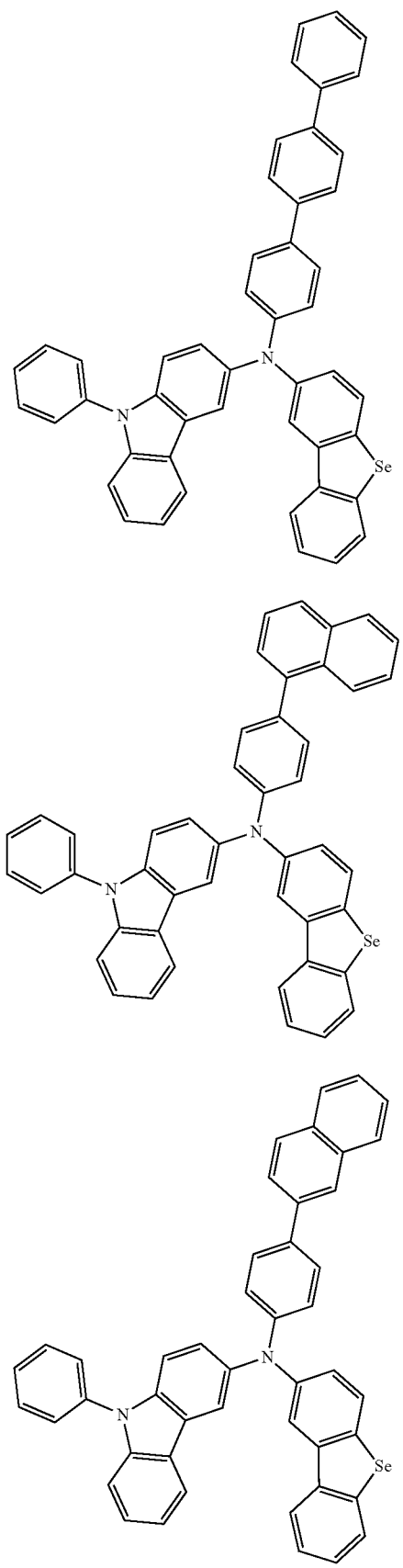
235
236
237
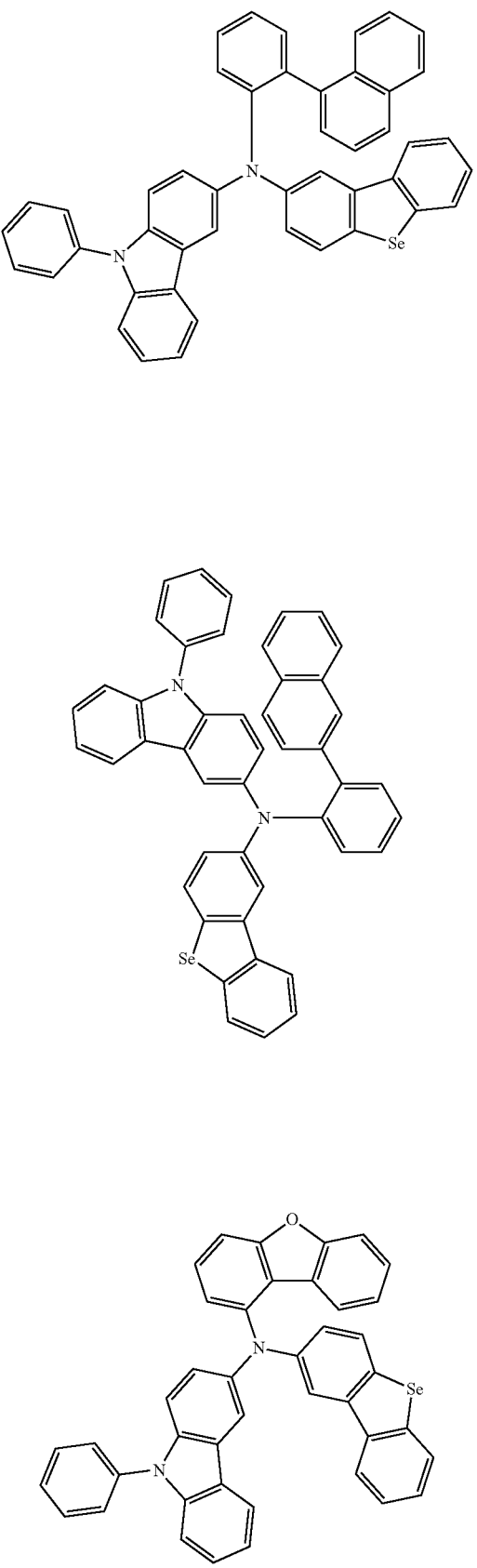
238
239

-continued

240

241

242

-continued

243

244

245

246
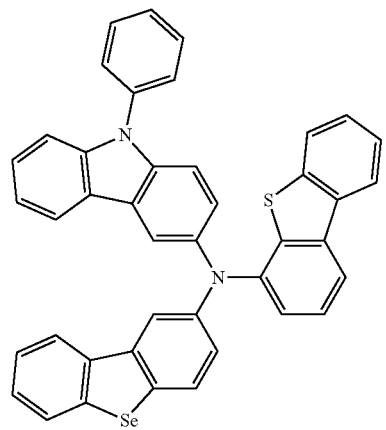
247
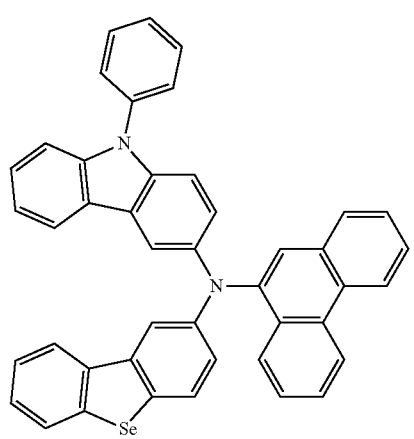
248
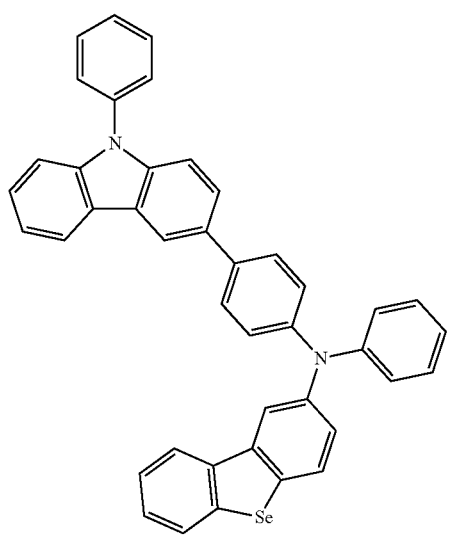
249
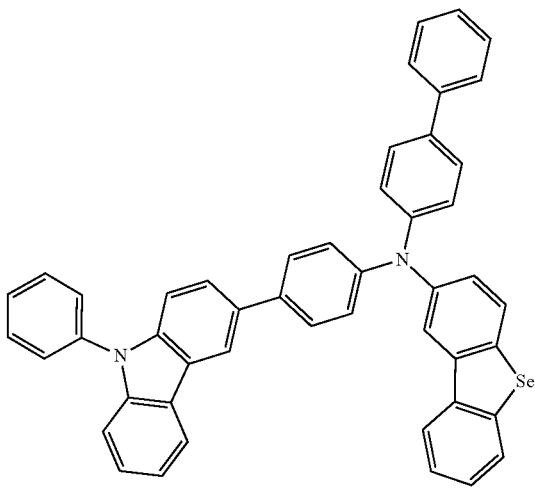
250
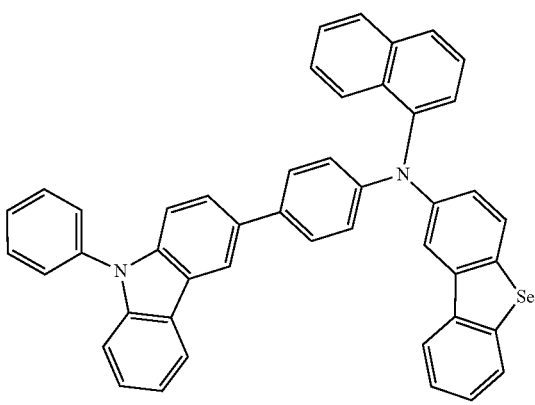
251

203
-continued
252
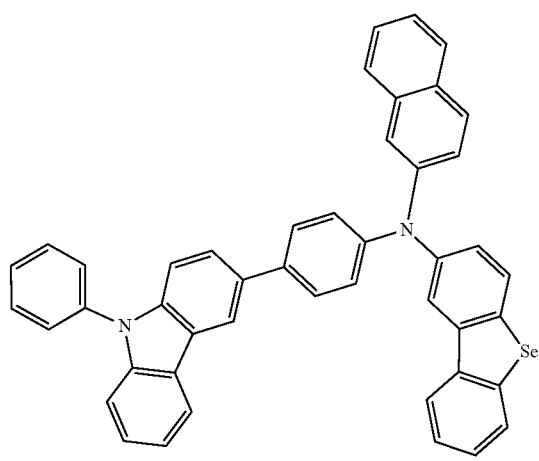
253
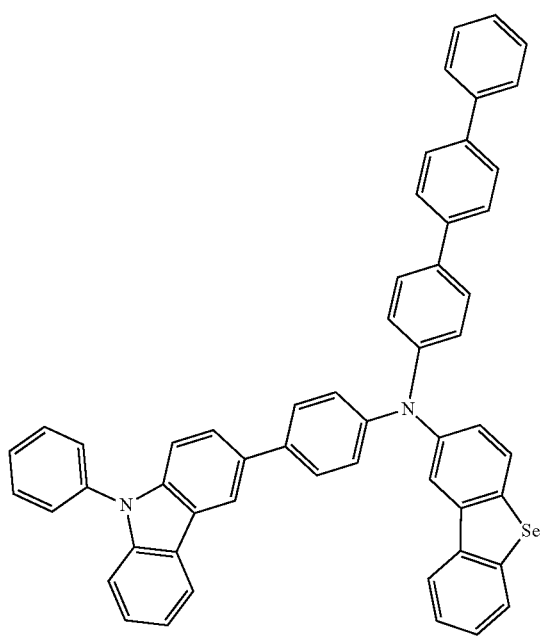
204
-continued
254
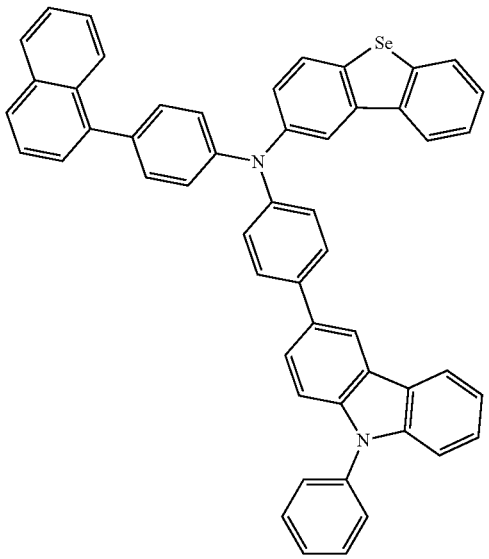
255
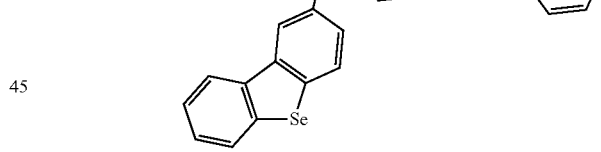
256
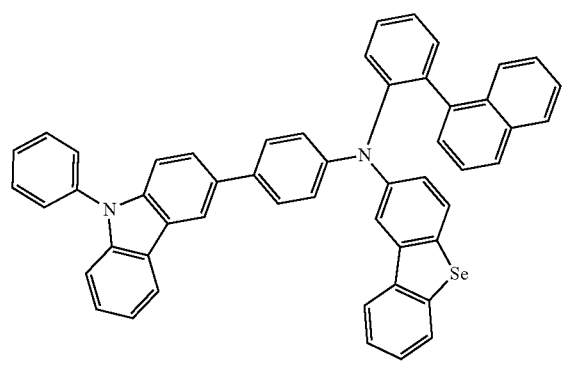

205
-continued
257
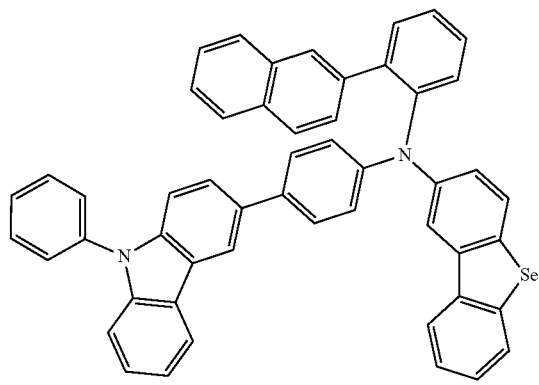
258
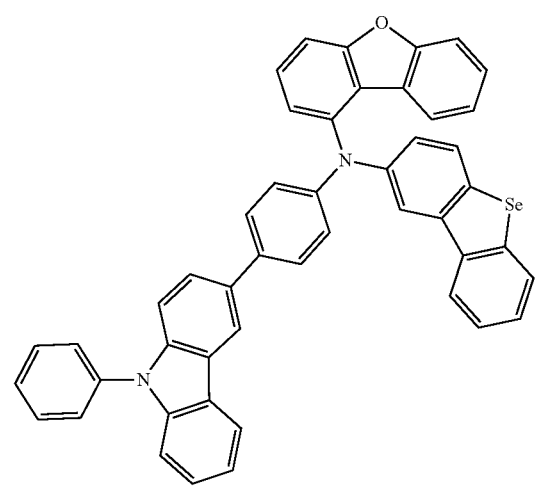
259
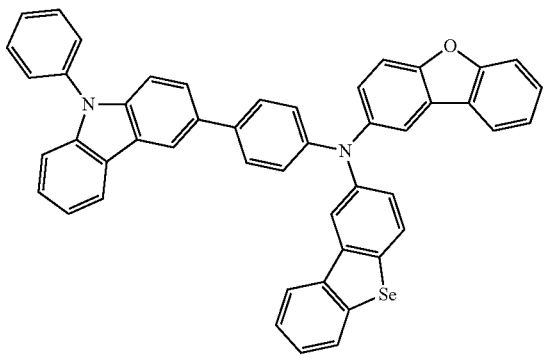
206
-continued
260
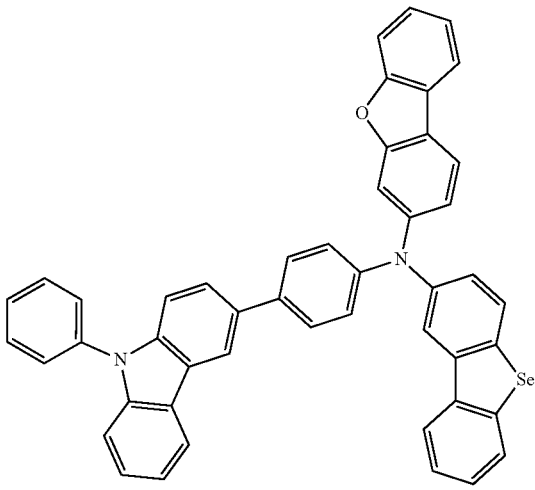
261
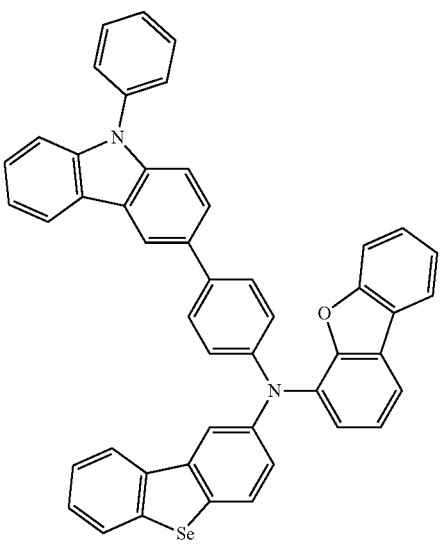
262
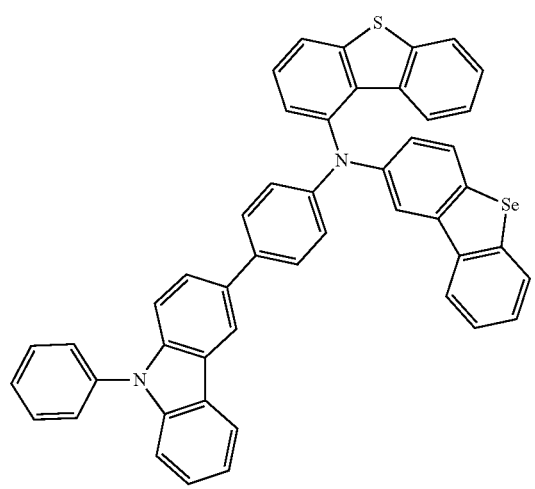

263
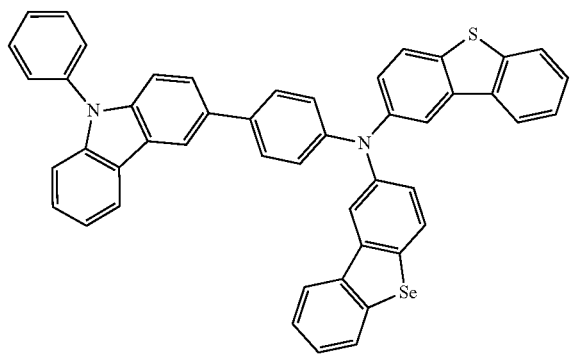
264
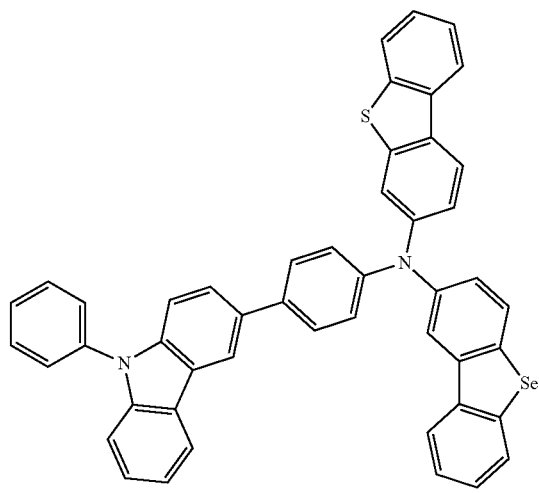
265
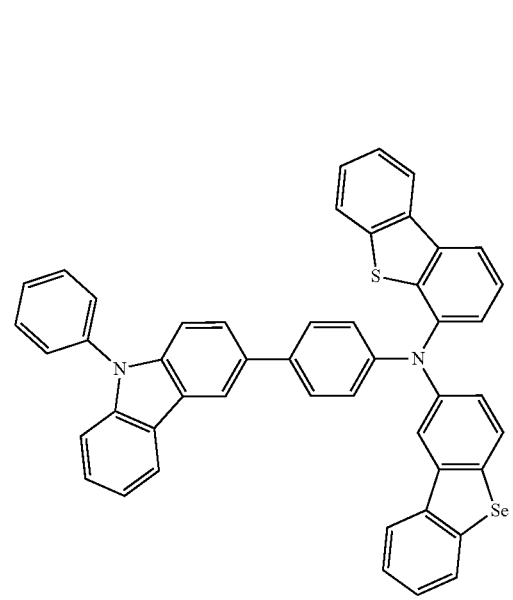
266
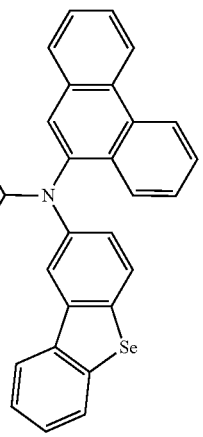
267
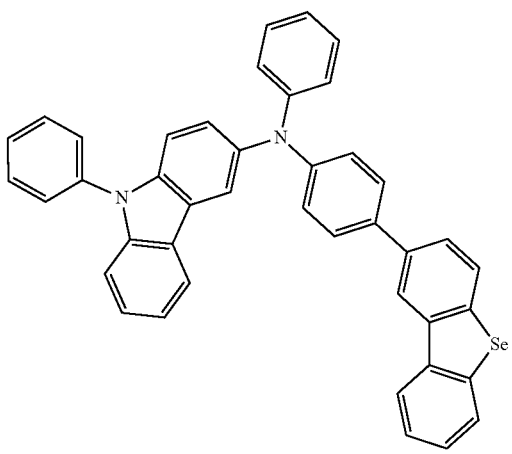
268
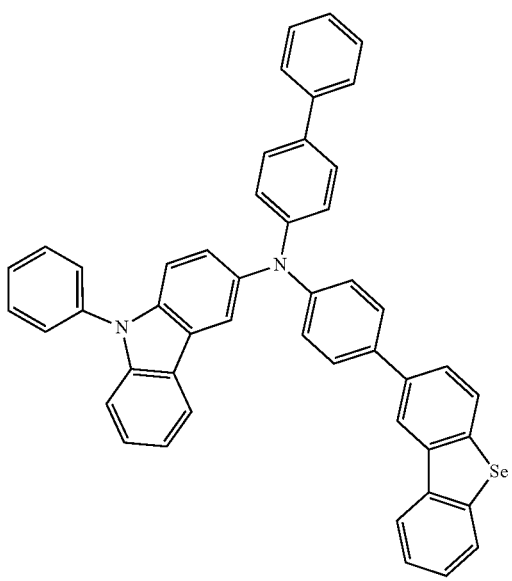

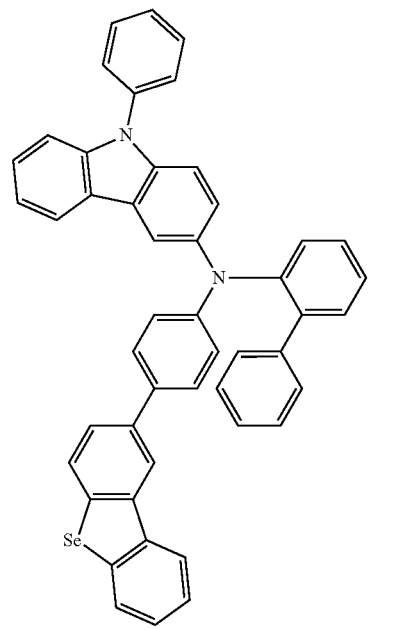
269
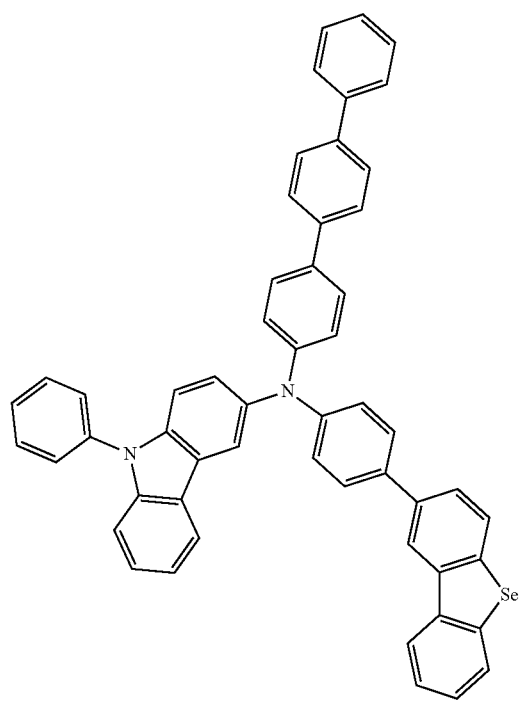
272
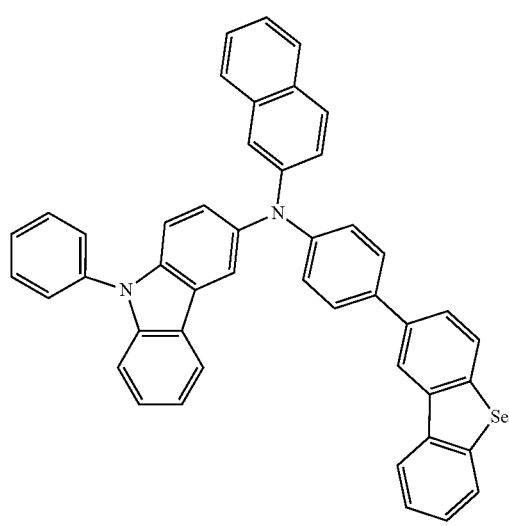
270
271
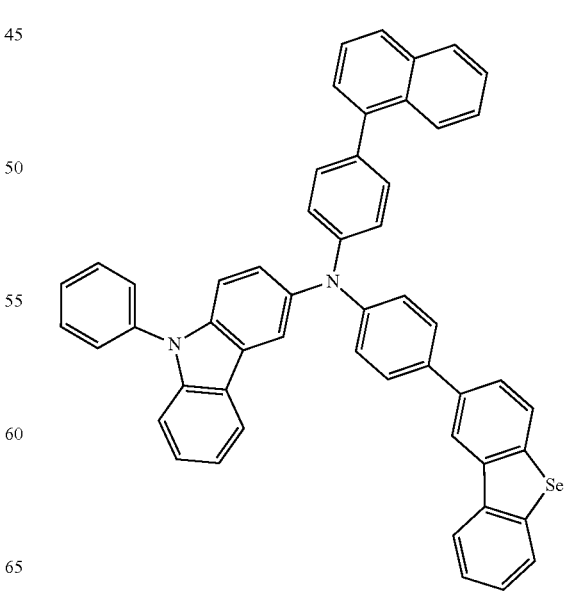
273

211
-continued
274
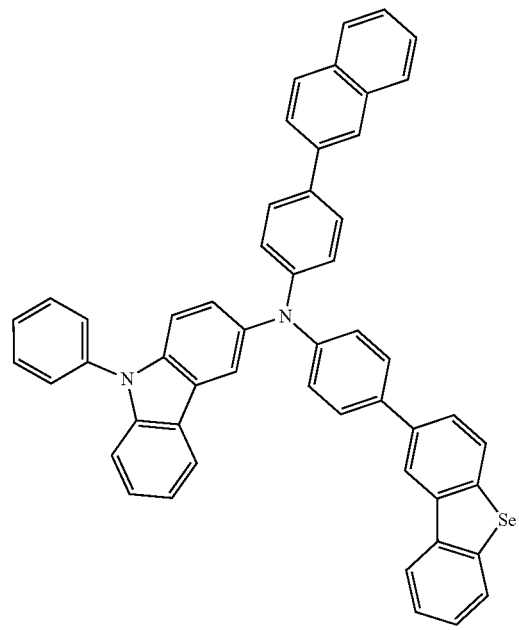
275
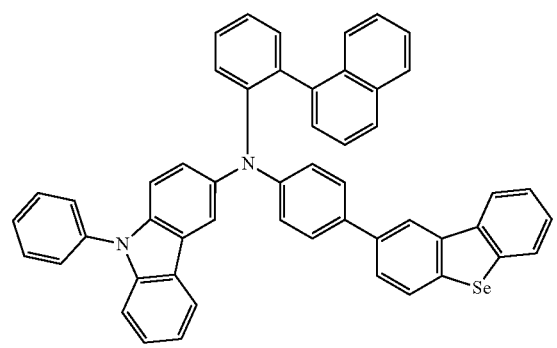
276
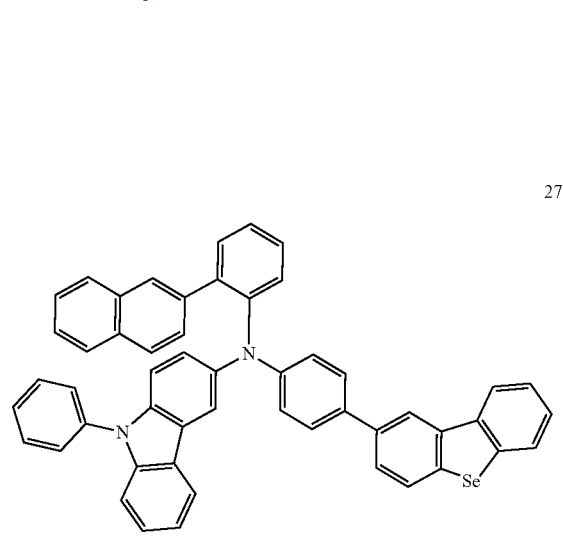
212
-continued
277
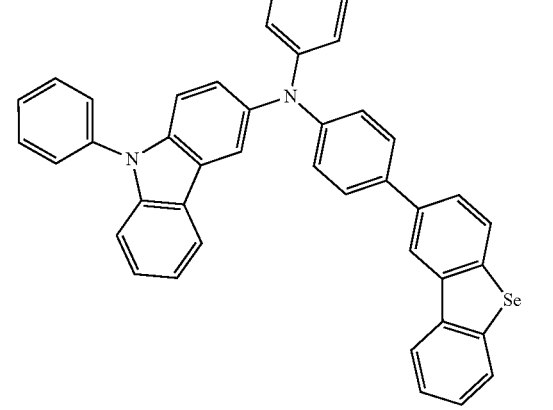
278
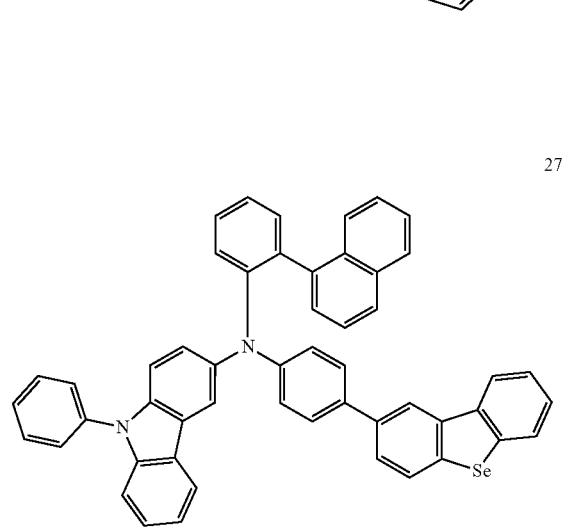
279
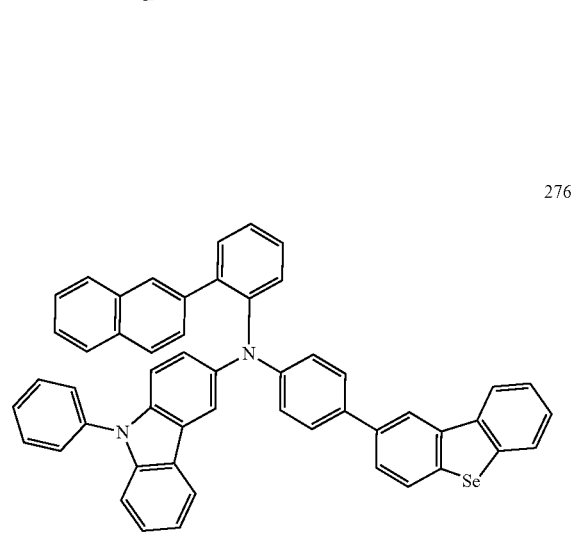

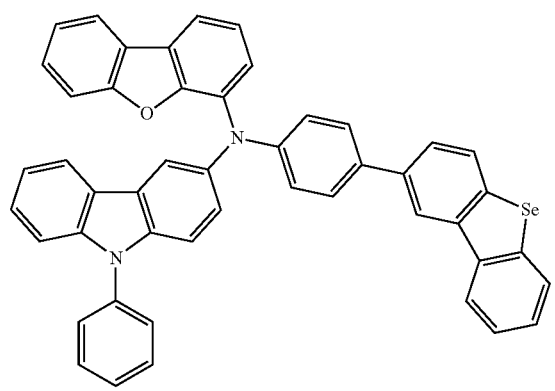
280
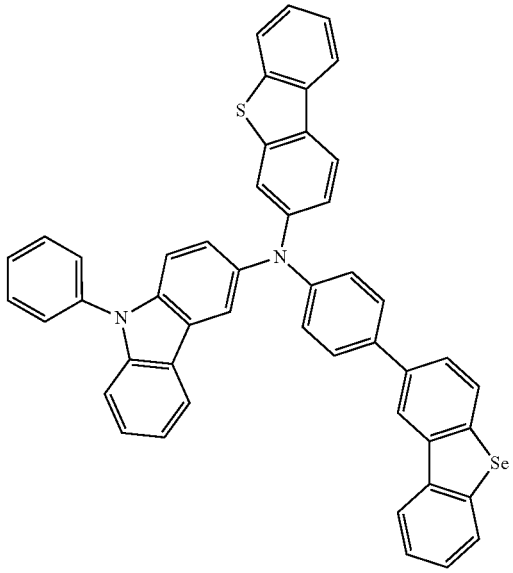
283
281
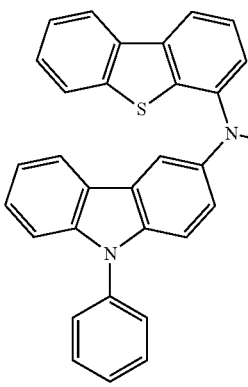
282
284
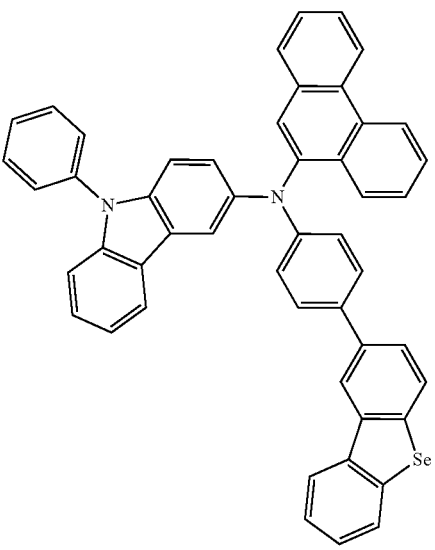
285

286
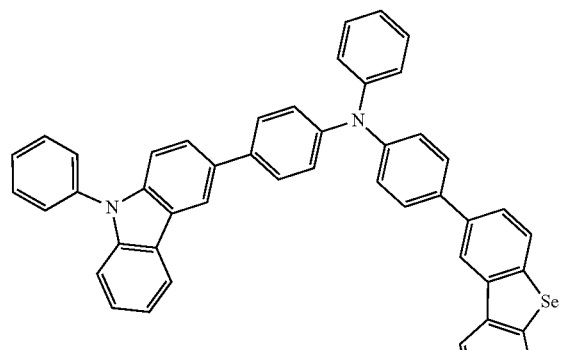
287
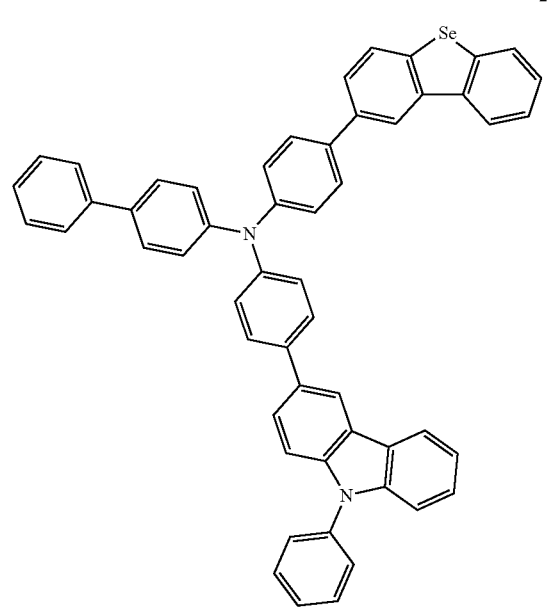
288
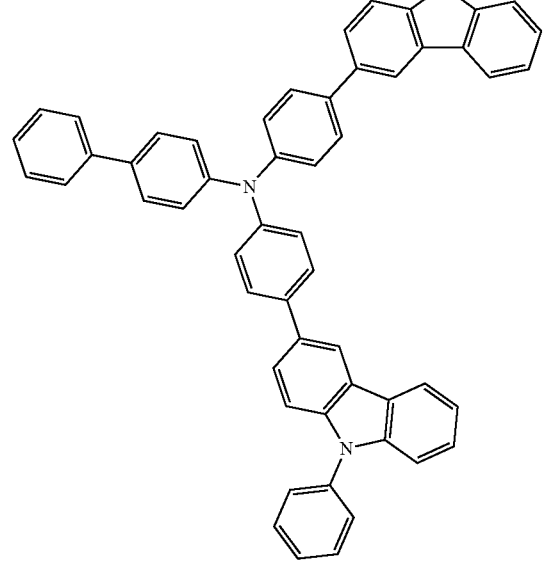
289
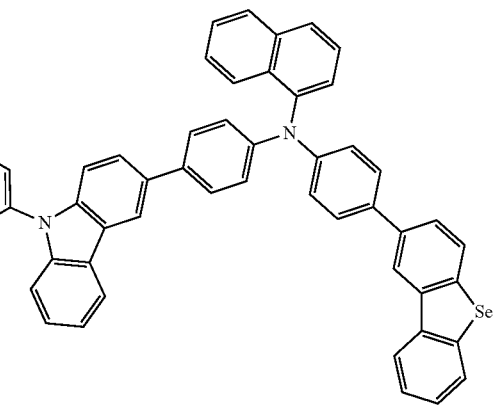
290
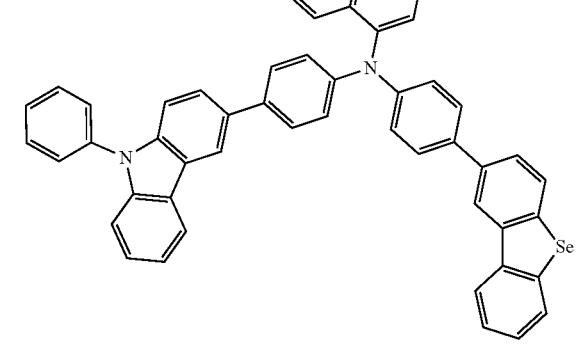
291
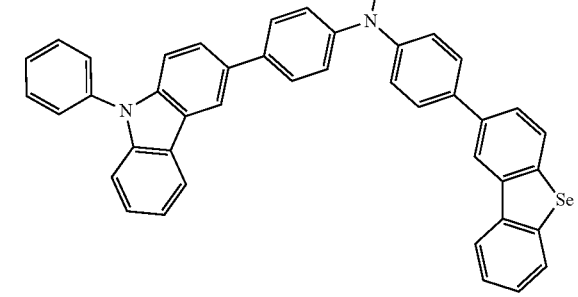

217
-continued
292
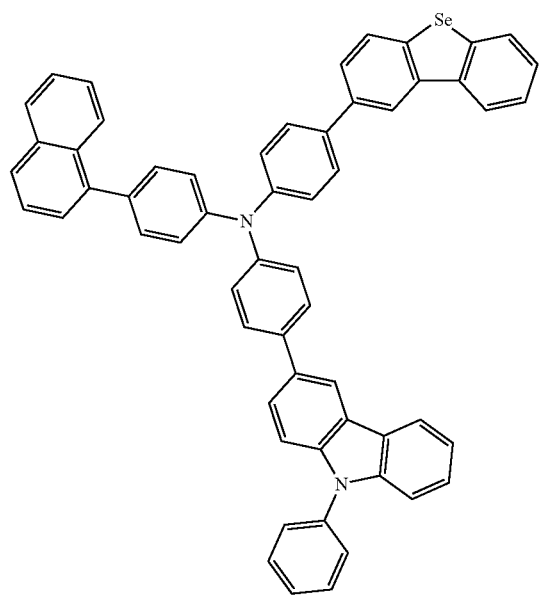
293
295
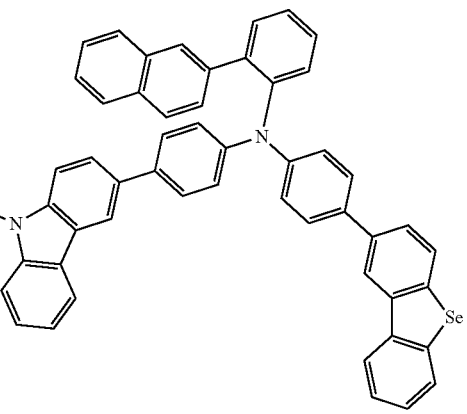
296
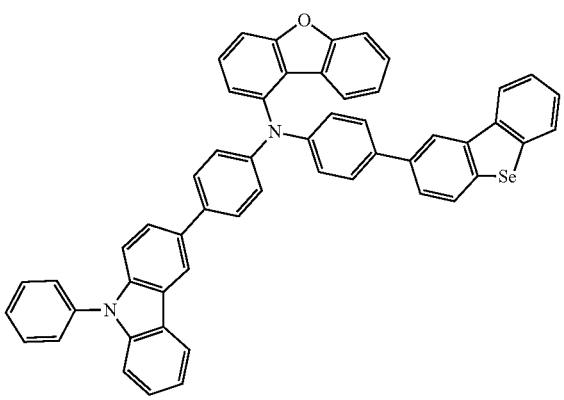
218
-continued
294
297
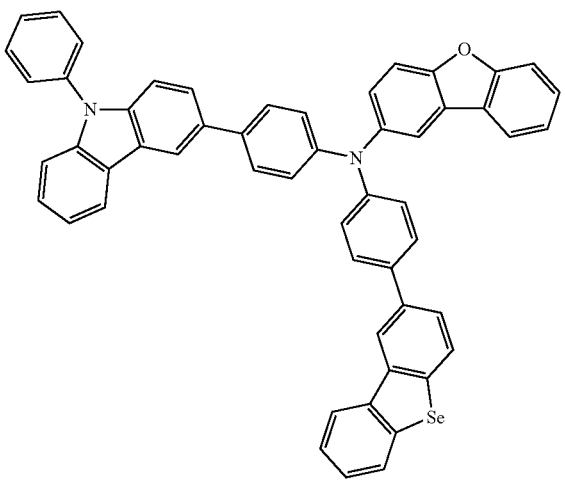

-continued
298
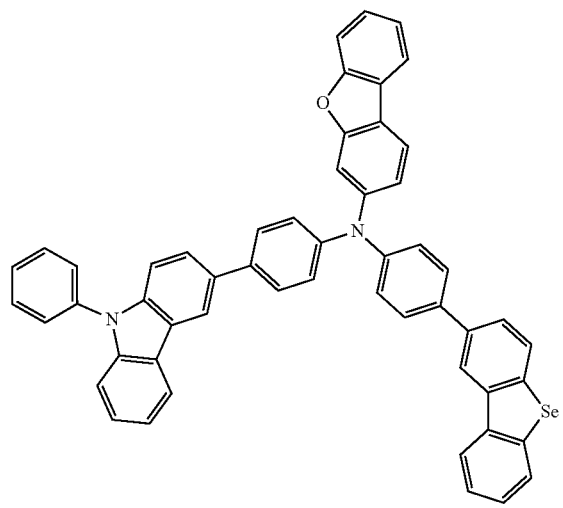
299
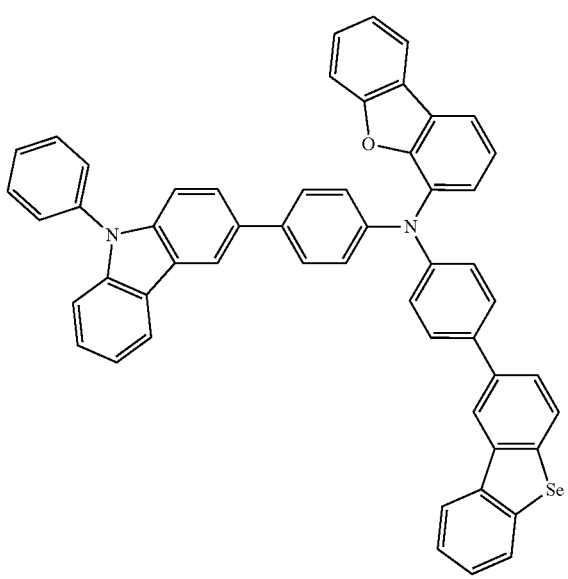
300
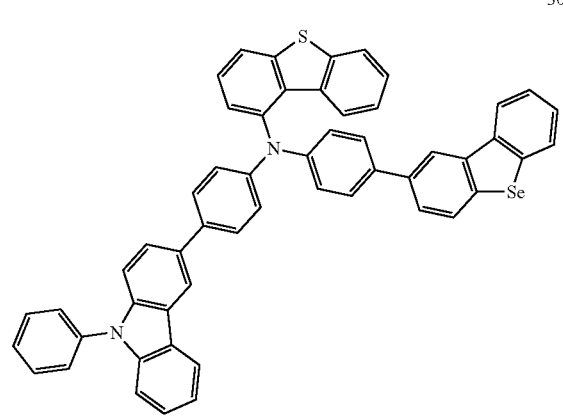
-continued
301
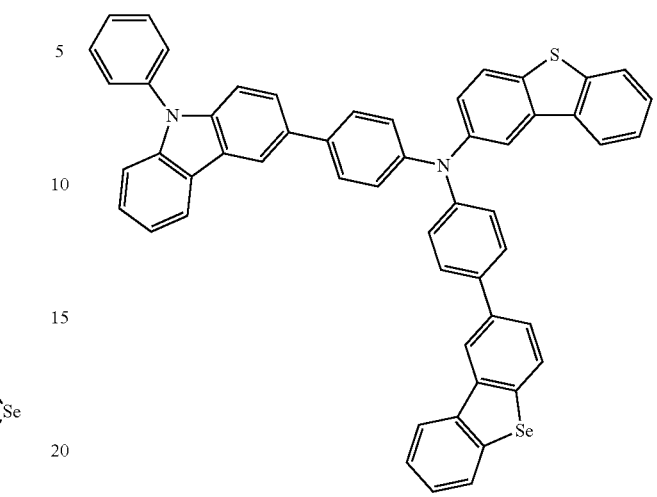
302
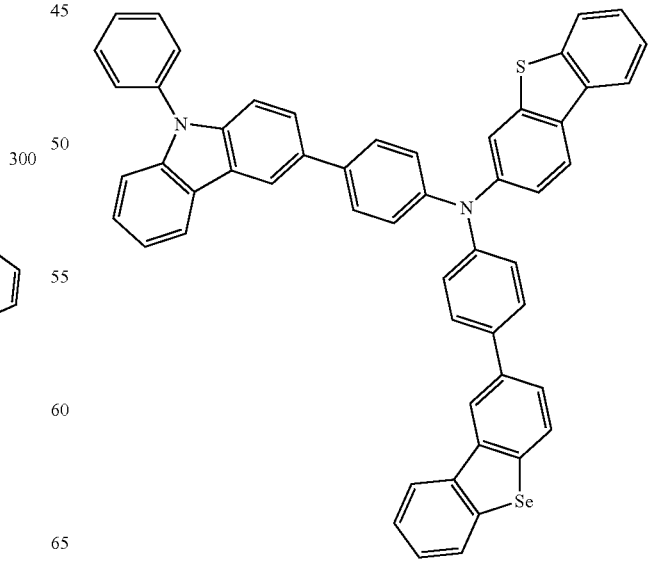

-continued

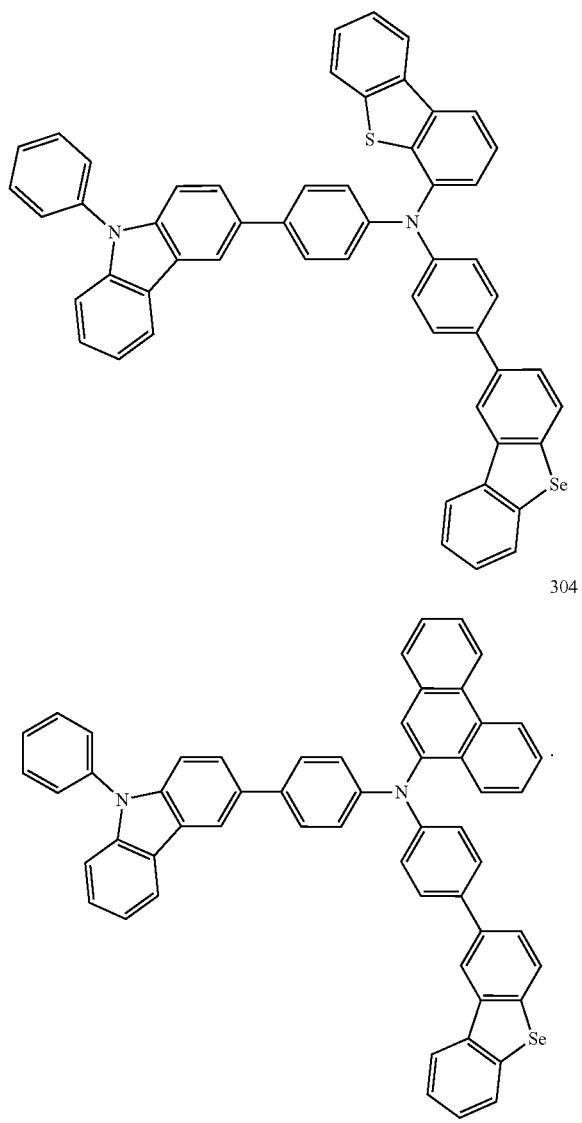

303

304

In the organic electroluminescence device 10 of an embodiment illustrated in FIGS. 1 to 4, the hole transport region HTR may include the amine compound represented by Formula 1 as a material. In some embodiments, the hole transport layer HTL or the hole injection layer HIL may include the amine compound represented by Formula 1 as a material. In some embodiments, the hole transport layer HTL may include the amine compound represented by Formula 1 as a hole transport material. However, the embodiment is not limited thereto.

The hole transport region HTR may include one kind (e.g., type) or two or more kinds (e.g., types) of the amine compounds of Formula 1 (e.g., the amine compounds in the Compound Group 1 described above). The hole transport region HTR may further include any suitable material in addition to the amine compound described above.

The hole injection layer HIL may include, for example, a phthalocyanine compound (such as copper phthalocyanine); N,N'-diphenyl-N,N'-bis-[4-(phenyl-m-tolyl-amino)-phenyl]-biphenyl-4,4'-diamine (DNTPD), 4,4',4''-[tris(3-methylphenyl)phenylamino]triphenylamine] (m-MTDATA), 4,4',4''-tris(N,N-diphenylamino)triphenylamine (TDATA), 4,4',4''-tris{N,-(2-naphthyl)-N-phenylamino)-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(naphthalene-1-yl)-N,N'-diphenyl-benzidine (NPB), triphenylamine-containing polyetherketone (TPAPEK), 4-isopropyl-4'-methyldiphenyliodonium tetrakis(pentafluorophenyl)borate, dipyrazino[2,3-f: 2',3'-h]quinoxaline-2,3,6,7,10,11X-hexacarbonitrile (HAT-CN), etc.

The hole transport layer HTL, for example, may include carbazole derivatives (such as N-phenyl carbazole and/or polyvinyl carbazole), fluorine derivatives, N,N'-bis(3-methylphenyl)-N,N'-diphenyl-[1,1-biphenyl]-4,4'-diamine (TPD), triphenylamine (derivatives such as 4,4',4''-tris(N-carbazolyl)triphenylamine (TCTA)), N,N'-di(1-naphtalene-1-yl)-N,N'-diphenyl-benzidine (NPB), 4,4'-cyclohexylidene bis[N,N-bis(4-methylphenyl]benzenamine] (TAPC), 4,4'-bis[N,N'-(3-tolyl)amino]-3,3'-dimethylbiphenyl (HMTPD), 1,3-bis(N-carbazolyl)benzene (mCP), etc.

The thickness of the hole transport region HTR may be from about 100 Å to about 10,000 Å, for example, from about 100 Å to about 5,000 Å. The thickness of the hole injection region HIL may be, for example, from about 30 Å to about 1,000 Å, and the thickness of the hole transport layer HTL may be from about 30 Å to about 1,000 Å. For example, the thickness of the electron blocking layer EBL may be from about 10 Å to about 1,000 Å. If the thicknesses of the hole transport region HTR, the hole injection layer HIL, the hole transport layer HTL and the electron blocking layer EBL respectively satisfy the above-described ranges, satisfactory (or suitable) hole transport properties may be achieved without a substantial increase in driving voltage.

The hole transport region HTR may further include, in addition to the above-described materials, a charge generating material to increase conductivity. The charge generating material may be dispersed uniformly or non-uniformly in the hole transport region HTR. The charge generating material may be, for example, a p-dopant. The p-dopant may be one of quinone derivatives, metal oxides, or cyano group-containing compounds, but is not limited thereto. For example, non-limiting examples of the p-dopant may include quinone derivatives (such as tetracyanoquinodimethane (TCNQ) and/or 2,3,5,6-tetrafluoro-7,7,8,8-tetracyanoquinodimethane (F4-TCNQ)), metal oxides (such as tungsten oxide and/or molybdenum oxide), etc., but are not limited thereto.

As described above, the hole transport region HTR may further include at least one of a hole buffer layer or an electron blocking layer EBL, in addition to the hole injection layer HIL and the hole transport layer HTL. The hole buffer layer, may compensate a resonance distance according to the wavelength of light emitted from an emission layer EML and may increase light emission efficiency. Materials which may be included in the hole transport region HTR may be used as materials included in the hole buffer layer. The electron blocking layer EBL is a layer that serves to prevent or reduce electrons from being injected from the electron transport region ETR to the hole transport region HTR.

The emission layer EML is provided on the hole transport region HTR. The thickness of the emission layer EML may be, for example, from about 100 Å to about 1000 Å, for example, from about 100 Å to about 300 Å. The emission layer EML may have a single layer formed of a single material, a single layer formed of a plurality of different materials, or a multilayer structure having a plurality of layers formed of a plurality of different materials.

In the organic electroluminescence device 10 of an embodiment, the emission layer EML may include an anthracene derivative, a pyrene derivative, a fluoranthene derivative, a chrysene derivative, a dihydrobenzanthracene derivative, or a triphenylene derivative. In some embodiments, the emission layer EML may include an anthracene derivative or a pyrene derivative.

The emission layer EML may include an anthracene derivative represented by Formula 4 below.

Formula 4

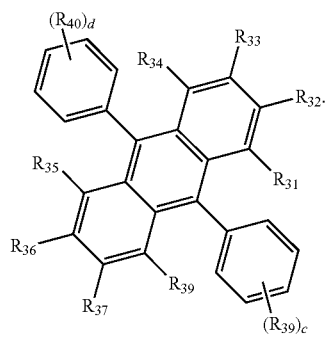

In the Formula, $R_{31}$ to $R_{40}$ may be each independently a hydrogen atom, a deuterium atom, a halogen atom, a substituted or unsubstituted silyl group, a substituted or unsubstituted alkyl group having 1 to 10 carbon atoms, a substituted or unsubstituted aryl group having 6 to 30 ring-forming carbon atom, or a substituted or unsubstituted heteroaryl group having 2 to 30 ring-forming carbon atoms, and/or may be bonded to an adjacent group to form a ring. For example, any of $R_{31}$ to $R_{40}$ may be bonded to an adjacent group to form a saturated hydrocarbon ring or an unsaturated hydrocarbon ring.

In Formula 4, c and d may be each independently an integer of 0 to 5.

Formula 4 may be represented by any one of Compounds 4-1 to 4-16 below.

4-1

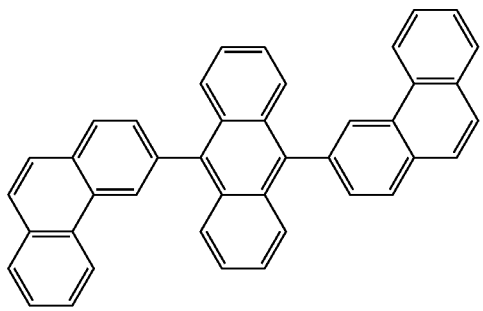

4-2

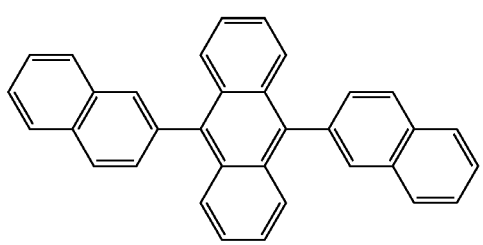

4-3

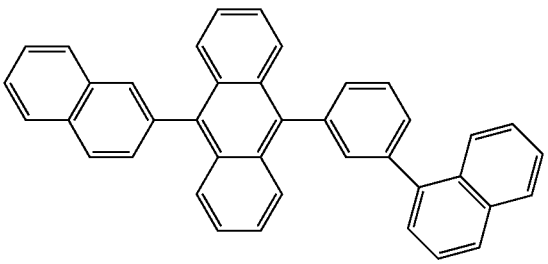

4-4

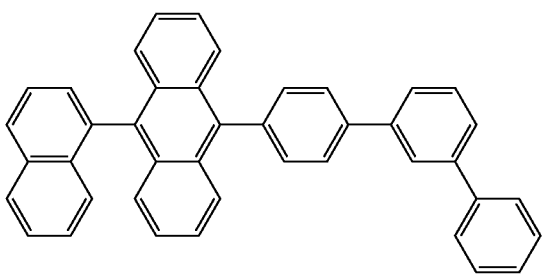

4-5

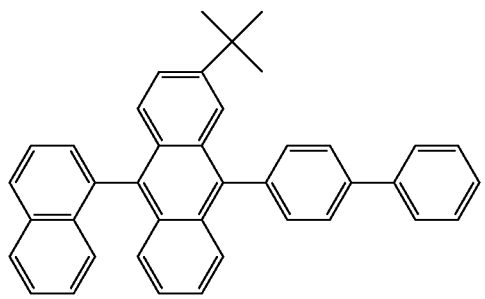

4-6

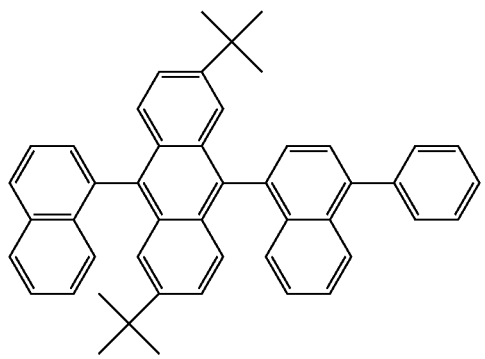

4-7

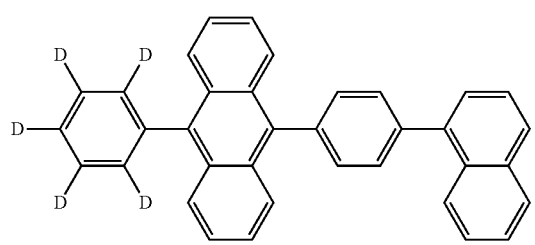

4-8
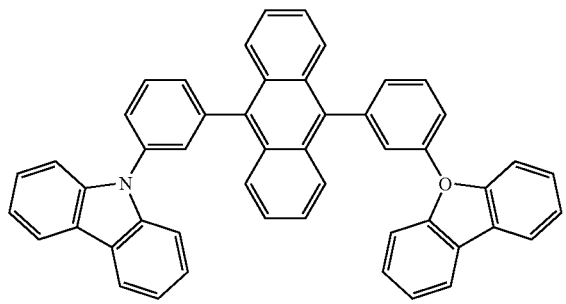

4-9
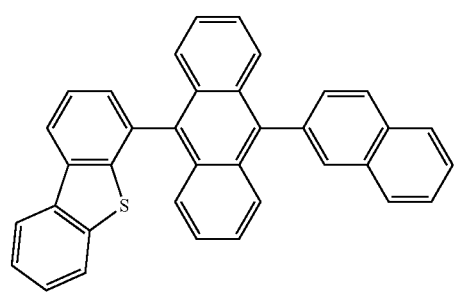

4-10
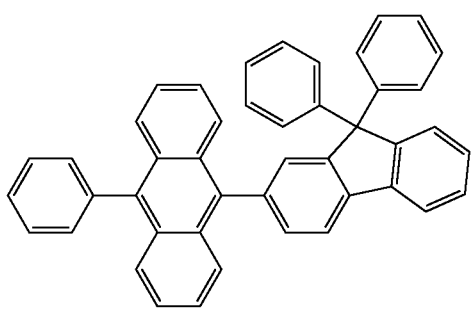

4-11
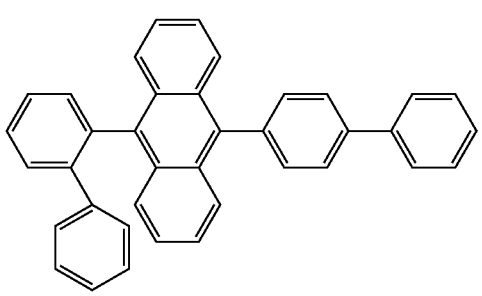

4-12
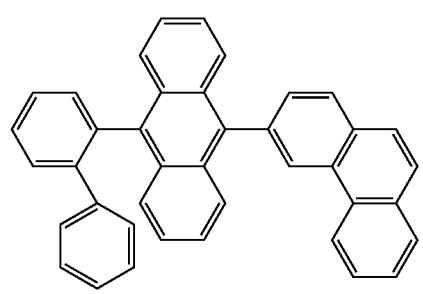

4-13
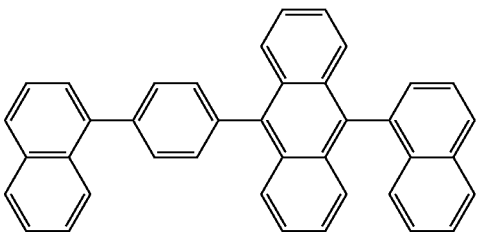

4-14
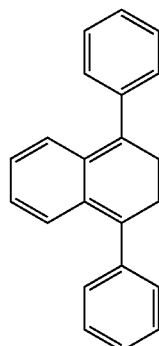

4-15
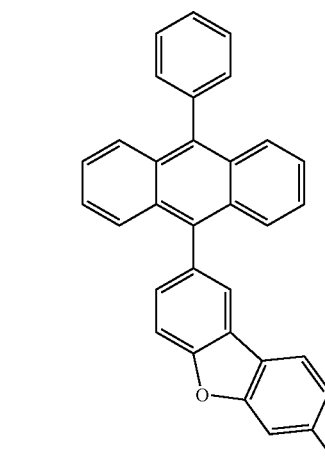

4-16
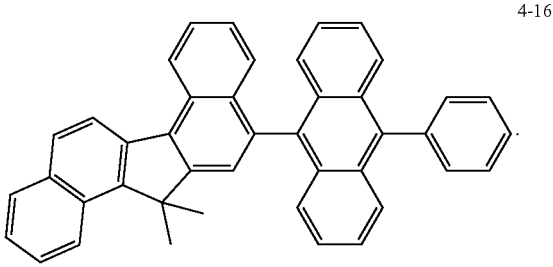

The emission layer EML may include any suitable host material as a host. For example, the emission layer EML may include at least one of bis[2-(diphenylphosphino)phenyl]ether oxide (DPEPO), 4,4'-bis(N-carbazolyl)-1,1'-biphenyl (CBP), 1,3-bis(carbazolyl-9-yl)benzene (mCP), 2,8-Bis(diphenylphosphoryl)dibenzo[b,d]furan (PPF), 4,4',4"-tris(carbazol-9-yl)-triphenylamine (TcTa), or 1,3,5-tris(1-phenyl-1H-benzo[d]imidazol-2-yl) benzene (TPBi). However, the embodiment is not limited thereto and, for example, tris(8-hydroxyquinolino)aluminum (Alq3), poly(N-vinylcarbazole) (PVK), 9,10-di(naphthalene-2-yl)anthracene (ADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), hexaphenyl cyclotriphosphazene (CP1), 1,4-bis(triphenylsilyl)benzene (UGH2), hexaphenylcyclotrisiloxane (DPSiO$_3$), octaphenylcyclotetrasiloxane (DPSiO$_4$), etc. as a host material.

In an embodiment, the emission layer EML may include styryl derivatives (e.g., 1,4-bis[2-(3-N-ethylcarbazoryl)vinyl]benzene (BCzVB), 4-(di-p-tolylamino)-4''-[(di-p-tolylamino)styryl]stilbene (DPAVB), and/or N-(4-((E)-2-(6-((E)-4-(diphenylamino)styryl)naphthalen-2-yl)vinyl) phenyl)-N-phenylbenzenamine (N-BDAVBi)), perylene and/or the derivatives thereof (e.g., 2,5,8,11-tetra-t-butylperylene (TBP)), pyrene and/or the derivatives thereof (e.g., 1,1-dipyrene, 1,4-dipyrenylbenzene, and/or 1,4-bis(N,N-diphenylamino)pyrene), etc. as a dopant material.

The emission layer EML may include the amine compound of an embodiment and any suitable phosphorescent dopant material. For example, a metal complex including iridium (Ir), platinum (Pt), osmium (Os), gold (Au), titanium (Ti), zirconium (Zr), hafnium (Hf), europium (Eu), terbium (Tb), or thulium (Tm) may be used as a phosphorescent dopant. In some embodiments, iridium (III)bis(4,6-difluorophenylpyridinato-N,C2' (FIrpic), bis(2,4-difluorophenylpyridinato) (Fir6), and/or platinum octaethyl porphyrin (PtOEP) may be used as a phosphorescent dopant. However, the embodiment is not limited thereto.

In some embodiments, the emission layer EML may further include any suitable phosphorescent host material, for example, BCPDS(bis(4-(9H-carbazol-9-yl)phenyl)diphenylsilane).

When the emission layer EML emits red light, the emission layer EML may further include, for example, a fluorescent material including PBD:Eu (DBM)$_3$(Phen)(tris (dibenzoylmethanato)phenanthoroline europium) and/or perylene. When the emission layer EML emits red, a dopant included in the emission layer EML may be, for example, a metal complex such as bis(1-phenylisoquinoline) acetylacetonate iridium (PIQIr(acac)), bis(1-phenylquinoline) acetylacetonate iridium (PQIr(acac)), tris(1-phenylquinoline) iridium (PQIr) and/or octaethylporphyrin platinum (PtOEP), an organometallic complex, rubrene and/or derivatives thereof, and/or 4-dicyanomethylene-2-(p-dimethylaminostyryl)-6-methyl-4H-pyran (DCM) and/or derivatives thereof.

When the emission layer EML emits green light, the emission layer EML may further include a fluorescent material including, for example, tris(8-hydroxyquinolino) aluminum (Alq3). When the emission layer EML emits green, a dopant included in the emission layer EML may be, for example, a metal complex (such as fac-tris(2-phenylpyridine) iridium (Ir(ppy)$_3$)), an organometallic complex, and/or coumarin and/or one or more derivatives thereof.

When the emission layer EML emits blue light, the emission layer EML may further include, for example, a fluorescent material including any one selected from the group consisting of spiro-DPVBi (spiro-DPVBi), spiro-6P (spiro-6P), distyryl-benzene (DSB), distyryl-arylene (DSA), polyfluorene-based polymer (PFO), and poly(p-phenylene vinylene)-based polymer (PPV). When the emission layer EML emits blue, a dopant included in the emission layer EML may be, for example, a metal complex (such as (4,6-F2ppy)$_2$Irpic), an organometallic complex, perylene and/or one or more derivatives thereof.

In the organic electroluminescence device 10 of an embodiment illustrated in FIGS. 1 to 4, the electron transport region ETR is provided on the emission layer EML. The electron transport region ETR may include at least one of a hole blocking layer HBL, an electron transport layer ETL, or an electron injection layer EIL, but the embodiment is not limited thereto.

The electron transport region ETR may have a single layer formed of a single material, a single layer formed of a plurality of different materials, or a multilayer structure including a plurality of layers formed of a plurality of different materials.

For example, the electron transport region ETR may have a single layer structure of an electron injection layer EIL or an electron transport layer ETL, and may have a single layer structure formed of an electron injection material and an electron transport material. In some embodiments, the electron transport region ETR may have a single layer structure formed of a plurality of different materials, or may have a structure in which an electron transport layer ETL/electron injection layer EIL, or a hole blocking layer HBL/electron transport layer ETL/electron injection layer EIL are stacked in the stated order from the emission layer EML, but is not limited thereto. The thickness of the electron transport region ETR may be, for example, from about 1,000 Å to about 1,500 Å.

The electron transport region ETR may be formed using one or more suitable methods such as a vacuum deposition method, a spin coating method, a cast method, a Langmuir-Blodgett (LB) method, an inkjet printing method, a laser printing method, a laser induced thermal imaging (LITI) method, etc.

When the electron transport region ETR includes the electron transport layer ETL, the electron transport region ETR may include an anthracene-based compound. However, the present disclosure is not limited thereto, and the electron transport region may include, for example, tris(8-hydroxyquinolinato)aluminum (Alq3), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d] imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), berylliumbis(benzoquinolin-10-olate (Bebq$_2$), 9,10-di(naphthalene-2-yl)anthracene (ADN), or a mixture thereof. The thickness of the electron transport layer ETL may be from about 100 Å to about 1,000 Å and may be, for example, from about 150 Å to about 500 Å. If the thickness of the electron transport layer ETL satisfies the above-described range, satisfactory (or suitable) electron transport properties may be obtained without a substantial increase in driving voltage.

When the electron transport region ETR includes the electron injection layer EIL, the electron transport region ETR may include a halogenated metal (such as LiF, NaCl, CsF, RbCl, RbI, and/or CuI), a lanthanide metal (such as Yb), a metal oxide (such as Li$_2$O and/or BaO), and/or lithium quinolate (Liq), but is not limited thereto. The electron injection layer EIL may also be formed of a mixture material of an electron transport material and an insulating organo-metal salt. The organo-metal salt may be a material having an energy band gap of about 4 eV or more. In some embodiments, the organo-metal salt may include, for example, one or more of metal acetates, metal benzoates, metal acetoacetates, metal acetylacetonates, or metal stearates. The thickness of the electron injection layer EIL may be from about 1 Å to about 100 Å, for example, from about 3 Å to about 90 Å. If the thickness of the electron injection layer EIL satisfies the above-described range, satisfactory (or suitable) electron injection properties may be obtained without a substantial increase in driving voltage.

As described above, the electron transport region ETR may include a hole blocking layer HBL. The hole blocking layer HBL may include, for example, at least one of 2,9-dimethyl-4,7-diphenyl-1,10-phenanthroline (BCP) or 4,7-diphenyl-1,10-phenanthroline (Bphen), but is not limited thereto.

The second electrode EL2 is provided on the electron transport region ETR. The second electrode EL2 may be a common electrode and/or a cathode. The second electrode EL2 may be a transmissive electrode, a transflective electrode or a reflective electrode. If the second electrode EL2 is the transmissive electrode, the second electrode EL2 may include a transparent metal oxide, for example, indium tin oxide (ITO), indium zinc oxide (IZO), zinc oxide (ZnO), and/or indium tin zinc oxide (ITZO).

If the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (e.g., a mixture of Ag and Mg). In some embodiments, the second electrode EL2 may have a multilayer structure including a reflective film or a transflective film formed of any of the above-described materials, and a transparent conductive film formed of indium tin oxide (ITO), indium zinc oxide (IZO), zinc oxide (ZnO), and/or indium tin zinc oxide (ITZO).

In some embodiments, the second electrode EL2 may be connected with an auxiliary electrode. If the second electrode EL2 is connected with the auxiliary electrode, the resistance of the second electrode EL2 may decrease.

Meanwhile, the organic electroluminescence device 10 of an embodiment may further include a capping layer CPL on the second electrode EL2. The capping layer CPL may include, for example, α-NPD, NPB, TPD, m-MTDATA, Alq3, CuPc, N4,N4,N4',N4'-tetra(biphenyl-4-yl) biphenyl-4,4'-diamine (TPD15), 4,4',4''-tris(carbazol sol-9-yl)triphenylamine (TCTA), etc.

The amine compound of the present embodiments may be included as a material for the organic electroluminescence device 10 in an organic layer other than the hole transport region HTR. The organic electroluminescence device 10 according to an embodiment of the present disclosure may include the above-described amine compound in at least one organic layer between the first electrode EL1 and the second electrode EL2, or in a capping layer CPL on the second electrode EL2.

In the organic electroluminescence device 10, as voltage is applied to each of the first electrode EL1 and the second electrode EL2, holes injected from the first electrode EL1 move through the hole transport region HTR to the emission layer EML, and electrons injected from the second electrode EL2 move through the electron transport region ETR to the emission layer EML. The electrons and holes recombine in the emission layer EML to form excitons, and these excitons fall from the excited state to the ground state to emit light.

In the organic electroluminescence device according to an embodiment of the present disclosure, as an amine compound included in the hole transport region HTR includes a carbazole group substituted to a central nitrogen atom of the amine compound, and dibenzoselenophene substituted to the central nitrogen atom, glass transition temperature (Tg) and melting point of the amine compound may increase due to a condensed polycyclic ring structure substituted to the central nitrogen atom. Accordingly, heat resistance and durability against heat generated when the organic electroluminescence device emits light are improved, thereby achieving improved light emission efficiency characteristics at a lower driving voltage, compared to a case of using an amine compound containing no condensed polycyclic ring in the emission layer.

In particular, the organic electroluminescence device of an embodiment that includes the amine compound in the hole transport layer, the amine compound including a central nitrogen atom, a carbazole group substituted to the central nitrogen atom, and a dibenzoselenophene group substituted to the central nitrogen atom, and including a substituted or unsubstituted aryl group or a substituted or unsubstituted heteroaryl group on the nitrogen atom of the carbazole group, may attain improved heat resistance and durability due to the condensed polycyclic ring structure of the amine compound. Accordingly, the amine compound of an embodiment may be used to improve life characteristics of the organic electroluminescence device.

Hereinafter, with reference to Examples and Comparative Examples, an amine compound according to an embodiment of the present disclosure, and an organic electroluminescence device of an embodiment using the amine compound will be described in more detail. However, Examples shown below are illustrated only for the understanding of the present disclosure, and the scope of the present disclosure is not limited thereto.

1. SYNTHESIS OF EXAMPLE COMPOUNDS

1) Synthesis Example of Compound 1

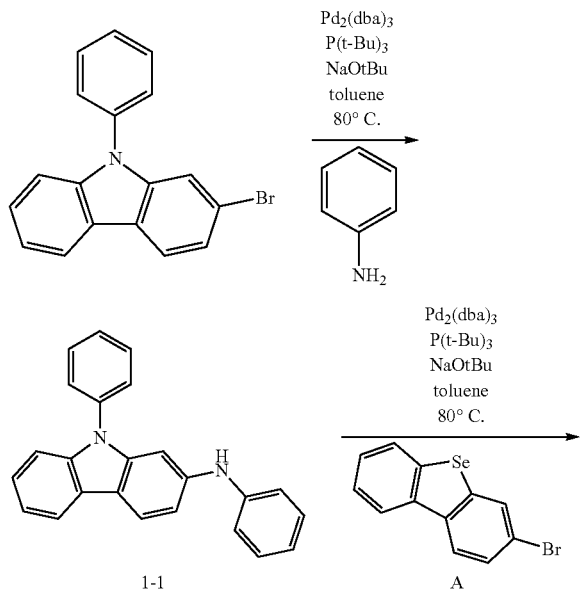

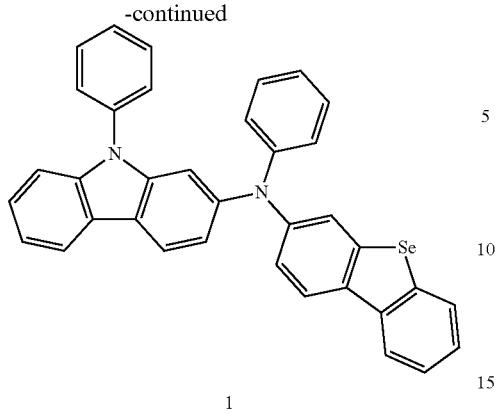

1

(1) Synthesis of Intermediate Compound 1-1

Reactants 2-bromo-9-phenyl-9H-carbazole (3.25 g), aniline (1.46 g), Pd$_2$(dba)$_3$ (0.46 g), P (t-Bu)$_3$ (0.21 g), and NaOtBu (2.44 g) were dissolved in toluene (50 ml) and stirred at 80° C. for 1 hour. After cooling the reaction solution to room temperature, the reaction was terminated with water, and extraction was carried out three times using ethyl ether. The separated organic layer was dried over anhydrous magnesium sulfate and distilled under reduced pressure, and the resulting residue was separated and purified by column chromatography to obtain Intermediate Compound 1-1 (3.39 g, yield: 70%).

(2) Synthesis of Compound 1

Compound 1 (3.76 g, yield: 65%) was obtained in substantially the same manner as used for the synthesis of Intermediate Compound 1-1, except that 3-bromodibenzo[b,d]selenophene (hereinafter Intermediate A) (3.77 g) was used instead of aniline, and Intermediate Compound 1-1 (3.39 g) was used instead of 2-bromo-9-phenyl-9H-carbazole.

2) Synthesis Example of Compound 2

Reaction Formula 2

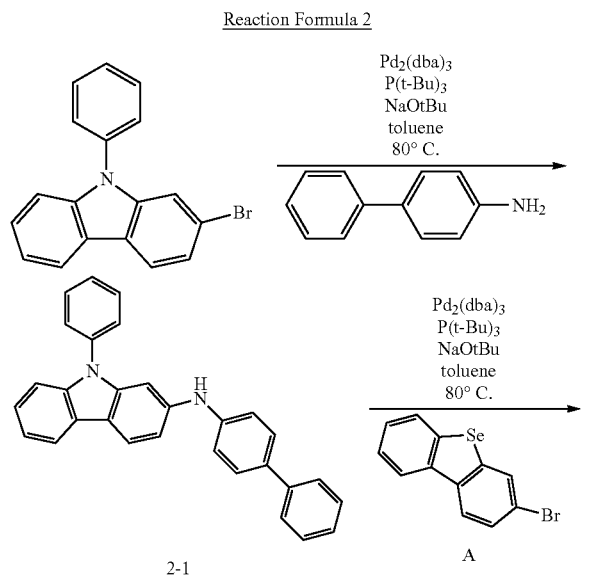

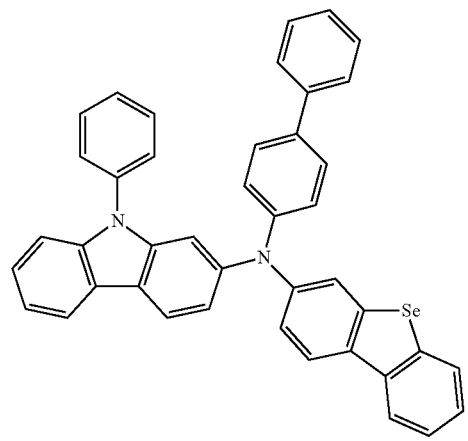

2

(1) Synthesis of Intermediate Compound 2-1

Intermediate Compound 2-1 (2.81 g, yield: 57%) was obtained in substantially the same manner as used for the synthesis of Intermediate Compound 1-1, except that 4-aminobiphenyl (2.53 g) was used instead of aniline.

(2) Synthesis of Compound 2

Compound 2 (4.16 g, yield: 65%) was obtained in substantially the same manner as used for the synthesis of Compound 1, except that Intermediate Compound 2-1 (4.10 g) was used instead of Intermediate Compound 1-1.

3) Synthesis Example of Compound 3

Reaction Formula 3

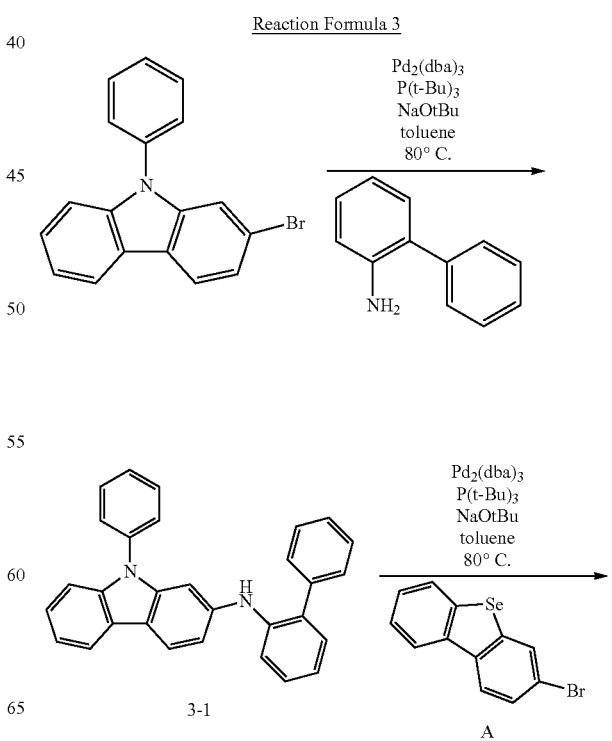

233
-continued

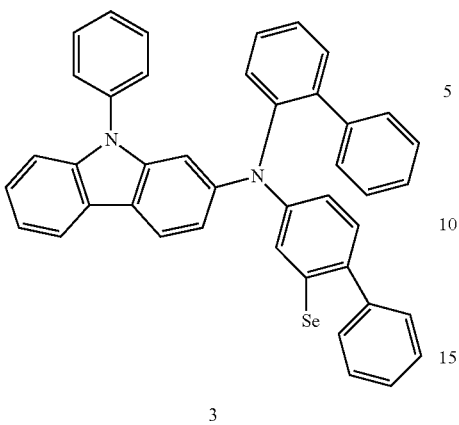

3

234
-continued

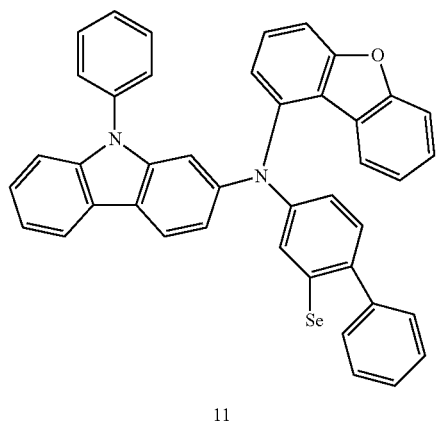

11

(1) Synthesis of Intermediate Compound 3-1

Intermediate Compound 3-1 (2.33 g, Yield: 57%) was obtained in substantially the same manner as used for the synthesis of Intermediate Compound 1-1, except that 2-aminobiphenyl (2.94 g) was used instead of aniline.

(2) Synthesis of Compound 3

Compound 3 (3.90 g, Yield: 61%) was obtained in substantially the same manner used for synthesis of Compound 1 except that Intermediate Compound 3-1 (4.10 g) was used instead of Intermediate Compound 1-1.

(1) Synthesis of Intermediate Compound 11-1

Intermediate Compound 11-1 (3.01 g, yield: 71%) was obtained in substantially the same manner as used for the synthesis of Intermediate Compound 1-1, except that 2-aminodibenzofuran (2.74 g) was used instead of aniline.

(2) Synthesis of Compound 11

Compound 11 (3.76 g, yield: 65%) was obtained in substantially the same manner as used for the synthesis of Compound 1, except that Intermediate Compound 11-1 (3.48 g) was used instead of Intermediate Compound 1-1.

4) Synthesis Example of Compound 11

Reaction Formula 11

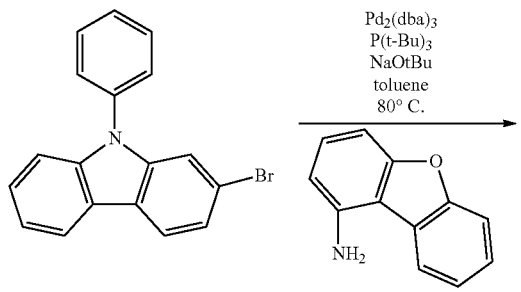

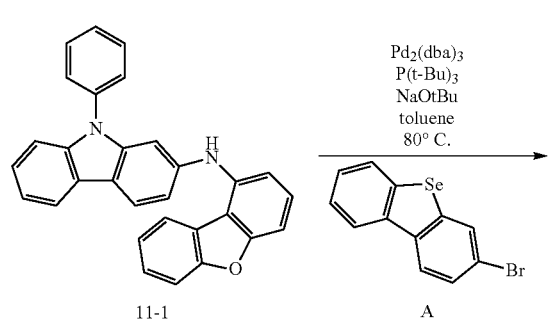

5) Synthesis Example of Compound 15

Reaction Formula 15

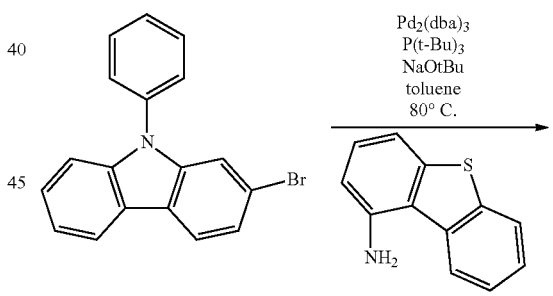

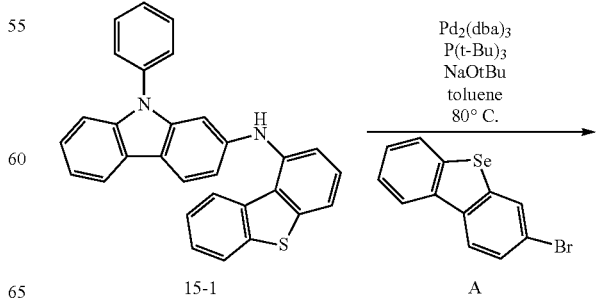

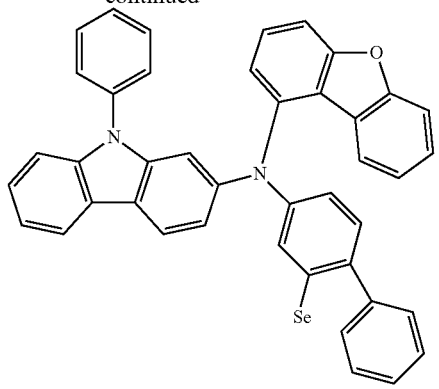

(1) Synthesis of Intermediate Compound 15-1
Intermediate Compound 15-1 (2.99 g, yield: 68%) was obtained in substantially the same manner as used for the synthesis of Intermediate Compound 1-1, except that 2-aminodibenzothiophene (2.98 g) was used instead of aniline.

(2) Synthesis of Compound 15
Compound 15 (4.35 g, Yield: 65%) was obtained in substantially the same manner as used for the synthesis of Compound 1, except that Intermediate Compound 15-1 (4.40 g) was used instead of Intermediate Compound 1-1.

6) Synthesis Example of Compound 21

Reaction Formula 21

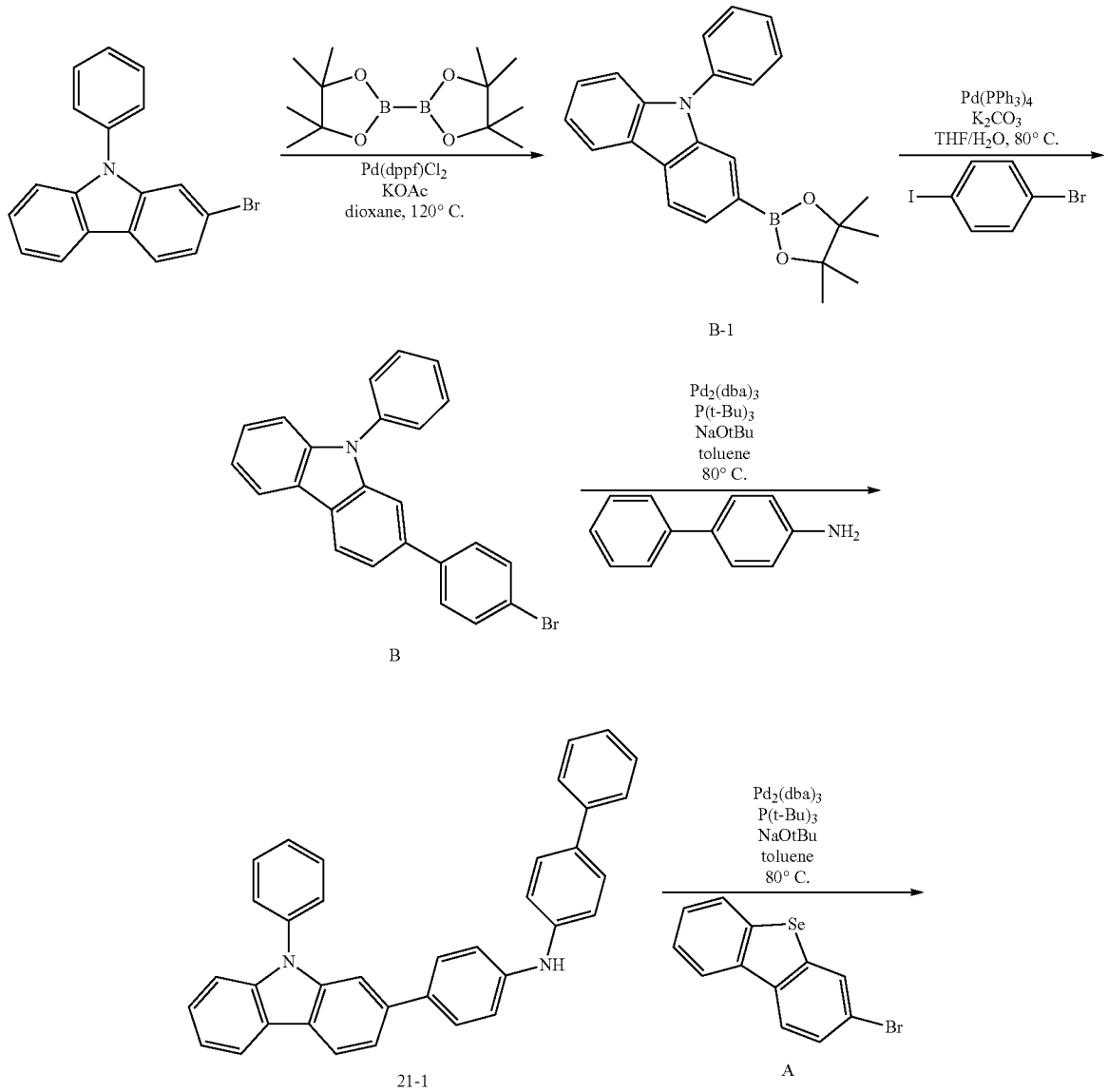

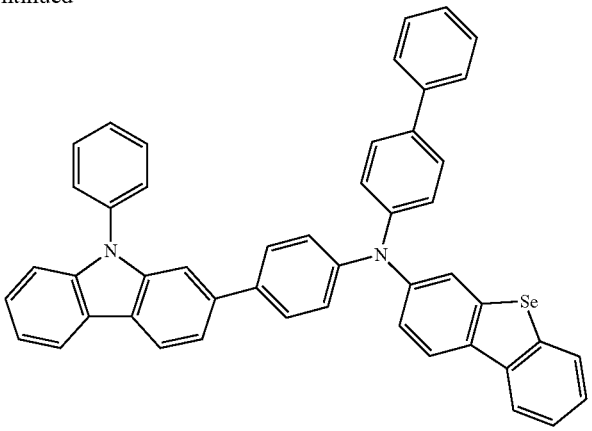

21

(1) Synthesis of Intermediate Compound B-1

2-bromo-9-phenyl-9H-carbazole (3.21 g), Pd(dppf)Cl$_2$ (0.39 g), KOAc (2.61 g), and bispinacolatodiboron (2.56 g) were dissolved in dioxane (50 ml) and stirred at 120° C. for 12 hours. After cooling the reaction solution to room temperature, the reaction was terminated with water, and extraction was carried out three times using methylene chloride (MC). The separated organic layer was dried over anhydrous magnesium sulfate and distilled under reduced pressure, and the resulting residue was separated and purified by column chromatography to obtain Intermediate Compound B-1 (2.98 g, yield: 81%).

(2) Synthesis of Intermediate Compound B

Intermediate Compound B-1 (3.69 g), Pd (PPh$_3$)$_4$ (0.48 g), K$_2$CO$_3$ (3.25 g), and 1-bromo-4-iodobenzene (2.40 g) were dissolved in THF/H$_2$O (100 ml/25 ml) and stirred at 80° C. for 12 hours. After cooling the reaction solution to room temperature, the reaction was terminated with water, and extraction was carried out three times using ethyl ether. The separated organic layer was dried over anhydrous magnesium sulfate and distilled under reduced pressure, and the resulting residue was separated and purified by column chromatography to obtain Intermediate Compound B (2.66 g, yield: 67%).

(3) Synthesis of Intermediate Compound 21-1

Intermediate Compound 21-1 (2.77 g, yield: 57%) was obtained in substantially the same manner as used for the synthesis of Intermediate Compound 1-1, except that 4-aminobiphenyl (2.53 g) was used instead of aniline, and Intermediate Compound B was used instead of 2-bromo-9-phenyl-9H-carbazole.

(4) Synthesis of Compound 21

Compound 21 (4.65 g, yield: 65%) was obtained in substantially the same manner as used for the synthesis of Compound 1, except that Intermediate Compound 21-1 (4.86 g) was used instead of Intermediate Compound 1-1.

7) Synthesis Example of Compound 77

Reaction Formula 77

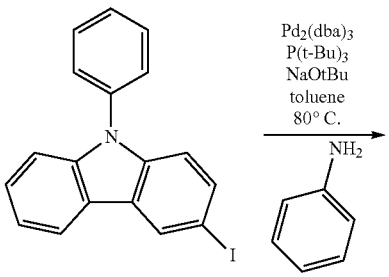

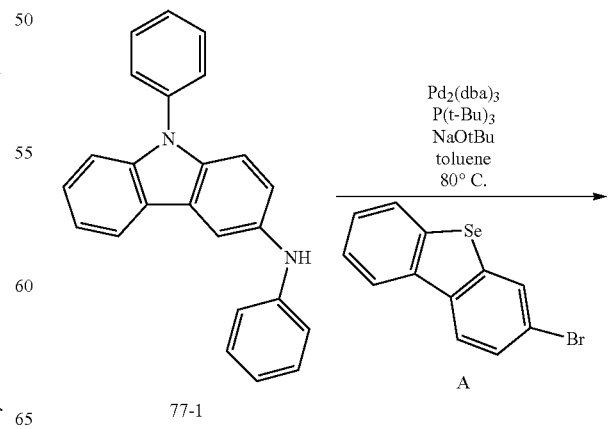

77-1

-continued

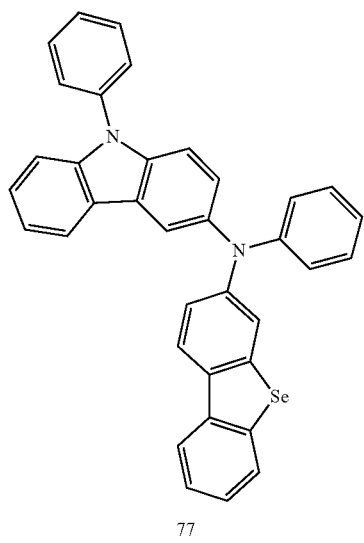

77

-continued

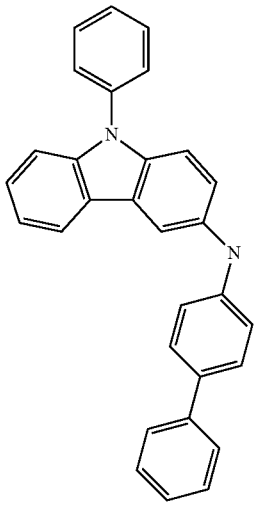

78-1

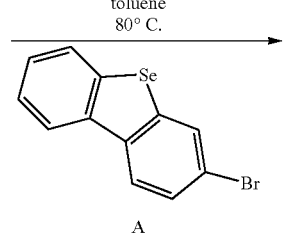

(1) Synthesis of Intermediate Compound 77-1

2-bromo-9-phenyl-9H-carbazole Compound 77-1 (2.24 g, yield: 67%) was obtained in substantially the same manner as used for the synthesis of Intermediate Compound 1-1, except that 3-iodo-9-phenyl-9H-carbazole (3.69 g) was used instead of 2-bromo-9-phenyl-9H-carbazole.

(2) Synthesis of Compound 77

Compound 77 (3.66 g, yield: 65%) was obtained in substantially the same manner as used for the synthesis of Compound 1, except that Intermediate Compound 77-1 (3.34 g) was used instead of Intermediate Compound 1-1.

8) Synthesis Example of Compound 78

Reaction Formula 78

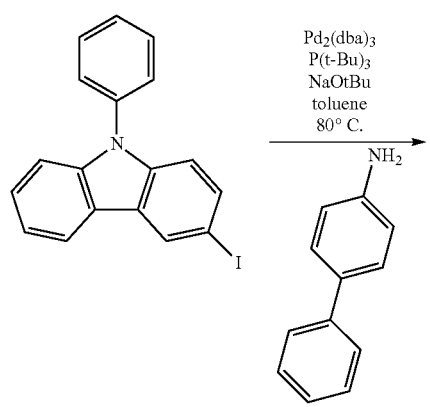

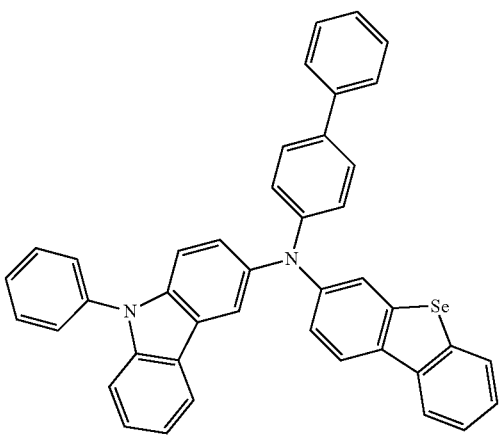

78

(1) Synthesis of Intermediate Compound 78-1

Intermediate Compound 78-1 (3.15 g, yield: 77%) was obtained in substantially the same manner as used for the synthesis of Intermediate Compound 1-1, except that 3-iodo-9-phenyl-9H-carbazole (3.69 g) was used instead of 2-bromo-9-phenyl-9H-carbazole, and 4-aminobiphenyl (2.54 g) was used instead of aniline.

(2) Synthesis of Compound 78

Compound 78 (4.80 g, yield: 75%) was obtained in substantially the same manner as used for the synthesis of Compound 1, except that Intermediate Compound 78-1 (4.09 g) was used instead of Compound 1-1.

9) Synthesis Example of Compound 87

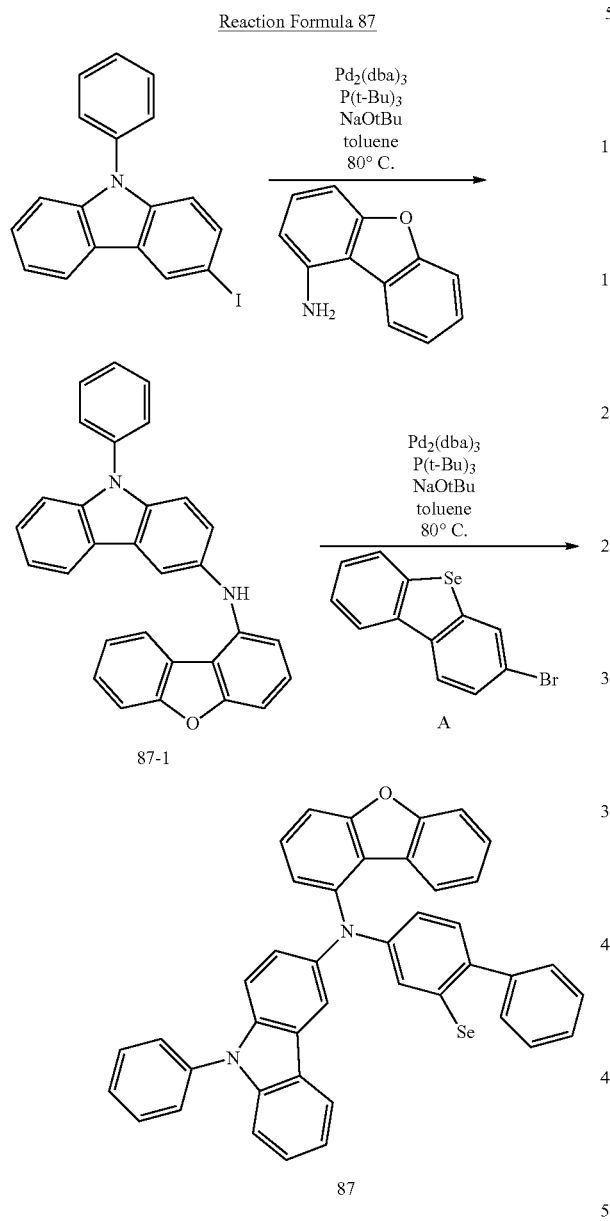

Reaction Formula 87

(1) Synthesis of Intermediate Compound 87-1

Intermediate Compound 87-1 (3.60 g, yield: 85%) was obtained in substantially the same manner as used for the synthesis of Intermediate Compound 1-1, except that 3-iodo-9-phenyl-9H-carbazole (3.69 g) was used instead of 2-bromo-9-phenyl-9H-carbazole, and 1-aminodibenzofuran (2.75 g) was used instead of aniline.

(2) Synthesis of Compound 87

Compound 87 (4.25 g, Yield: 65%) was obtained in substantially the same manner as used for the synthesis of Compound 1, except that Intermediate Compound 87-1 (4.24 g) was used instead of Intermediate Compound 1-1.

10) Synthesis Example of Compound 91

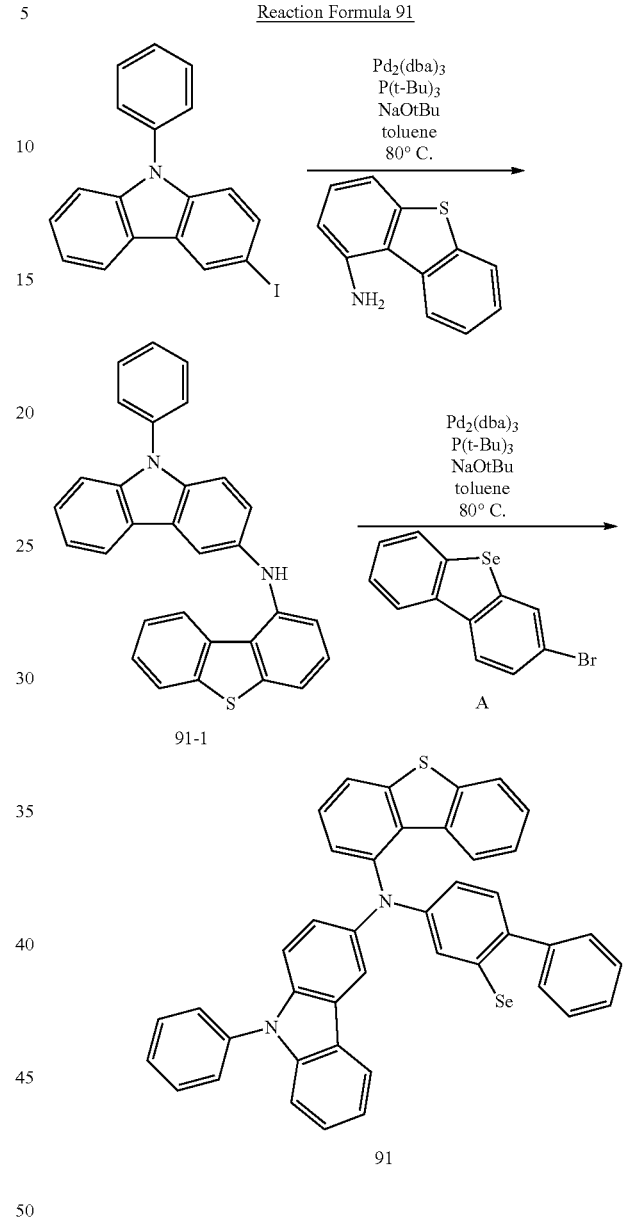

Reaction Formula 91

(1) Synthesis of Intermediate Compound 91-1

Intermediate Compound 91-1 (2.59 g, yield: 59%) was obtained in substantially the same manner as used for the synthesis of Intermediate Compound 1-1, except that 3-iodo-9-phenyl-9H-carbazole (3.69 g) was used instead of 2-bromo-9-phenyl-9H-carbazole, and 1-aminodibenzothiophene (2.98) was used instead of aniline.

(2) Synthesis of Compound 91

Compound 91 (4.22 g, Yield: 63%) was obtained in substantially the same manner as used for the synthesis of Compound 1, except that Intermediate Compound 91-1 (4.40 g) was used instead of Intermediate Compound 1-1.

11) Synthesis Example of Compound 153
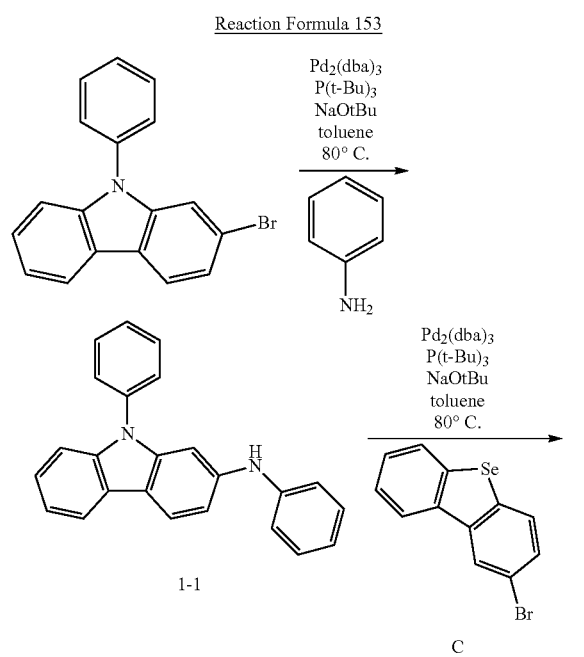
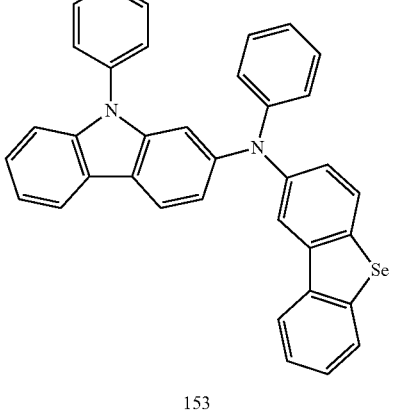
(1) Synthesis of Compound 153
Compound 153 (3.67 g, yield: 65%) was obtained in substantially the same manner as used for the synthesis method of Compound 1, except that Intermediate C (4.64 g) was used instead of Intermediate A (4.64 g).
12) Synthesis Example of Compound 154
Reaction Formula 154
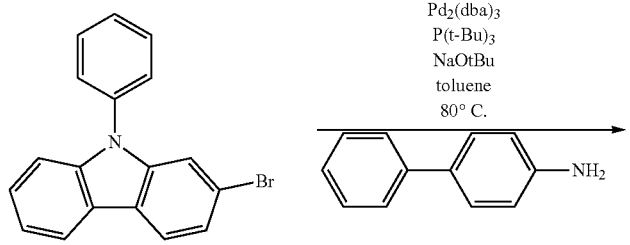
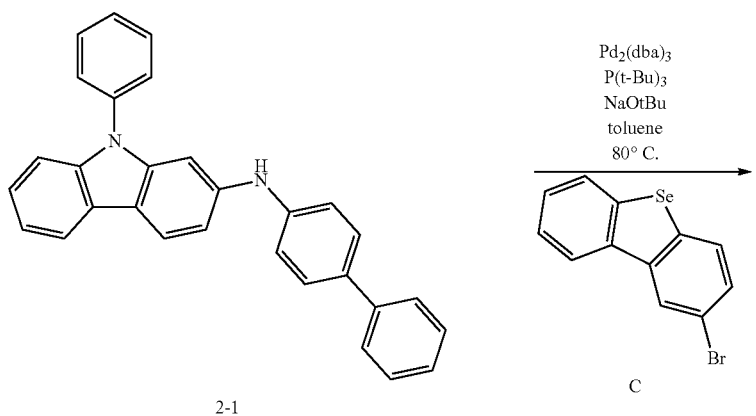

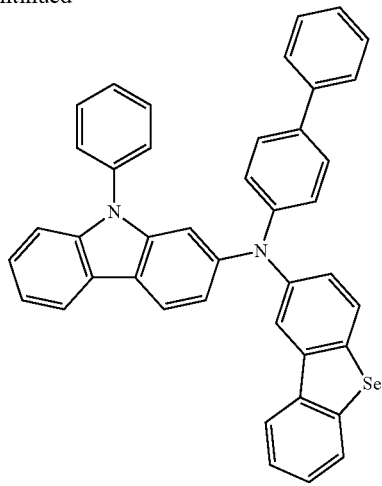

154

(1) Synthesis of Compound 154

Compound 154 (4.67 g, yield: 73%) was obtained in substantially the same manner as used for the synthesis of Compound 2, except that Intermediate C (4.64 g) was used instead of Intermediate A (4.64 g).

13) Synthesis Example of Compound 163

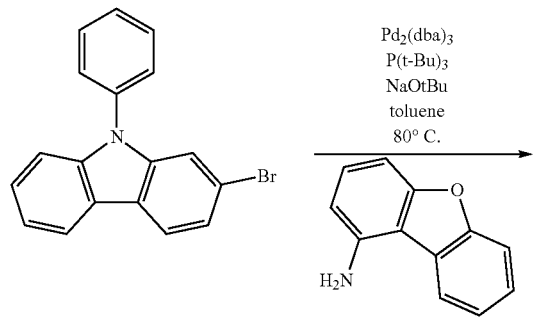

Reaction Formula 163

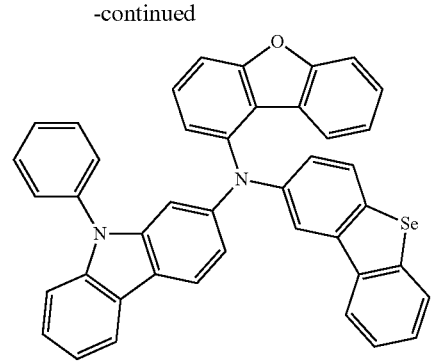

163

(1) Synthesis of Compound 163

Compound 163 (3.99 g, yield: 61%) was obtained in substantially the same manner as used for the synthesis of Compound 11, except that Intermediate C (4.64 g) was used instead of Intermediate A (4.64 g).

14) Synthesis Example of Compound 167

Reaction Formula 167

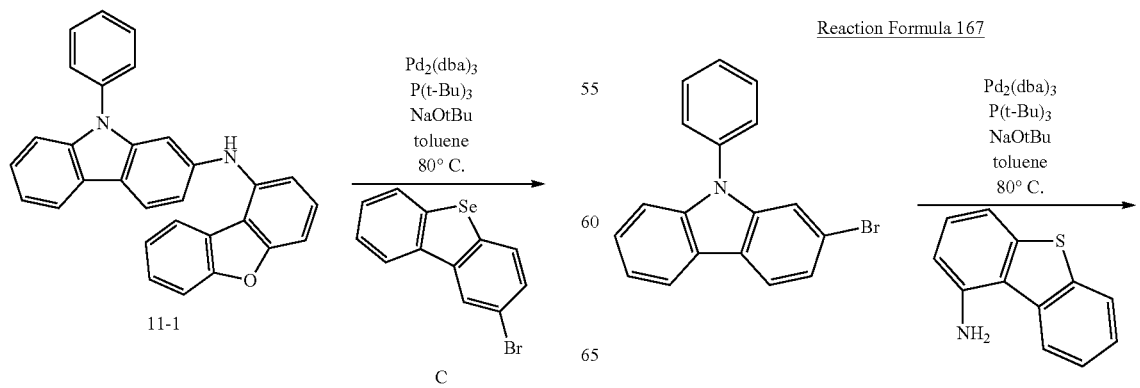

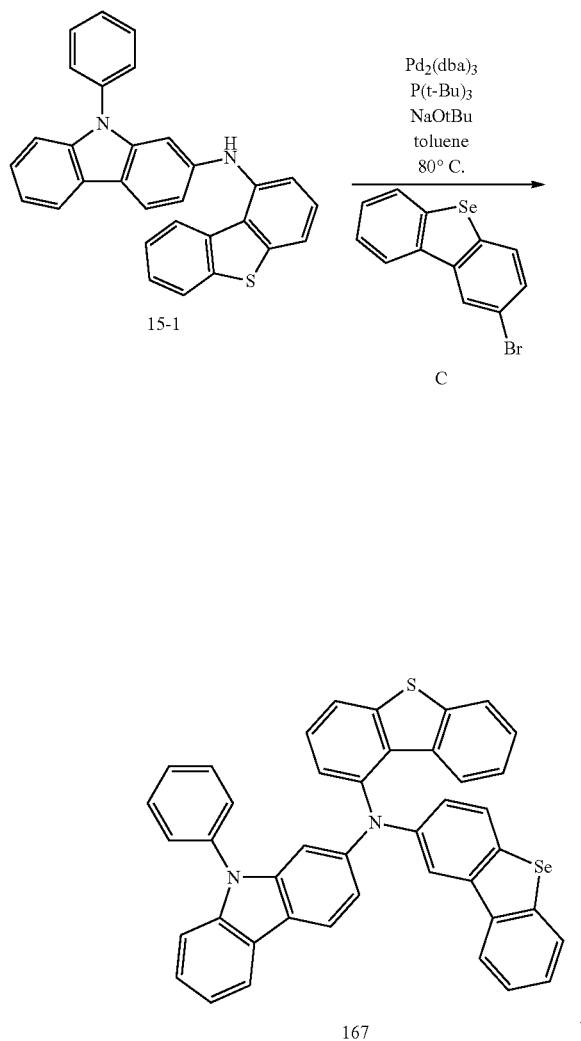

(1) Synthesis of Compound 167

Compound 167 (4.89 g, yield: 67%) was obtained in substantially the same manner as used for the synthesis of Compound 15, except that Intermediate C (4.64 g) was used instead of Intermediate A (4.64 g).

15) Synthesis Example of Compound 229

Reaction Formula 229

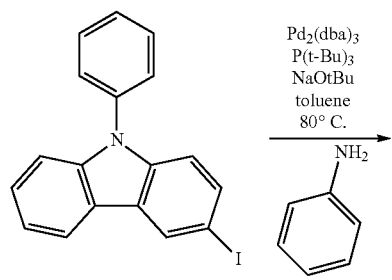

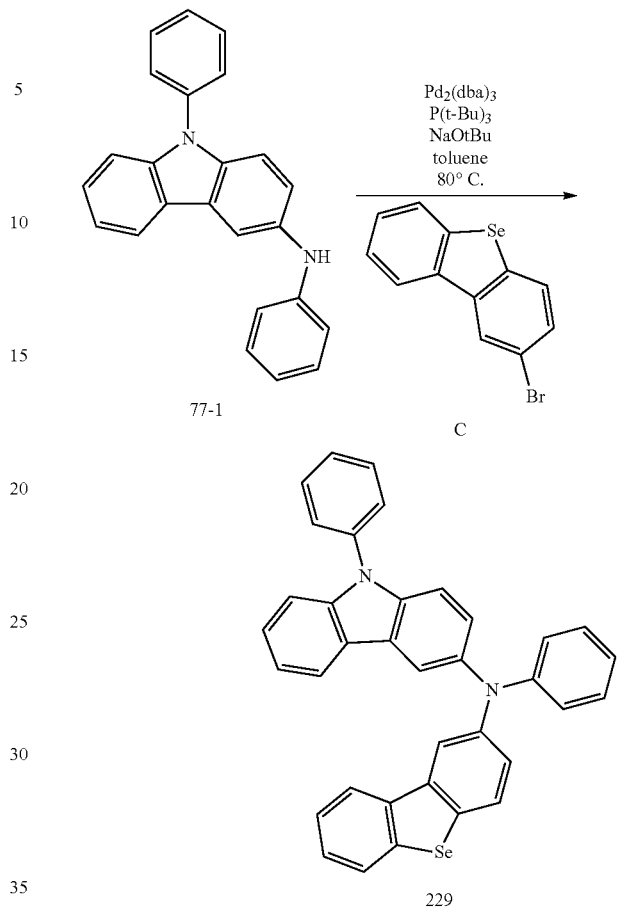

(1) Synthesis of Compound 229

Compound 229 (4.57 g, yield: 81%) was obtained in substantially the same manner as used for the synthesis of Compound 77, except that Intermediate C (4.64 g) was used instead of Intermediate A (4.64 g).

16) Synthesis Example of Compound 230

Reaction Formula 230

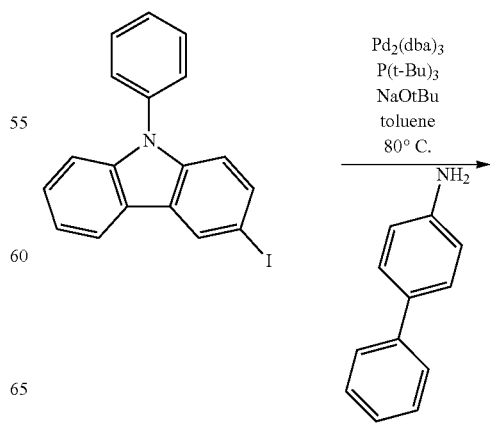

249
-continued

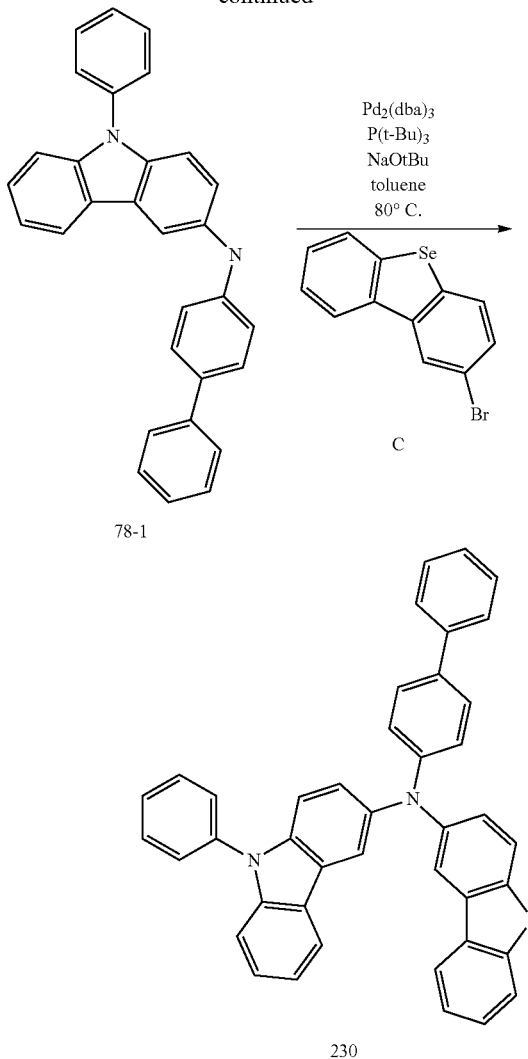

250
-continued

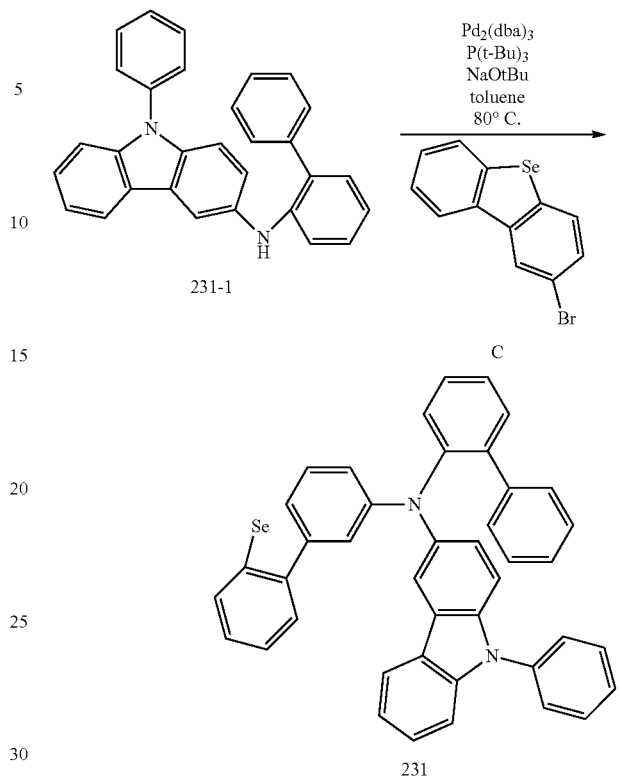

(1) Synthesis of Compound 230

Compound 230 (5.05 g, yield: 79%) was obtained in substantially the same manner as used for the synthesis of Compound 78, except that Intermediate C (4.64 g) was used instead of Intermediate A (4.64 g).

17) Synthesis Example of Compound 231

Reaction Formula 231

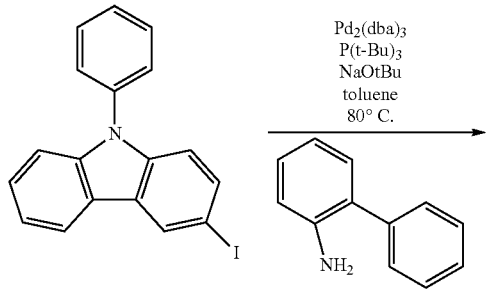

(1) Synthesis of Intermediate Compound 231-1

Intermediate Compound 231-1 (2.70 g, yield: 66%) was obtained in substantially the same manner as used for the synthesis of Intermediate Compound 3-1, except that 3-iodo-9-phenyl-9H-carbazole (3.69 g) was used instead of 2-bromo-9-phenyl-9H-carbazole.

(2) Synthesis of Compound 231

Compound 231 (4.10 g, yield: 65%) was obtained in substantially the same manner as used for the synthesis of Compound 1, except that Intermediate C (4.64 g) was used instead of Intermediate A (4.64 g), and Intermediate Compound 231-1 was used instead of Intermediate Compound 1-1.

18) Synthesis Example of Compound 239

Reaction Formula 239

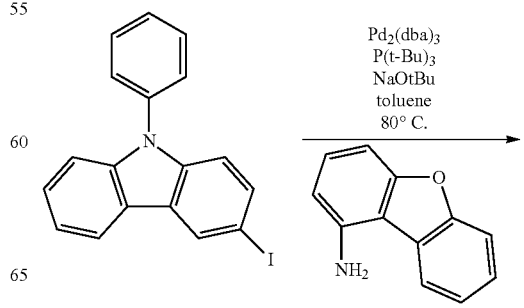

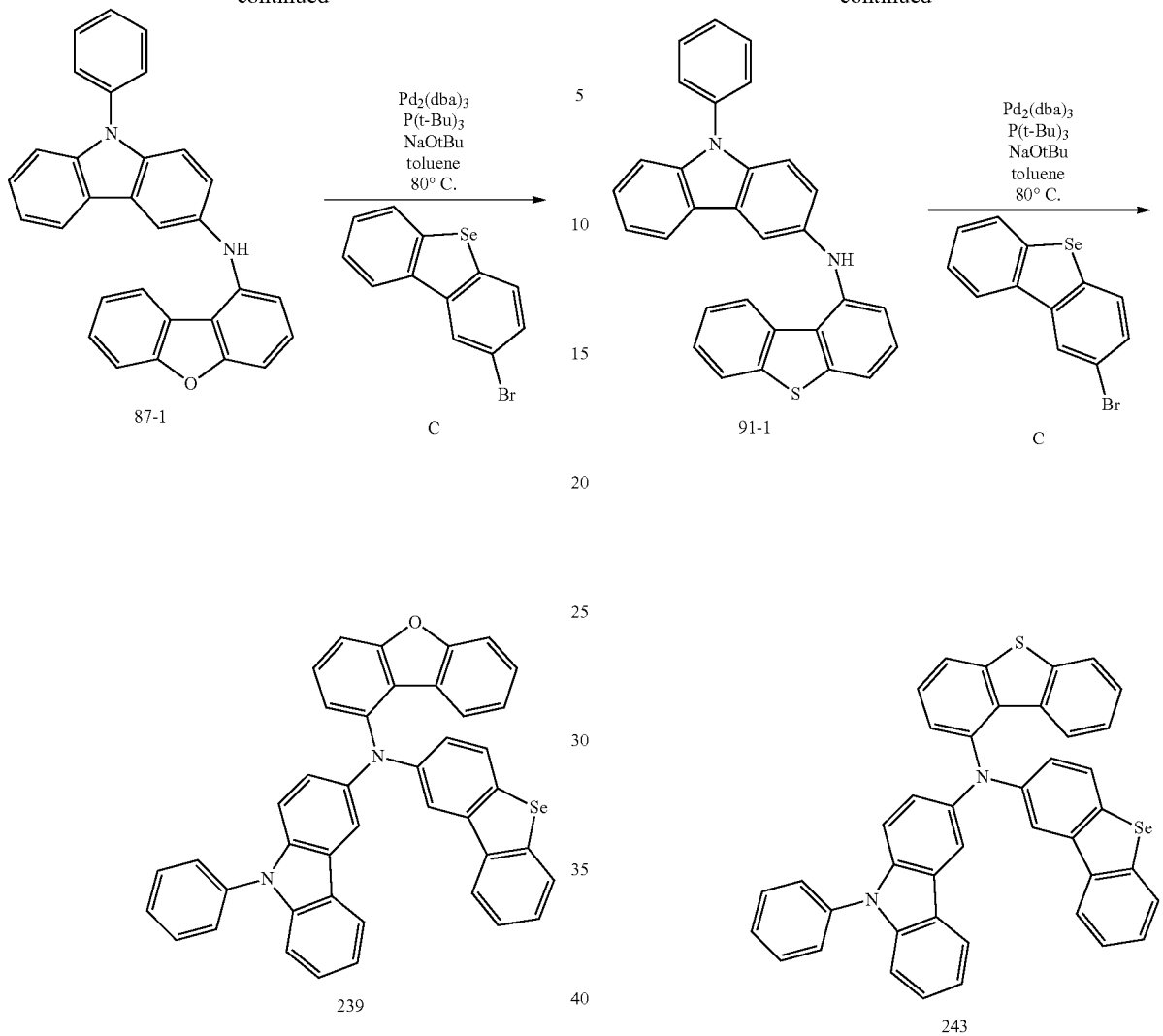

(1) Synthesis of Compound 239

Compound 239 (4.38 g, yield: 67%) was obtained in substantially the same manner as used for the synthesis of Compound 87, except that Intermediate C (4.64 g) was used instead of Intermediate A.

19) Synthesis Example of Compound 243

(1) Synthesis of Compound 243

Compound 243 (4.89 g, yield: 73%) was obtained in substantially the same manner as used for the synthesis of Compound 91, except that Intermediate C (4.64 g) was used instead of Intermediate A.

20) Synthesis Example of Compound 249

Reaction Formula 243

Reaction Formula 249

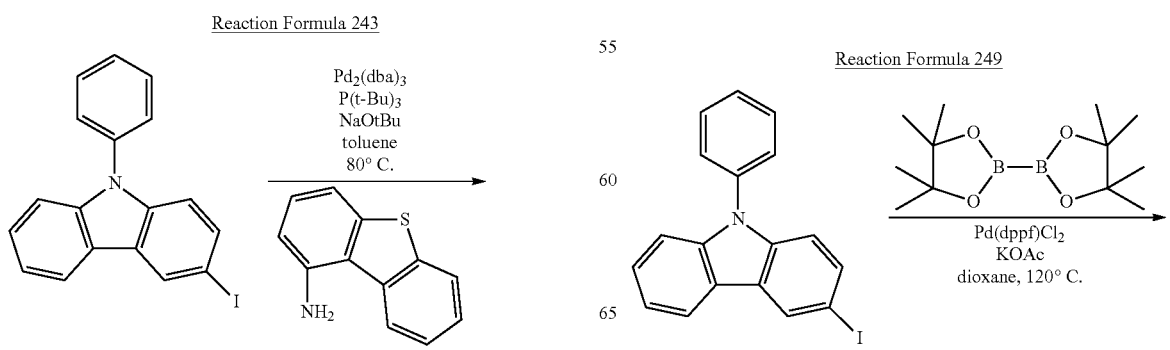

-continued

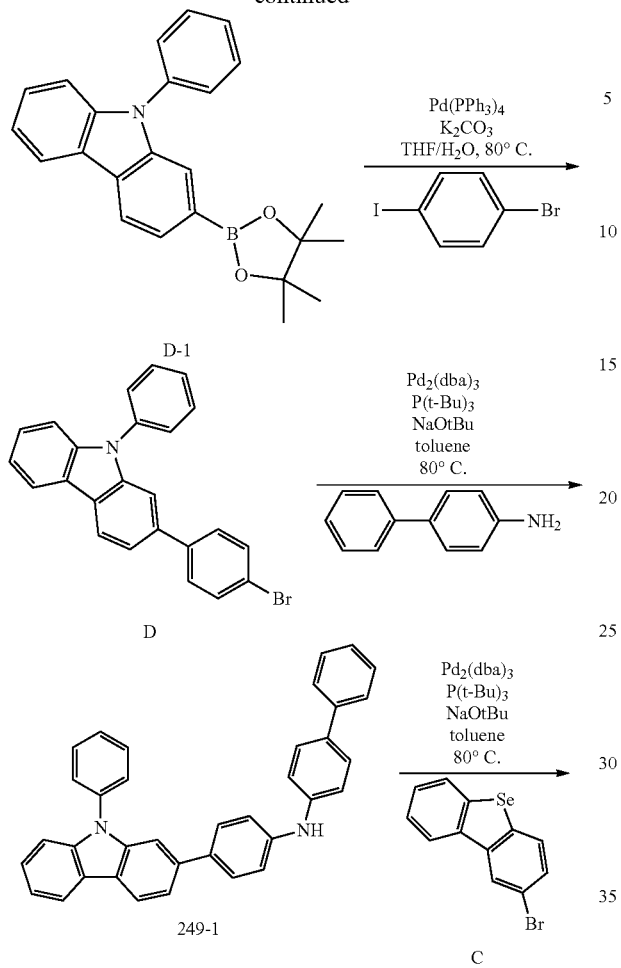

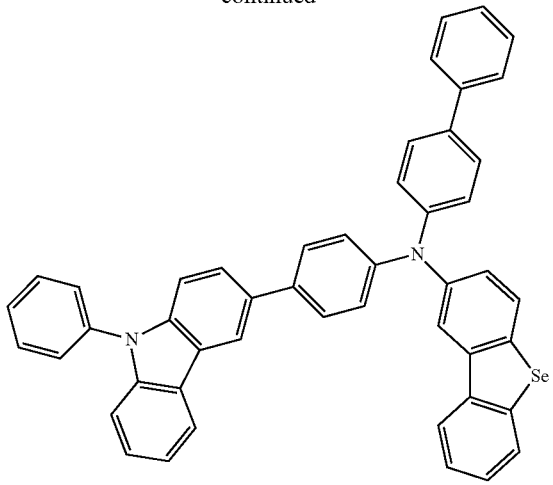

249

(1) Synthesis of Compound 249

Compound 249 (4.08 g, yield: 57%) was obtained in substantially the same manner as used for the synthesis of Compound 21, except that 3-iodo-9-phenyl-9H-carbazole (3.69 g) was used instead of 2-bromo-9-phenyl-9H-carbazole, and Intermediate C (4.64 g) was used instead of Intermediate A.

$^1$H NMR and Mass Spectrometry/Fast Atom Bombardment (MS/FAB) of the synthesized compounds are shown in Table 1 below.

TABLE 1

| No. of Compound | 1H NMR (CDCl3, 400 MHz) | MS/FAB Found | calc |
|---|---|---|---|
| Compound 1 | 8.55(d, 1H), 8.24(d, 1H), 7.94(d, 1H) 7.77-7.73 (m, 2H), 7.62 (dd, 2H), 7.58-7.45 (m, 6H), 7.37-7.16 (m, 8H), 7.08-7.00(m, 3H) | 564.11 | 563.11 |
| Compound 2 | 8.55(d, 1H), 8.24(d, 1H), 7.94(d, 1H) 7.77-7.73 (m, 4H), 7.62-7.35 (m, 16H), 7.30-7.25 (m, 4H), 7.16 (dd, 1H), | 640.14 | 639.14 |
| Compound 3 | 8.55(d, 1H), 8.24(d, 1H), 8.10 (d, 1H) 7.94 (d, 1H), 7.88-7.77 (dd, 2H), 7.62-7.25 (m, 18H), 7.14-7.08 (m, 4H), | 640.14 | 639.14 |
| Compound 11 | 8.55(d, 1H), 8.24(d, 1H), 7.98-7.94 (dd, 2H), 7.88-7.77 (dd, 2H), 7.62-7.16 (m, 19H), 6.91 (d, 1H), | 654.12 | 653.12 |
| Compound 15 | 8.55(d, 1H), 8.45(d, 1H), 8.24(d, 1H) 7.94-7.93 (dd, 2H), 7.77-7.73 (dd, 2H), 7.62-7.25 (m, 18H), 7.16 (d, 1H), | 670.10 | 669.10 |
| Compound 21 | 8.55(d, 1H), 8.31(d, 1H), 7.94-7.91(dd, 2H) 7.77-7.73 (m, 5H), 7.62-7.35 (m, 22H), 7.16 (d, 1H), | 716.17 | 715.17 |
| Compound 77 | 8.55(d, 1H), 7.94(d, 1H), 7.77-7.73(dd, 2H) 7.62-7.45 (m, 9H), 7.35-7.16 (m, 6H), 7.08-7.00 (dd, 3H), | 564.11 | 563.11 |
| Compound 78 | 8.55(d, 1H), 7.94(d, 1H), 7.77-7.73(m, 4H) 7.62-7.35 (m, 21H), 7.16 (dd, 1H) | 640.14 | 639.14 |
| Compound 87 | 8.55(d, 1H), 7.98-7.94(dd, 2H), 7.77-7.73(dd, 2H) 7.62-7.25 (m, 19H), 7.16 (d, 1H), 6.91 (d, 1H), | 654.12 | 653.12 |

TABLE 1-continued

| No. of Compound | 1H NMR (CDCl3, 400 MHz) | MS/FAB Found | calc |
|---|---|---|---|
| Compound 91 | 8.55(d, 1H), 8.45(d, 1H), 7.94-7.93(dd, 2H), 7.77-7.73 (dd, 2H), 7.62-7.30 (m, 19H), 7.16 (d, 1H) | 670.10 | 669.10 |
| Compound 153 | 8.55(d, 1H), 8.24(d, 1H), 7.94(d, 1H), 7.77(d, 1H), 7.62-7.45 (m, 9H), 7.35-7.00 (m, 11H) | 564.11 | 563.11 |
| Compound 154 | 8.55(d, 1H), 8.24(d, 1H), 7.94(d, 1H), 7.77-7.75(dd, 3H), 7.62-7.25 (m, 21H), 7.16 (dd, 1H) | 640.14 | 639.14 |
| Compound 155 | 8.55(d, 1H), 8.24(d, 1H), 8.10(d, 1H), 7.94(d, 1H), 7.77(d, 1H), 7.62-7.25 (m, 19H), 7.16-7.08 (m, 4H) | 640.14 | 639.14 |
| Compound 163 | 8.55(d, 1H), 8.24(d, 1H), 7.98-7.79(dd, 2H), 7.77(d, 1H), 7.77(d, 1H), 7.62-7.16 (m, 19H), 6.91 (d, 1H) | 654.12 | 653.12 |
| Compound 167 | 8.55(d, 1H), 8.45(d, 1H), 8.24(d, 1H), 7.97-7.93(dd, 2H), 7.77(d, 1H), 7.62-7.25 (m, 19H), 7.16 (dd, 1H) | 670.10 | 669.10 |
| Compound 229 | 8.55(d, 1H), 7.94(d, 1H), 7.77(d, 1H), 7.62-7.45(m, 10H) 7.35-7.16 (m, 8H), 7.08-7.00 (dd, 3H) | 564.11 | 563.11 |
| Compound 230 | 8.55(d, 1H), 7.94(d, 1H), 7.77-7.75(dd, 3H), 7.62-7.28(m, 22H) 7.16 (dd, 1H) | 640.14 | 639.14 |
| Compound 231 | 8.55(d, 1H), 8.10(d, 1H), 7.97(d, 1H), 7.77(d, 1H) 7.62-7.28 (m, 20H), 7.16-7.08(m, 4H) | 640.14 | 639.14 |
| Compound 239 | 8.55(d, 1H), 7.98-7.94(dd, 2H), 7.77(d, 1H), 7.62-7.27(m, 20H) 7.16 (dd, 1H), 6.91(dd, 1H) | 654.12 | 653.12 |
| Compound 243 | 8.55(d, 1H), 8.45(d, 1H), 7.94-7.93(dd, 2H), 7.77(d, 1H) 7.62-7.35 (m, 20H), 7.16(dd, 1H) | 670.10 | 669.10 |
| Compound 249 | 8.55(d, 1H), 7.99-7.89(m, 3H), 7.77-7.75(m, 4H), 7.77(d, 1H) 7.62-7.35 (m, 22H), 7.16(dd, 1H) | 716.17 | 715.17 |

2. MANUFACTURE AND EVALUATION OF ORGANIC ELECTROLUMINESCENCE DEVICE CONTAINING AMINE COMPOUND (Manufacture of Organic Electroluminescence Device)

Organic electroluminescence devices of an embodiment, each including the amine compound of an embodiment in a hole transport region, and organic electroluminescence devices, each including a comparative example compound in a hole transport region, were manufactured as follows.

For an anode, an ITO glass substrate (Corning, 15 Ω/cm2 (1200 Å)) was cut to a size of about 50 mm×50 mm×0.7 mm, and the cut ITO glass substrates were washed by ultrasonic waves using isopropyl alcohol and distilled water for about 5 minutes respectively, irradiated with ultraviolet rays for about 30 minutes, cleansed by exposing to ozone, and then installed in a vacuum deposition apparatus.

2-TNATA was vacuum-deposited on the ITO glass substrate to form a hole injection layer having a thickness of about 600 Å, and then a Comparative Example Compound or an Example Compound was vacuum-deposited to a thickness of about 300 Å on the hole injection layer to form a hole transport layer.

On the hole transport layer, 9,10-di (naphthalen-2-yl) anthracene (hereinafter referred to as DNA) as a blue fluorescent host and 4,4'-bis [2-(4-(N, N-diphenylamino) phenyl)vinyl] biphenyl (hereinafter referred to as DPAVBi) as a blue fluorescent dopant were co-deposited at a weight ratio of 98:2 to form an emission layer having a thickness of about 300 Å.

Thereafter, Alq3 was deposited to a thickness of about 300 Å on the emission layer to form an electron transport layer, LiF (an alkali metal halide) was deposited to a thickness of about 10 Å to form an electron injection layer, and Al was vacuum-deposited to a thickness of about 3000 Å to form a LiF/Al cathode electrode, thus manufacturing an organic electroluminescence device.

The materials of each layer used in the manufacture of the organic electroluminescence devices are as follows.

(Functional Layer Compounds)
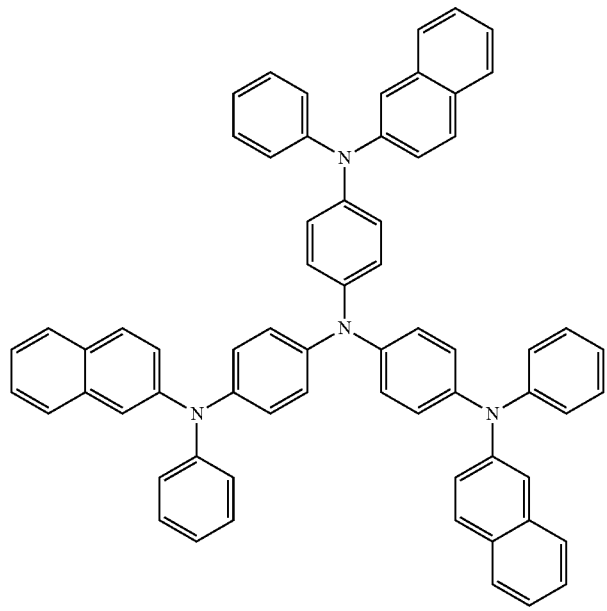
2-NATA
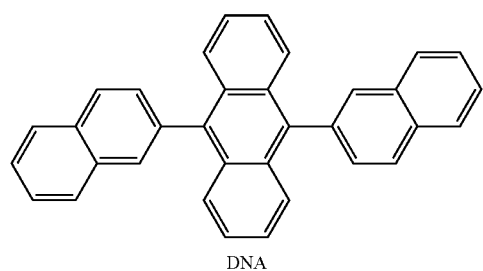
DNA
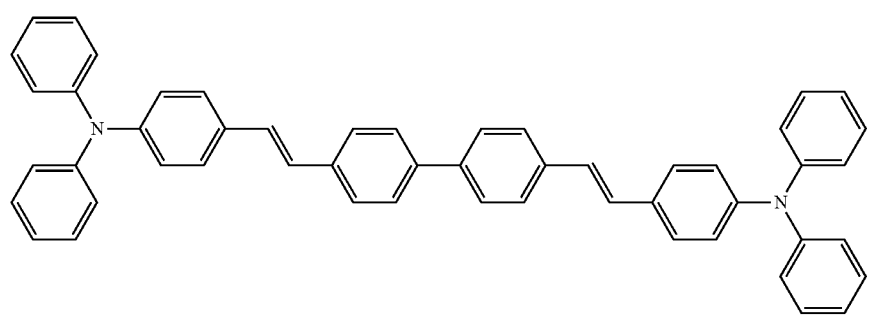

Comparative Example Compounds
c1
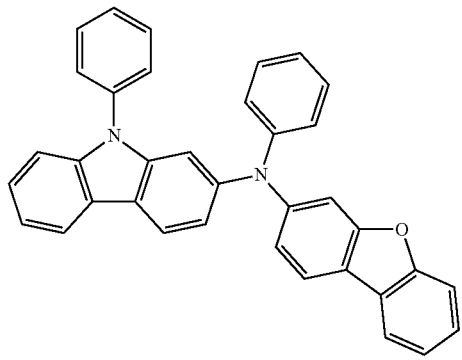
c2
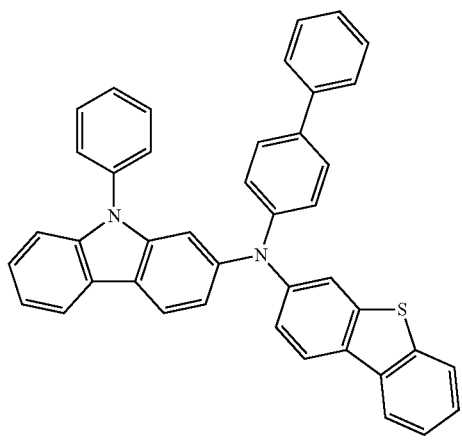
c3
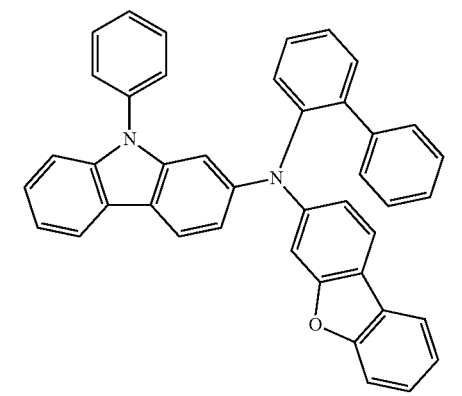
c4
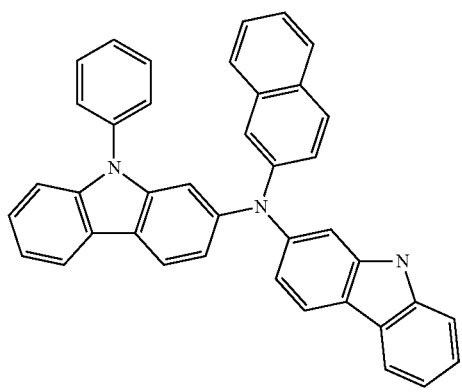
c5
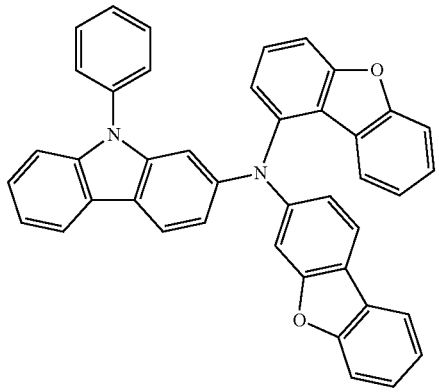
c6
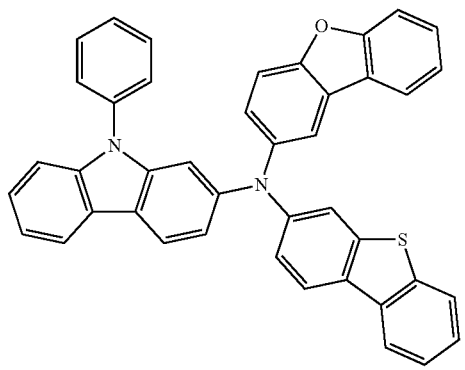
c7
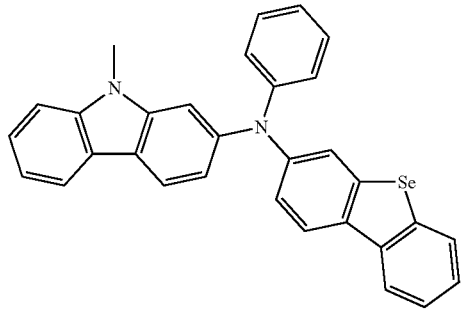

(Characteristic Evaluation of Organic Electroluminescence Devices)

TABLE 2

| Examples of manufactured devices | Hole transport material | Driving voltage (V) | Current density (mA/cm$^2$) | Luminance (cd/m$^2$) | Efficiency (cd/A) | Emitted color | Half-life (hr @100 mA/cm$^2$) |
|---|---|---|---|---|---|---|---|
| Example 1 | Compound 1 | 4.20 | 50 | 3440 | 8.88 | Blue | 330 |
| Example 2 | Compound 2 | 4.24 | 50 | 3750 | 7.50 | Blue | 325 |
| Example 3 | Compound 3 | 4.32 | 50 | 3603 | 7.21 | Blue | 354 |
| Example 4 | Compound 11 | 4.26 | 50 | 3572 | 7.14 | Blue | 360 |
| Example 5 | Compound 15 | 4.45 | 50 | 3345 | 6.69 | Blue | 366 |
| Example 6 | Compound 21 | 4.56 | 50 | 3420 | 6.84 | Blue | 345 |
| Example 7 | Compound 77 | 4.14 | 50 | 3521 | 7.04 | Blue | 355 |
| Example 8 | Compound 78 | 4.35 | 50 | 3412 | 6.82 | Blue | 361 |
| Example 9 | Compound 87 | 4.63 | 50 | 3542 | 7.08 | Blue | 331 |
| Example 10 | Compound 91 | 4.50 | 50 | 3613 | 7.22 | Blue | 372 |
| Example 11 | Compound 97 | 4.11 | 50 | 3341 | 6.68 | Blue | 368 |
| Example 12 | Compound 153 | 4.23 | 50 | 3455 | 6.91 | Blue | 345 |
| Example 13 | Compound 154 | 4.55 | 50 | 3332 | 6.66 | Blue | 363 |
| Example 14 | Compound 155 | 4.30 | 50 | 3522 | 7.04 | Blue | 366 |
| Example 15 | Compound 163 | 4.63 | 50 | 3412 | 6.82 | Blue | 340 |
| Example 16 | Compound 167 | 4.21 | 50 | 3458 | 6.91 | Blue | 330 |
| Example 17 | Compound 173 | 4.44 | 50 | 3436 | 6.87 | Blue | 348 |
| Example 18 | Compound 229 | 4.41 | 50 | 3487 | 6.97 | Blue | 386 |
| Example 19 | Compound 230 | 4.31 | 50 | 3456 | 6.91 | Blue | 384 |
| Example 20 | Compound 231 | 4.48 | 50 | 3675 | 7.35 | Blue | 346 |
| Example 21 | Compound 239 | 4.36 | 50 | 3666 | 7.33 | Blue | 356 |
| Example 22 | Compound 243 | 4.22 | 50 | 3645 | 7.29 | Blue | 357 |
| Example 23 | Compound 249 | 4.00 | 50 | 3652 | 7.30 | Blue | 354 |
| Comparative Example 1 | Compound c1 | 4.80 | 50 | 3155 | 6.31 | Blue | 297 |
| Comparative Example 2 | Compound c2 | 4.76 | 50 | 3260 | 6.52 | Blue | 289 |
| Comparative Example 3 | Compound c3 | 4.67 | 50 | 3330 | 6.66 | Blue | 312 |
| Comparative Example 4 | Compound c4 | 4.77 | 50 | 3065 | 6.13 | Blue | 326 |
| Comparative Example 5 | Compound c5 | 5.12 | 50 | 3385 | 6.77 | Blue | 288 |
| Comparative Example 6 | Compound c6 | 5.11 | 50 | 2970 | 5.94 | Blue | 312 |
| Comparative Example 7 | Compound c7 | 4.94 | 50 | 3275 | 6.55 | Blue | 299 |

Examples 1 to 23 are light emitting devices in which Compounds 1, 2, 3, 11, 15, 21, 77, 78, 87, 91, 97, 153, 154, 155, 163, 167, 173, 229, 230, 231, 239, 243, and 249 are applied to a hole transport layer. Comparative Examples 1 to 7 are light emitting devices in which Comparative Examples Compounds c1 to c7 are applied to a hole transport layer. Referring to the results of Table 2 above, it is seen that the light emitting devices of Examples 1 to 23 have a low driving voltage, improved luminance and efficiency, and an improved lifetime compared to Comparative Examples 1 to 7.

In Examples 1 to 23, the amine compound includes a condensed polycyclic ring containing a hetero atom (more specifically, a carbazole group, a dibenzoselenophene group, and an aryl group or a heteroaryl group substituted on a central nitrogen atom), and further includes an aryl group or a heteroaryl group substituted to a nitrogen atom of the carbazole group.

In addition, in the amine compound of the present embodiments, a substituted or unsubstituted aryl group or a substituted or unsubstituted heteroaryl group may be linked between the central nitrogen atom and the substituents by a linker to allow the amine compound including a plurality of condensed polycyclic rings to have improved heat resistance and durability against heat. Accordingly, the organic electroluminescence device including the amine compound containing a condensed polycyclic ring (such as a carbazole group and a dibenzoselenophene group of Examples 1 to 23) in the hole transport region may have high efficiency and long-life characteristics.

Comparative Example Compounds c1 to c6 include a central nitrogen atom, a carbazole group substituted to the central nitrogen atom, and an aryl group or heteroaryl group substituted to the central nitrogen atom, but instead of a dibenzoselenophene group, have a dibenzofuran group, a dibenzothiophenyl group, or a carbazole group linked to the central nitrogen atom. Accordingly, Comparative Examples 1 to 6, which include Comparative Example Compounds c1 to c6 in the hole transport layer have an increased driving voltage and decreased light emission efficiency and device life as compared with most of Examples 1 to 23.

Comparative Example Compound c7 includes a central nitrogen atom, a carbazole group substituted to the central nitrogen atom, a phenyl group substituted to the central nitrogen atom, and a dibenzoselenophene group substituted to the central nitrogen atom. However, in Comparative Example Compound c7, a methyl group is substituted to a nitrogen atom of the carbazole group instead of an aryl group or a heteroaryl group. Accordingly, Comparative Example 7 including Comparative Example Compound c7 in the emission layer has reduced light emission efficiency and device life as compared with Examples 1 to 23.

It is believed, therefore, that the organic light emitting device according to an embodiment of the present disclosure that includes a central nitrogen atom, a carbazole group substituted to the central nitrogen atom, a dibenzoselenophene group substituted to the central nitrogen atom, and an aryl group or a heteroaryl group substituted to the central nitrogen atom, and an aryl group or a heteroaryl group substituted to a nitrogen atom of the carbazole group may obtain improved life and efficiency characteristics due to a stable structure having improved heat resistance and durability.

An organic electroluminescence device of an embodiment may have high efficiency and increased lifetime characteristics.

An amine compound of an embodiment may be applied to a hole transport region of an organic electroluminescence device to contribute to allowing the organic electroluminescence device to have high efficiency and long-life.

The term "and/or" includes one or more combinations which may be defined by relevant elements. Expressions such as "at least one of," "one of," and "selected from," when preceding a list of elements, modify the entire list of elements and do not modify the individual elements of the list. Further, the use of "may" when describing embodiments of the present disclosure refers to "one or more embodiments of the present disclosure."

As used herein, the terms "use," "using," and "used" may be considered synonymous with the terms "utilize," "utilizing," and "utilized," respectively.

In addition, the terms "substantially," "about," and similar terms are used as terms of approximation and not as terms of degree, and are intended to account for the inherent deviations in measured or calculated values that would be recognized by those of ordinary skill in the art.

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein Although the present disclosure has been described with reference to example embodiments of the present disclosure, it will be understood that the present disclosure should not be limited to these example embodiments but that various changes and modifications can be made by those skilled in the art without departing from the spirit and scope of the present disclosure.

Accordingly, the technical scope of the present disclosure is not intended to be limited to the contents set forth in the detailed description of the specification, but is intended to be defined by the appended claims and their equivalents.

What is claimed is:

1. An organic electroluminescence device comprising:

a first electrode;

a second electrode facing the first electrode; and a plurality of organic layers between the first electrode and the second electrode, wherein at least one of the plurality of organic layers comprises an amine compound, the amine compound comprises a central nitrogen atom, a carbazole group substituted to the central nitrogen atom, and a dibenzoselenophene group substituted to the central nitrogen atom, and a nitrogen atom of the carbazole group is substituted with a substituted or unsubstituted aryl group or a substituted or unsubstituted heteroaryl group, wherein the plurality of organic layers comprise a hole transport region, an emission layer, and an electron transport region, and the hole transport region comprises the amine compound, and wherein the amine compound is represented by Formula 1:

Formula 1

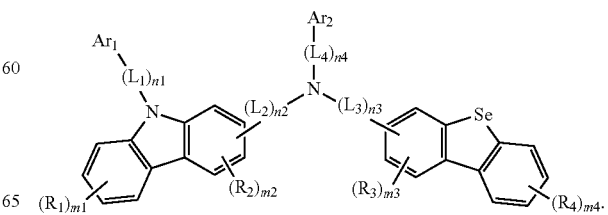

wherein in Formula 1,

Ar$_1$ and Ar$_2$ are each independently a substituted or unsubstituted aryl group having 6 to 60 ring-forming carbon atoms, or a substituted or unsubstituted heteroaryl group having 3 to 60 ring-forming carbon atoms, L$_1$ to L$_4$ are each independently a direct linkage, a substituted or unsubstituted arylene group having 6 to 60 ring-forming carbon atoms, or a substituted or unsubstituted heteroarylene group having 3 to 60 ring-forming carbon atoms, R$_1$ to R$_4$ are each independently a hydrogen atom, a deuterium atom, a halogen atom, a substituted or unsubstituted alkyl group having 1 to 20 carbon atoms, a substituted or unsubstituted aryl group having 6 to 60 ring-forming carbon atoms, or a substituted or unsubstituted heteroaryl group having 3 to 60 ring-forming carbon atoms, m$_1$ to m$_4$ are each independently an integer of 0 to 4, and n$_1$ to n$_4$ are each independently an integer of 0 to 1.

2. The organic electroluminescence device of claim 1, wherein the amine compound further comprises, a substituted or unsubstituted aryl group or a substituted or unsubstituted heteroaryl group, substituted to the central nitrogen atom.

3. The organic electroluminescence device of claim 1, wherein the amine compound further comprises, a substituted or unsubstituted arylene group or a substituted or unsubstituted heteroarylene group, connecting the central nitrogen atom and the carbazole group and the central nitrogen atom and the dibenzoselenophene group, respectively.

4. The organic electroluminescence device of claim 1, wherein the hole transport region comprises a hole transport layer and a hole injection layer, and
the hole transport layer comprises the amine compound.

5. The organic electroluminescence device of claim 1, wherein the amine compound represented by Formula 1 is represented by Formula 1-1:

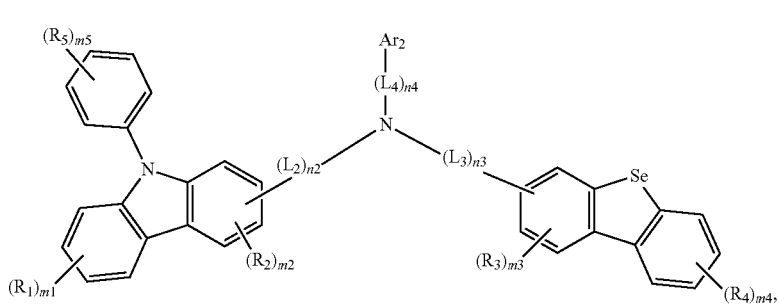

Formula 1-1 wherein in Formula 1-1,
Ar$_2$, L$_2$ to L$_4$, R$_1$ to R$_4$, m$_1$ to m$_4$, and n$_2$ to n$_4$ are the same as defined in Formula 1,
R$_5$ is a hydrogen atom, a deuterium atom, a halogen atom, a substituted or unsubstituted alkyl group having 1 to 20 carbon atoms, a substituted or unsubstituted aryl group having 6 to 60 ring-forming carbon atoms, or a substituted or unsubstituted heteroaryl group having 3 to 60 ring-forming carbon atoms, and
m is an integer of 0 to 5.

6. The organic electroluminescence device of claim 1, wherein the amine compound represented by Formula 1 is represented by any one of Formulae 2-1 to 2-4:

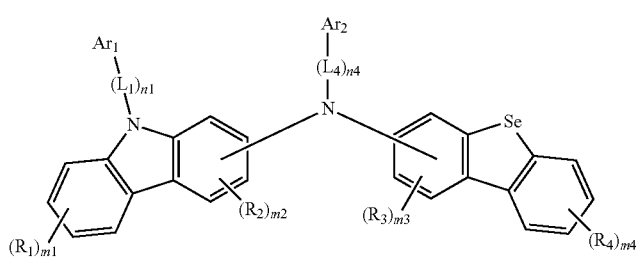

Formula 2-1

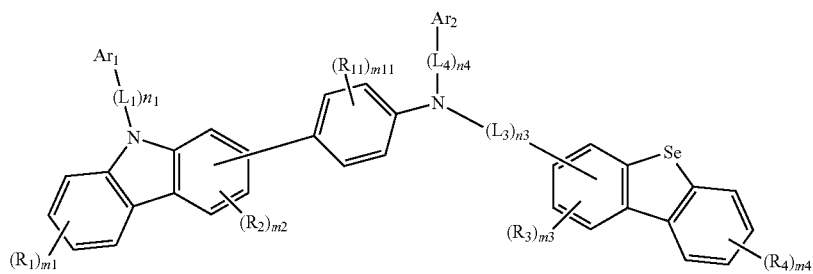
Formula 2-2

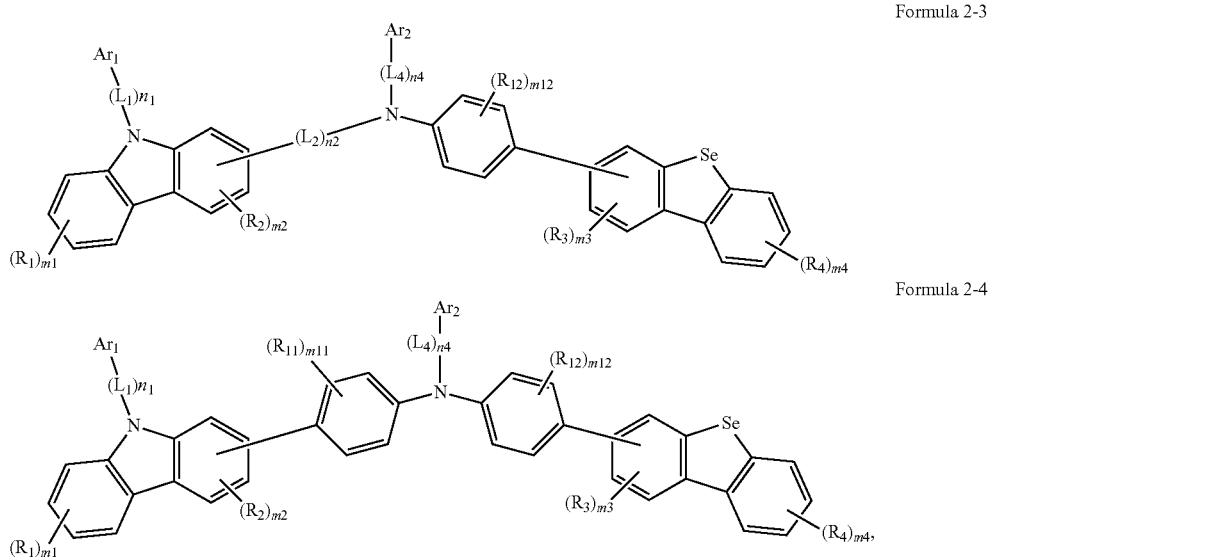
Formula 2-3

Formula 2-4 wherein in Formulae 2-1 to 2-4, $Ar_1$, $Ar_2$, $L_1$ to $L_4$, $R_1$ to $R_4$, $m_1$ to $m_4$, and $n_1$ to $n_4$ are the same as defined in Formula 1, $R_{11}$ and $R_{12}$ are each independently a hydrogen atom, a deuterium atom, a halogen atom, a substituted or unsubstituted alkyl group having 1 to 20 carbon atoms, a substituted or unsubstituted aryl group having 6 to 60 ring-forming carbon atoms, or a substituted or unsubstituted heteroaryl group having 3 to 60 ring-forming carbon atoms, and $m_{11}$ and $m_{12}$ are each independently an integer of 0 to 4.

7. The organic electroluminescence device of claim 1, wherein the amine compound represented by Formula 1 is represented by any one of Formulae 3-1 to 3-4:

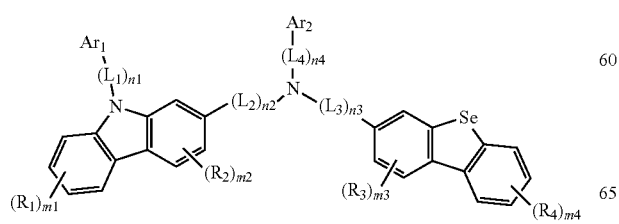
Formula 3-1

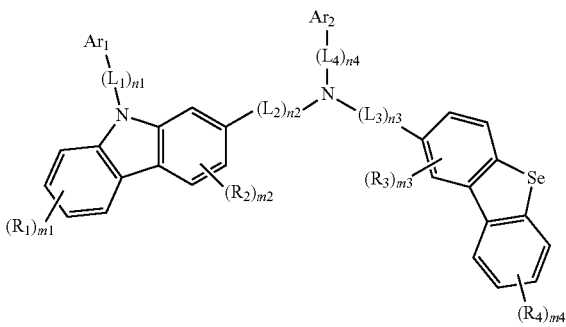
Formula 3-2

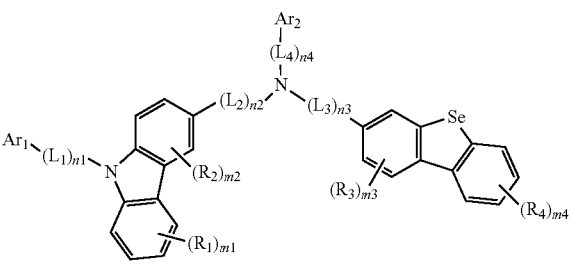
Formula 3-3

Formula 3-4

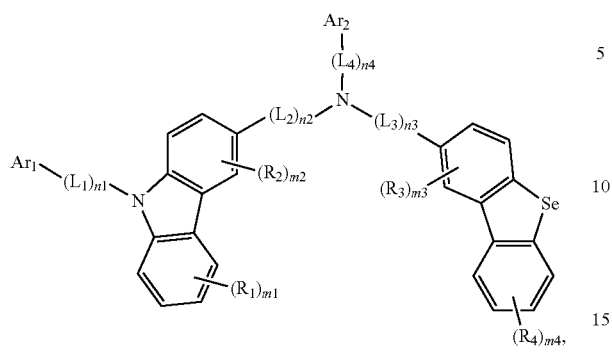

wherein in Formulae 3-1 to 3-4,

Ar$_1$, Ar$_2$, L$_1$ to L$_4$, R$_1$ to R$_4$, m$_1$ to m$_4$, and n$_1$ to n$_4$ are the same as defined in Formula 1.

8. The organic electroluminescence device of claim 1, wherein Ar$_2$ is a substituted or unsubstituted phenyl group, a substituted or unsubstituted naphthyl group, a substituted or unsubstituted phenanthrenyl group, a substituted or unsubstituted dibenzofuranyl group, or a substituted or unsubstituted dibenzothiophenyl group.

9. The organic electroluminescence device of claim 1, wherein the amine compound represented by Formula 1 is any one of compounds represented by Compound Group 1:

Compound Group 1

1

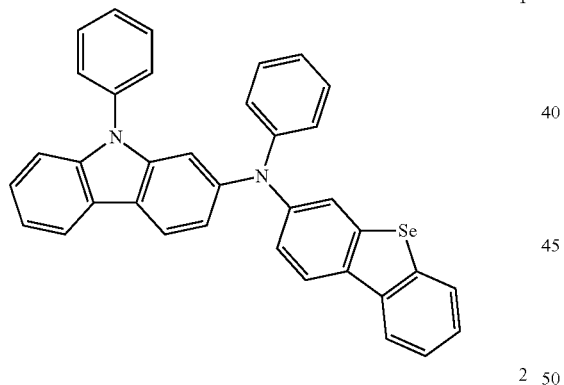

2

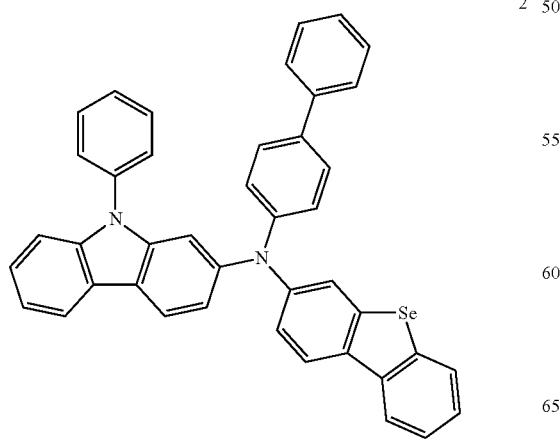

3

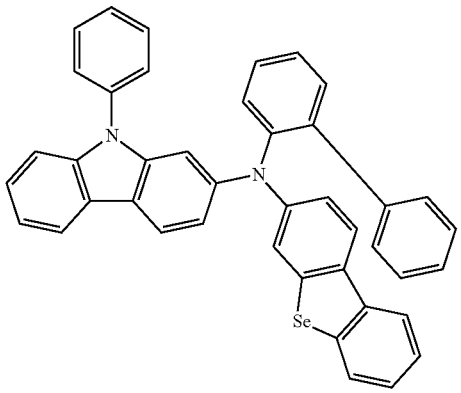

4

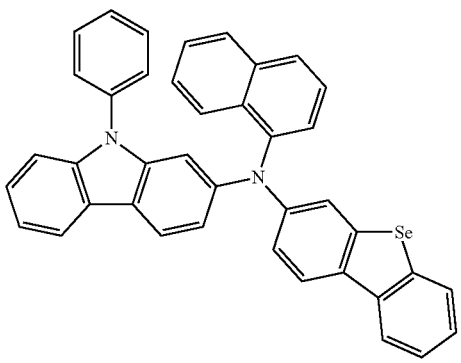

5

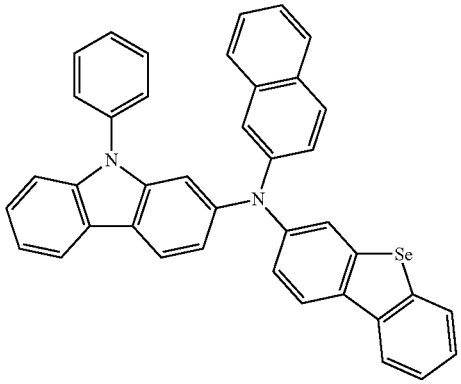

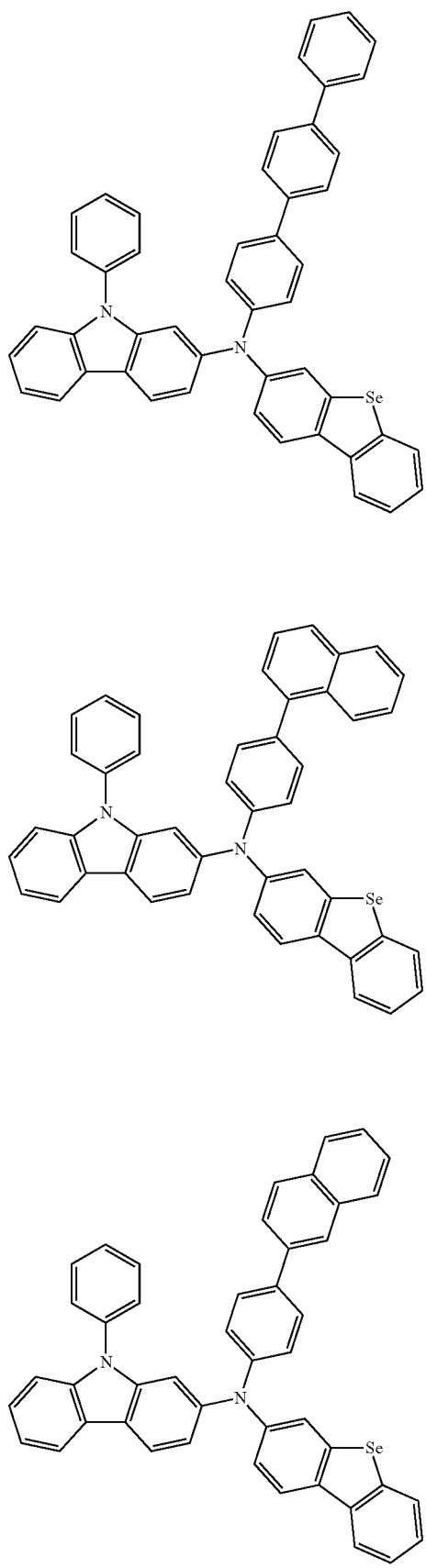
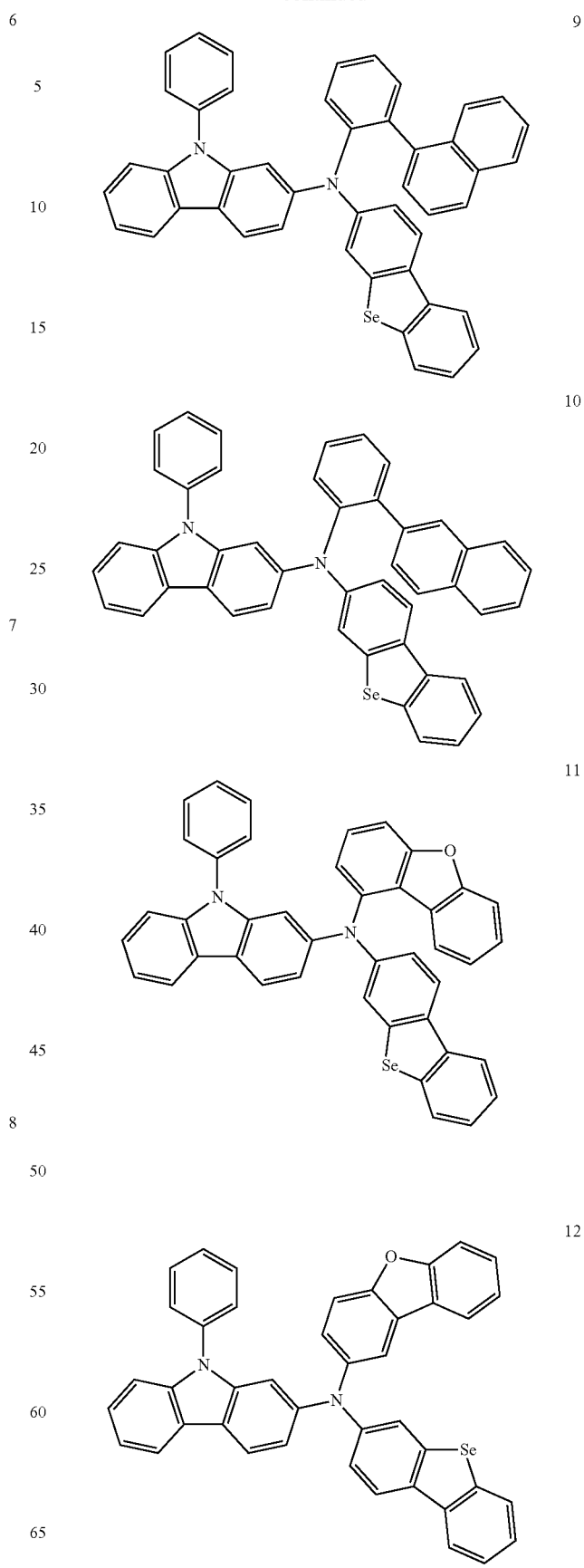

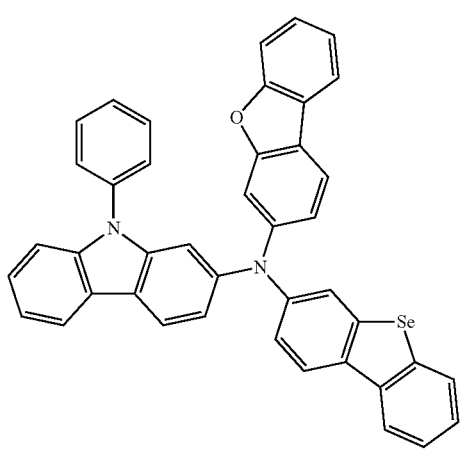
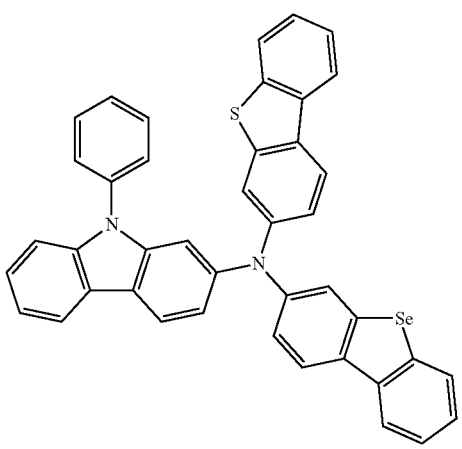

21
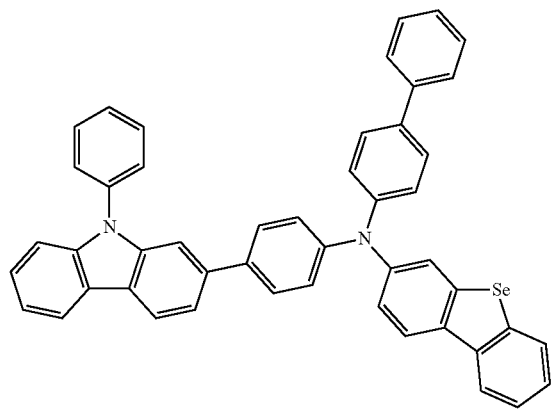
22
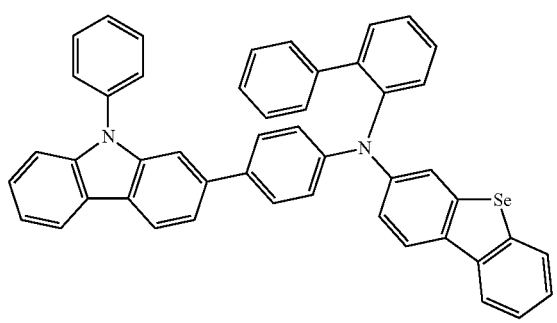
23
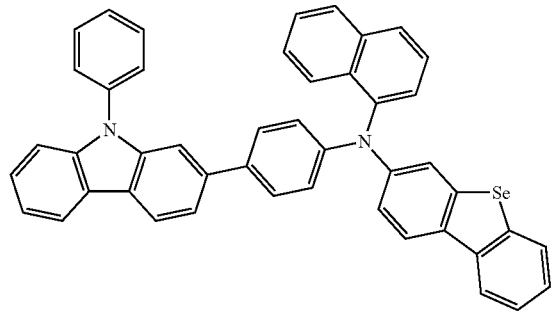
24
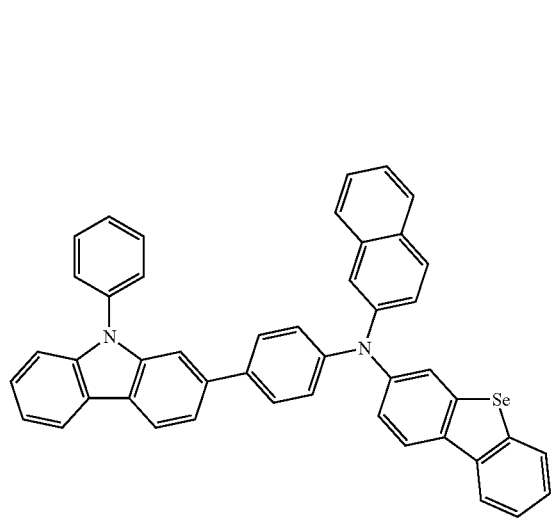
25
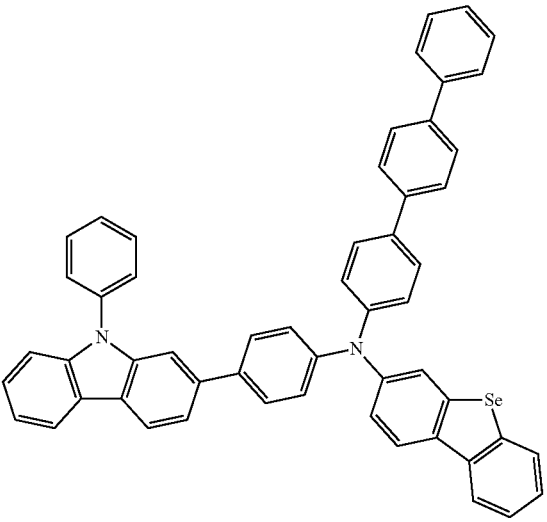
26
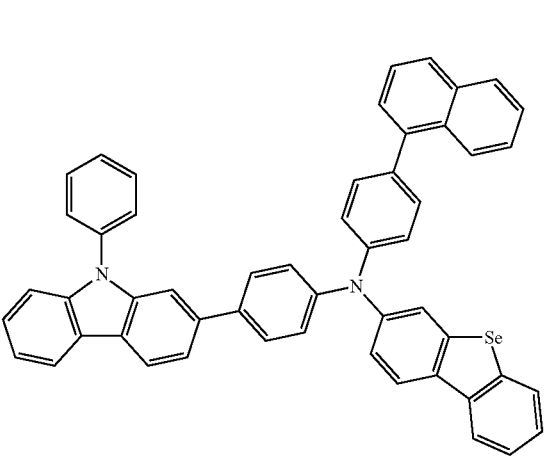
27
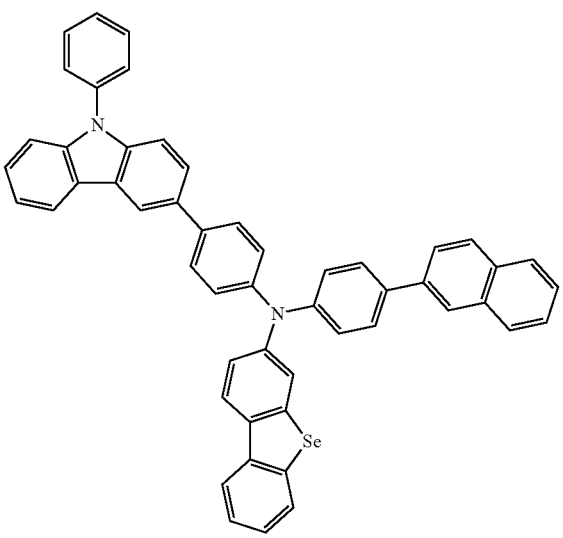

28
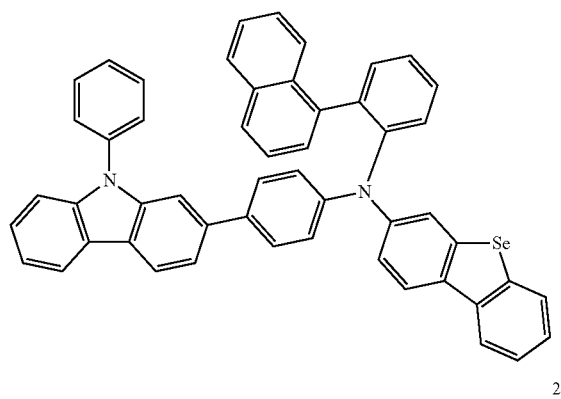
29
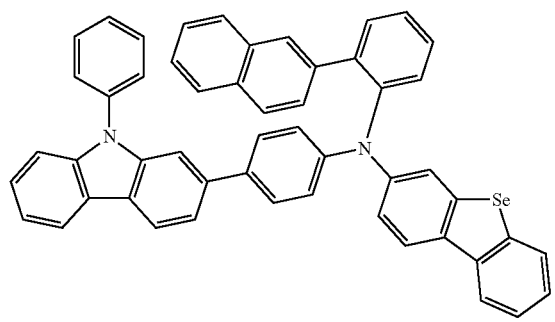
30
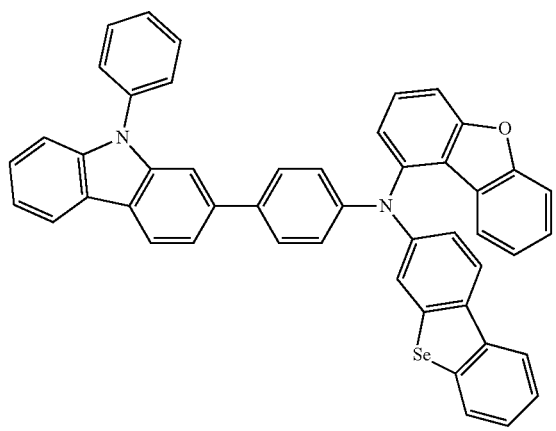
31
32
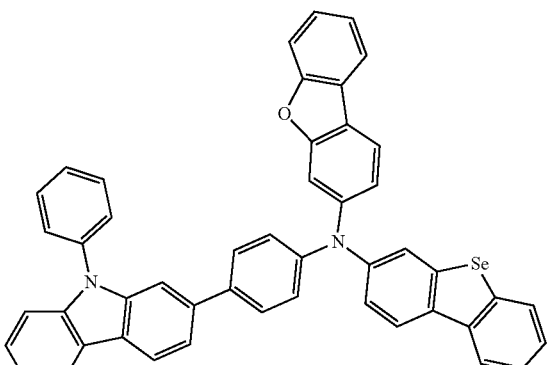
33
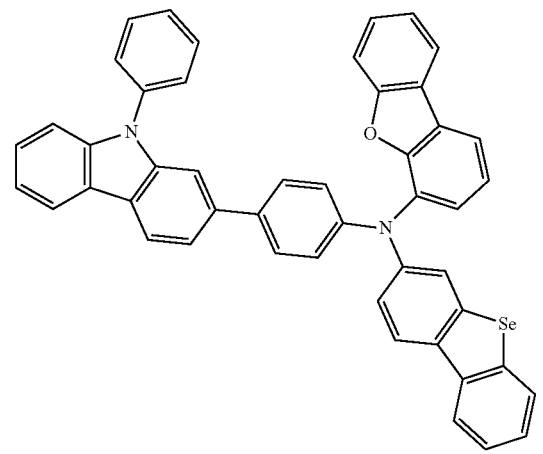
34
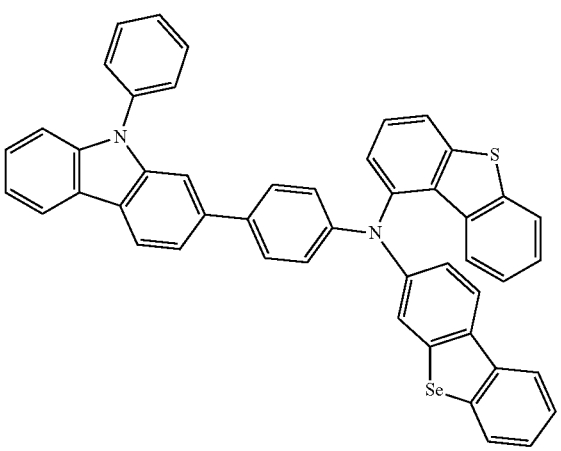

279
-continued
35
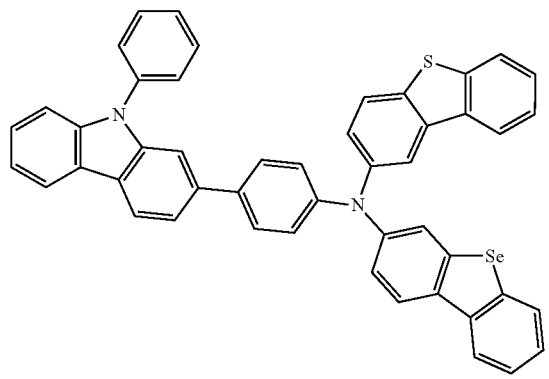
36
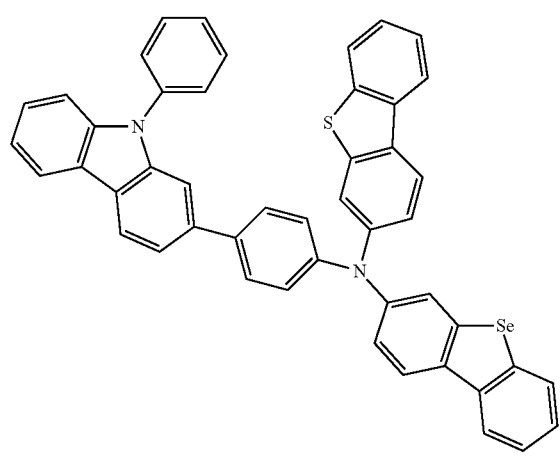
37
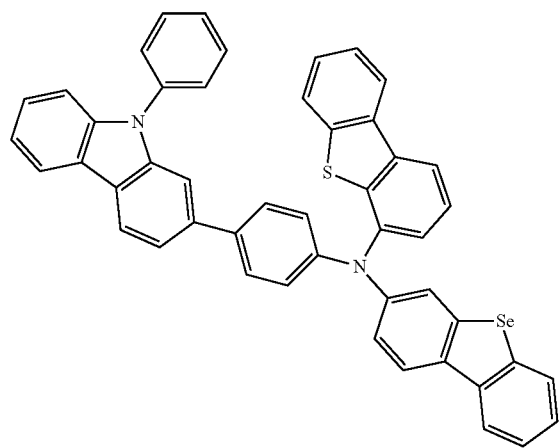
280
-continued
38
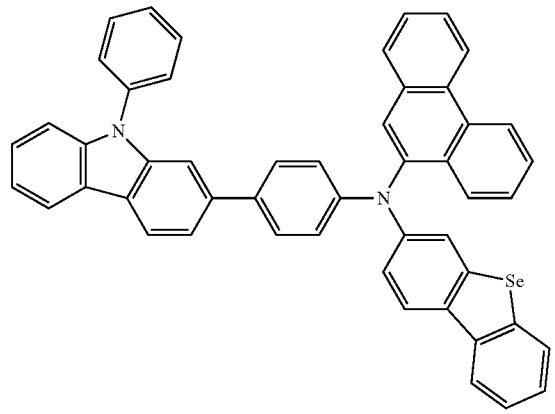
39
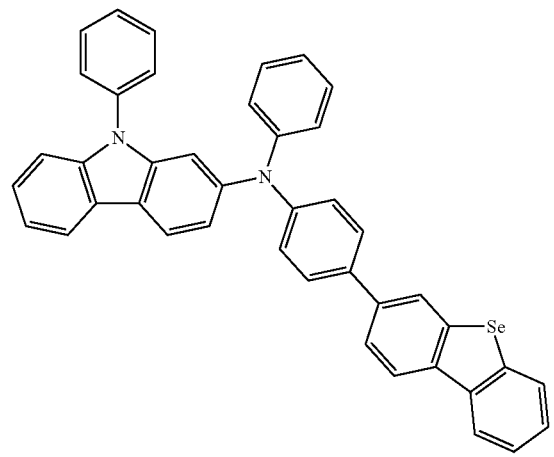
40
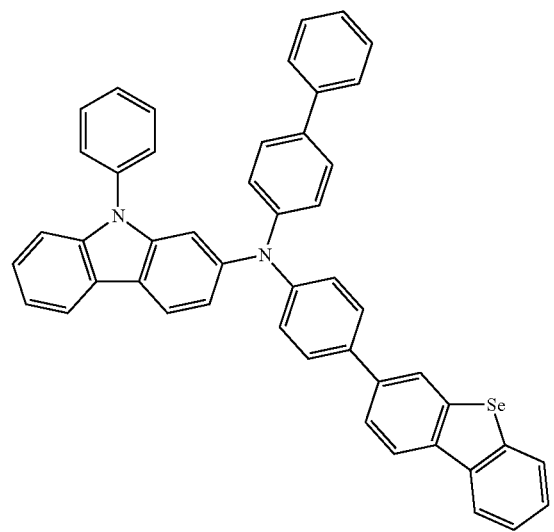

281
-continued
41
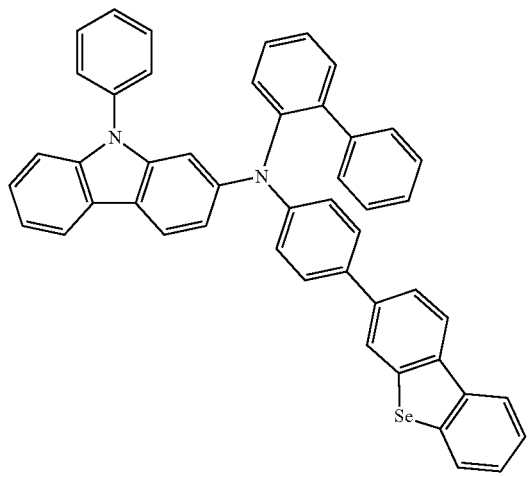
42
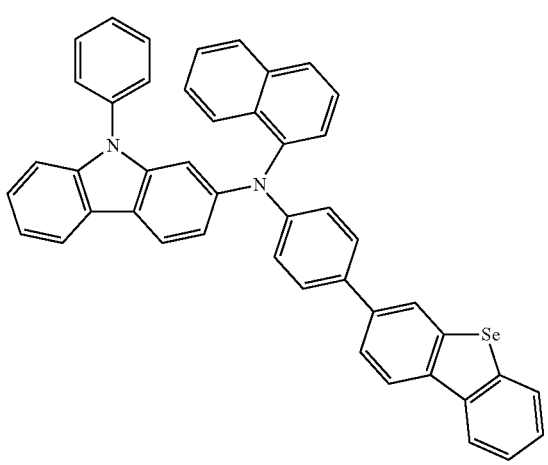
43
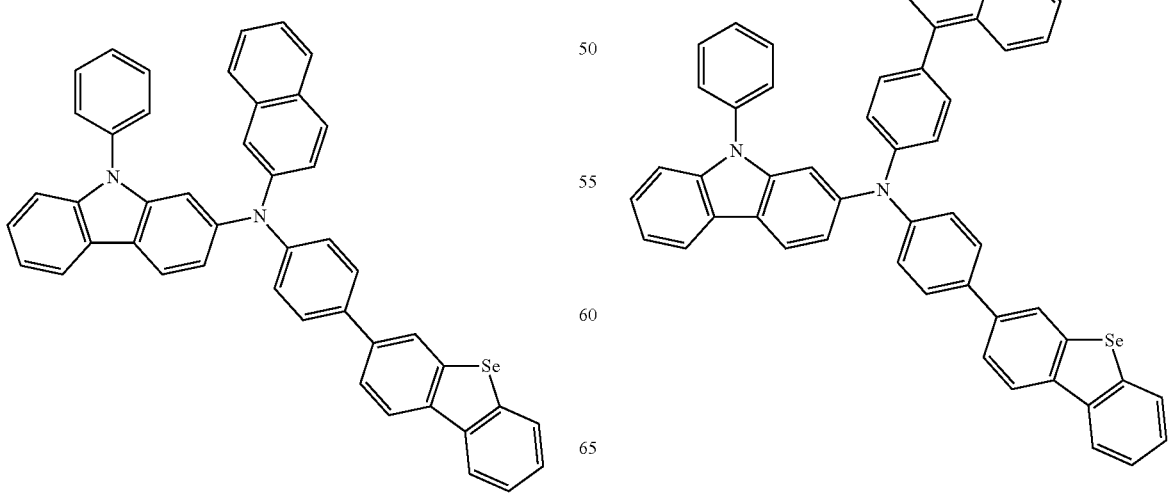
282
-continued
44
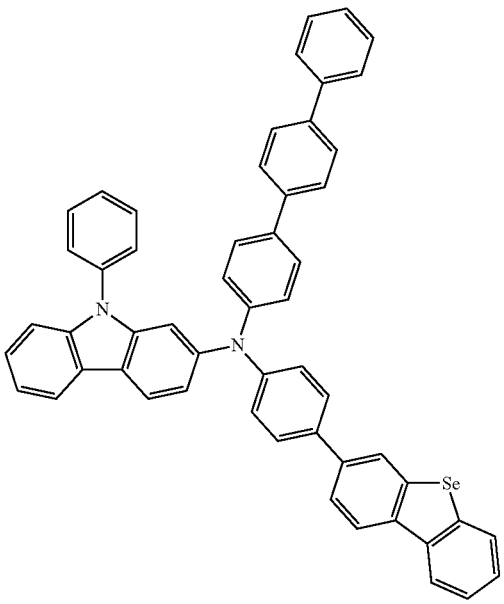
45

283
-continued
46
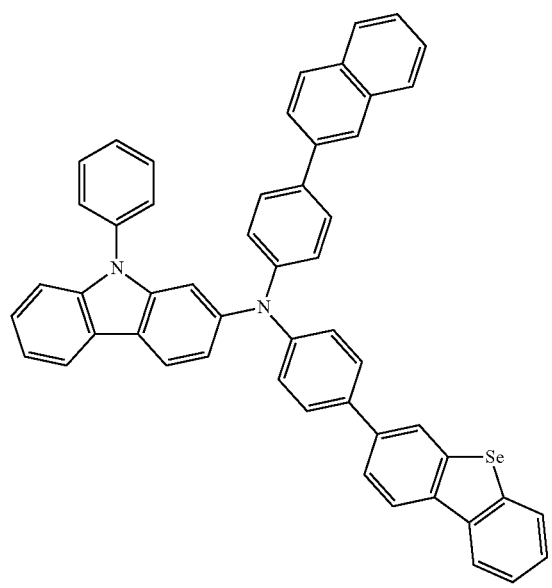
47
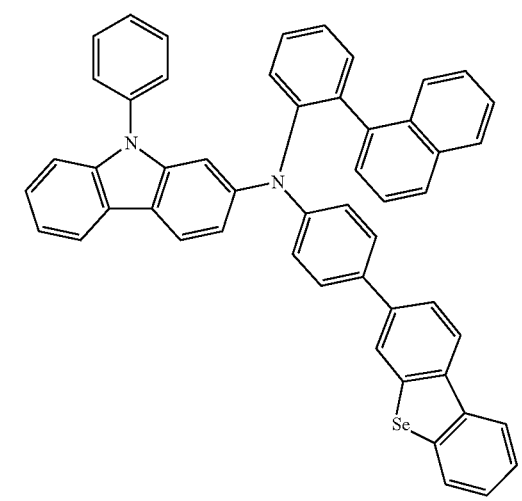
48
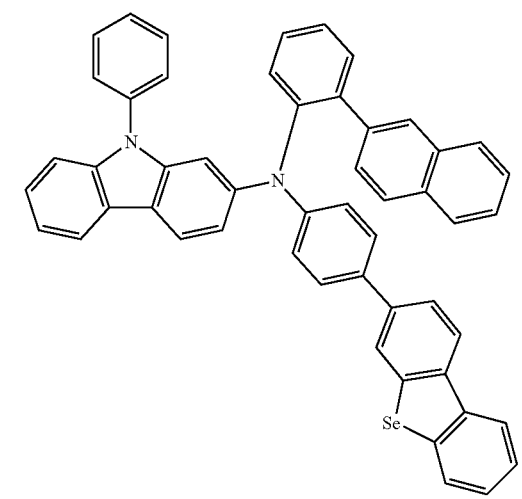
284
-continued
49
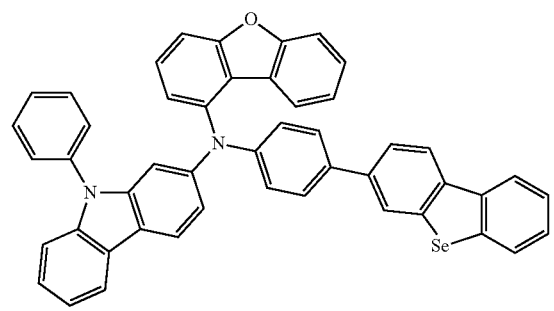
50
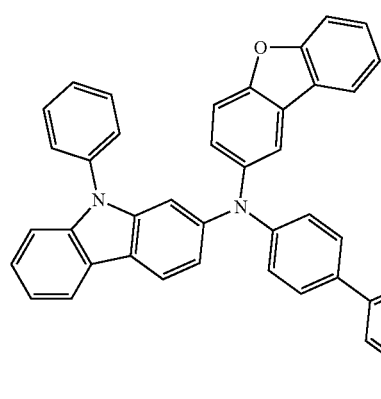
51
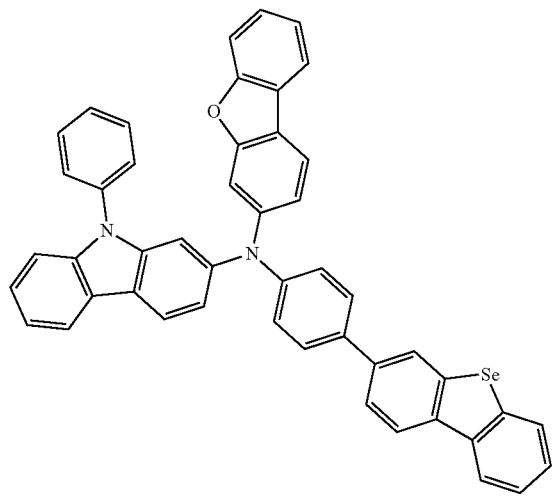

52
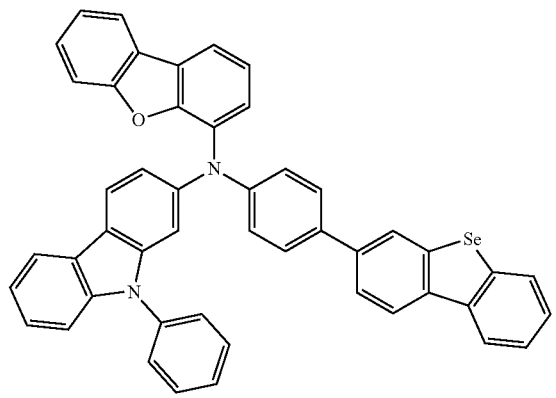
53
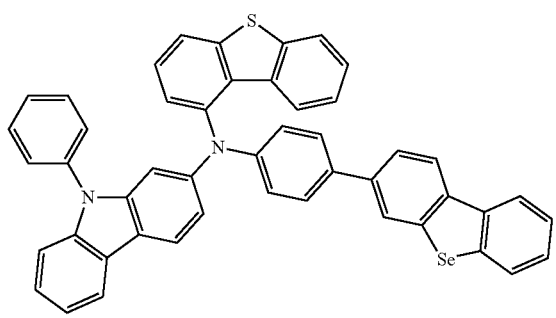
54
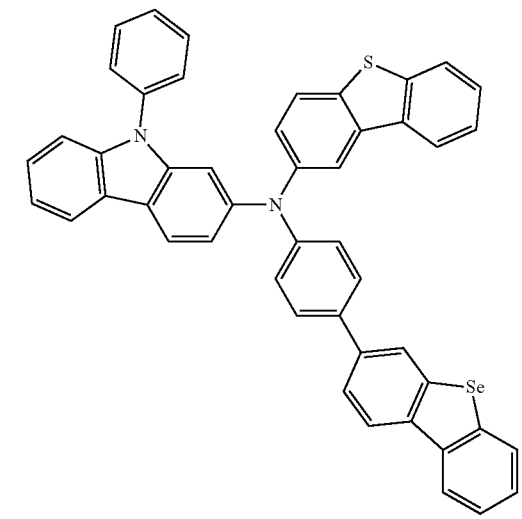
55
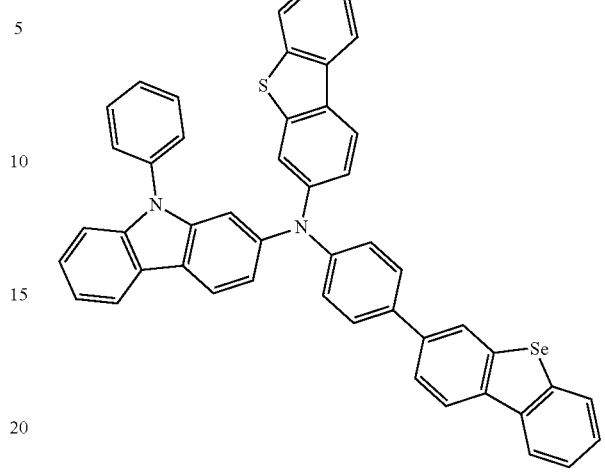
56
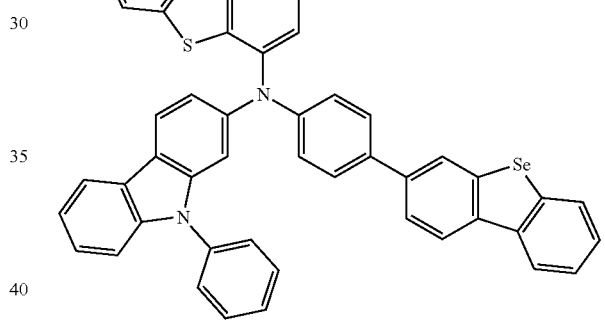
57
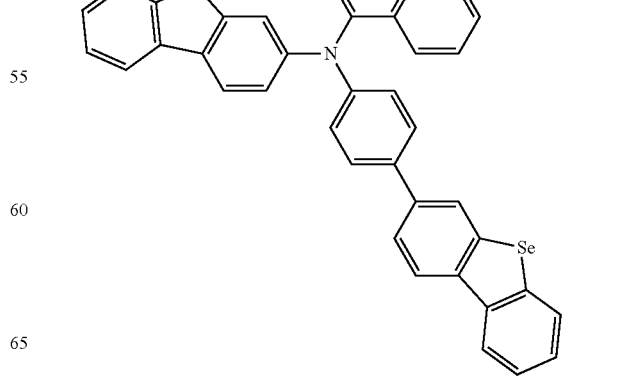

287
-continued
58
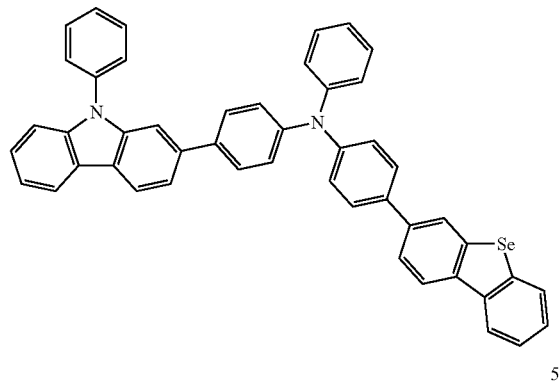
59
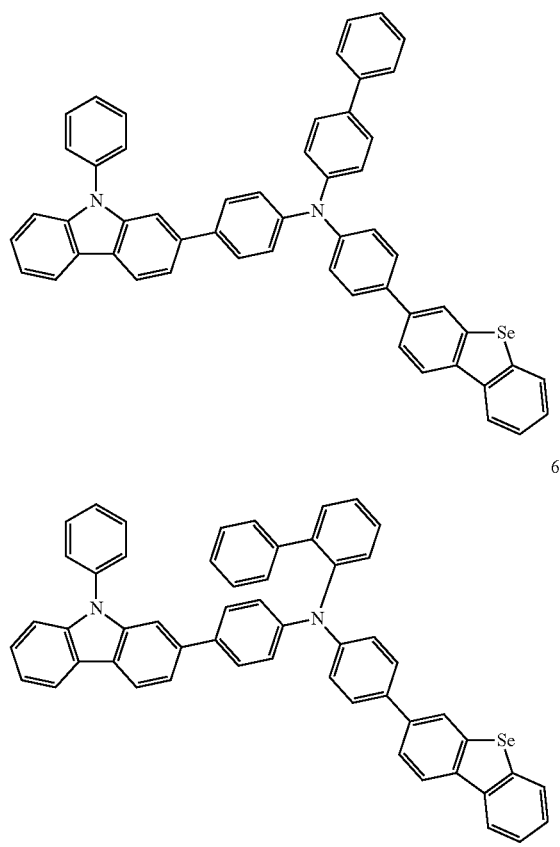
60
61
288
-continued
62
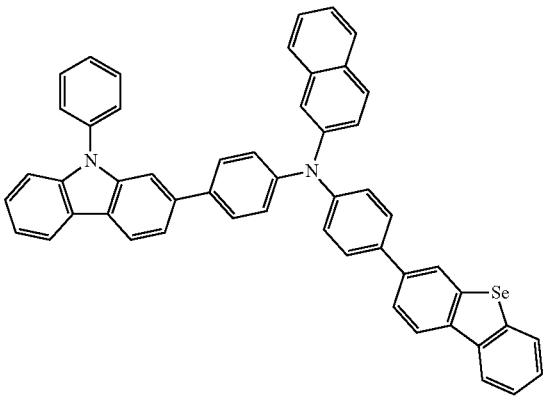
63
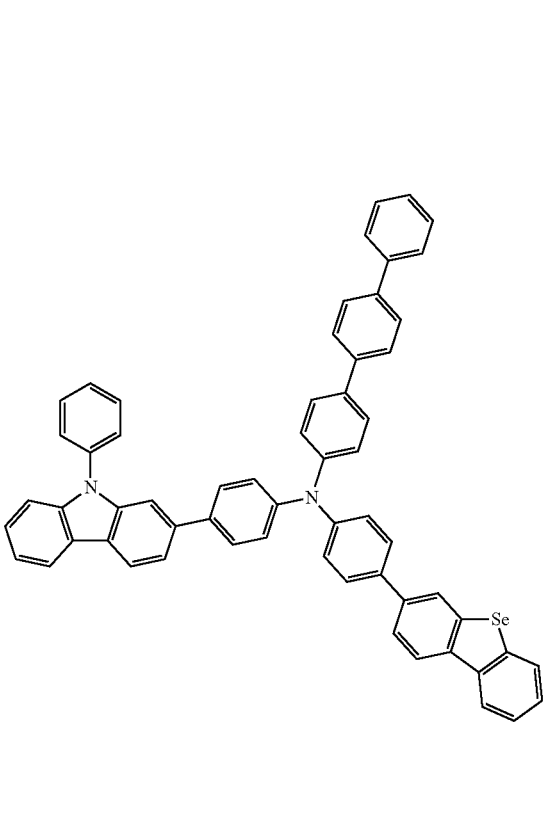
64
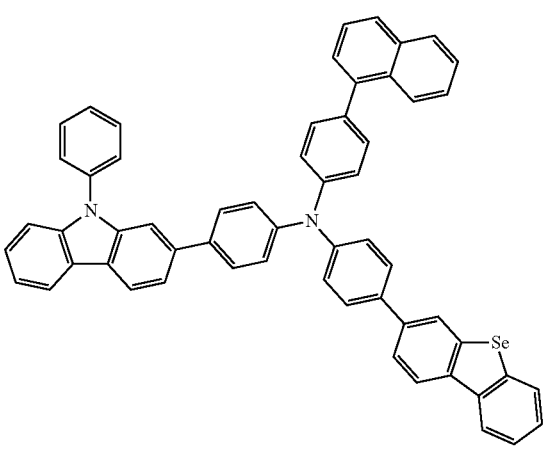

289
-continued
65
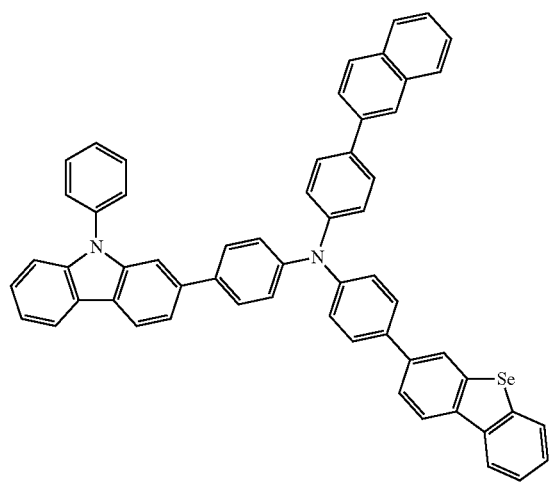
66
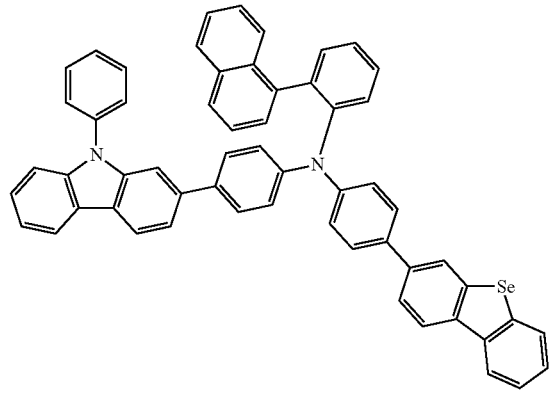
67
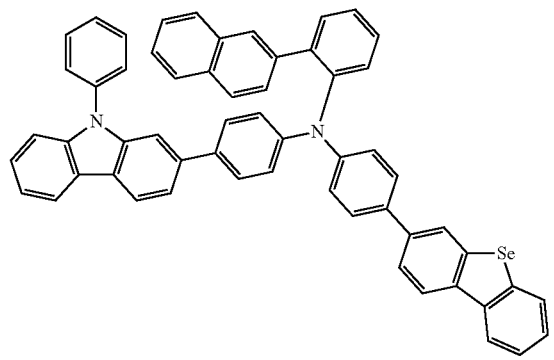
290
-continued
68
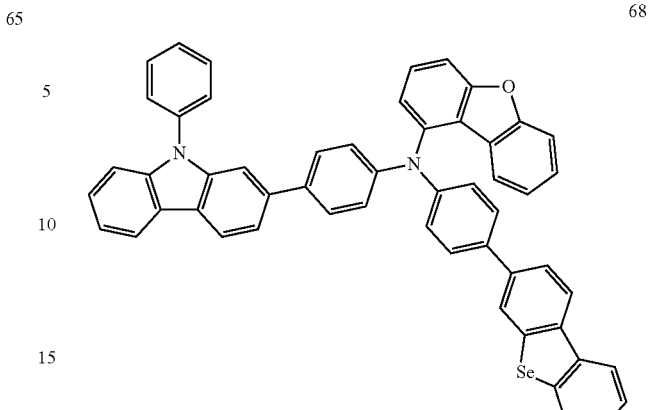
69
70

291
-continued
292
-continued
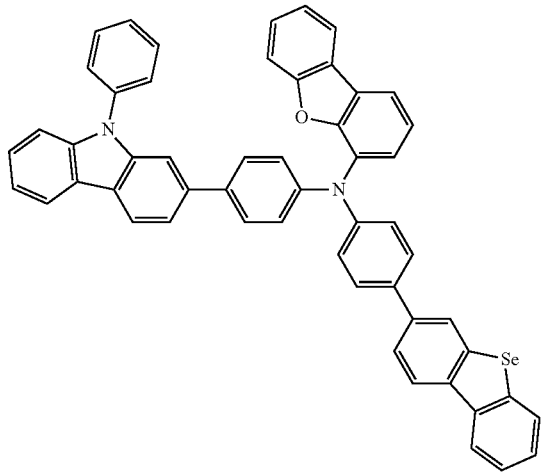
71
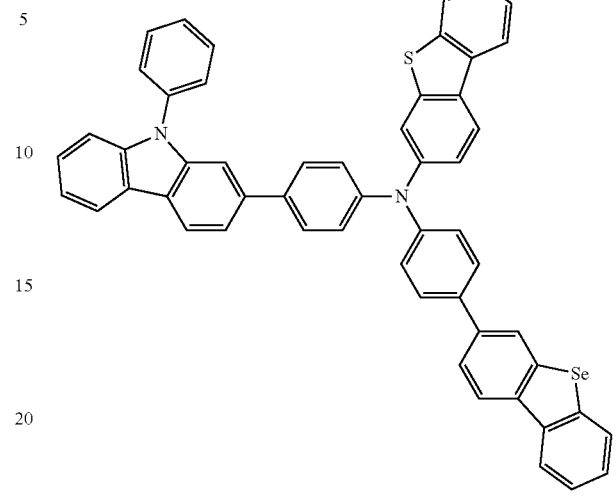
74
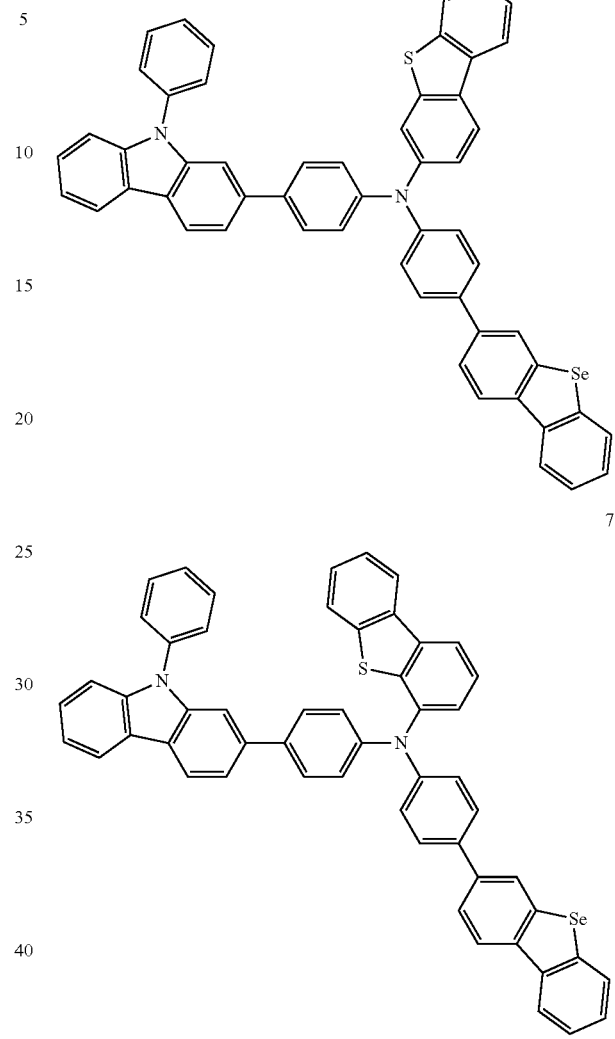
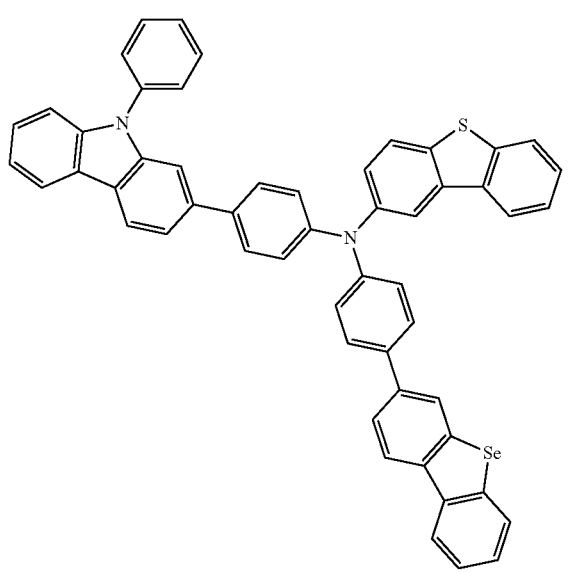
73
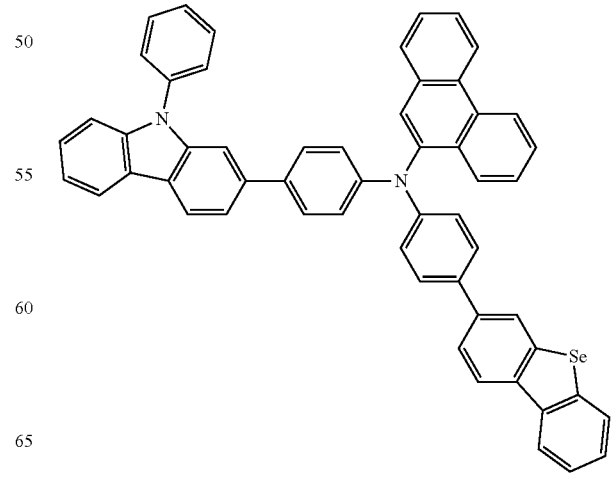
76

77
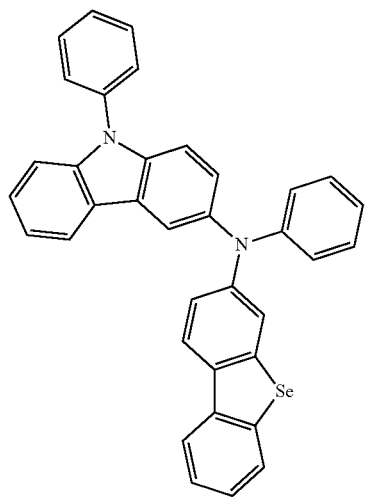
78
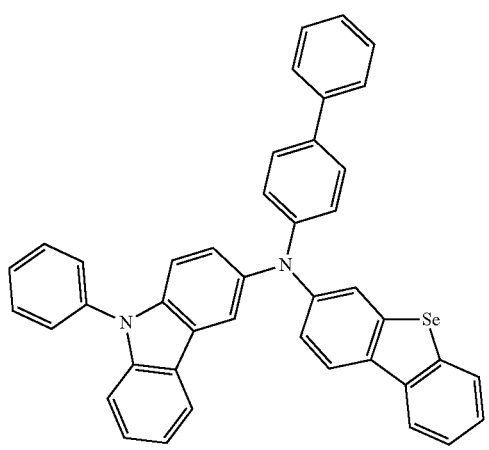
79
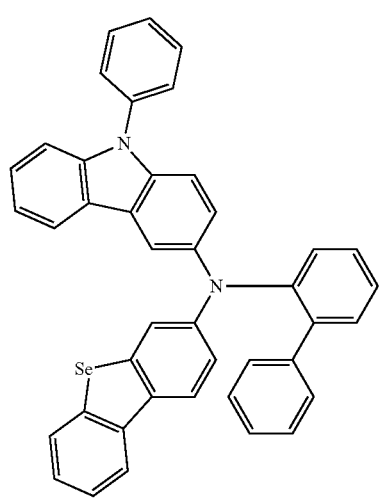
80
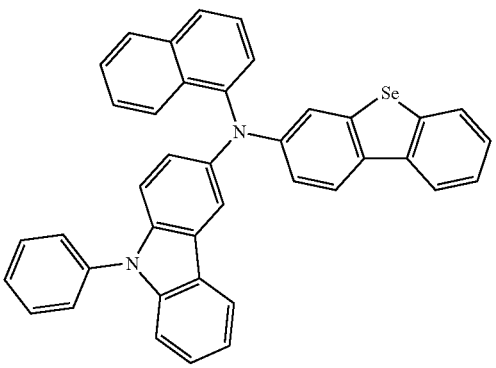
81
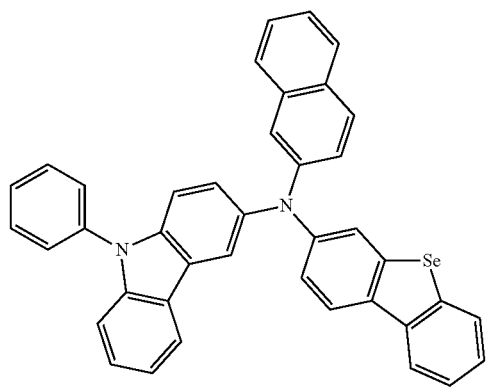
82
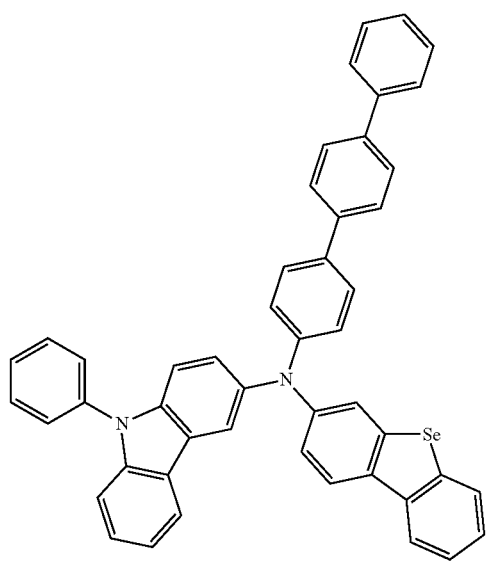

295
-continued
83
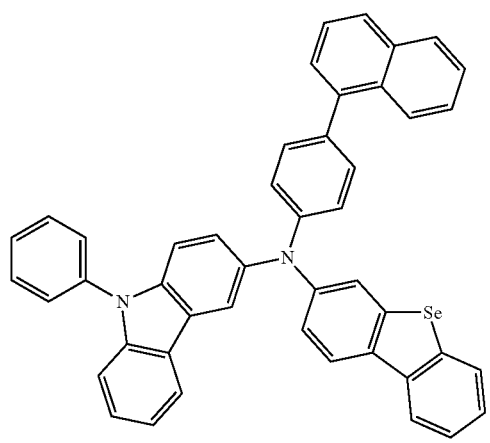
84
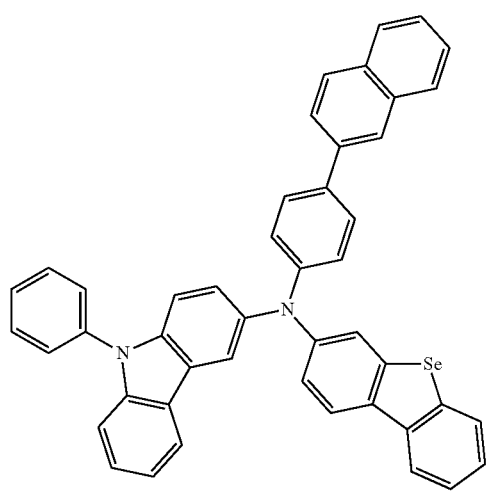
85
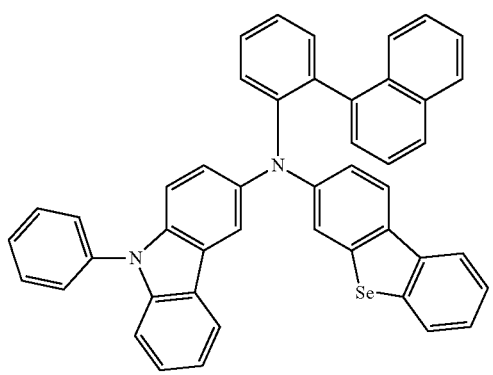
296
-continued
86
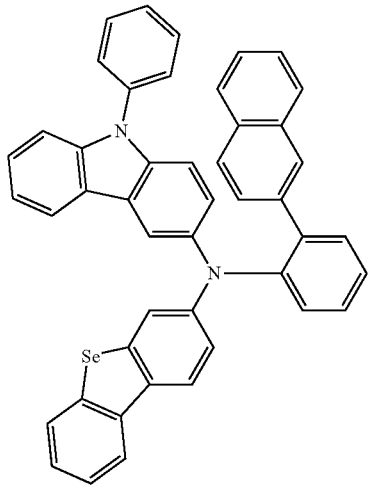
87
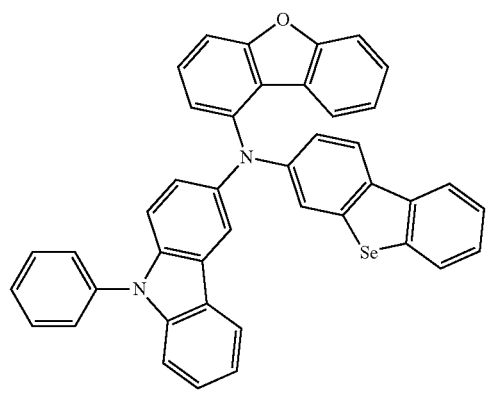
88
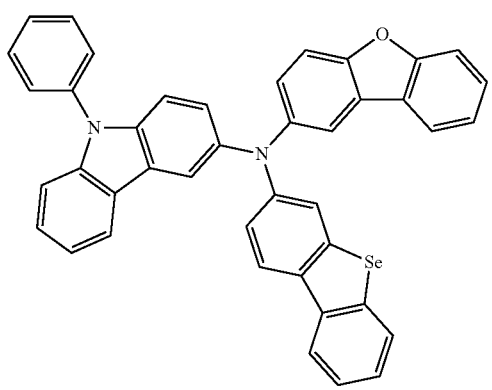

-continued
89
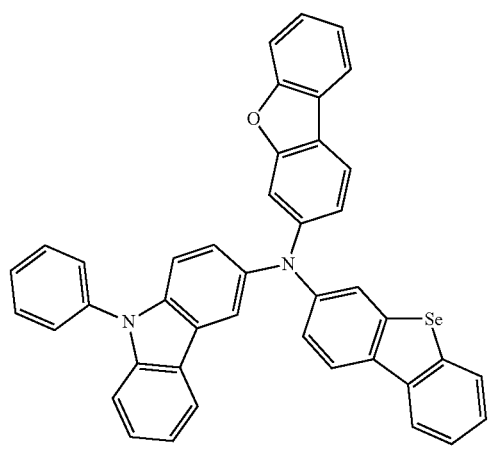
90
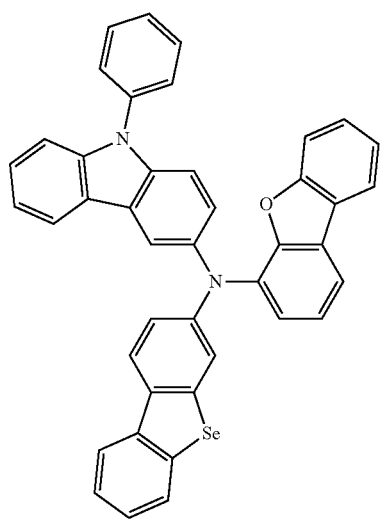
91
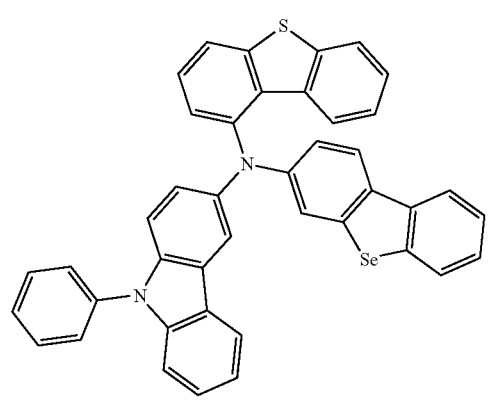
-continued
92
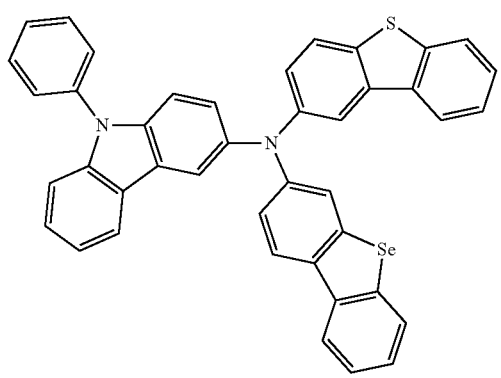
93
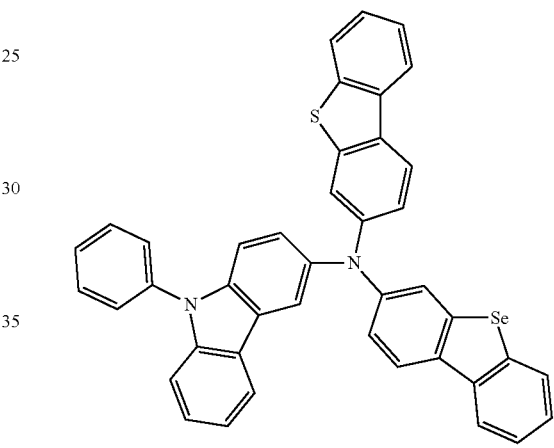
94
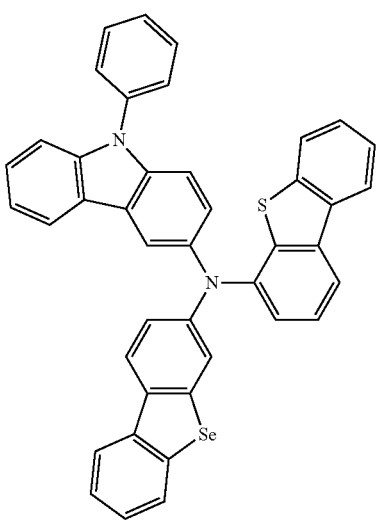

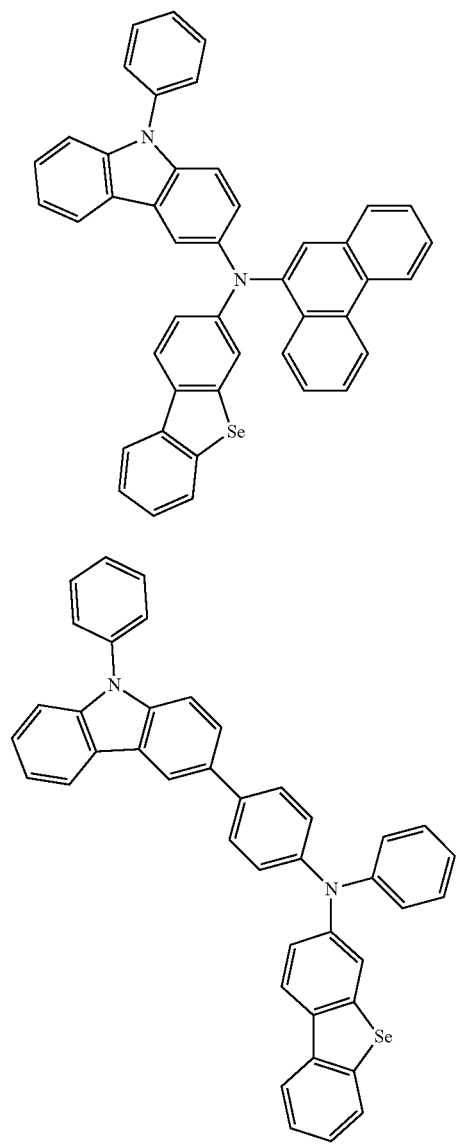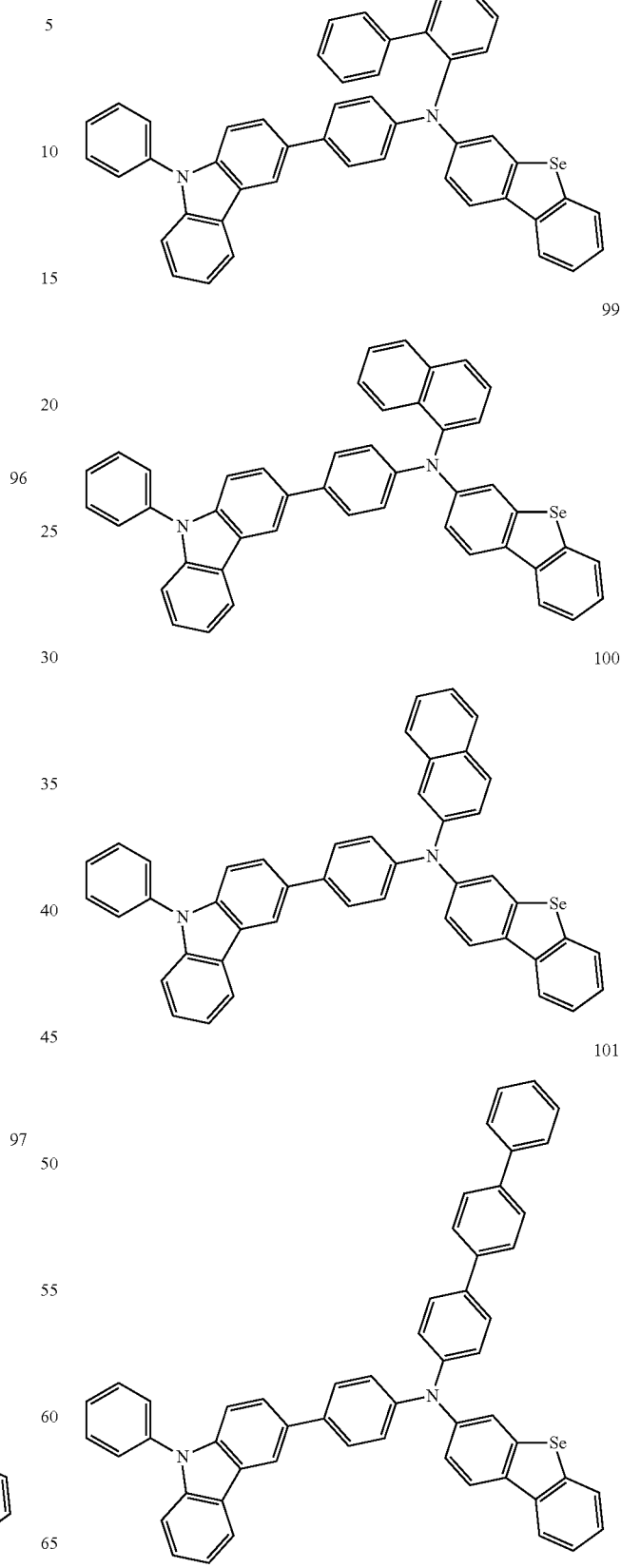

-continued
102
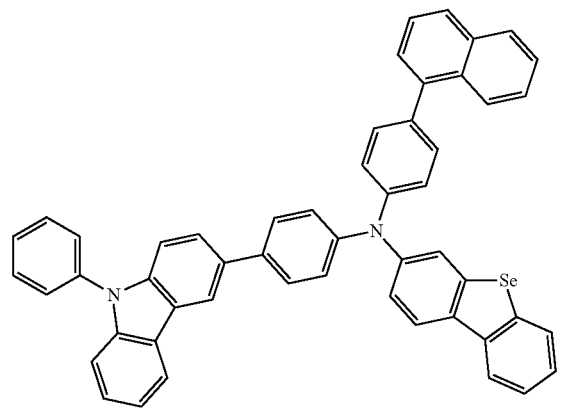
105
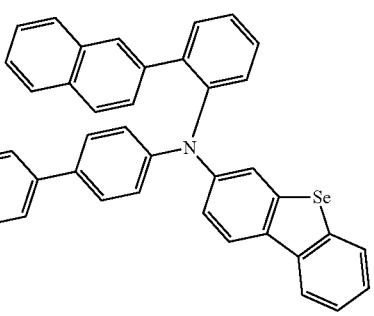
103
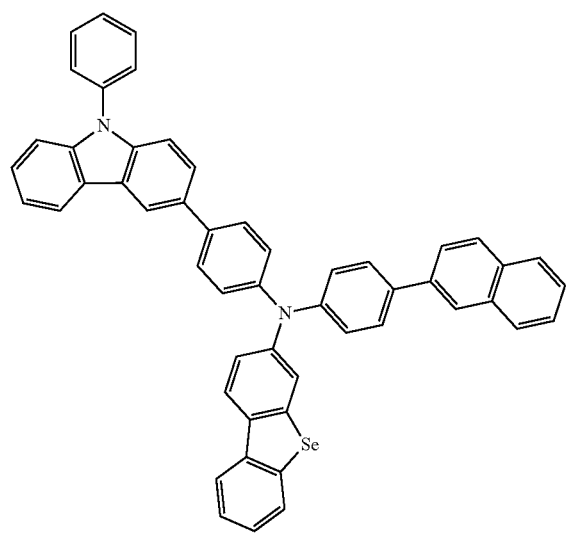
106
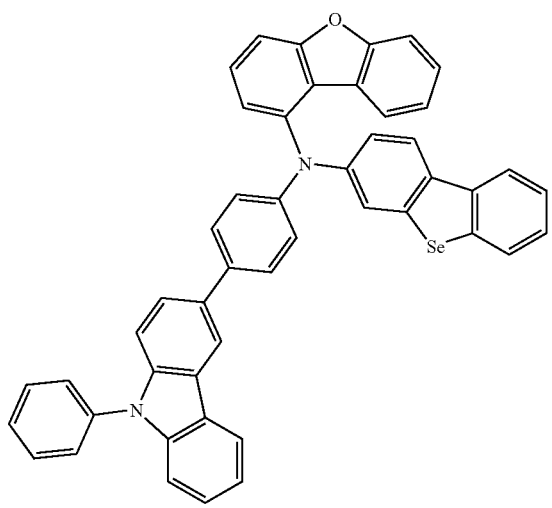
104
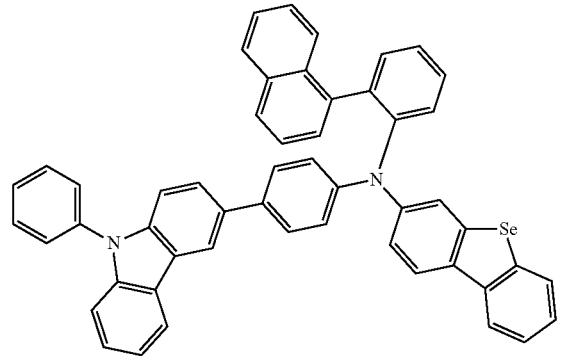
107
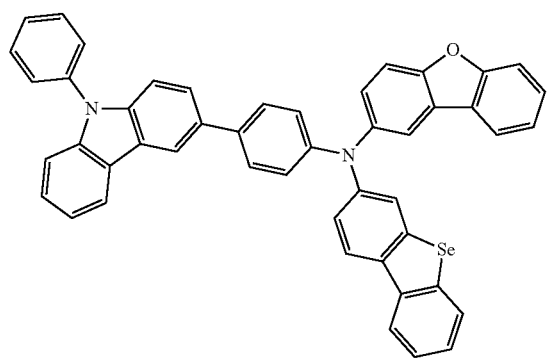

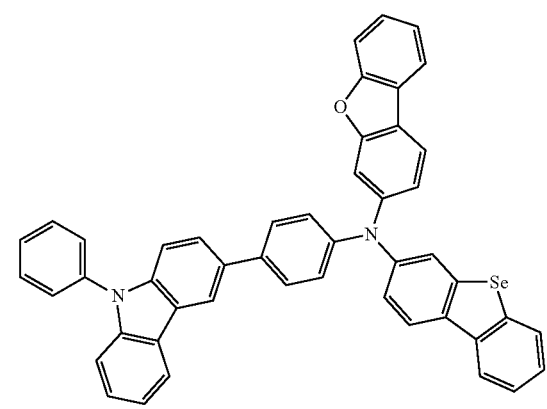
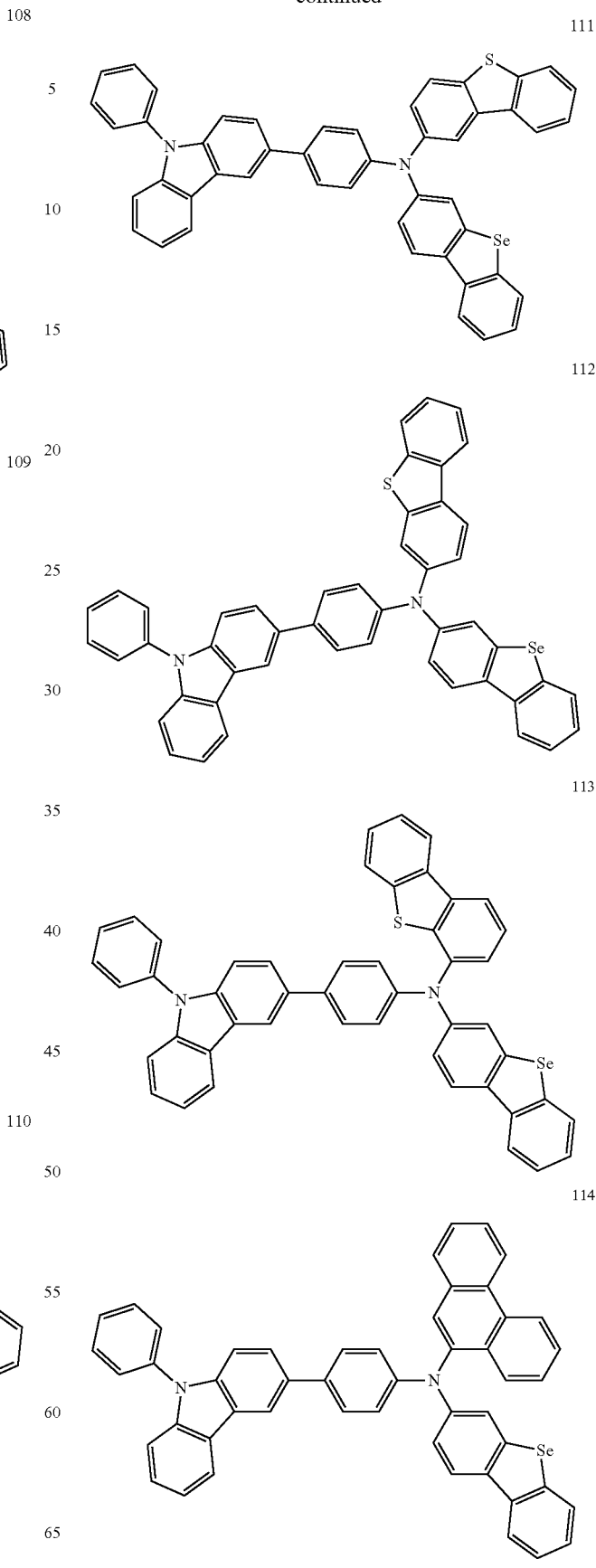

305
-continued
115
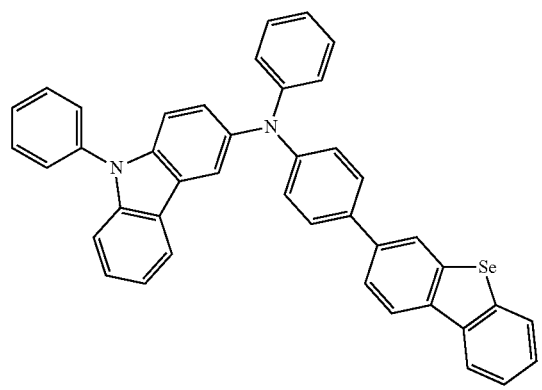
116
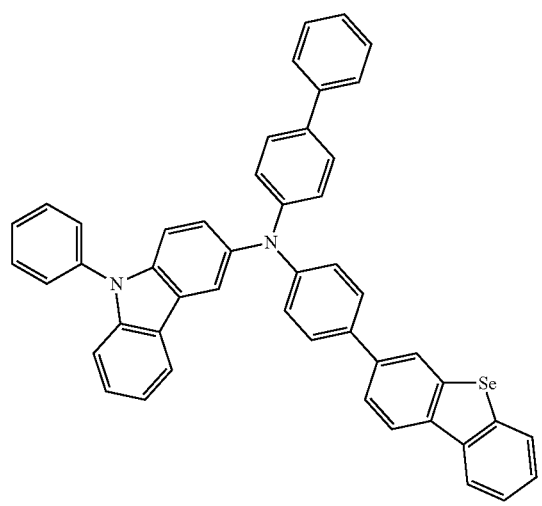
117
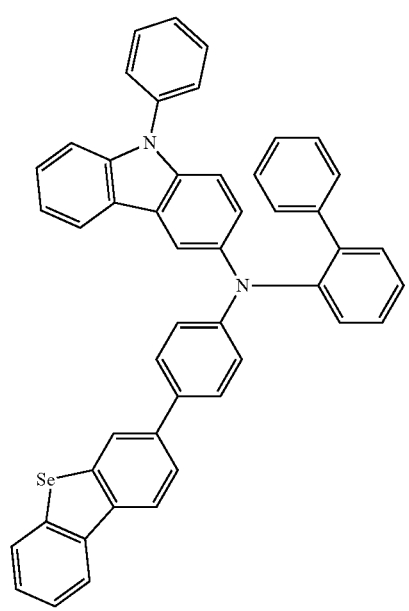
306
-continued
118
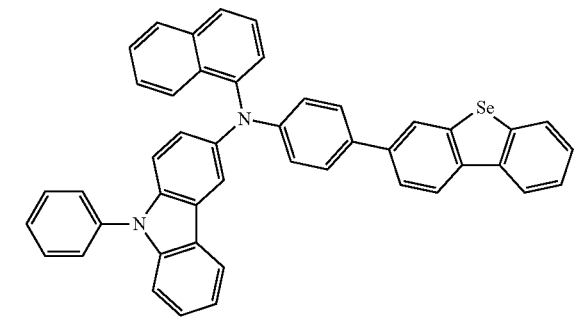
119
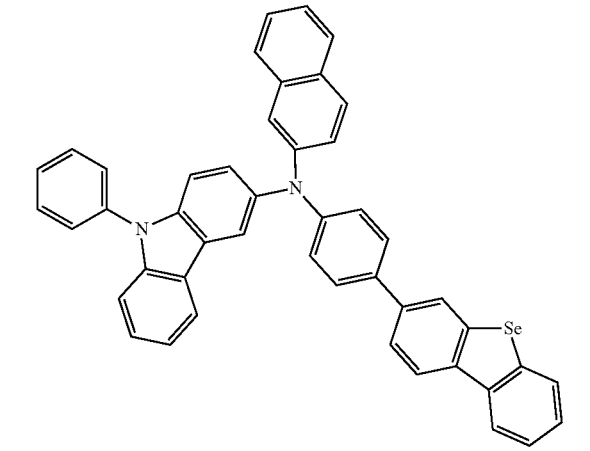
120
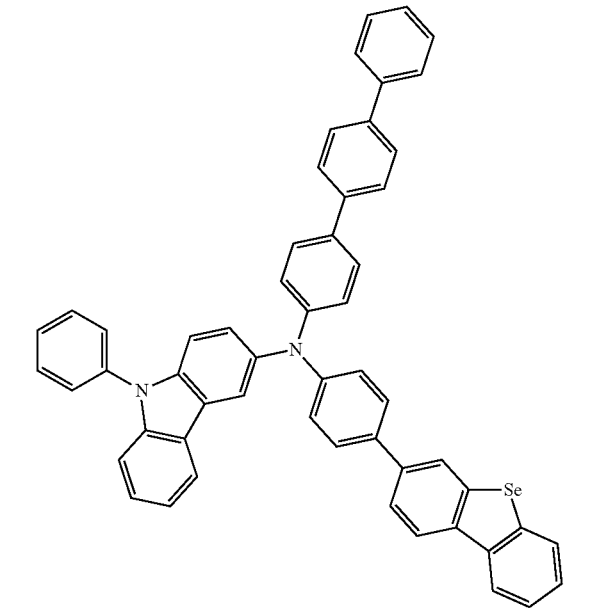

121
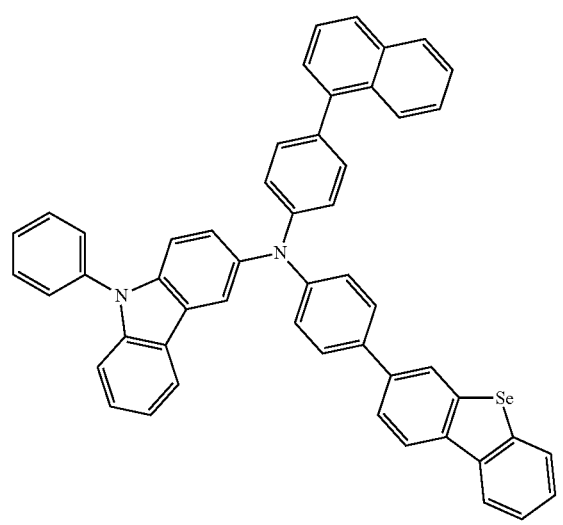
124
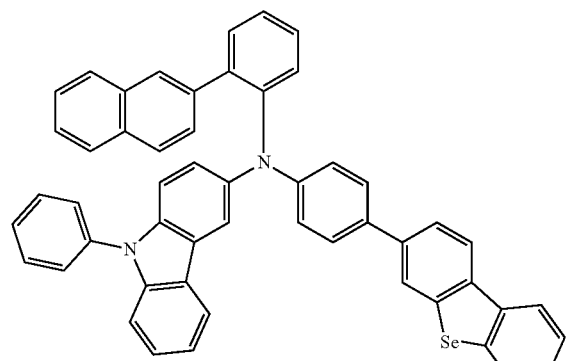
122
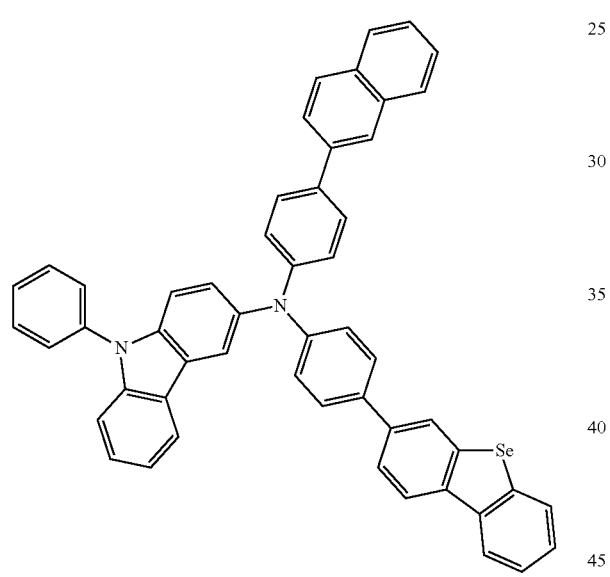
125
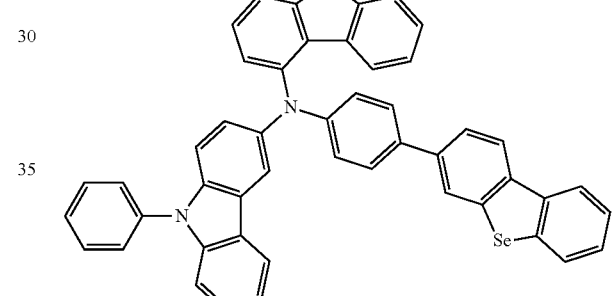
123
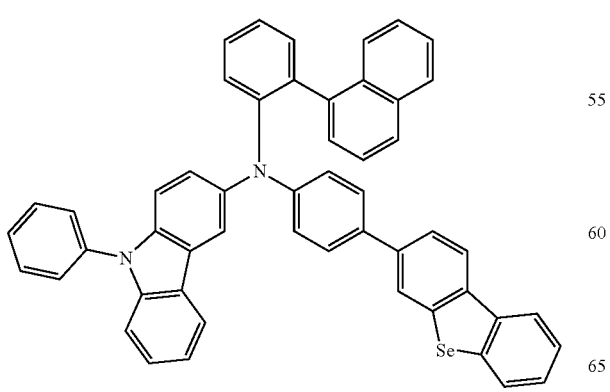
126
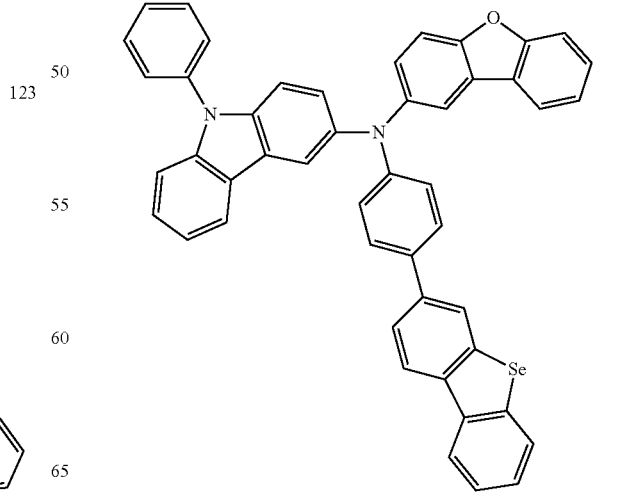

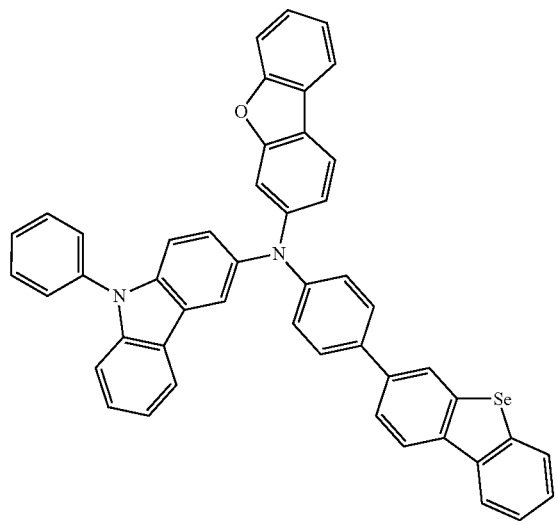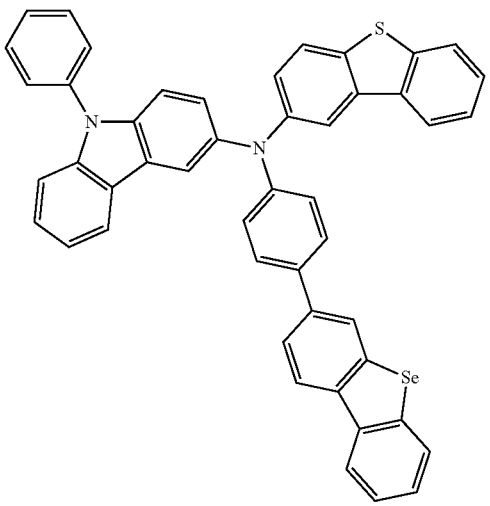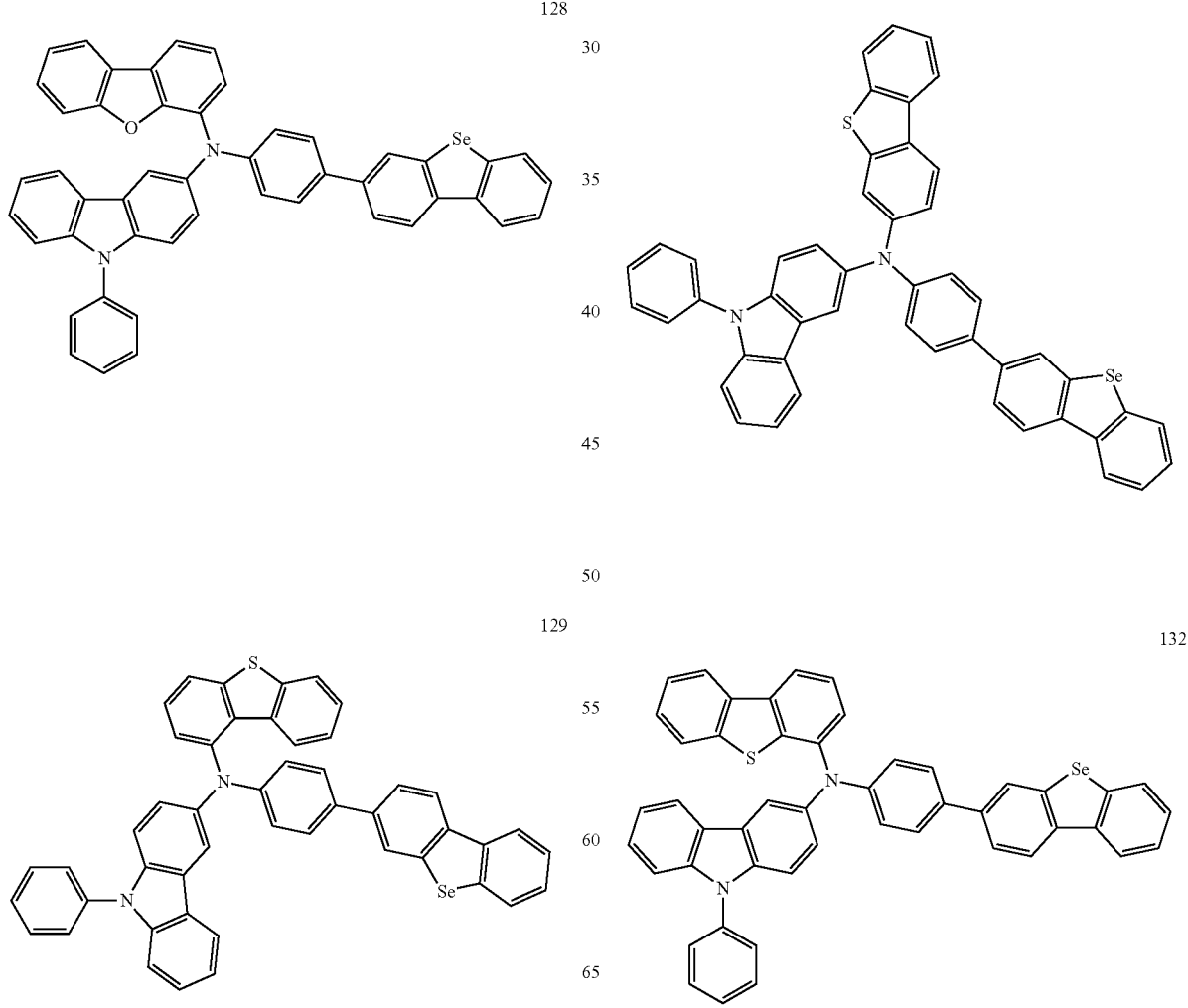

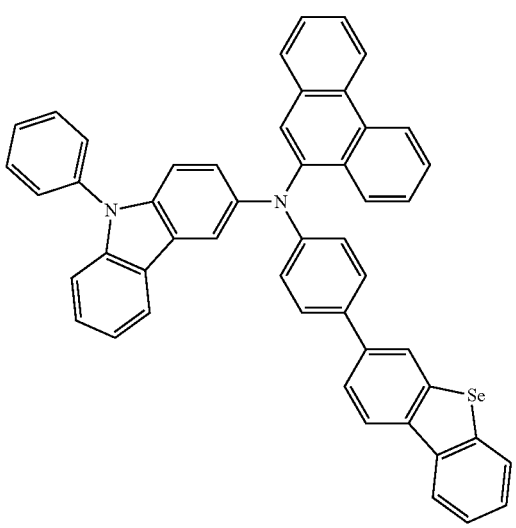
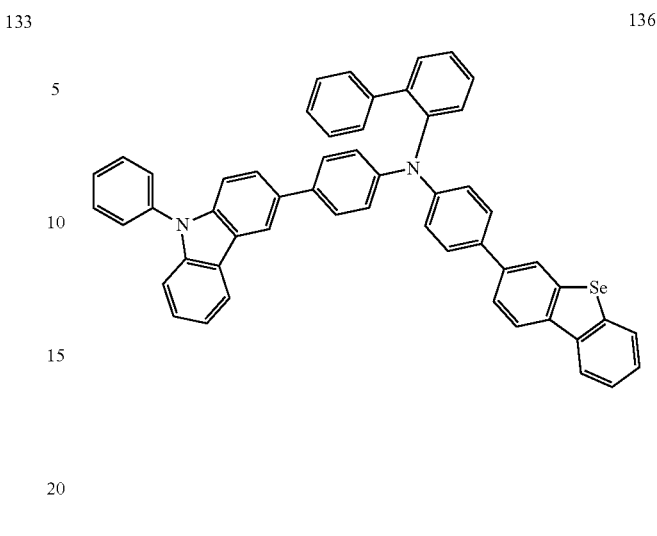

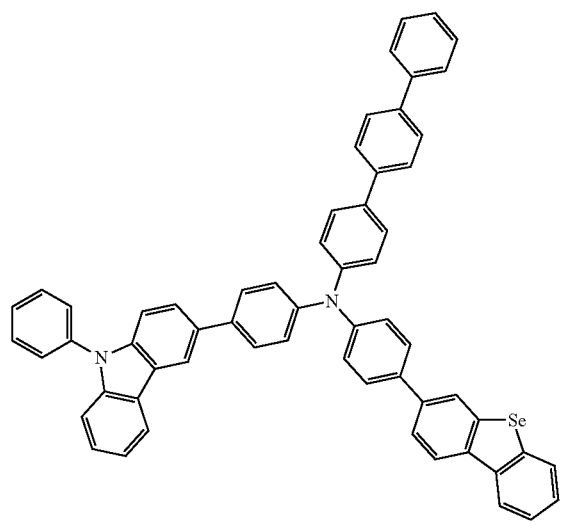

146
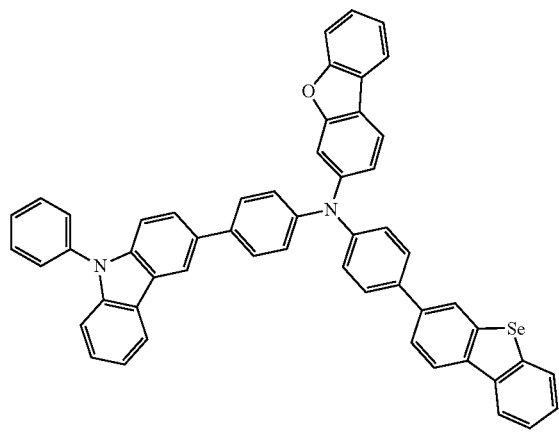
147
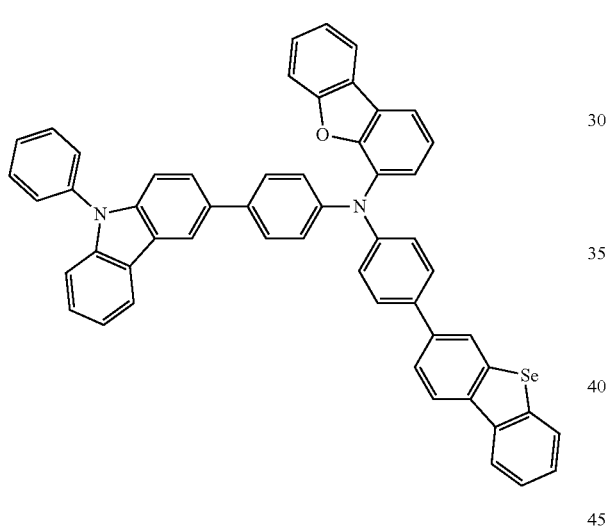
148
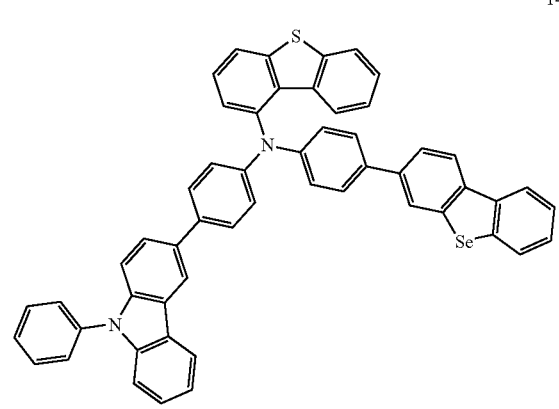
149
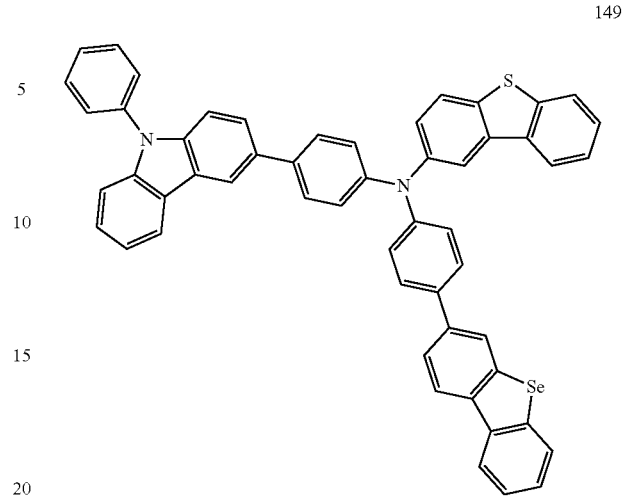
150
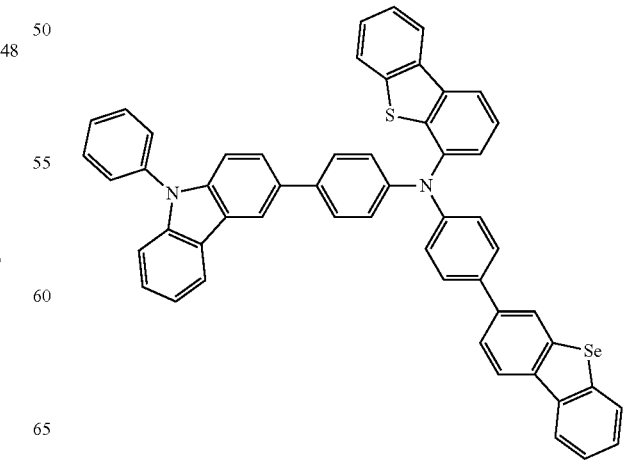
151

152
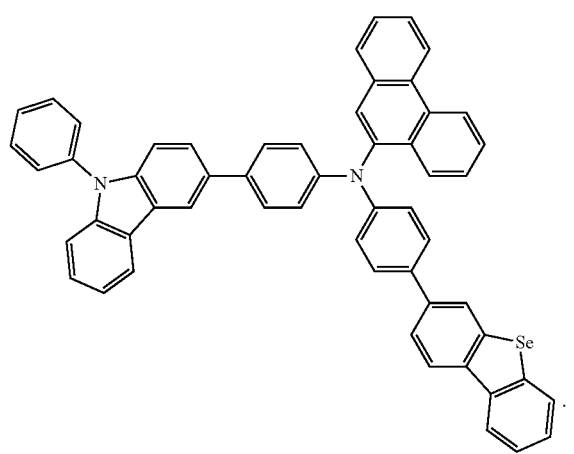
155
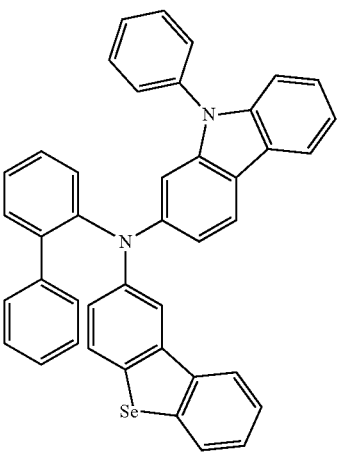
153
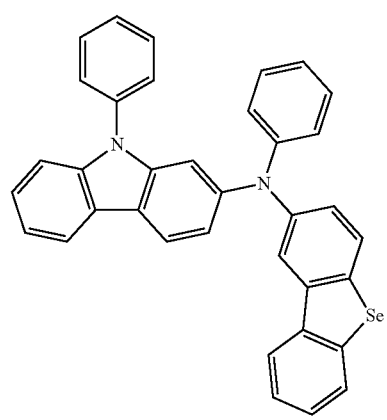
156
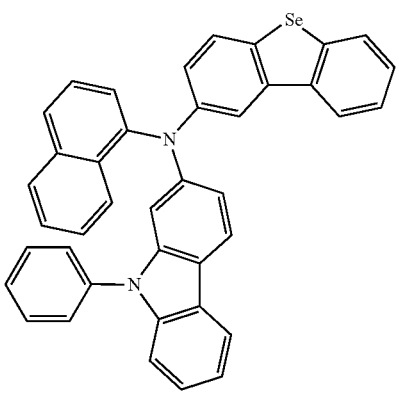
154
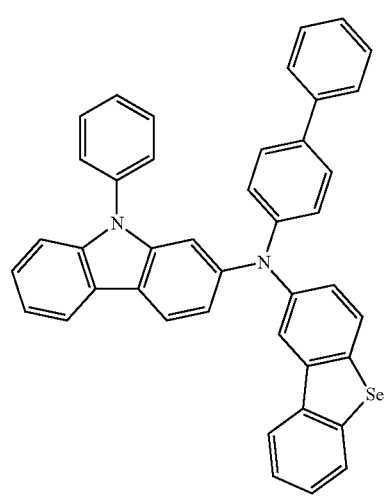
157
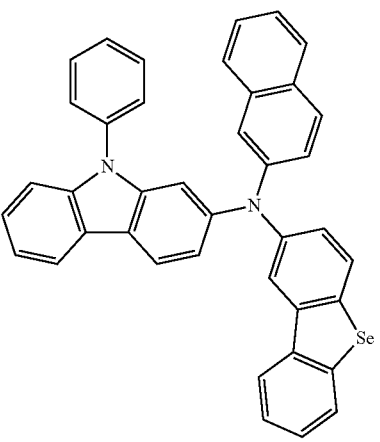

158
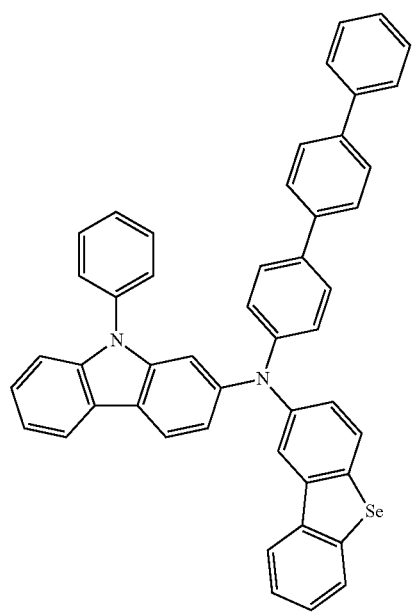
159
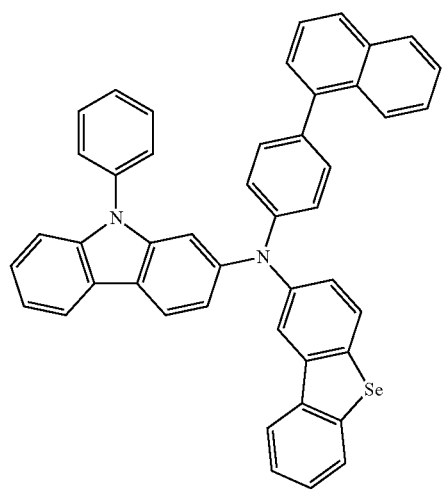
160
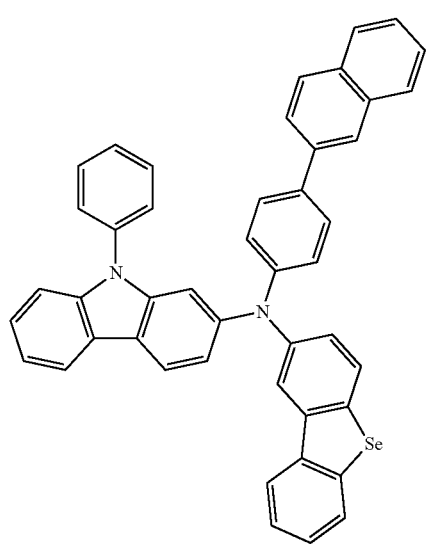
161
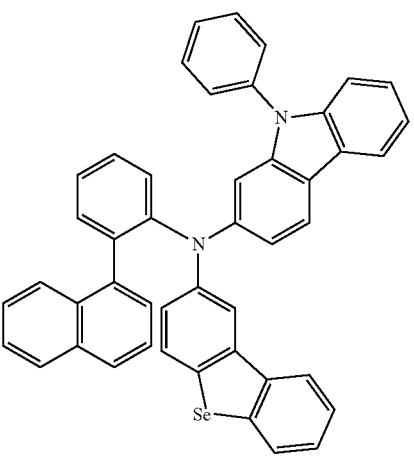
162
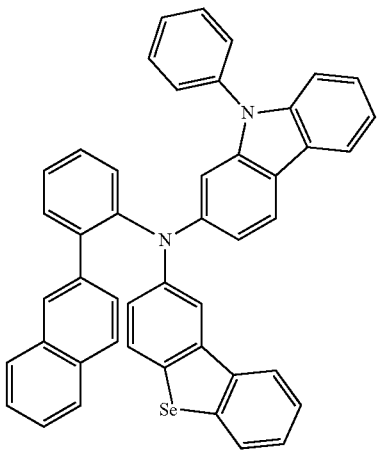
163
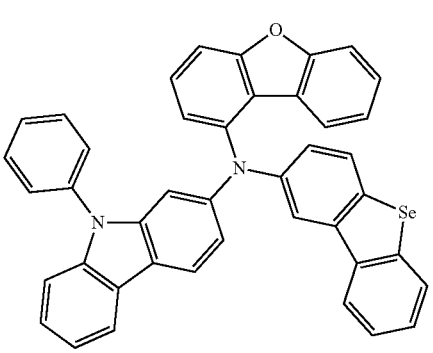

321
-continued
322
-continued
164
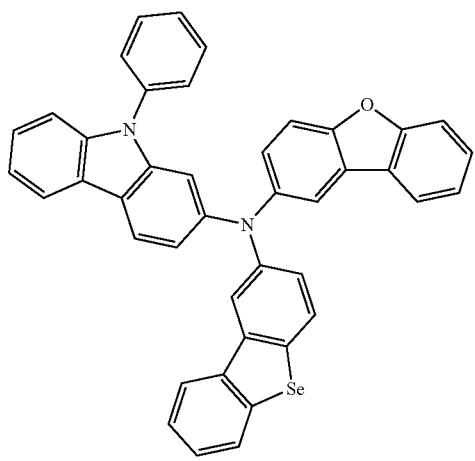
168
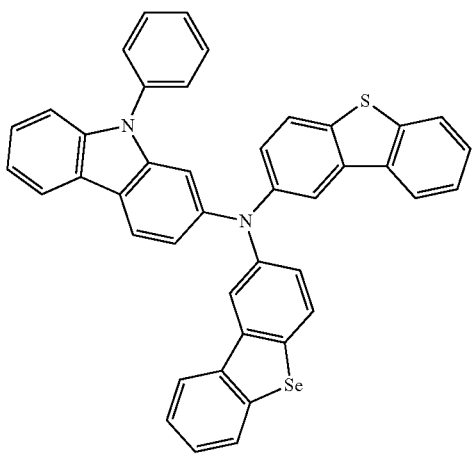
165
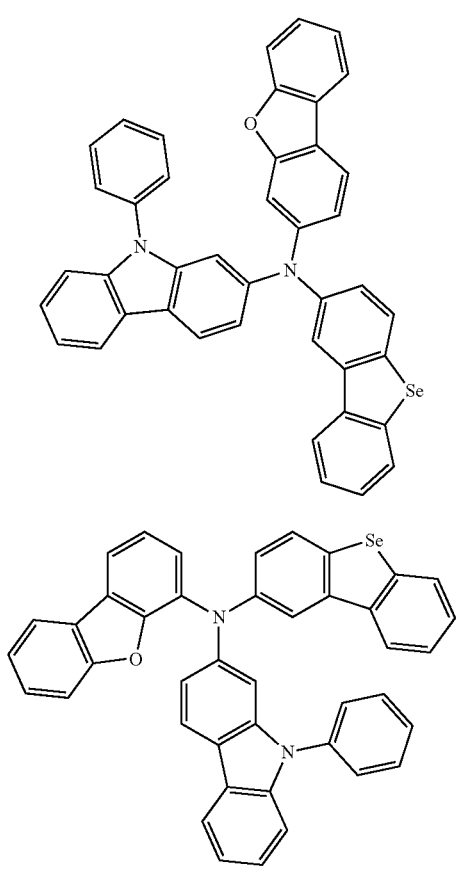
169
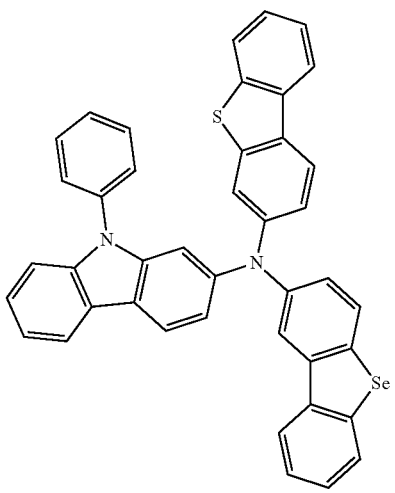
166
167
170
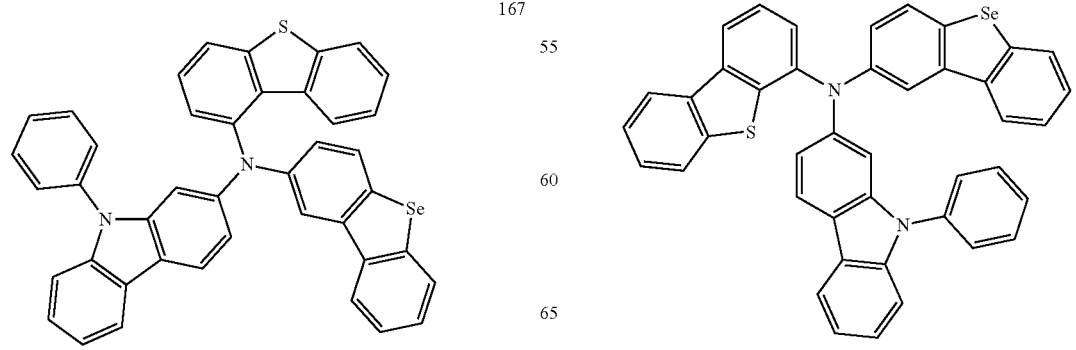

323
-continued
171
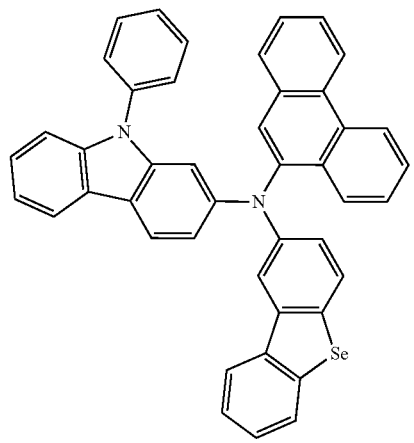
172
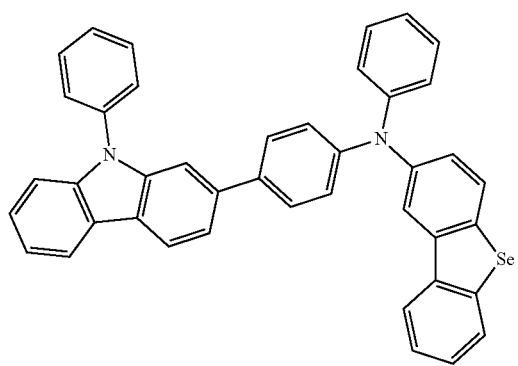
173
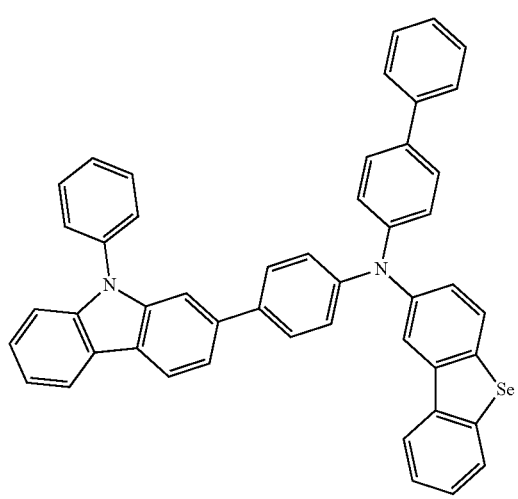
324
-continued
174
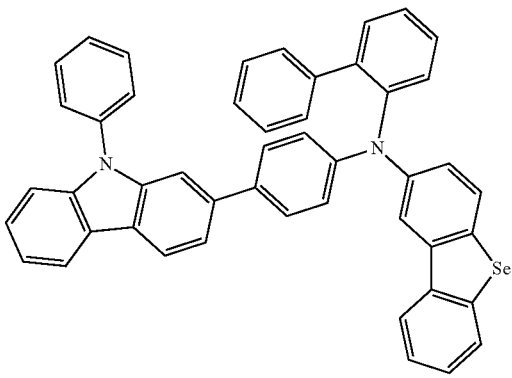
175
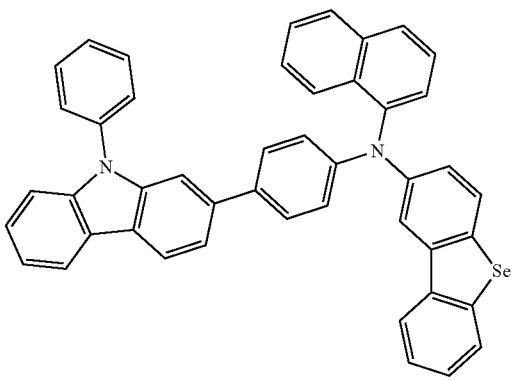
176
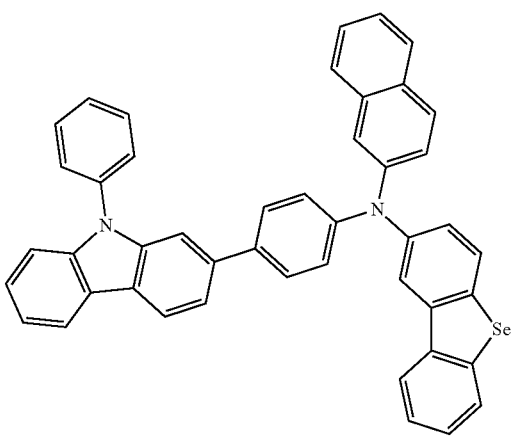

-continued
177
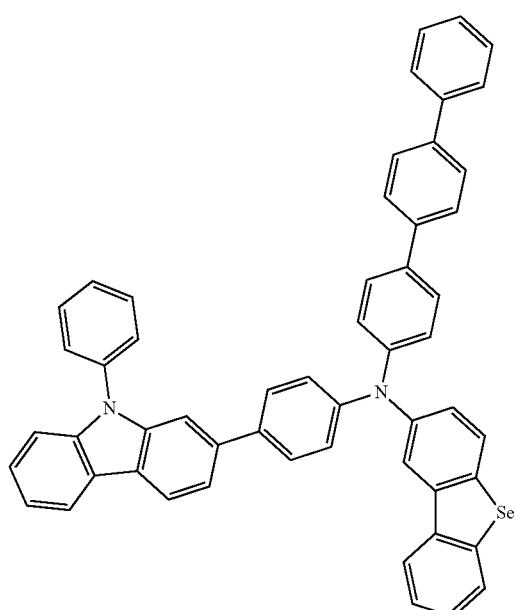
178
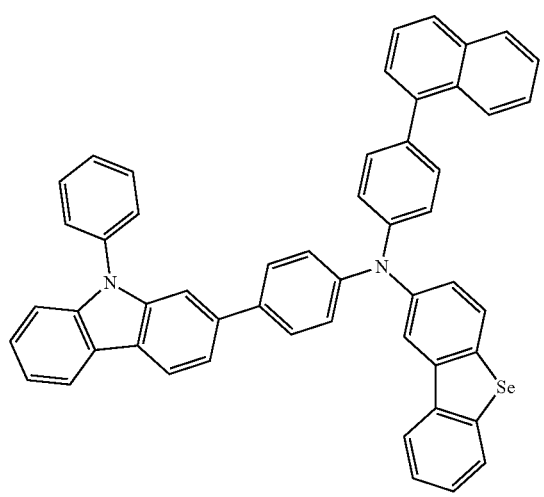
179
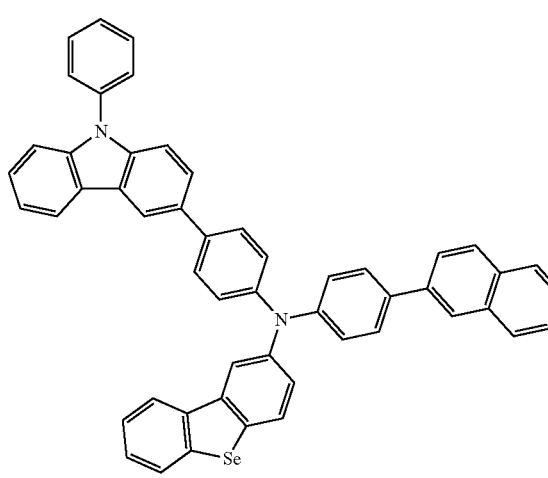
-continued
180
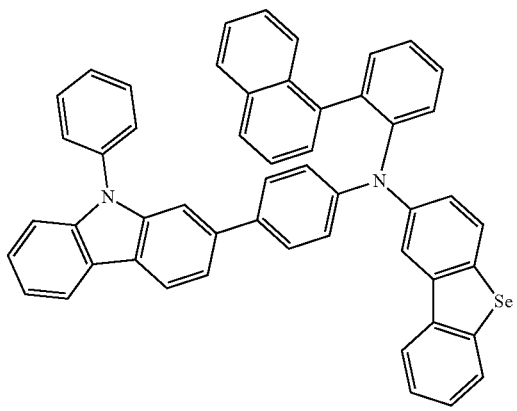
181
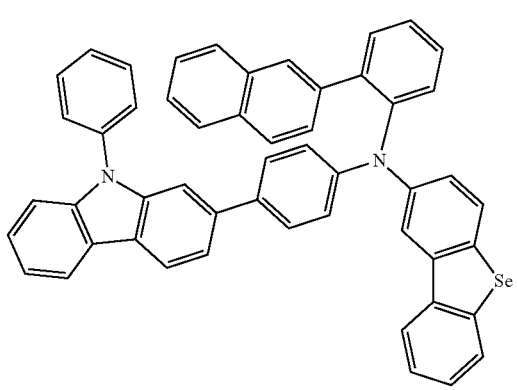
182
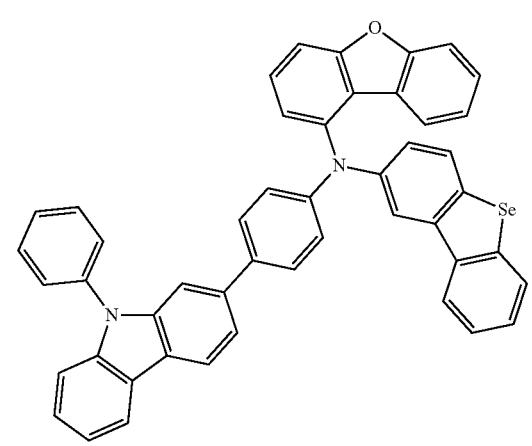

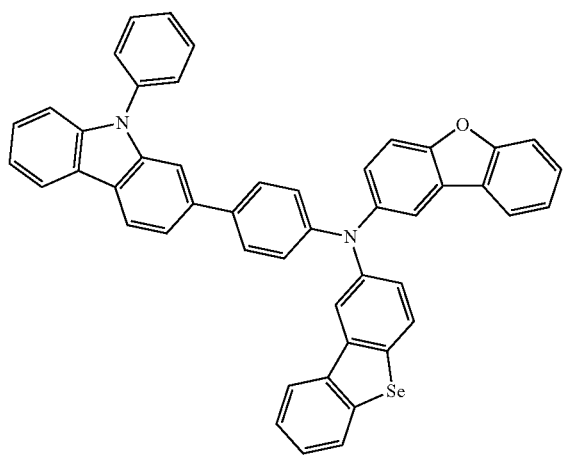
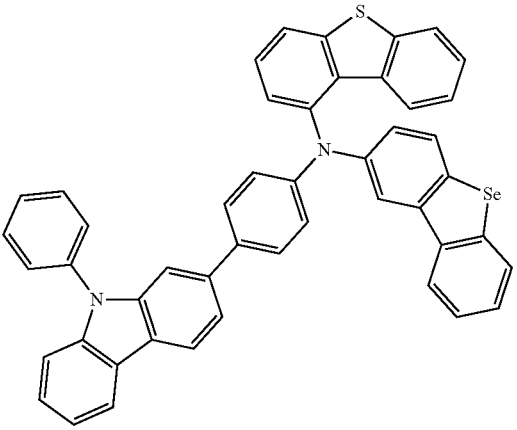

329
-continued
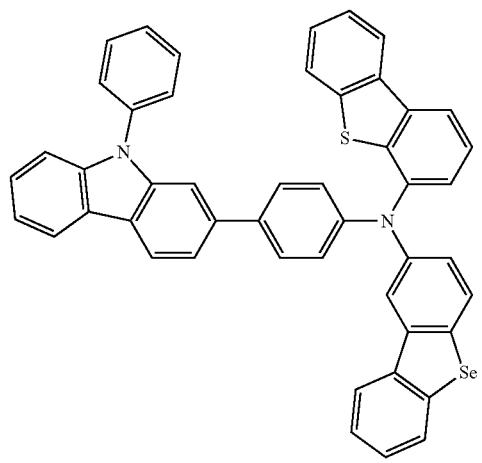
189
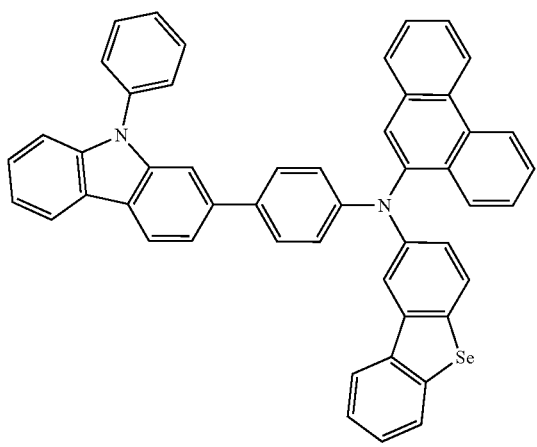
190
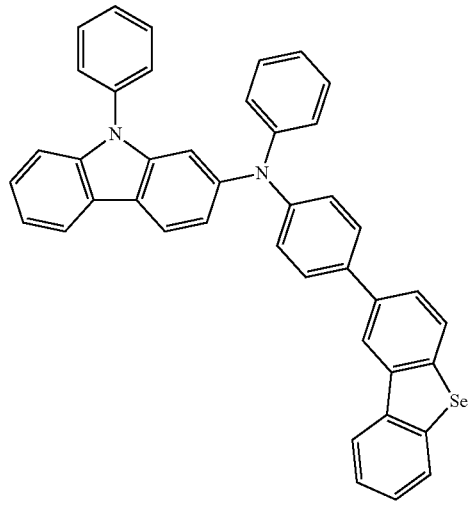
191
330
-continued
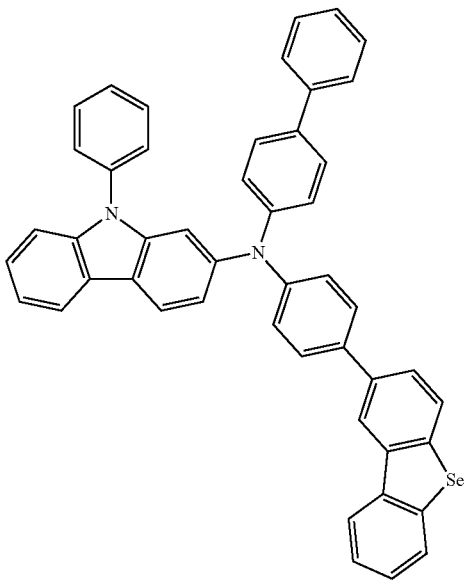
192
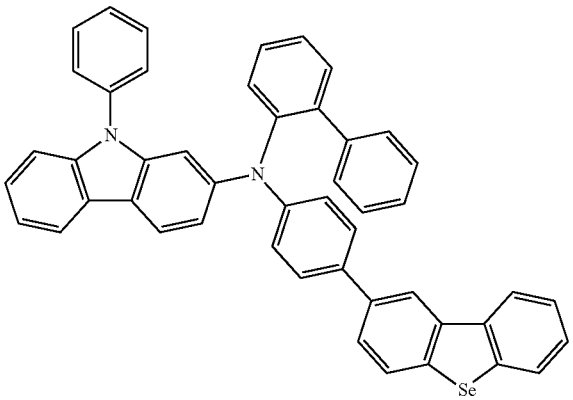
193
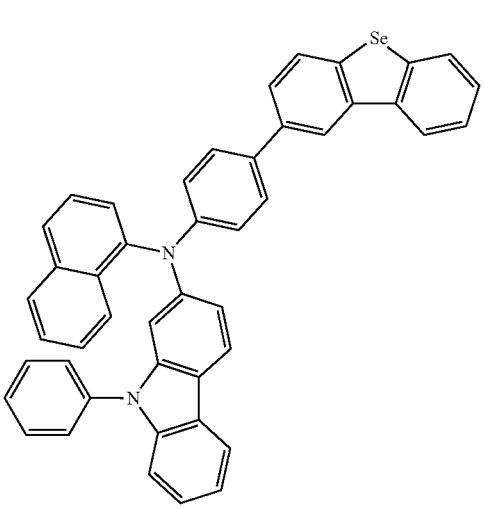
194

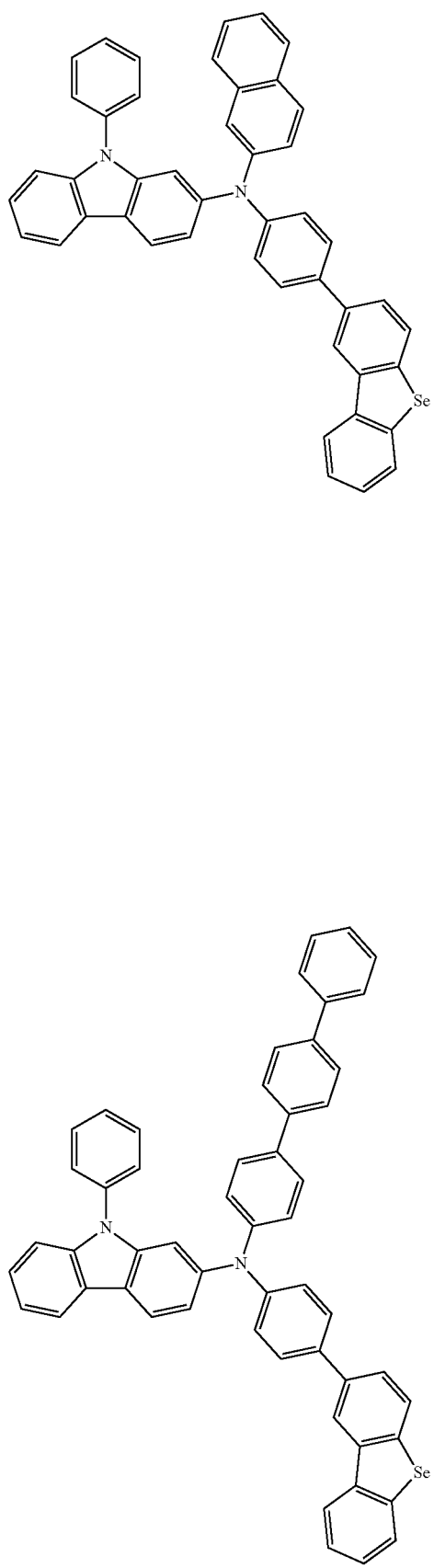
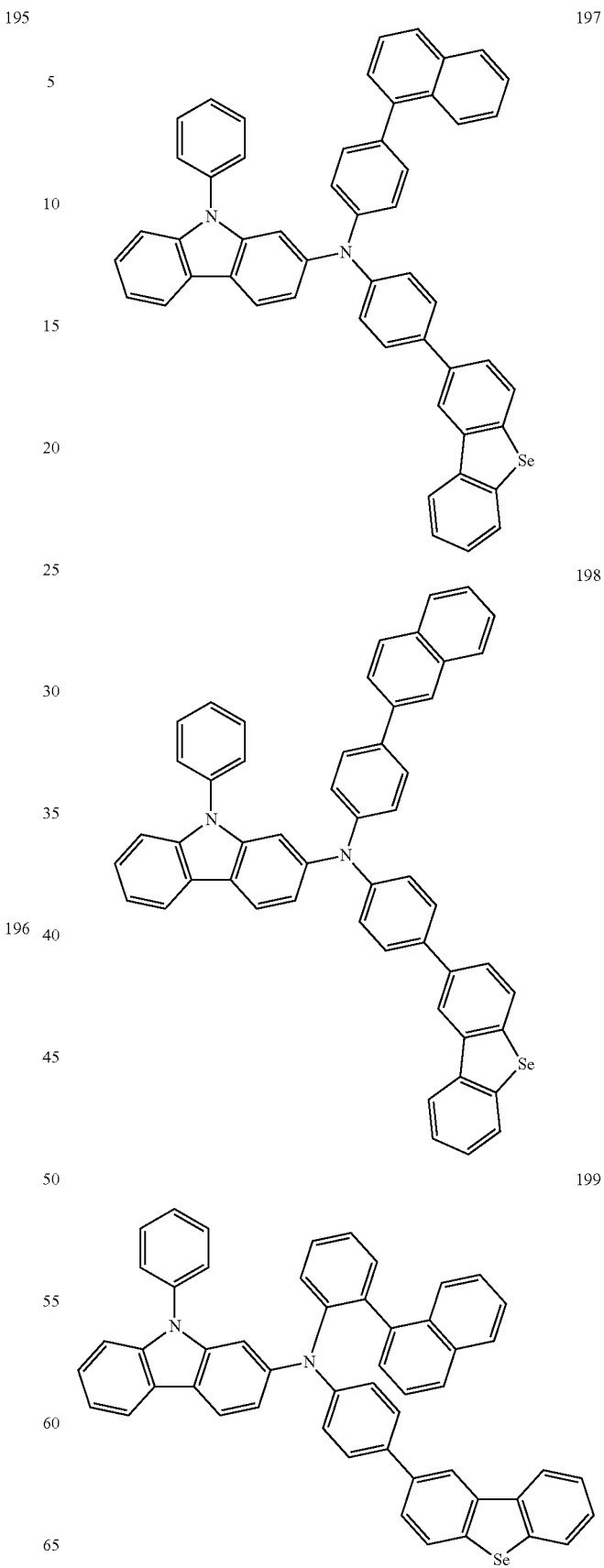

333
-continued
200
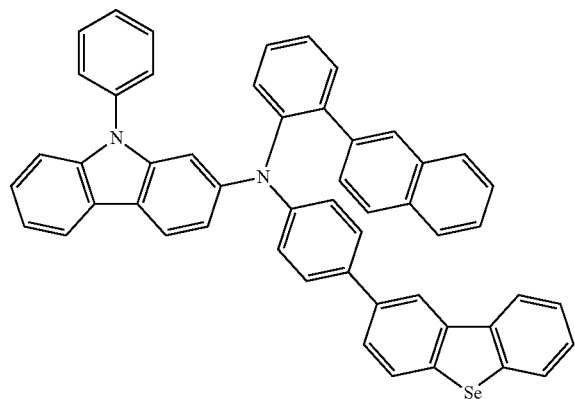
201
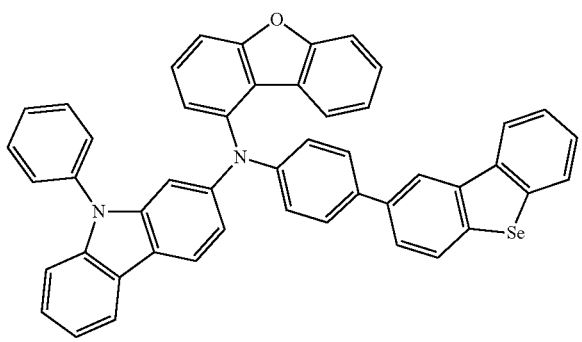
202
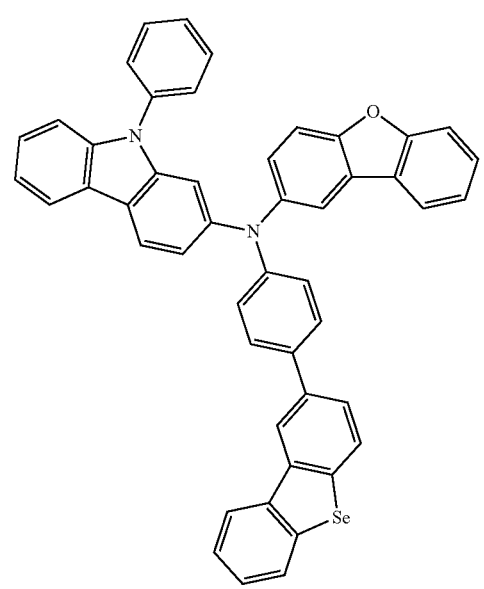
334
-continued
203
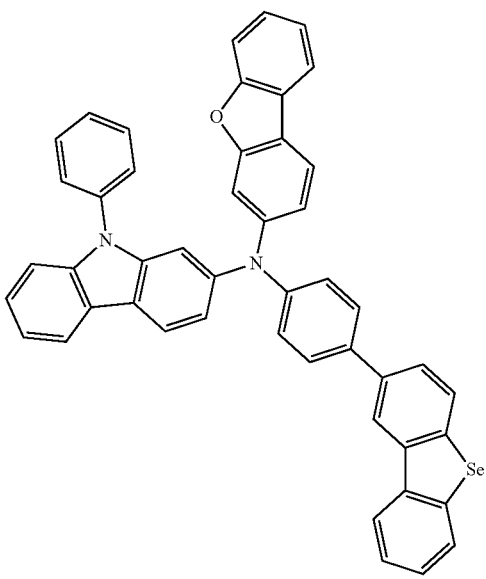
204
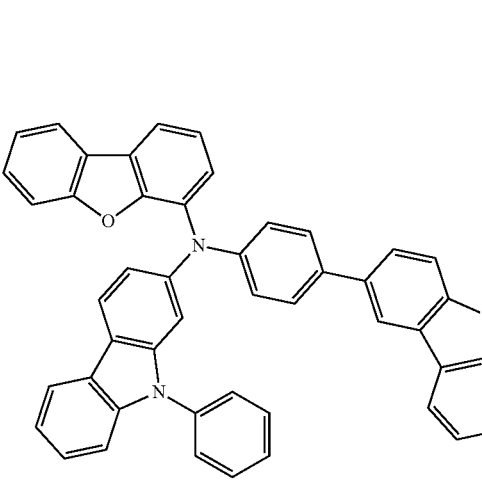
205
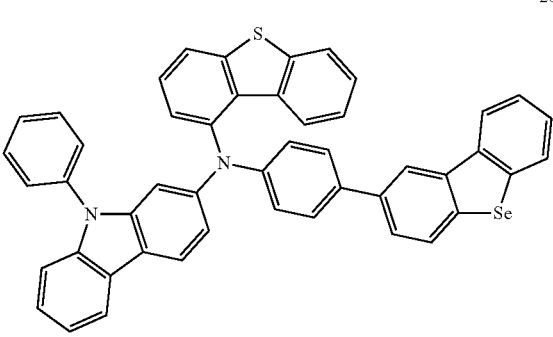

335
-continued
206
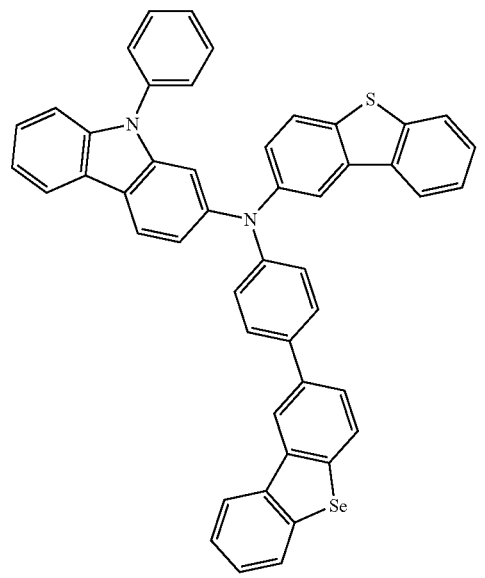
207
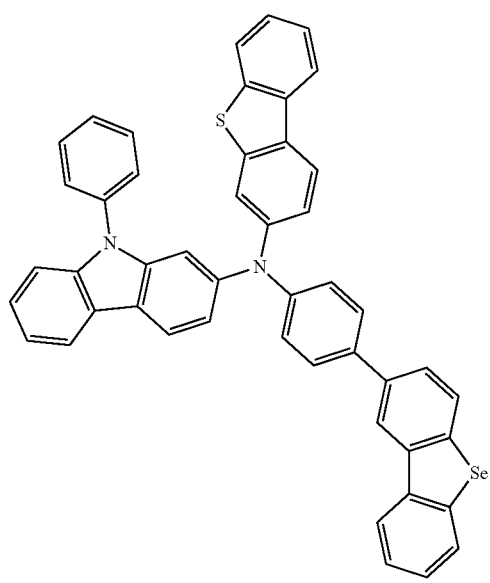
208
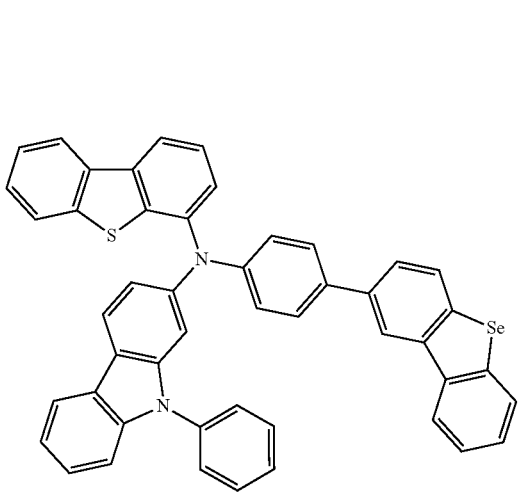
336
-continued
209
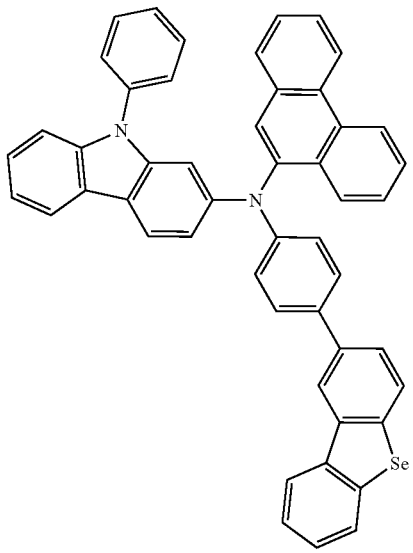
210
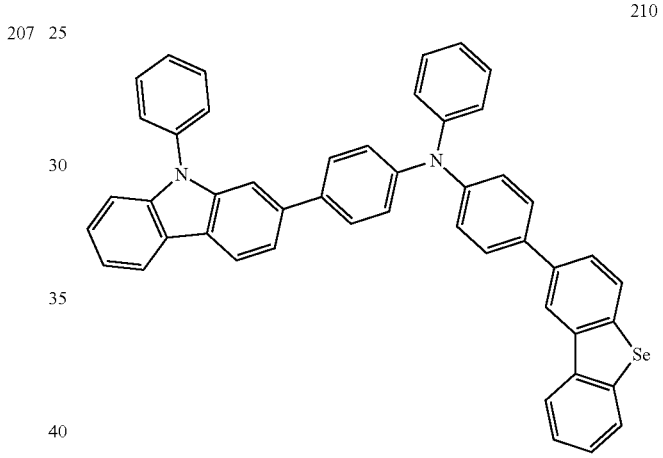
211
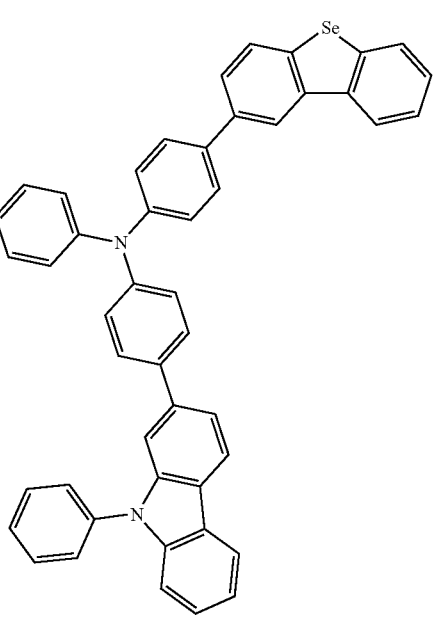

337
-continued
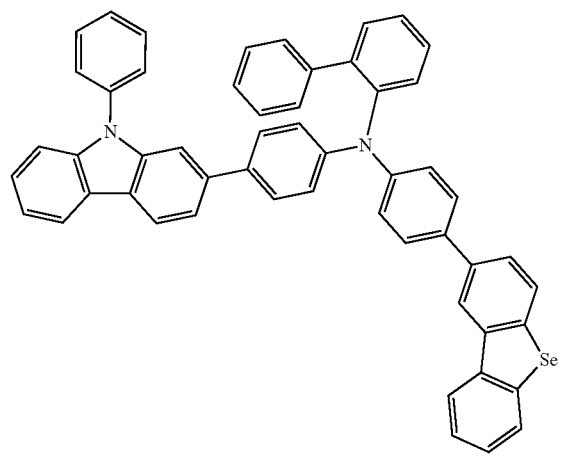
212
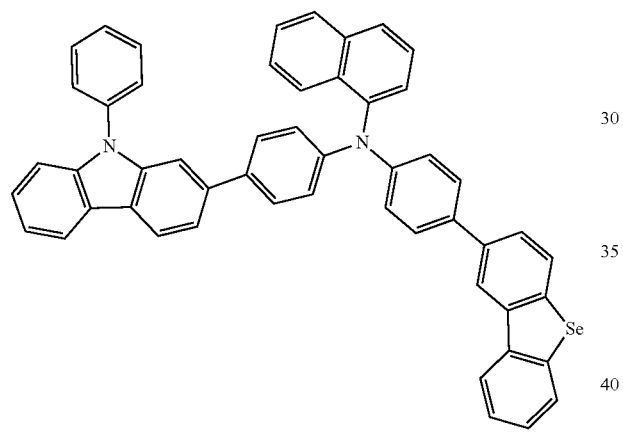
213
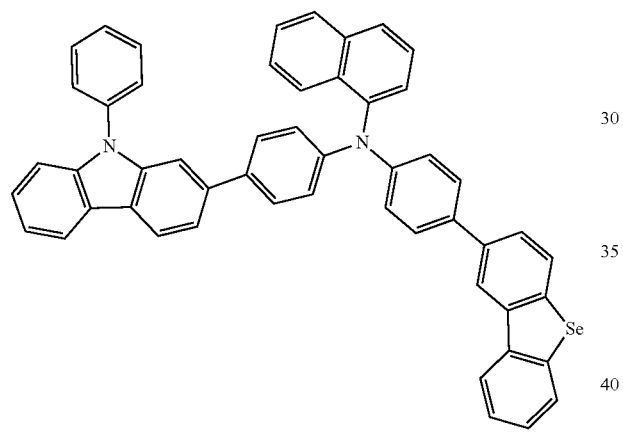
214
338
-continued
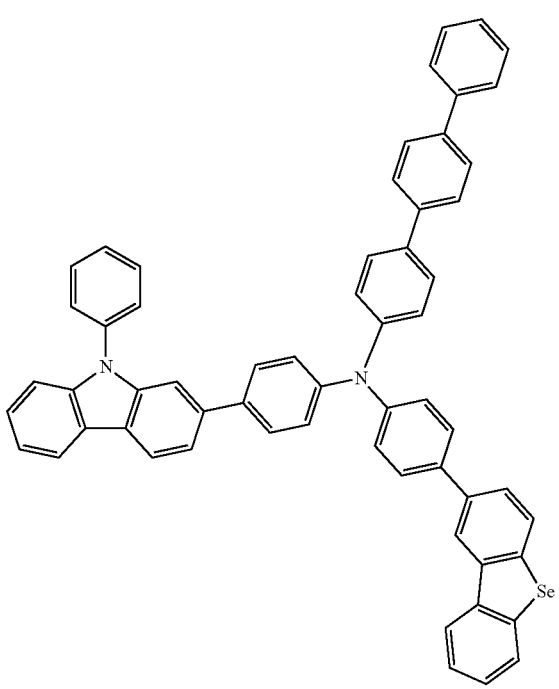
215
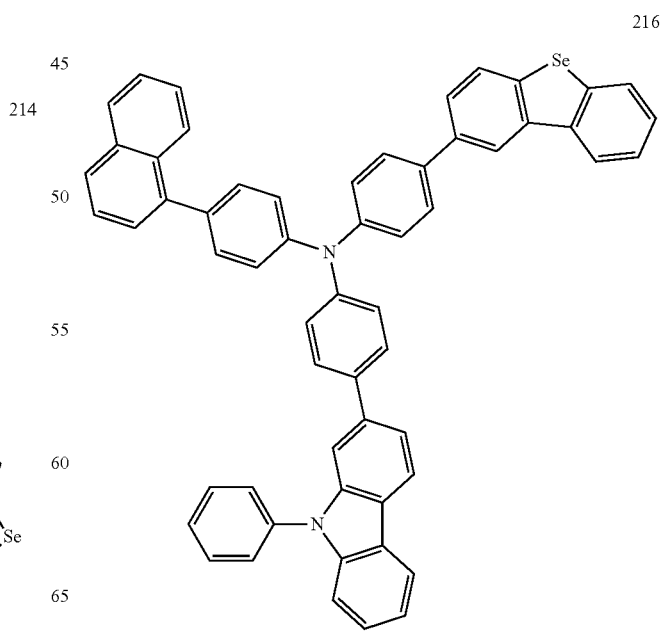
216

339
-continued
217
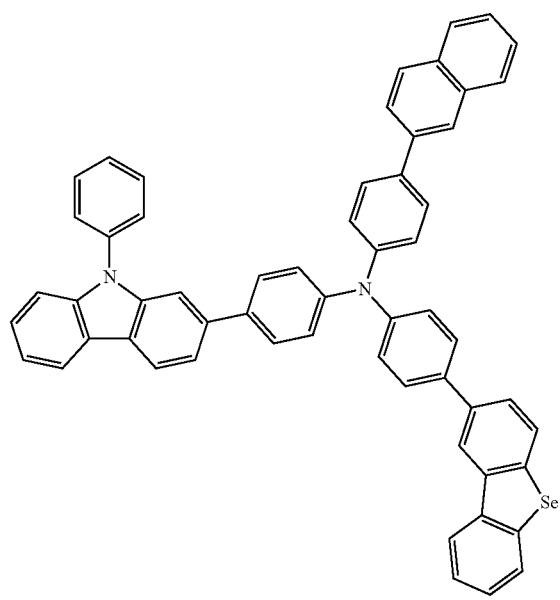
218
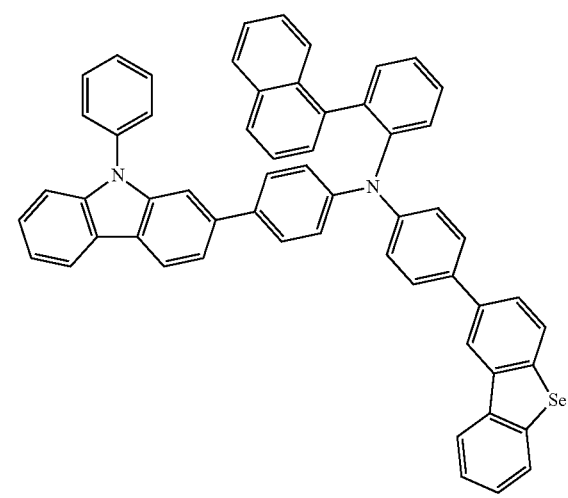
219
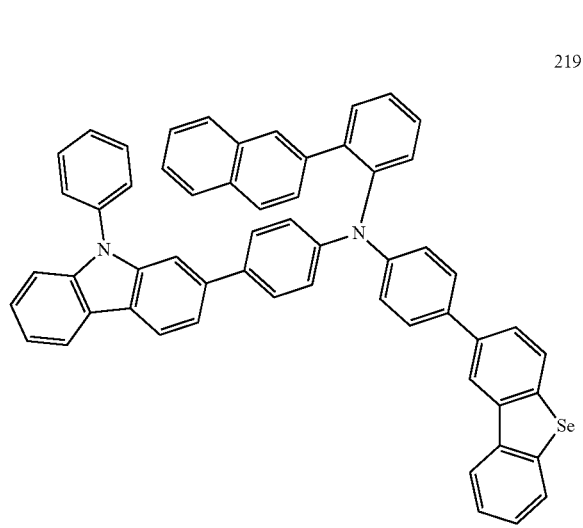
340
-continued
220
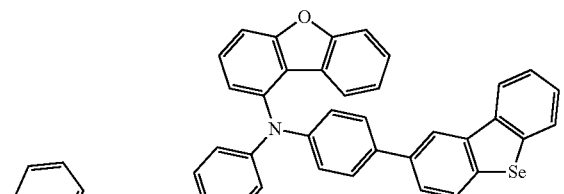
221
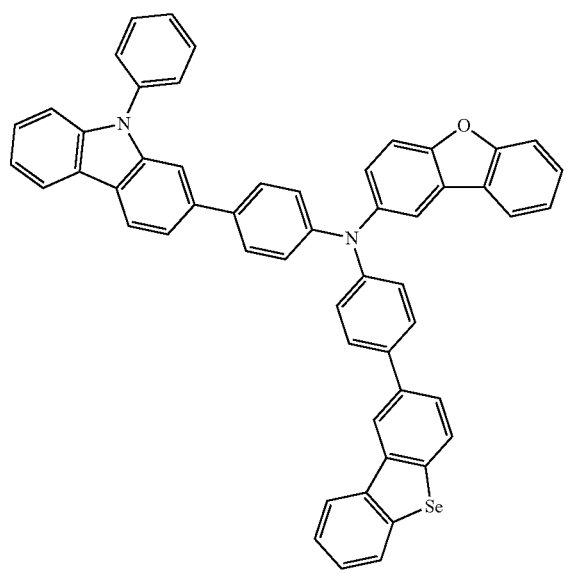
222
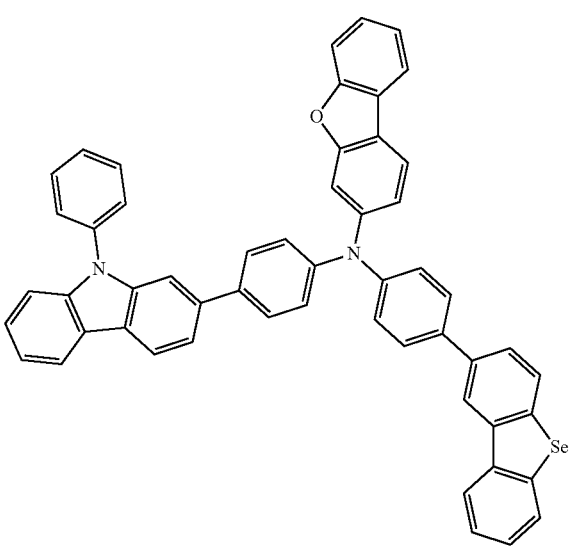

341
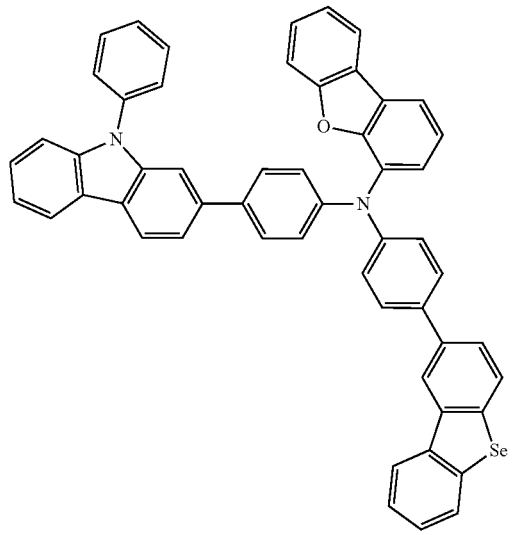
223
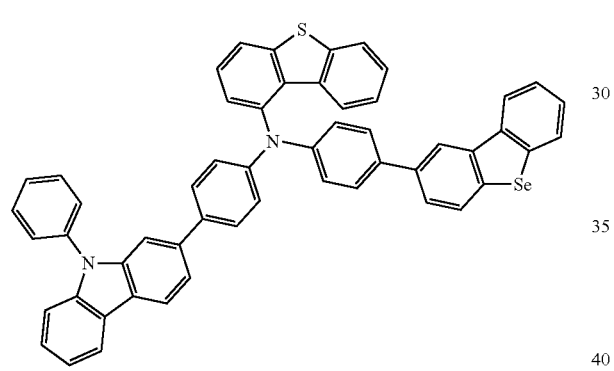
224
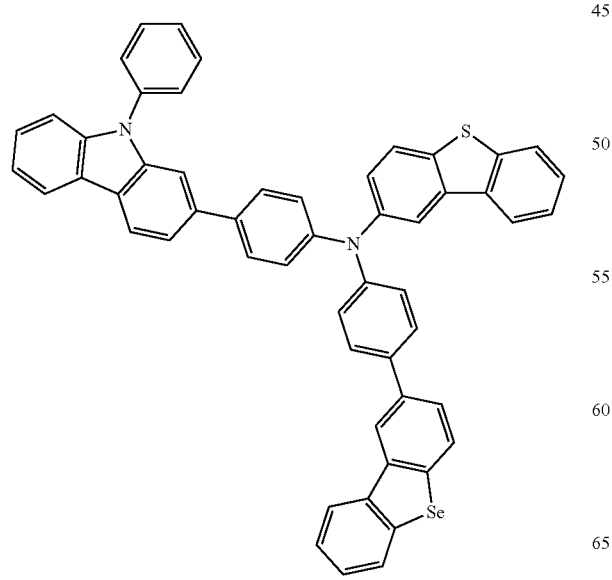
225
342
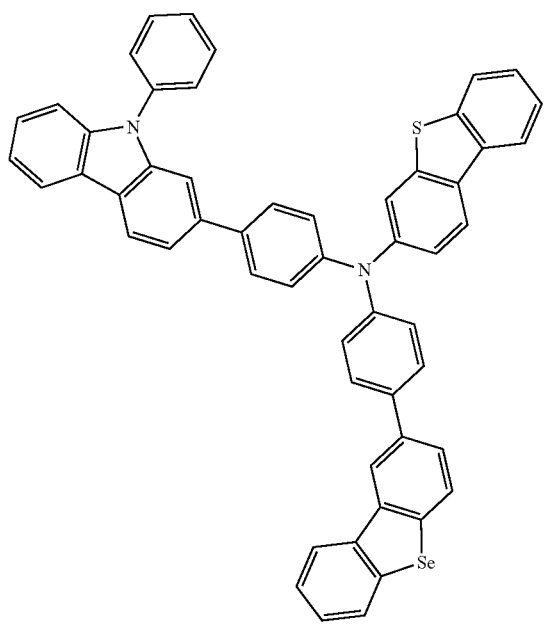
226
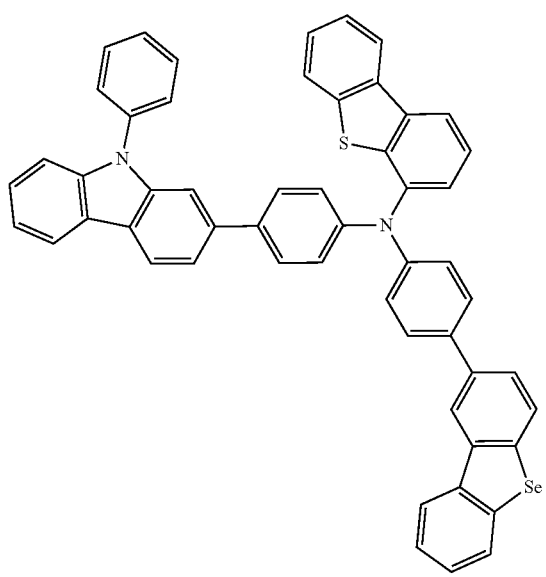
227

-continued
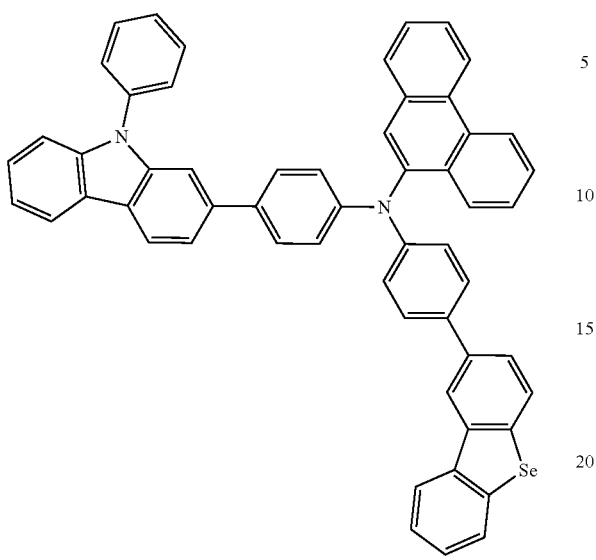
228
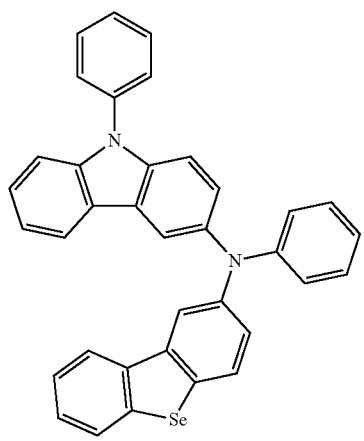
229
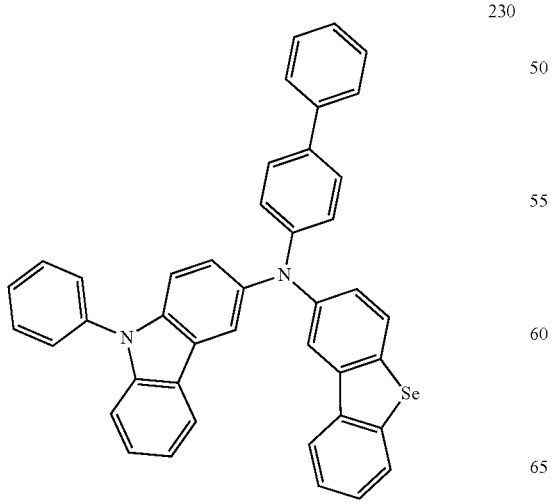
230
-continued
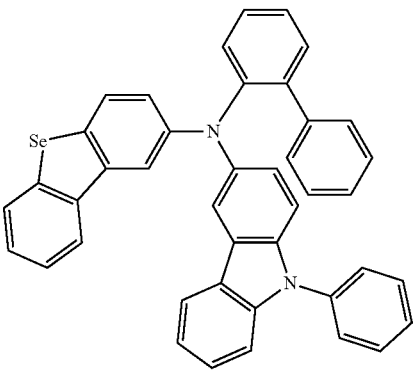
231
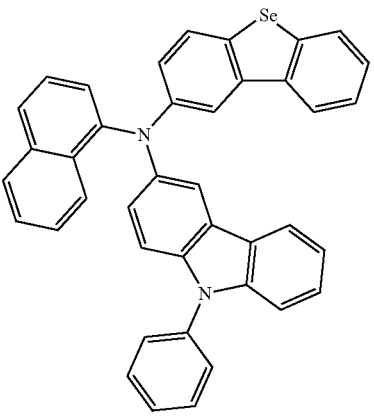
232
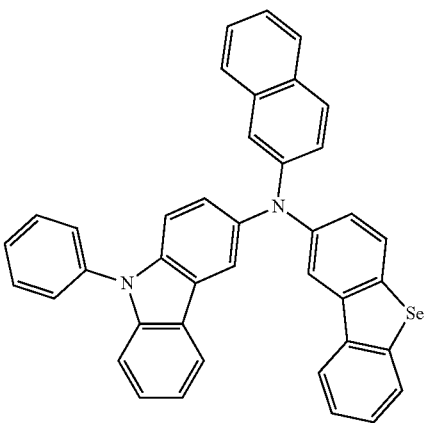
233

345
-continued
234
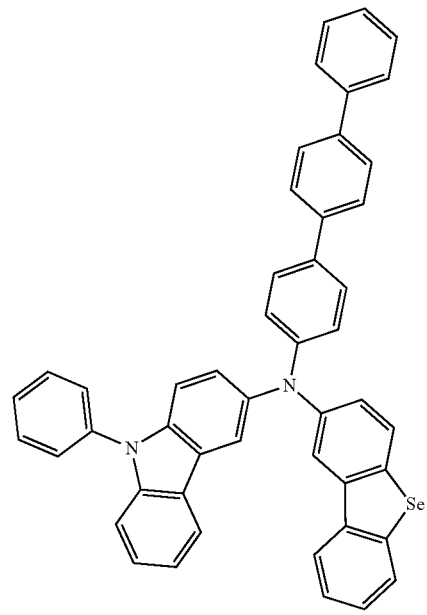
235
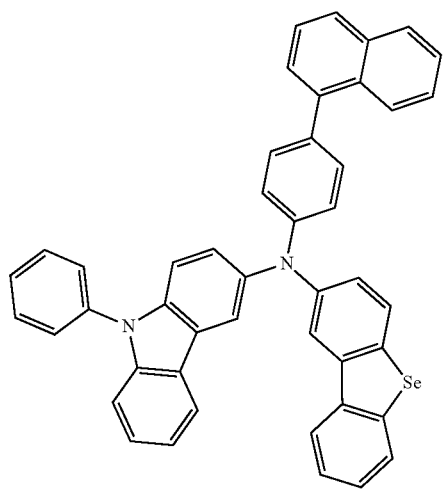
236
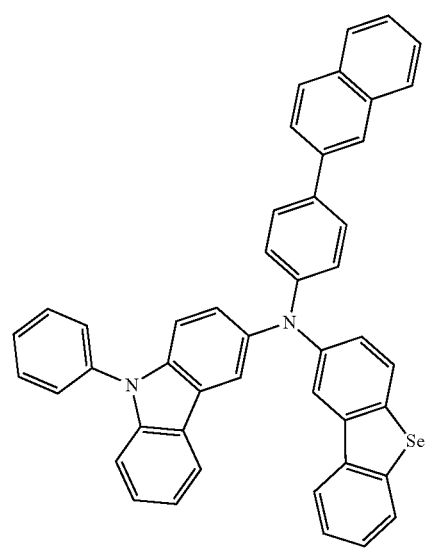
346
-continued
237
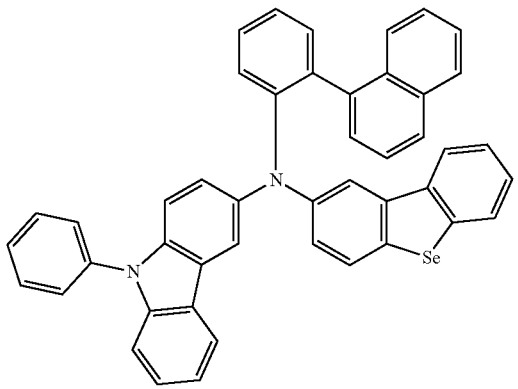
238
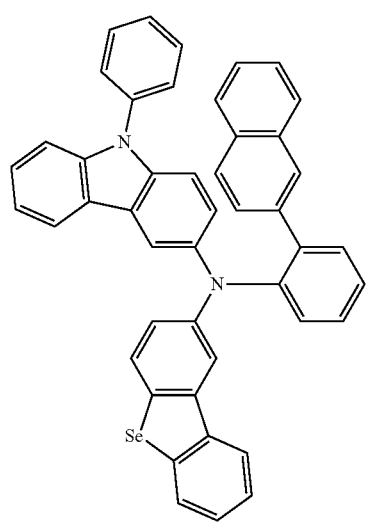
239
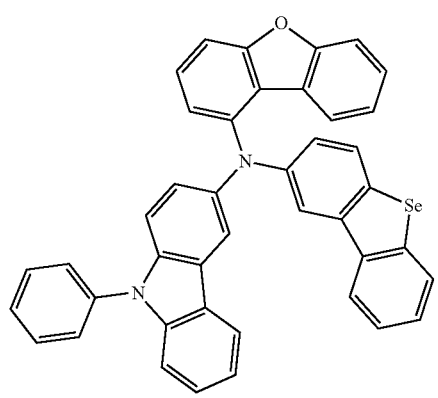

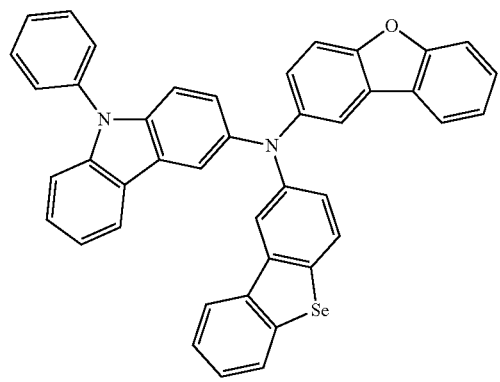
240
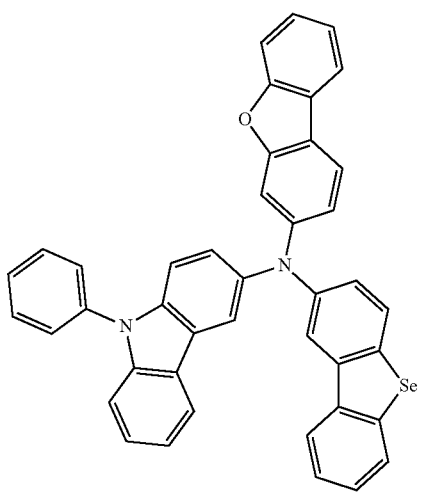
241
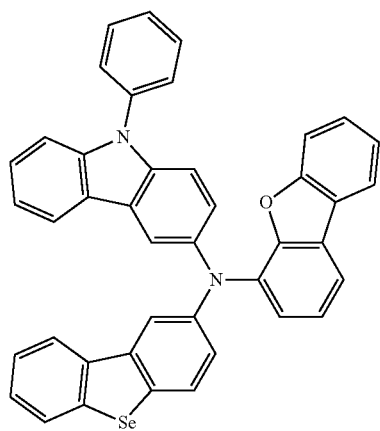
242
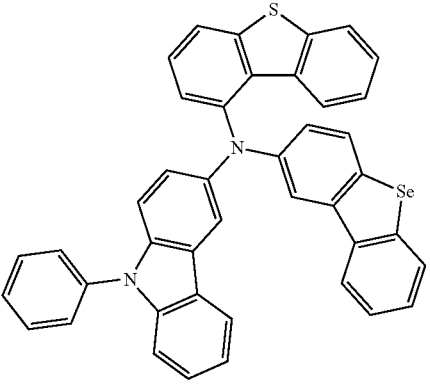
243
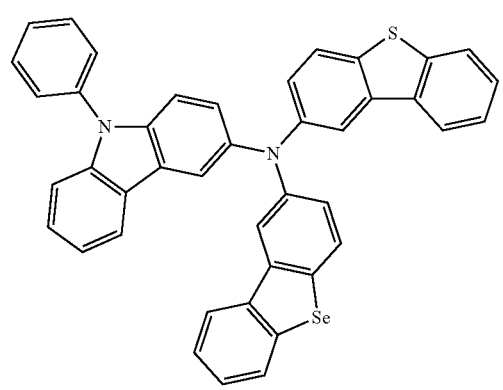
244
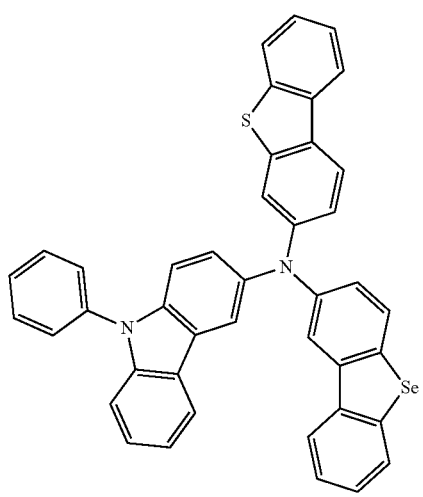
245

246
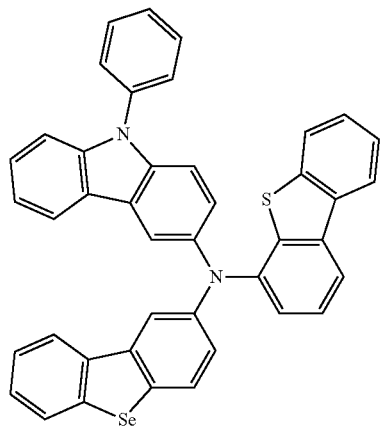
249
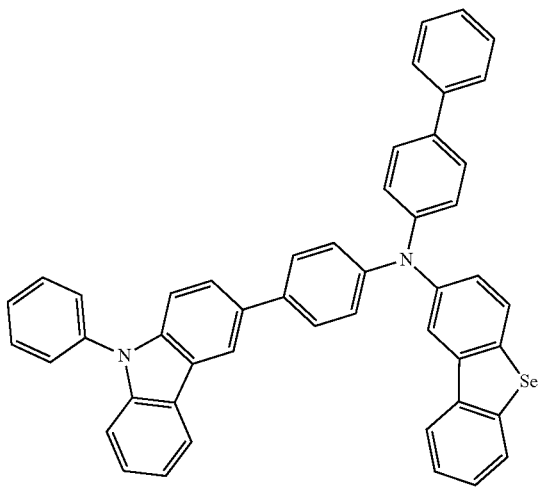
247
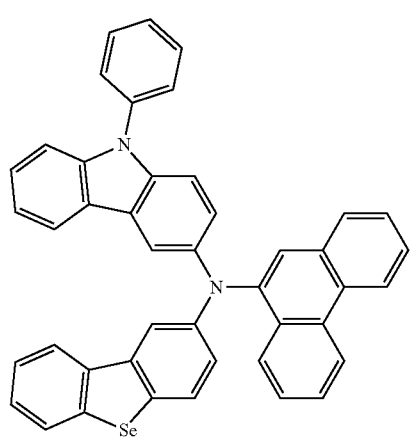
250
248
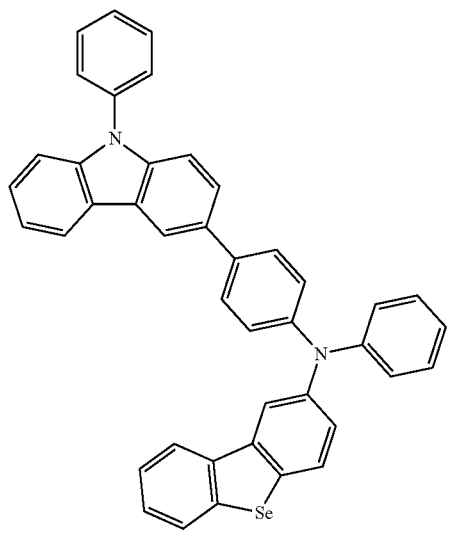
251
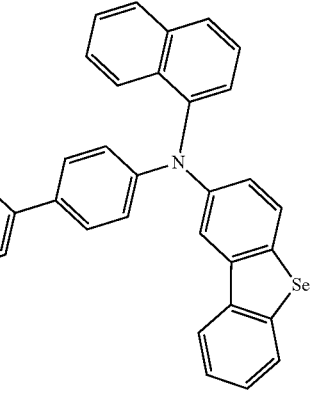

351
-continued
252
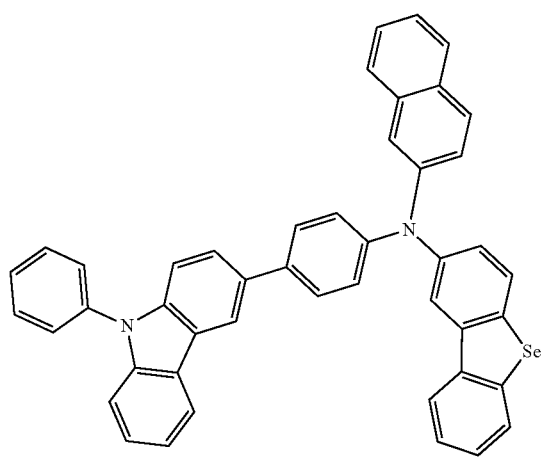
253
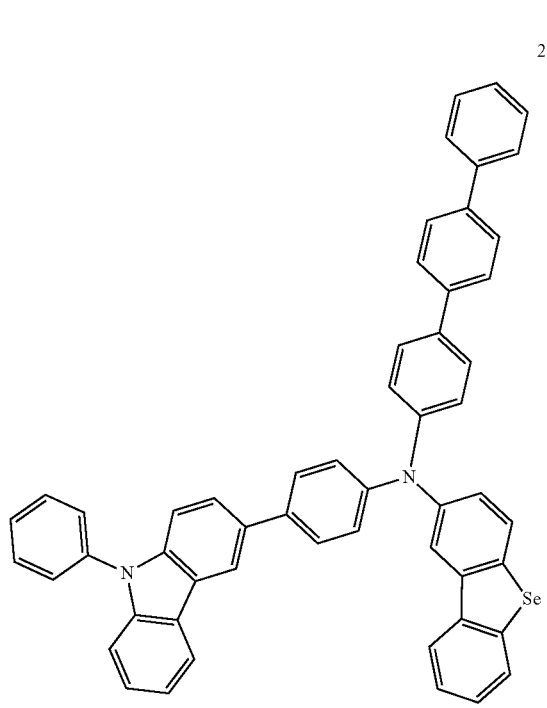
352
-continued
254
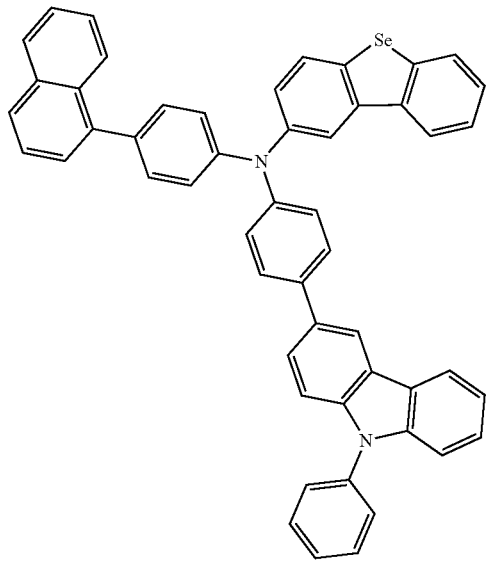
255
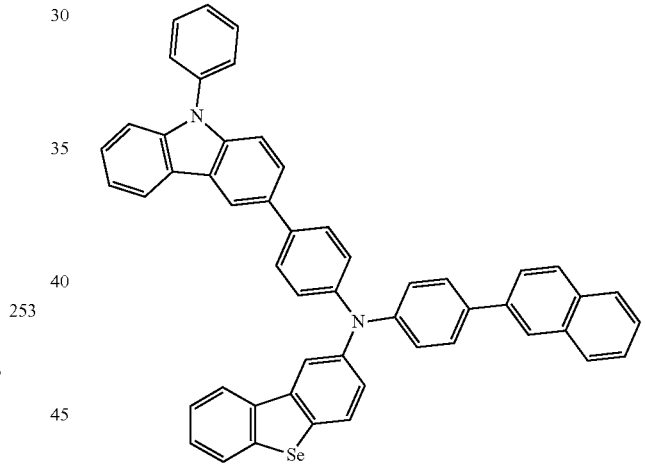
256
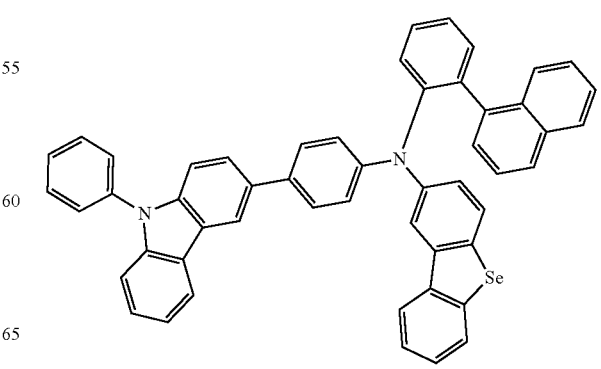

257
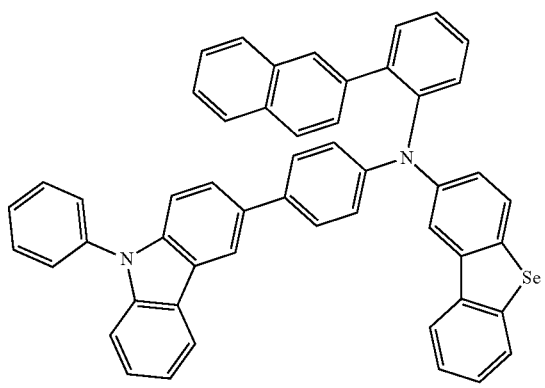
258
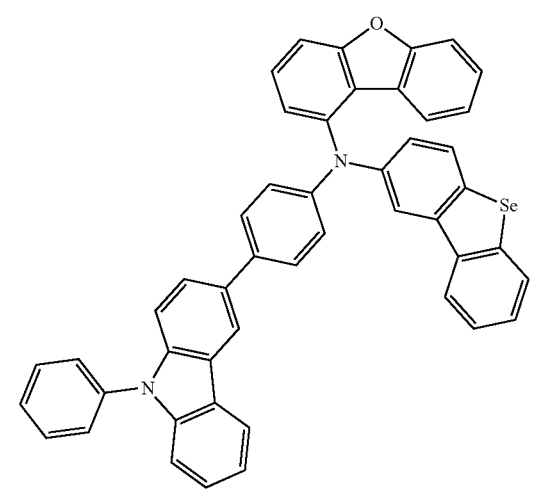
259
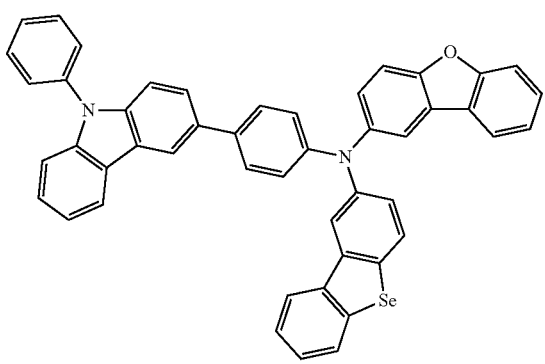
260
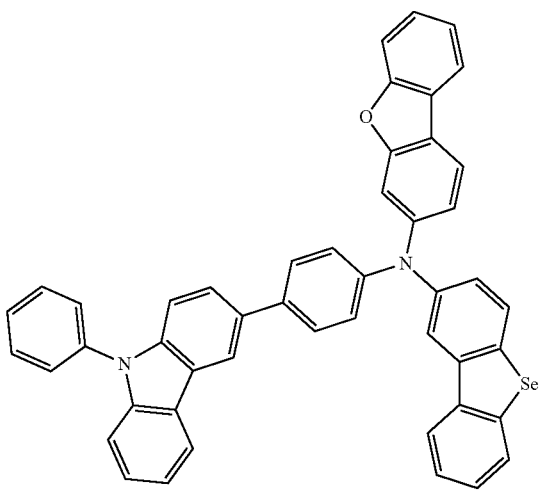
261
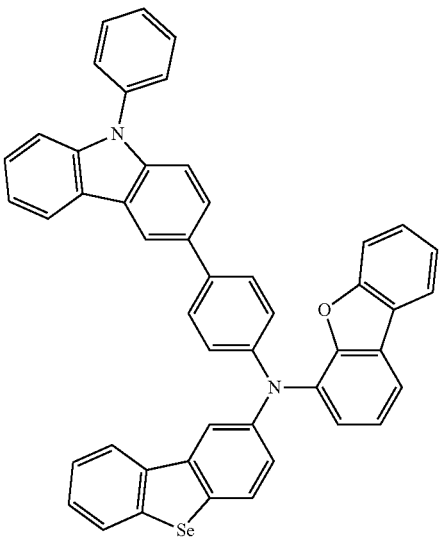
262
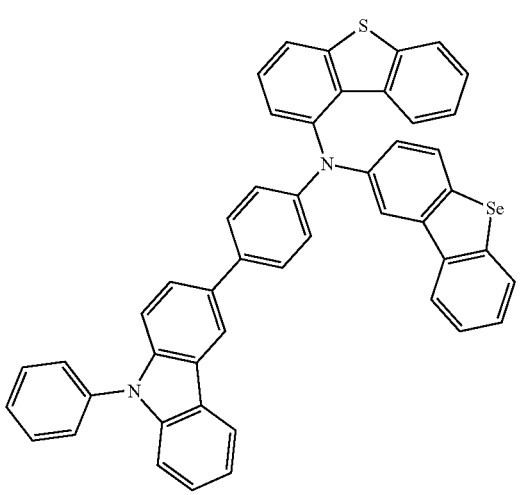

263
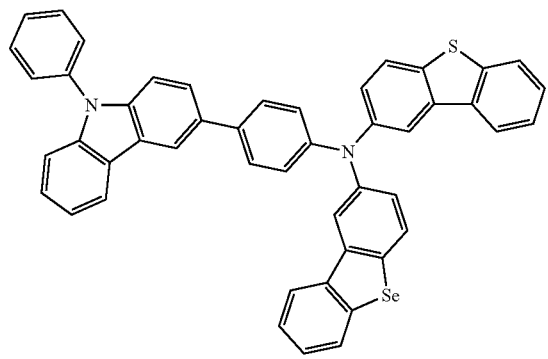
264
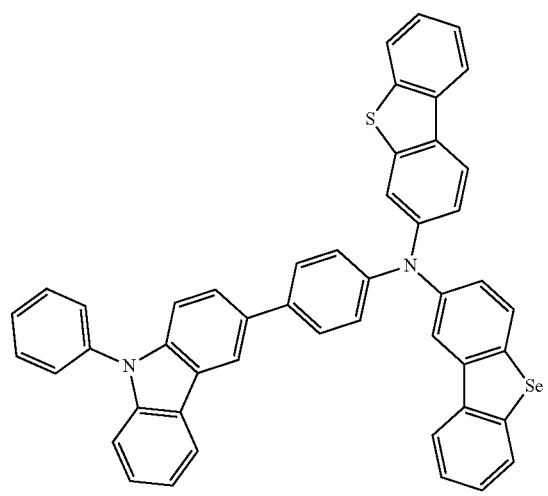
265
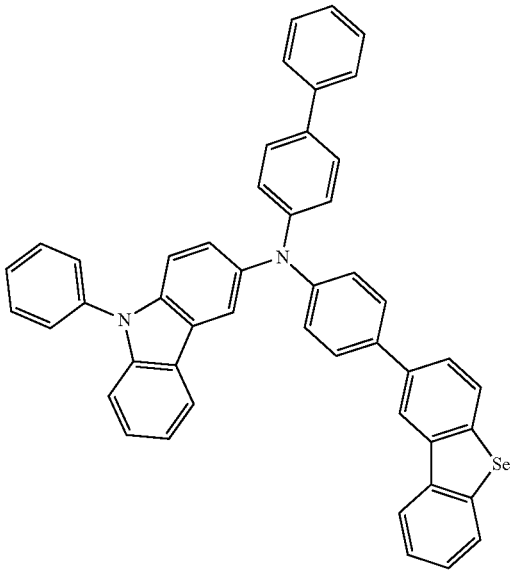
266
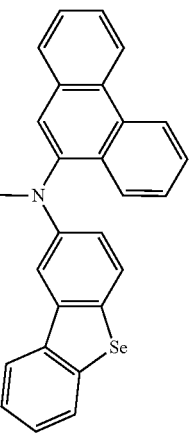
267
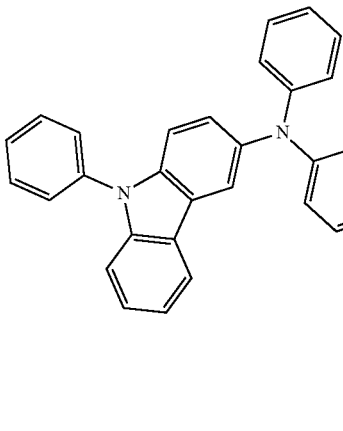
268

269
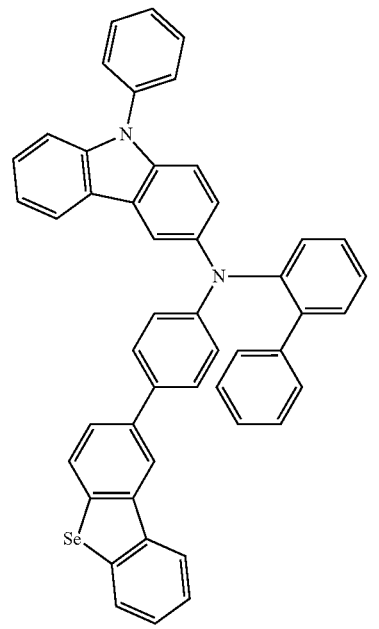
270
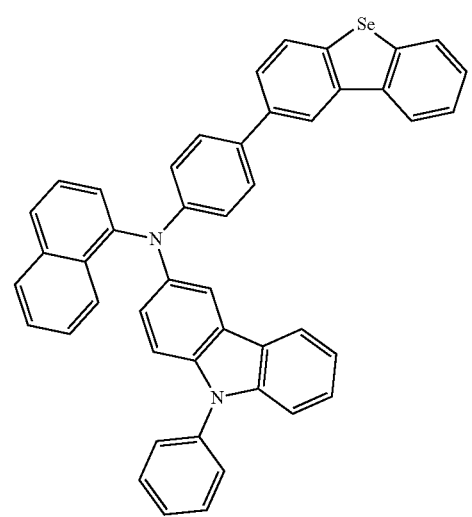
271
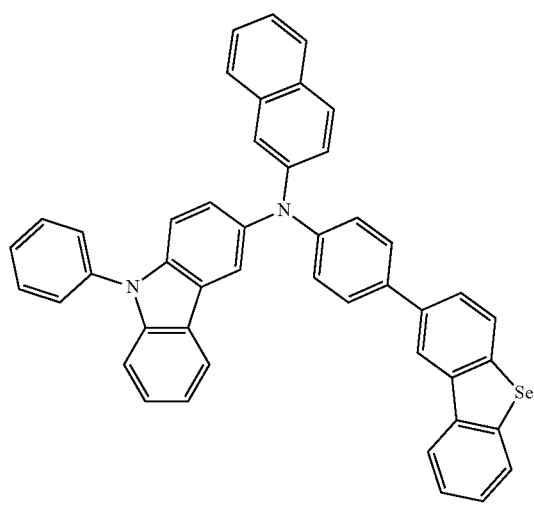
272
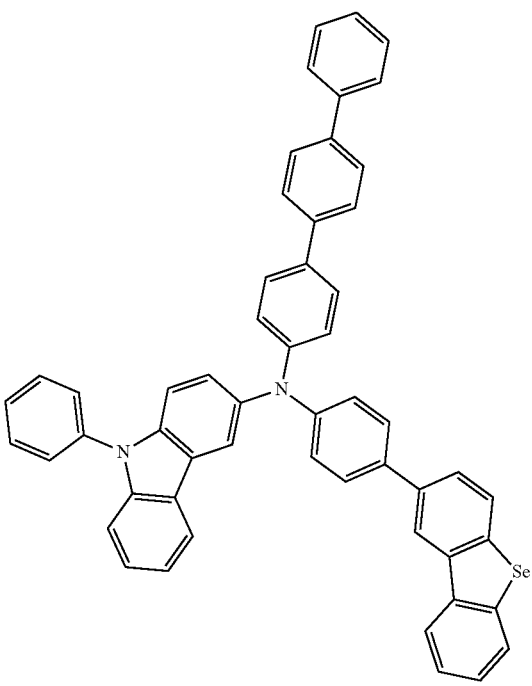
273
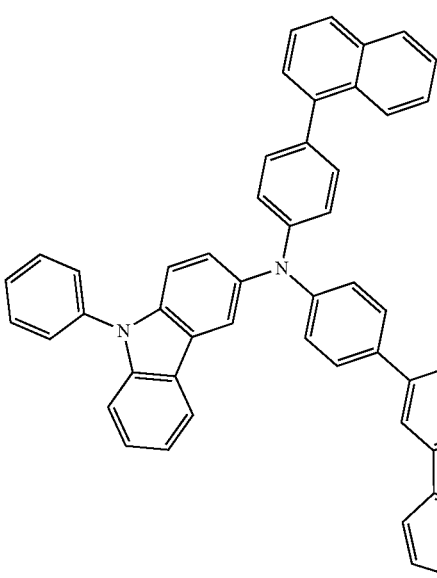

359
-continued
274
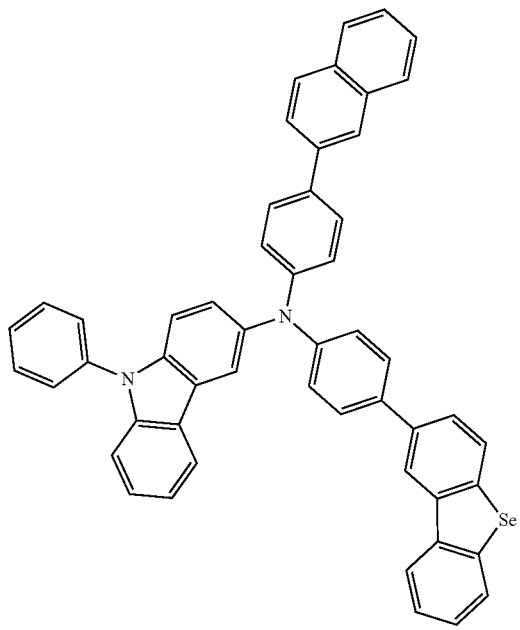
275
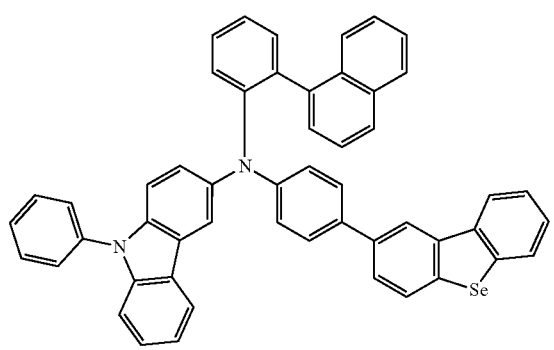
276
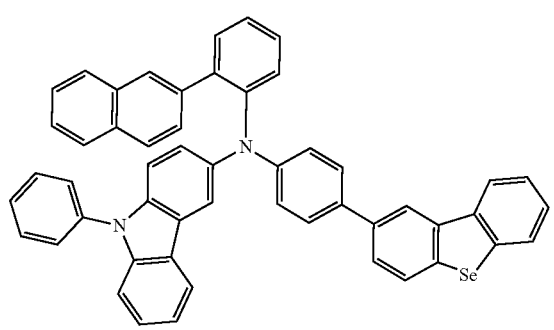
360
-continued
277
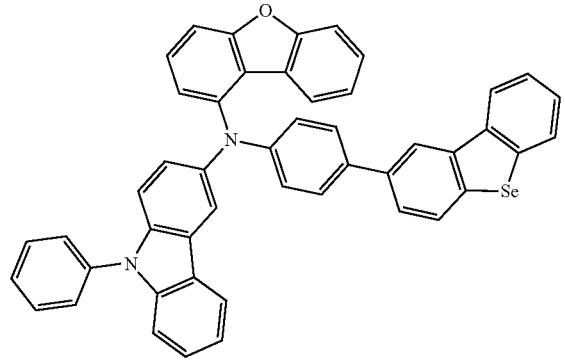
278
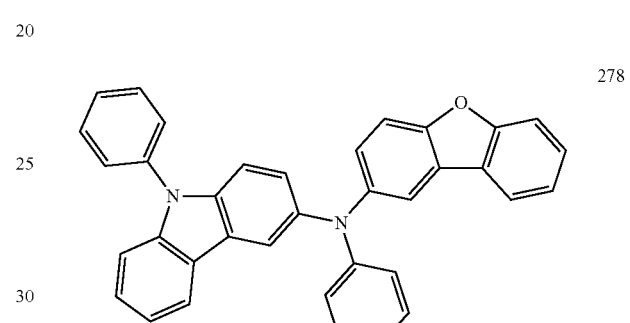
279
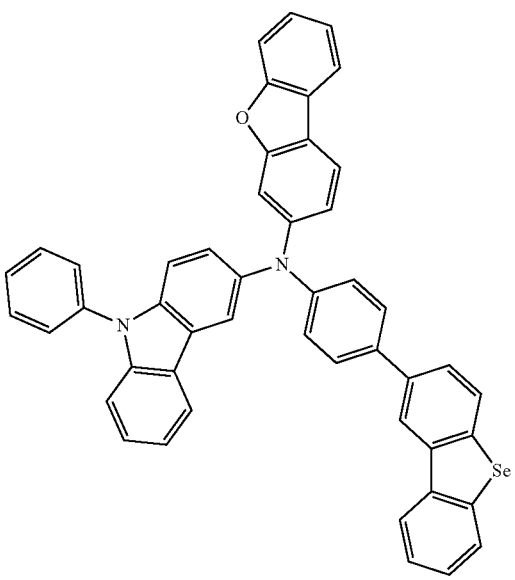

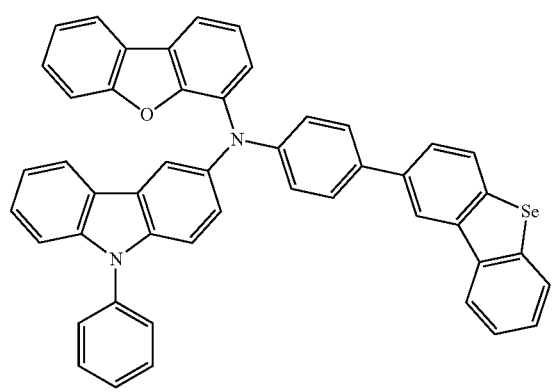
280
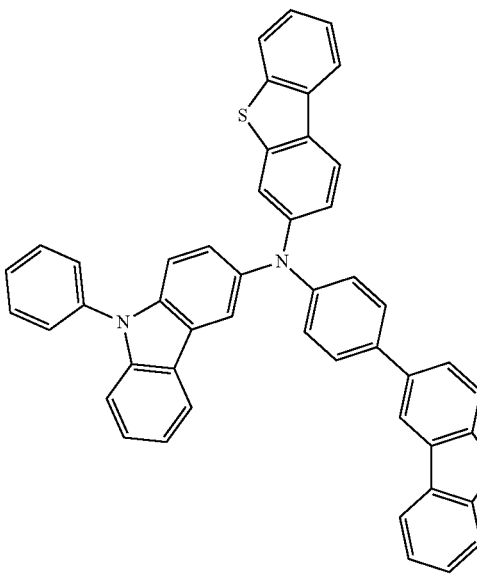
283
281
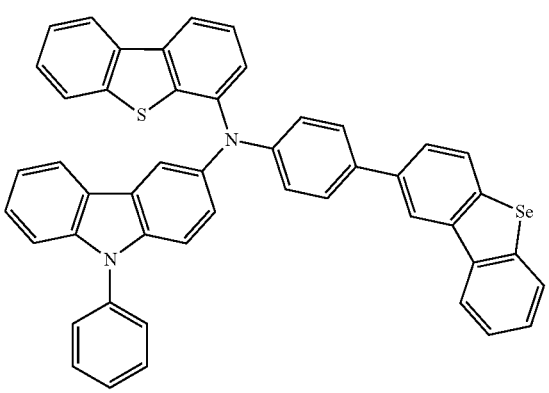
284
282
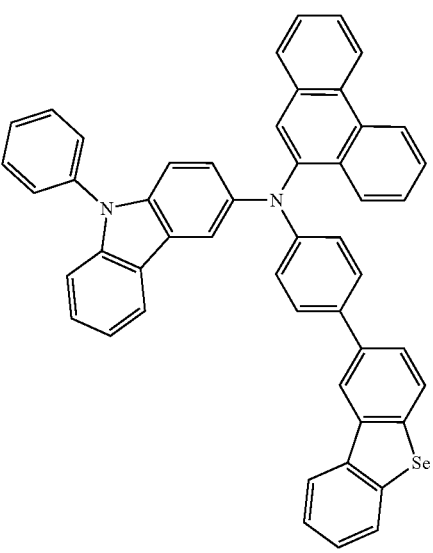
285

-continued
286
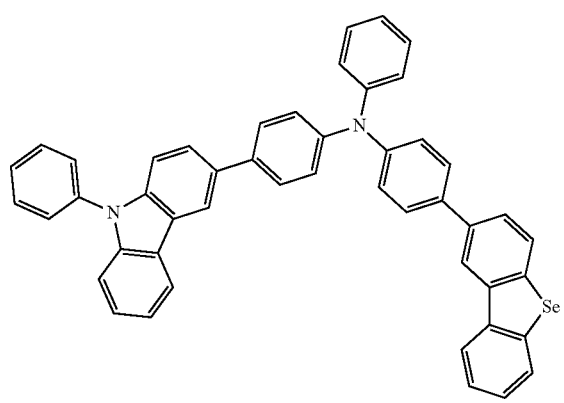
288
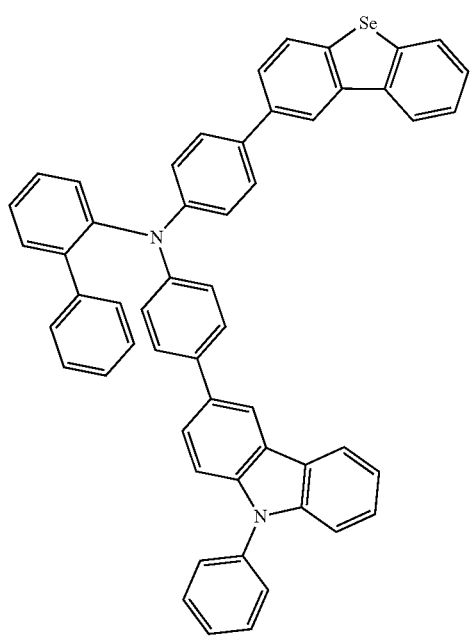
287
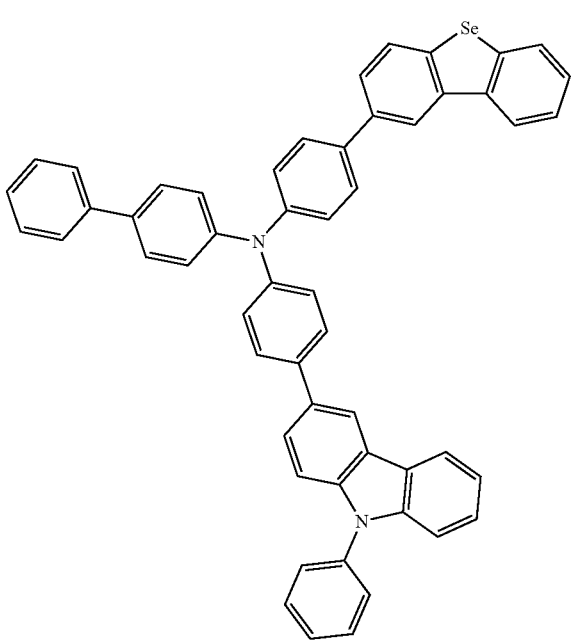
289
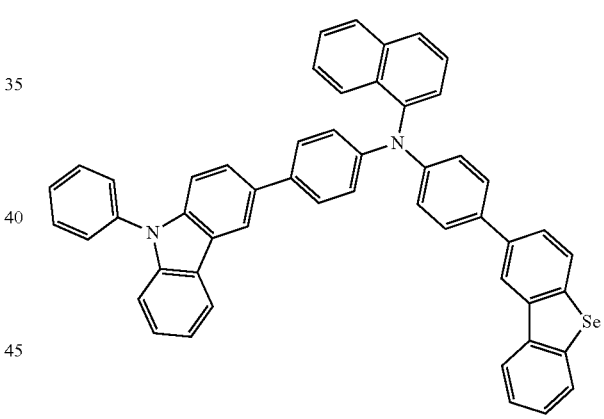
290
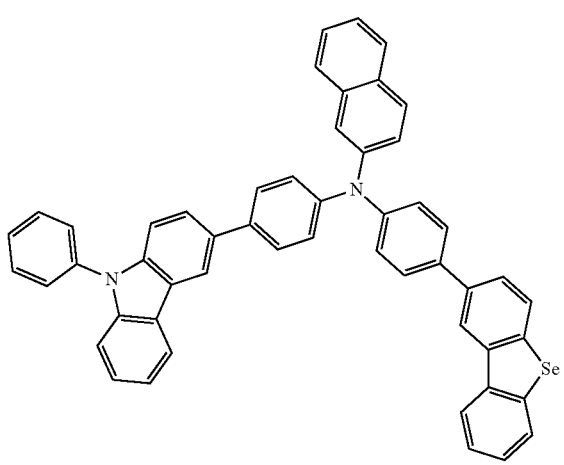

-continued
291
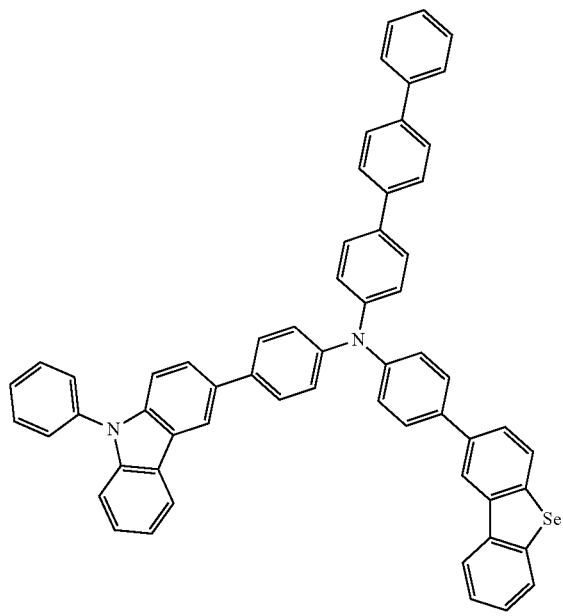
292
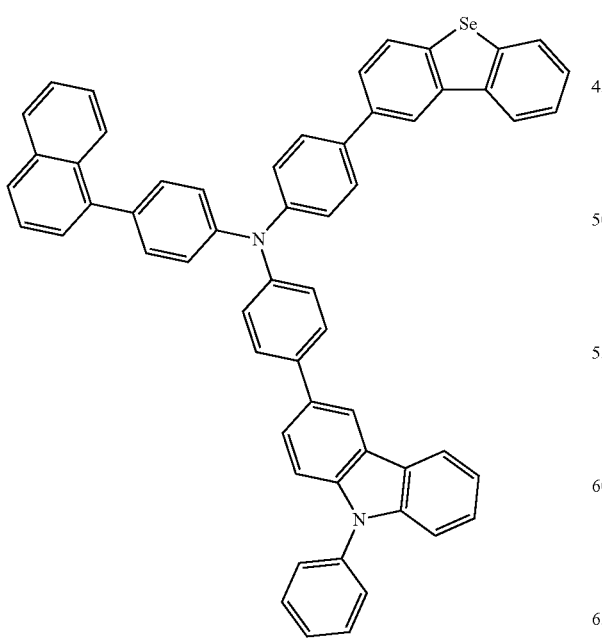
293
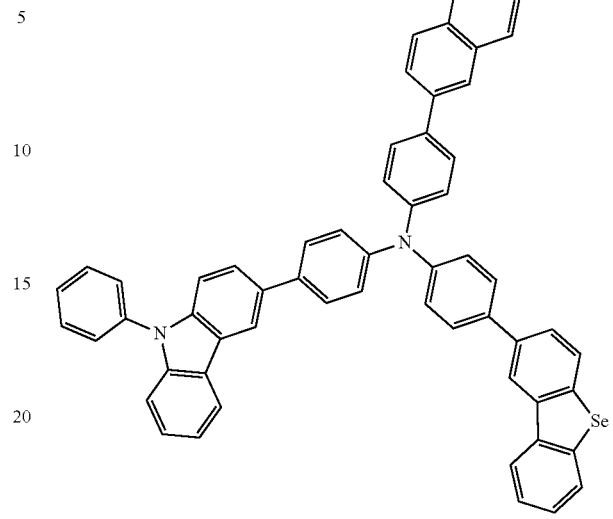
294
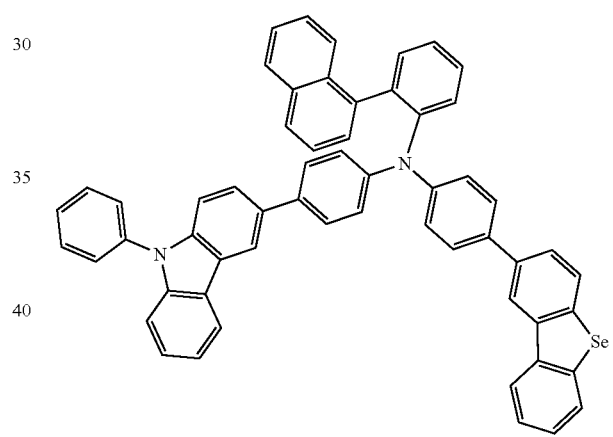
295
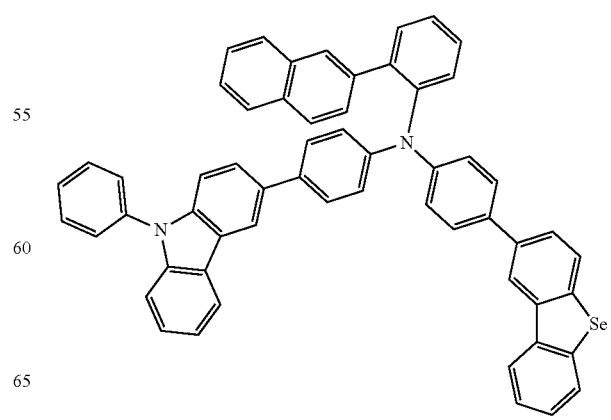

296
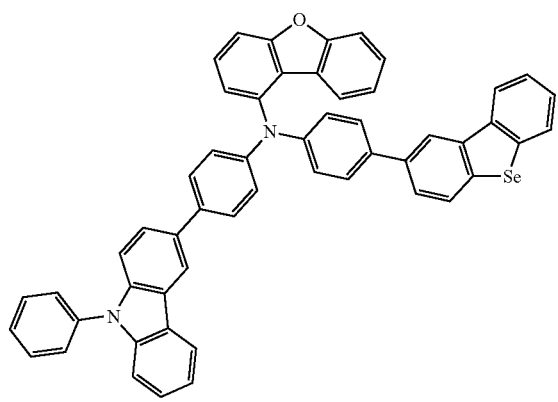
297
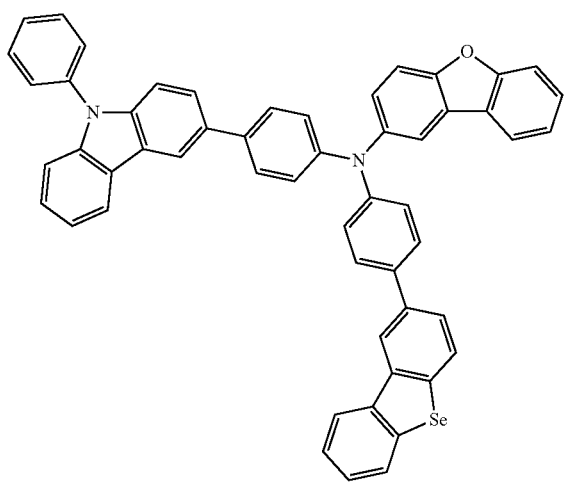
298
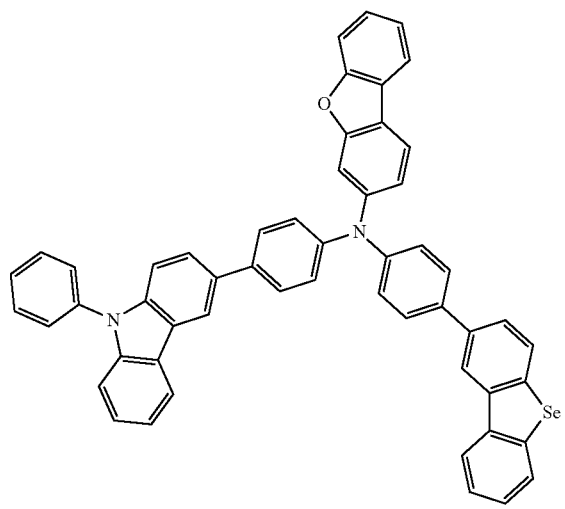
299
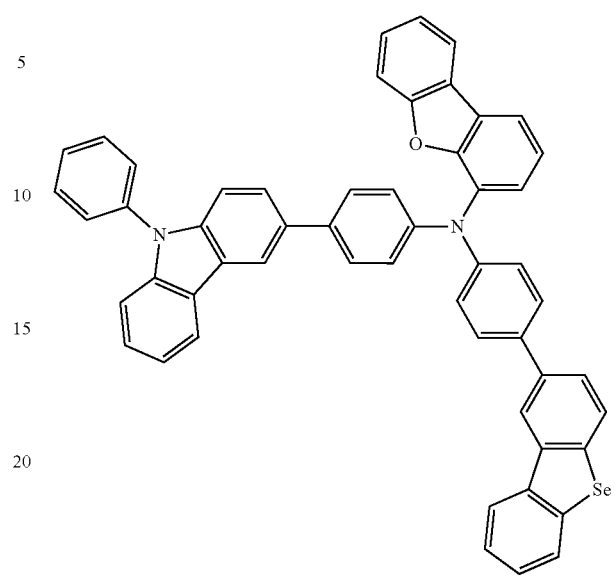
300
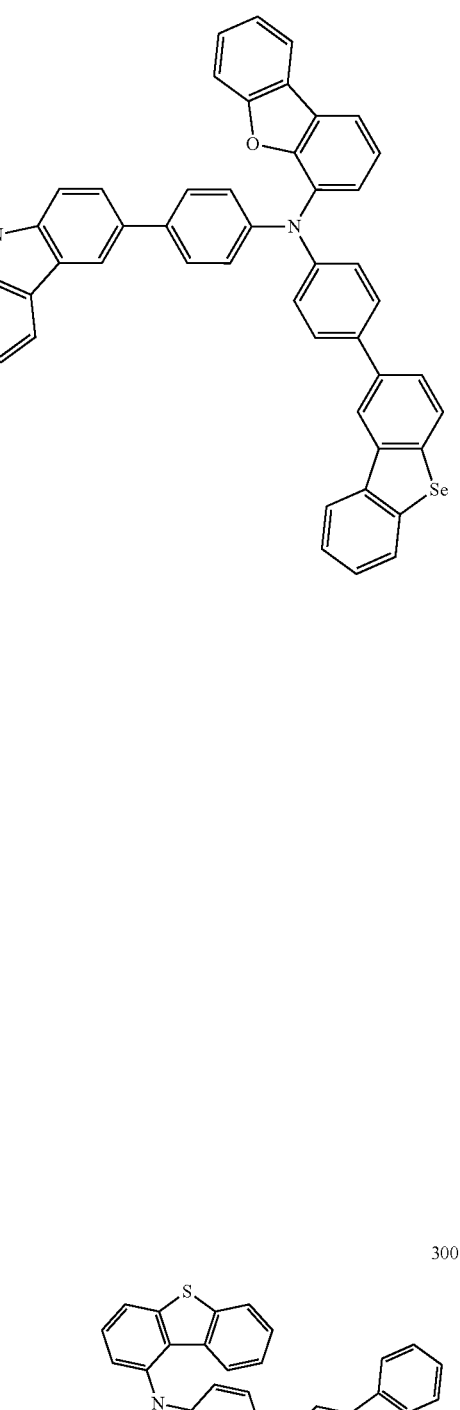

369
-continued
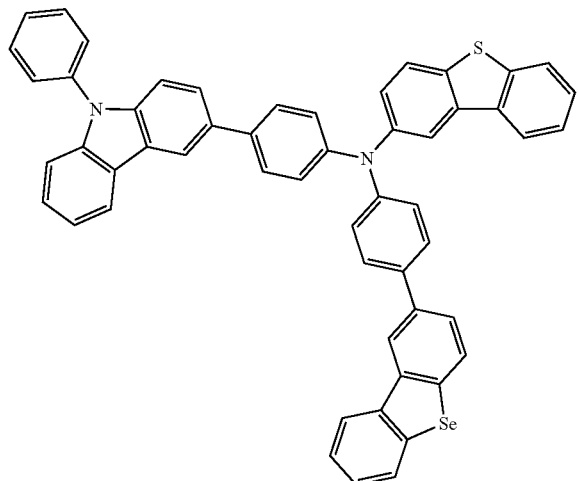
301
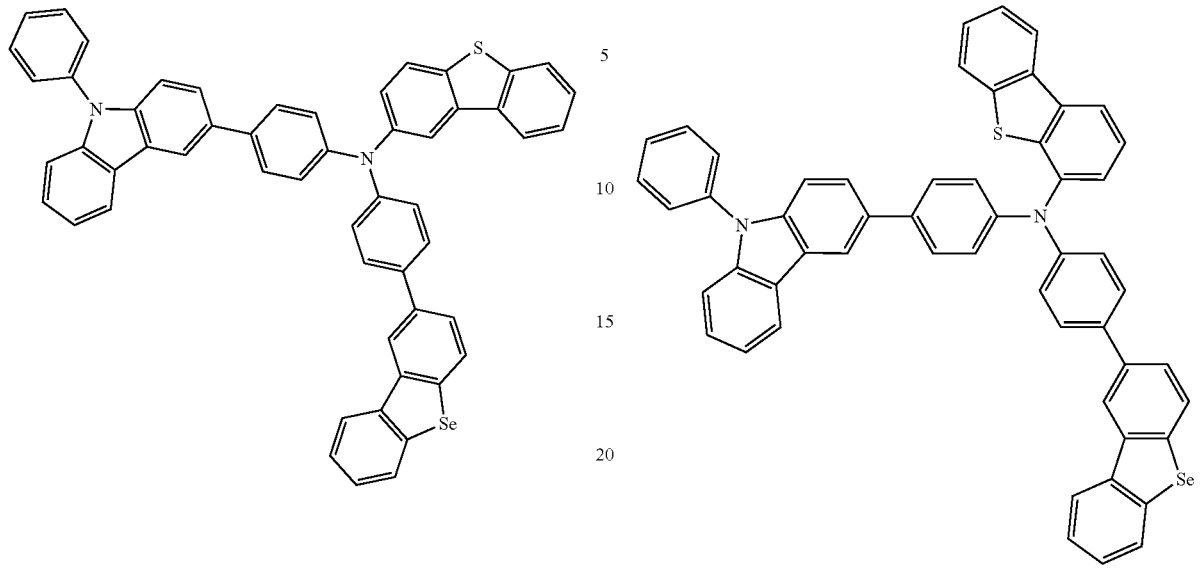
370
-continued
303
304
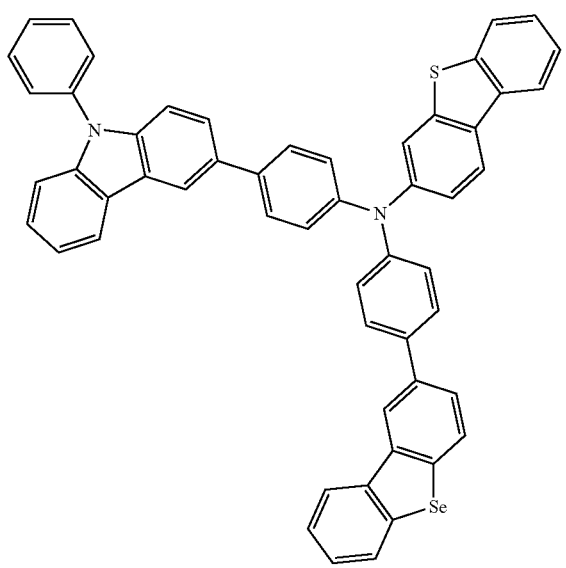
302
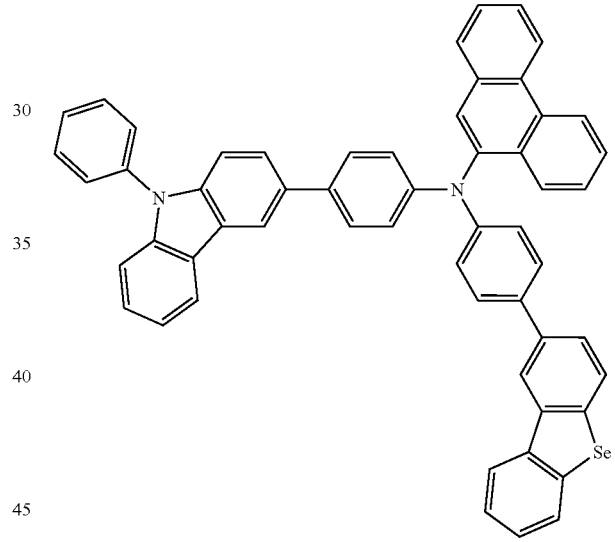
* * * * *

UNITED STATES PATENT AND TRADEMARK OFFICE
CERTIFICATE OF CORRECTION

PATENT NO. : 11,737,356 B2
APPLICATION NO. : 16/997595
DATED : August 22, 2023
INVENTOR(S) : Dongjun Kim et al.

Page 1 of 2

It is certified that error appears in the above-identified patent and that said Letters Patent is hereby corrected as shown below:

In the Claims

In Column 264, Lines 58-65, in Claim 1, in Formula 1, delete

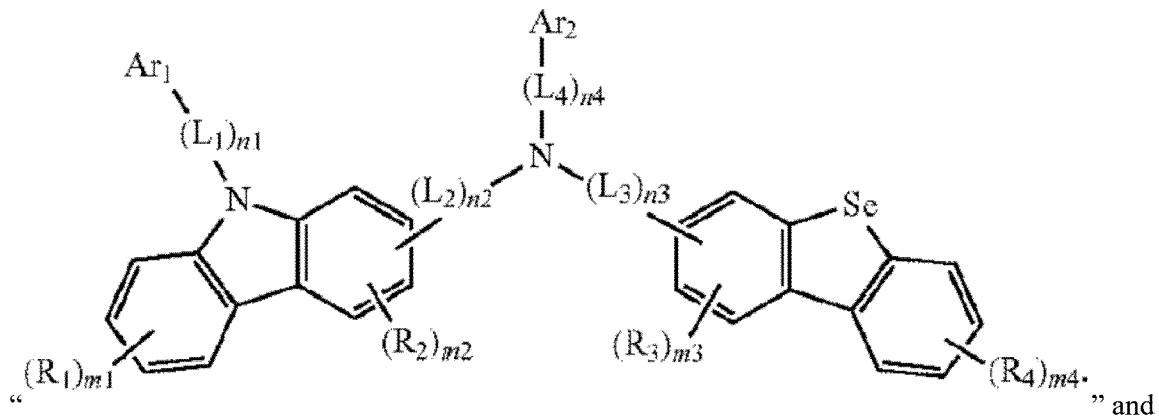

" and

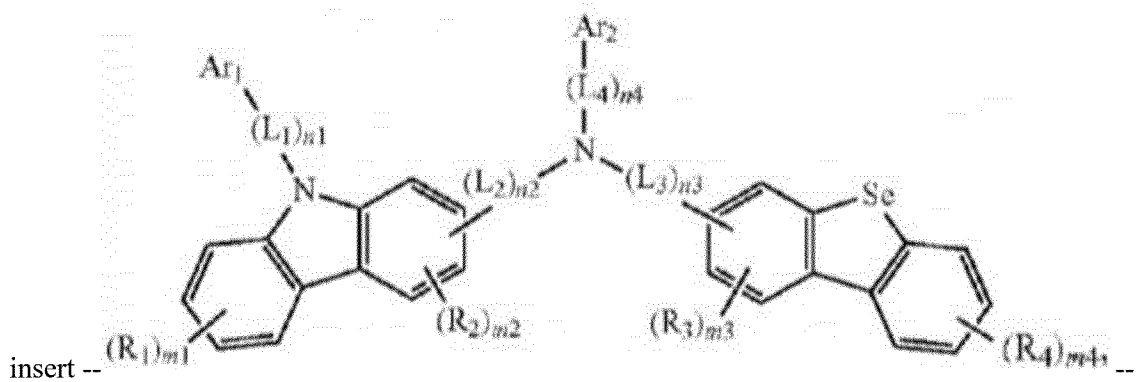

insert -- --.

In Column 266, Line 51, in Claim 5, delete "m" and insert -- $m_5$ --.

Signed and Sealed this
Twenty-sixth Day of March, 2024

Katherine Kelly Vidal
*Director of the United States Patent and Trademark Office*

CERTIFICATE OF CORRECTION (continued)
U.S. Pat. No. 11,737,356 B2

In Column 370, Lines 26-46, in Claim 9, in Compound Group 304, after " 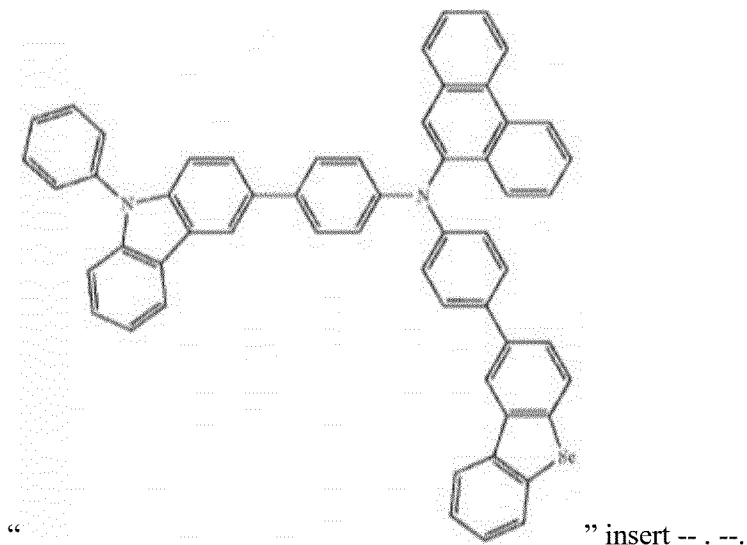 " insert -- . --.